US011953506B2

(12) United States Patent
Parekh et al.

(10) Patent No.: US 11,953,506 B2
(45) Date of Patent: Apr. 9, 2024

(54) MONITORING INFLAMMATION STATUS

(71) Applicant: Mologic Limited, Thurleigh (GB)

(72) Inventors: Gita Parekh, Wooton (GB); Paul Davis, Sharnbrook (GB)

(73) Assignee: MOLOGIC LIMITED, Thurleiogh (GB)

(*) Notice: Subject to any disclaimer, the term of this patent is extended or adjusted under 35 U.S.C. 154(b) by 658 days.

(21) Appl. No.: 16/783,567

(22) Filed: Feb. 6, 2020

(65) Prior Publication Data

US 2020/0241008 A1 Jul. 30, 2020

Related U.S. Application Data

(63) Continuation of application No. 15/122,304, filed as application No. PCT/GB2015/050602 on Mar. 2, 2015, now abandoned.

(30) Foreign Application Priority Data

Feb. 28, 2014 (GB) .................................... 1403605

(51) Int. Cl.
G01N 33/68 (2006.01)

(52) U.S. Cl.
CPC ..... G01N 33/6893 (2013.01); G01N 33/6863 (2013.01); *G01N 2800/12* (2013.01); *G01N 2800/7095* (2013.01)

(58) Field of Classification Search
CPC ........... G01N 33/6893; G01N 33/6863; G01N 2800/12; G01N 2800/7095
See application file for complete search history.

(56) References Cited

U.S. PATENT DOCUMENTS

| | | | |
|---|---|---|---|
| 7,214,542 B2 | 5/2007 | Hutchinson | |
| 2003/0049715 A1 | 3/2003 | Welsch | |
| 2006/0154234 A1* | 7/2006 | Winther | G01N 33/5005 435/6.14 |
| 2006/0211026 A1* | 9/2006 | Belloni | C12Q 1/6883 435/6.14 |
| 2008/0044843 A1* | 2/2008 | Perlee | G01N 33/6893 436/87 |
| 2008/0227117 A1* | 9/2008 | Fehniger | G01N 33/6893 530/382 |
| 2009/0054374 A1 | 2/2009 | Kennedy | |
| 2009/0068685 A1* | 3/2009 | Streeper | G01N 33/57423 435/7.23 |
| 2011/0183887 A1* | 7/2011 | Pilon | A61K 38/17 514/1.5 |
| 2013/0040844 A1* | 2/2013 | Wyss-Coray | C07K 16/18 435/7.1 |
| 2013/0261016 A1* | 10/2013 | Debad | G01N 33/57423 506/9 |
| 2014/0030735 A1* | 1/2014 | Merali | A61K 31/7072 435/23 |
| 2014/0094505 A1* | 4/2014 | Chan | G01N 33/6893 435/6.12 |
| 2015/0072349 A1* | 3/2015 | Diamandis | G01N 33/57434 435/6.12 |

FOREIGN PATENT DOCUMENTS

| | | |
|---|---|---|
| CA | 2714714 A1 | 1/2012 |
| WO | 2006118522 A1 | 11/2006 |
| WO | 2008144041 A1 | 11/2008 |
| WO | 2011084233 A1 | 7/2011 |
| WO | 2013156794 A1 | 10/2013 |

OTHER PUBLICATIONS

Nash (J. Cystic Fibrosis 2012 11: Supplemental S92) (Year: 2012).*
Woodruff (Pro. Am. Thorac Soc 2011 8:350-355). (Year: 2011).*
Villar-Alvarez (European Respiratory Journal 2011 vol. 38, p. 735; total 2 pages) (Year: 2011).*
Intellectual Property India. Examination report for application 201617029043, dated Mar. 13, 2020.
Abbot, J., et al., "What Defines a Pulmonary Exacerbation? The Perceptions of Adults with Cystic Fibrosis". Journal of Cystic Fibrosis, 8, (2009) 356-359.
Bilton, D., et al., "Pulmonary Exacerbation: Towards a Definition for use in Clinical Trials. Report from the EuroCareCF Working Group on Outcome Parameters in Clinical Trials", Journal of Cystic Fibrosis, vol. 10, Suppl 2, (2011) S79-S81.
Cappuzzo, F., et al., "Doxycycline treatment for lymphangioleiomyomatosis with urinary monitoring for MMPs", New England Journal of Medicine, vol. 354, No. 24, Jun. 15, 2006.
Chinese Office Action for CN201580022399.6 dated Aug. 2, 2018.
Chinese Office Action for CN201580022399.6 dated Nov. 16, 2017.
Combined Search and Examination Report for GB1403605.7 dated Nov. 14, 2014.
Dahlen, I, et al., "Inflammatory Markers in Acute Exacerbations of Obstructive Pulmonary Disease: Predictive Value in Relation to Smoking History", Respiratory Medicine (1999) 93, 744-751.
Downey, D. G., et al., "The Relationship of Clinical and inflammatory Markers to Outcome in Stable Patients with Cystic Fibrosis", Pediatric Pulmonology, vol. 42, (2007) 216-220.
European Office Action for EP15708260.3 dated Feb. 21, 2018.

(Continued)

*Primary Examiner* — Changhwa J Cheu
(74) *Attorney, Agent, or Firm* — Quarles & Brady LLP

(57) ABSTRACT

Methods for monitoring inflammation status of a subject comprise determining levels of at least one neutrophil activation marker, or at least three markers, in urine samples taken from the subject at multiple time points, wherein increased levels of the at least one neutrophil activation marker, or at least one of the markers, in a urine sample are indicative of or predictive of an exacerbation of inflammation and/or wherein decreased levels of the at least one neutrophil activation marker, or at least one of the markers, in a urine sample following an increase are indicative or predictive of recovery from, or successful treatment of, an exacerbation of inflammation. Corresponding systems, test kits and computer programs are provided.

8 Claims, 53 Drawing Sheets

Specification includes a Sequence Listing.

(56) References Cited

OTHER PUBLICATIONS

European Office Action for EP15708260.3 dated Jul. 20, 2018.
European Office Action for EP2015708260.3 dated Jul. 13, 2017.
Gunay, O., et al., "Effects of Physical Exercise on Lung Injury and Oxidant Stress in Children with Asthma", Allergol Immunopathol, vol. 40, (2012) 20-24.
Huang, JT., et al., "Clinical Validity of Plasma and Urinary Desmosine as Biomarkers for Chronic Obstructive Pulmonary Disease", Edinburgh Research Explorer, vol. 67, No. 6, (2011) 502-508.
International Preliminary Report on Patentability for PCT/GB2015/050602 dated May 9, 2016.
International Search Report and Written Opinion for PCT/GB2015/050602 dated Aug. 4, 2015.
Laguna, T. A., et al., "Urinary Desmosine: A Biomarker of Structural Lung Injury During CF Pulmonary Exacerbation", Pediatr Pulmonol, vol. 47, No. 9, (2012) 1-3.
Michel, O., et al., "Dose-Response Relationship to Inhaled Endotoxin in Normal Subjects", American Journal of Respiratory and Critical Care Medicine, vol. 156, No. 4, Oct. 1, 1997, pp. 1157-1164.
Parekh, G., et al., "Urinary Biomarkers at Exacerbation of Chronic Obstructive Pulmonary Disease (COPD)", I \American Thoracic Society, (2014).
Pulmonary Exacerbations in Cystic Fibrosis Information Sheet, Children's Hospital of Illinois, Yale School of Medicine, (2006).
Search Report for GB1403605.7 dated Dec. 24, 2014.
Stockfelt, L., et al., "Effects on Airways of Short-term Exposure to Two Kinds of Wood Smoke in a Chamber Study of Healthy Humans", Inhalation Toxicology, vol. 24(1-4), (2012) 47-59.
Verhave, J. C., et al., "Clinical value of inflammatory urinary biomarkers in overt diabetic nephropathy: A prospective study", Diabetes Research and Clinical Practice, vol. 101, No. 3, Jul. 20, 2013, pp. 333-340.
Wagner, B. D., et al. "The applicability of urinary creatinine as a method of specimen normalization in the cystic fibrosis population." Journal of Cystic Fibrosis 9.3 (2010): 212-216.
Written Opinion for PCT/GB2015/050602 dated Jan. 29, 2016.

* cited by examiner

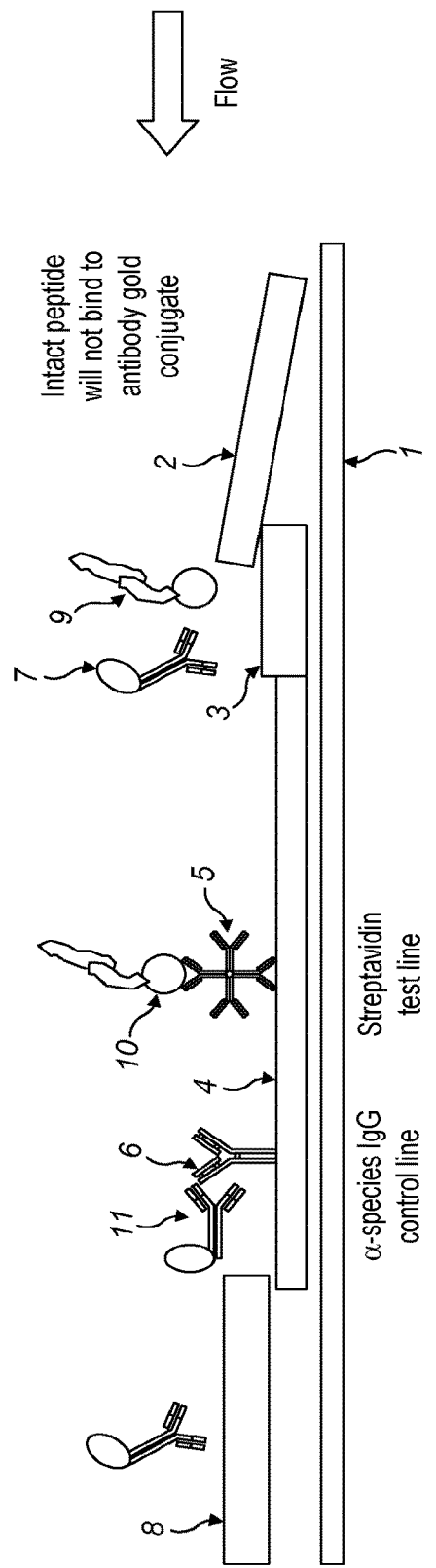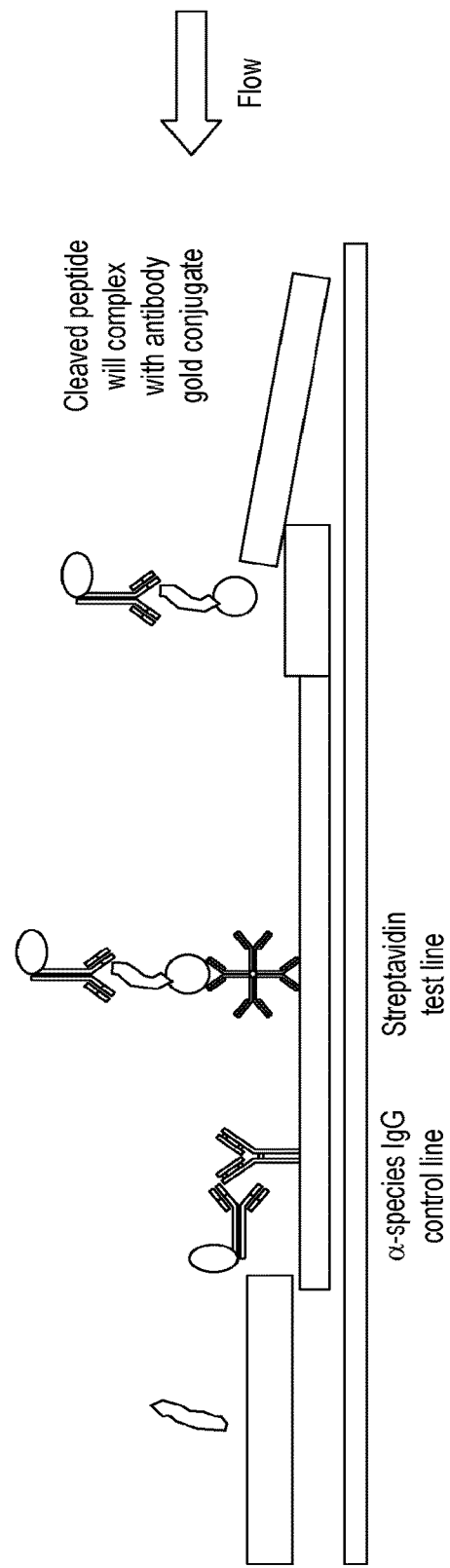

1,2-bis(Bromomethyl) benzene
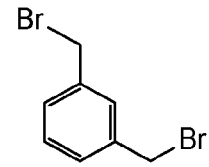
1,3-bis(Bromomethyl) benzene
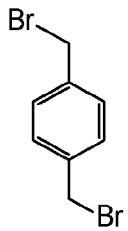
1,4-bis(Bromomethyl) benzene
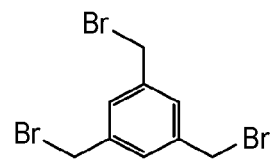
1,3,5-tris(Bromomethyl) benzene
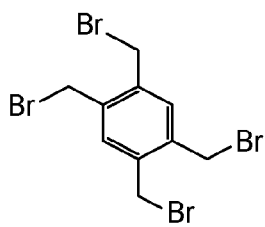
1,2,4,5-tetrakis(Bromomethyl) benzene
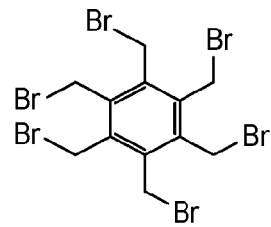
1,2,3,4,5,6-hexakis(Bromomethyl) benzene
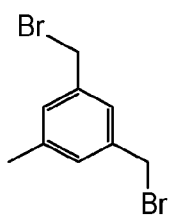
1,3-bis(bromomethyl)-5-methylbenzene
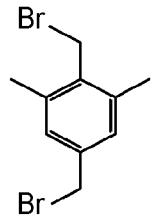
2,5-bis(bromomethyl)-1,3-dimethylbenzene
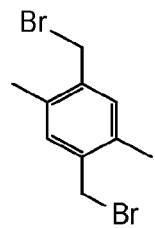
2,5-bis(bromomethyl)-1,4-dimethylbenzene
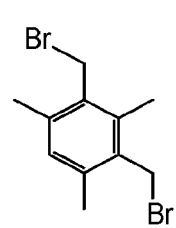
2,5-bis(bromomethyl)-1,4-dimethylbenzene
*FIG. 14*

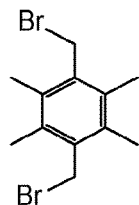
3,6-bis(bromomethyl)durene
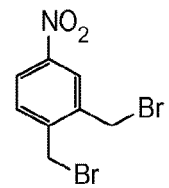
3,4-bis(bromomethyl)-nitrobenzene
2,3-bis(bromomethyl)-nitrobenzene
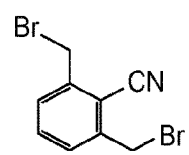
2,6-bis(bromomethyl)-benzonitrile
1,3-bis(bromomethyl)-5-methoxybenzene
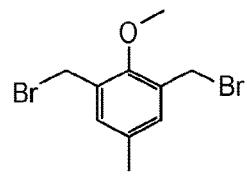
1,3-bis(bromomethyl)-2-methoxy-5-methylbenzene
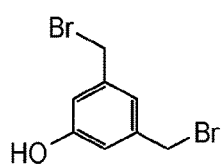
1,3-bis(bromomethyl)-5-hydroxybenzene
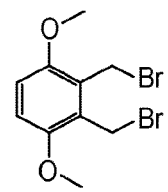
2,3-bis(bromomethyl)-1,4-dimethoxybenzene
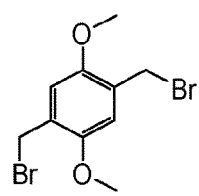
2,5-bis(bromomethyl)-1,4-dimethoxybenzene
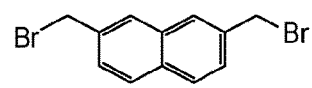
2,7-bis(bromomethyl)-naphthalene
*FIG. 14 Cont'd*

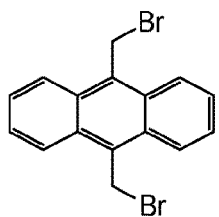
1,4-bis(bromomethyl)-naphthalene
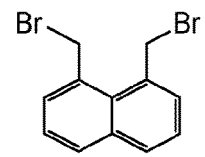
1,8-bis(bromomethyl)-naphthalene
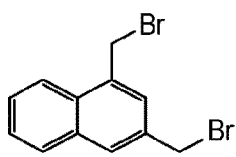
1,3-bis(bromomethyl)-naphthalene
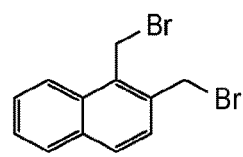
1,2-bis(bromomethyl)-naphthalene
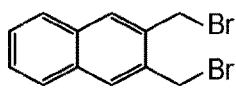
2,3-bis(bromomethyl)-naphthalene
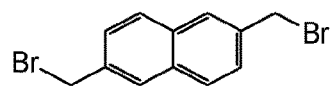
2,6-bis(bromomethyl)-naphthalene
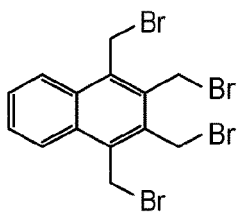
1,2,3,4-tetrakis(bromomethyl)-naphthalene
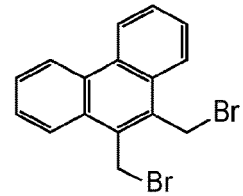
9,10-bis(bromomethyl)-phenanthrene
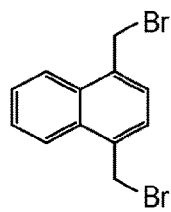
5,10-bis(bromomethyl)-anthracene
1-(bromomethyl)-3-[3(bromoethyl)benzyl]benzene
*FIG. 14* Cont'd Testing algorithm on 2nd baseline-onset samples 16 patients provided a 2nd baseline-onset sample before
(as indicated by '-') or after the previously analysed recovery samples

| ID | TIMP2 | MMP Onset 1 | A1AT | Days since recovery | TIMP2 | MMP Onset 2 | A1AT |
|---|---|---|---|---|---|---|---|
| 1 | -51.3 | 115.6 | 21.8 | 140 | 96.7 | 5626.3 | 444.3 |
| 5 | 18.7 | 522.1 | 180.0 | 560 | 434.7 | -100.0 | -45.8 |
| 6 | 83.8 | 347.7 | 58.5 | -499 | -82.9 | 91.8 | -10.2 |
| 10 | 40.9 | 0 | 832.8 | 260 | 69.2 | 110.1 | 264.2 |
| 11 | 291.9 | 243.6 | 49.5 | 57 | 40.0 | -55.5 | -55.4 |
| 20 | 3.9 | 0 | 302.0 | 96 | 2.6 | 0 | 38.5 |
| 23 | -60.9 | 4.8 | -100.0 | 168 | 171.5 | 661.9 | 1592.8 |
| 25 | -0.8 | 0 | 44.6 | -320 | 12.6 | 0 | -16.4 |
| 27 | 3.5 | 0 | -70.4 | 321 | 108.3 | 1.8 | 894.7 |
| 29 | 117.9 | -89.6 | 0 | -800 | 71.2 | 4.0 | 3.0 |
| 30 | 81.9 | -100.0 | 2315.3 | -30 | 1174.5 | 0 | 139.9 |
| 33 | -40.0 | 11.6 | -100.0 | -336 | -81.0 | 2.5 | 162.4 |
| 34 | 179.8 | 4.5 | -14.3 | -757 | 58.0 | -100.0 | 40.8 |
| 39 | -50.5 | 0 | -56.3 | 260 | -34.2 | 0 | -26.4 |
| 40 | 30.0 | 0 | -24.4 | -109 | 324.6 | 0 | 475.9 |
| 44 | 58.6 | 0 | -79.7 | 41 | 184.6 | 21.7 | 7422.7 |

No result (rows 27, 39) / No result (row 39, right side)

88% sensitivity                94% sensitivity

FIG. 27

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 1

Gly Pro Gln Gly Ile Phe Gly Gln
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Cys Gly Pro Gln Gly Ile Phe Gly Gln Cys
1               5                   10

<210> SEQ ID NO 3
<211> LENGTH: 25
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: BINDING
<222> LOCATION: (1)..(1)
<223> OTHER INFORMATION: Biotinylated

<400> SEQUENCE: 3

Gly Pro Gln Gly Ile Phe Gly Gln Glu Ser Ile Arg Leu Pro Gly Cys
1               5                   10                  15

Pro Arg Gly Val Asn Pro Val Val Ser
            20                  25

<210> SEQ ID NO 4
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: BINDING
<222> LOCATION: (1)..(1)
<223> OTHER INFORMATION: Bound to pegylated (PEG)-Biotin via the PEG
      spacer group
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MOD_RES
<222> LOCATION: (7)..(7)
<223> OTHER INFORMATION: ACETYLATION

<400> SEQUENCE: 4

Asp Ala Glu Glu Ala Glu Glu Gly Pro Gln Gly Ile Phe Gly Gln Glu
1               5                   10                  15

Ser Ile Arg Leu Pro Gly Cys Pro Arg Gly Val Asn Pro Val Val Ser
            20                  25                  30

<210> SEQ ID NO 5
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: BINDING
<222> LOCATION: (24)..(24)
<223> OTHER INFORMATION: Biotinylated

<400> SEQUENCE: 5

Ser Ile Arg Leu Pro Gly Cys Pro Arg Gly Val Asn Pro Val Val Ser
1               5                   10                  15

Gly Pro Gln Gly Ile Phe Gly Gln
            20

<210> SEQ ID NO 6
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (27)..(27)
<223> OTHER INFORMATION: ACETYLATION
<220> FEATURE:
<221> NAME/KEY: MOD_RES
<222> LOCATION: (30)..(30)
<223> OTHER INFORMATION: ACETYLATION
<220> FEATURE:
```

```
<221> NAME/KEY: SITE
<222> LOCATION: (30)..(31)
<223> OTHER INFORMATION: Glu and Asp linked via polyethylene glycol
      (PEG) spacer group
<220> FEATURE:
<221> NAME/KEY: BINDING
<222> LOCATION: (31)..(31)
<223> OTHER INFORMATION: Biotinylated

<400> SEQUENCE: 6

Ser Ile Arg Leu Pro Gly Cys Pro Arg Gly Val Asn Pro Val Val Ser
1               5                   10                  15

Gly Pro Gln Gly Ile Phe Gly Gln Ala Glu Glu Ala Glu Glu Asp
            20                  25                  30
```

MONITORING INFLAMMATION STATUS

CROSS-REFERENCE TO RELATED APPLICATIONS

The present application is a continuation of U.S. application Ser. No. 15/122,304, filed Aug. 29, 2016, which is the U.S. National Stage of International Application PCT/GB2015/050602, filed on Mar. 2, 2015, which International Application was published on Sep. 3, 2015 as International Publication No. WO2015/128681. The International Application claims priority to British Patent Application No. GB 1403605.7, filed on Feb. 28, 2014, the contents of which are incorporated herein by reference in their entireties.

FIELD OF THE INVENTION

The present invention relates to the identification of markers that predict or identify an inflammatory event. In particular, the invention relates to prediction and identification of exacerbation events, more specifically pulmonary exacerbations, based upon measuring urinary markers. The invention permits monitoring of inflammatory status by an individual by providing a personalised home use test.

BACKGROUND TO THE INVENTION

There are a number of different disorders of the respiratory tract, many of which have an inflammatory component. Examples included chronic obstructive pulmonary disease (COPD) and cystic fibrosis (CF).

The chronic infection and inflammation of lung disease can cause a progressive decline of lung function resulting in daily symptoms such as cough and sputum production. There are intermittent episodes of acute worsening of symptoms, more commonly referred to as pulmonary exacerbations. Pulmonary exacerbations (PEx) are a major cause of morbidity, mortality and hospital admission.

DESCRIPTION OF THE INVENTION

It would be useful to be able to accurately monitor subjects to predict PEx events before they happen, or identify the early onset of a PEx. This would allow early interventions to minimize the inflammatory damage caused by the PEx. Ideally, this can be achieved in a home self-testing approach. The inventors have discovered that urine samples are a useful source of markers which can predict PEx events, enabling home testing for predicting PExs. The markers may be indicative of neutrophil activation and thus may be termed "neutrophil activation markers".

Accordingly, in a first aspect, the invention provides a method for monitoring inflammation status of a subject, the method comprising determining levels of at least one (neutrophil activation) marker in urine samples taken from the subject at multiple time points, wherein increased levels of the at least one neutrophil activation marker in a urine sample are indicative of or predictive of an exacerbation of inflammation.

The method is preferably implemented in a system or kit for home use monitoring.

Accordingly, the invention also provides a system or test kit for monitoring inflammation status in a subject, comprising:
a. One or more testing devices for determining levels of at least one (neutrophil activation) marker in a urine sample
b. A processor; and
c. A storage medium comprising a computer application that, when executed by the processor, is configured to:
  i. Access and/or calculate the determined levels of the at least one neutrophil activation marker in the urine sample on the one or more testing devices
  ii. Calculate whether there is an increased or decreased level (or whether the level remains the same) of the at least one neutrophil activation marker in the urine sample; and
  iii. Output from the processor the current inflammation status of the subject, wherein increased levels of the at least one neutrophil activation marker in a urine sample are indicative of or predictive of an exacerbation of inflammation.

The invention also relates to a corresponding computer application for use in the system or test kit.

The inventors have determined that specific and sensitive results may be achieved by combining a plurality of urinary markers in order to monitor or predict PEx events. Accordingly, the invention also provides a method for monitoring inflammation status of a subject, the method comprising determining levels of at least 2, 3, 4, 5, 6, 7, 8, 9, 10 or more markers in urine samples taken from the subject at multiple time points, wherein increased levels of at least one of the markers in a urine sample indicates or predicts an exacerbation of inflammation.

Similarly, the invention also provides a system or test kit for monitoring inflammation status in a subject, comprising:
a. One or more testing devices for determining levels of at least 2, 3, 4, 5, 6, 7, 8, 9, 10 or more markers in a urine sample
b. A processor; and
c. A storage medium comprising a computer application that, when executed by the processor, is configured to:
  i. Access and/or calculate the determined levels of each marker in the urine sample on the one or more testing devices
  ii. Calculate whether there is an increased or decreased level (or whether the level remains the same) of at least one of the markers in the urine sample; and
  iii. Output from the processor the current inflammation status of the subject, wherein increased levels of at least one of the markers in a urine sample are indicative of or predictive of an exacerbation of inflammation.

The invention also relates to a corresponding computer application for use in the system or test kit.

According to all aspects of the invention, the markers are useful for monitoring of inflammation. Thus as well as proving useful for identifying or predicting an inflammatory event such as a PEx, the markers may also be useful for indicating a recovery from, or successful treatment of, the inflammatory event. Accordingly, in some embodiments decreased levels of the at least one marker in a urine sample following an increase are indicative or predictive of recovery from, or successful treatment of, an exacerbation of inflammation. The decrease may be down to pre-exacerbation levels and then may be measured on an on-going basis to ensure they are maintained thereafter. The invention may thus be used in conjunction with and to guide treatment of individual subjects. The invention may be used to monitor on-going treatment and to assist with determination of whether treatments should be altered (e.g. the dosage adjusted, level of intervention altered), stopped or replaced with an alternative. Similarly, stable levels of markers in urine of subjects may indicate the condition is being managed and the inflammatory status is stable.

The invention may be applicable to identifying bacterial or viral causes of an exacerbation in some embodiments.

In specific embodiments according to all aspects of the invention the monitored inflammation status is lung inflammation status. In further embodiments, the exacerbation of inflammation that is indicated and/or predicted is a pulmonary exacerbation.

The subject is a mammalian subject, typically a human. In certain embodiments, the subject is suffering from a respiratory disorder. More specifically, the respiratory disorder may be chronic obstructive pulmonary disease (COPD) or cystic fibrosis (CF). The inventors have accumulated data showing the effectiveness of this approach in these specific disease conditions. COPD represents a collection of lung diseases including chronic bronchitis, emphysema and chronic obstructive airways disease and thus any of these lung diseases may be monitored according to the invention. The invention may also be applicable to monitoring of asthma and interstitial lung disease (ILD). The invention may also be applied to bronchiectasis.

It should be noted that the invention is performed in vitro based upon isolated urine samples. The urine sample may be a mid-stream urine sample in some embodiments. The methods of the invention may include steps of obtaining a urine sample for testing in some embodiments. Similarly, in some embodiments, the systems and test kits include suitable vessels for receiving a urine sample. Those vessels may be specifically adapted for urine collection and may be different depending upon the gender of the subject. Commercially available examples include the Peezy MSU Urine Collection Device (Williams Medical). The container may be coloured to protect any light sensitive analytes.

By "marker" is meant a molecule indicative of inflammation, typically indicative of neutrophil activation. In some embodiments, the at least one marker is selected from a signalling molecule or an effector/effector inhibitor molecule. It should be noted that throughout the specification the term "the at least one marker" includes "at least one of the markers" where levels of a plurality of markers are being detected. Signalling molecules may be responsible for recruitment of the molecules that cause inflammatory damage. The effector molecules cause inflammatory damage. They may be enzymes. The effector inhibitor molecules inhibit the activity of the effector molecules. They may be enzyme inhibitors.

In some embodiments the effector molecule is selected from a protease activity, Neutrophil gelatinase-associated lipocalin (NGAL), calprotectin or myeloperoxidase (MPO). The effector molecule, in particular NGAL activity, may be either free or in complex. In further embodiments, the protease activity is selected from matrix metalloproteinase (MMP) activity, human neutrophil elastase (HNE) activity and cathepsin G activity. There are various MMPs which may usefully be detected, as discussed in further detail herein. In specific embodiments, MMP activity comprises MMP9 and/or MMP8 activity.

According to the invention, levels of effector inhibitor molecules may additionally or alternatively be determined. In specific embodiments, the effector inhibitor molecule comprises, consists essentially of or consists of (i.e. is) a protease inhibitor molecule. In some embodiments, the protease inhibitor molecule is selected from Tissue Inhibitor of metalloproteinase (TIMP), cystatin c, secreted leukocyte protease inhibitor (SLPI) and alpha-1 antitrypsin (A1AT).

According to the invention, levels of signalling molecules may additionally or alternatively be determined. In specific embodiments, the signalling molecule is selected from ICAM-1, IL-6, IL-1β, IL-8, N-formyl-Met-Leu-Phe (fMLP), IL-6 induced fibrinogen, fragments of complement proteins and cytokine induced beta-2-microglobulin (B2M).

In certain embodiments, the at least one marker comprises or further comprises a molecule produced as a consequence of inflammation. In specific embodiments, the molecule produced as a consequence of inflammation comprises a degradation product of protease activity, such as an extracellular matrix breakdown product and/or a product of oxidative damage such as chlorinated peptides and/or metabolites such as lactic acid and free fatty acid. Examples of extracellular matrix breakdown products include collagen breakdown products such as Ac-PGP, elastin fragments/peptides, desmosine. In specific embodiments, however, the levels of desmosine are not measured. In some embodiments, levels of large elastin fragments (LEF) may be measured.

Specific markers useful in the method include TIMP1, a tissue inhibitor of metalloproteinases, and cystatin c, a lysosomal proteinase inhibitor. Other useful markers which may be employed in combination include MMP level or activity and A1AT level or activity. The markers may be selected from those listed in FIG. 1 in some embodiments. In certain embodiments, the marker or markers is/are selected from TIMP (in particular TIMP2), NGAL, A1AT, IL-6, FMLP, creatinine, cystatin c, HSA, RBP4 and beta 2 microglobulin. IL-8 may also be a useful marker. Desmosine may be a useful marker when measured by ELISA. Each of these markers has been shown to be individually useful in indicating an inflammatory exacerbation (see Table 1 and Example 2 herein). Other specific marker combinations which may be useful in the invention include:

B2M and calprotectin or IL-6

B2M and calprotectin and HNE (activity or expression level)

B2M and calprotectin and HNE (activity or expression level) and A1AT

B2M and IL-6 and MMP (activity or expression level)

B2M and IL-6 and MMP (activity or expression level) and desmosine (preferably measured by ELISA) or HNE (activity or expression level)

Desmosine (preferably measured by ELISA) and IL-8 or IL-6 or A1AT

Desmosine (preferably measured by ELISA) and A1AT and FMLP

TIMP2 and desmosine (optionally measured by lateral flow) or MMP (activity or level) or IL-1beta or IL-6

TIMP2 and desmosine (optionally measured by lateral flow) and IL-6

TIMP2 and desmosine (optionally measured by lateral flow) and IL-6 and MMP (activity or expression level)

TIMP2 and IL-6 and desmosine (optionally measured by ELISA)

TIMP2 and IL-6 and desmosine (optionally measured by ELISA) and MMP (activity or expression level)

TIMP2 and MMP (activity or expression level) and A1AT or IL-6

TIMP2 and MMP (activity or expression level) and A1AT and desmosine (optionally measured by ELISA)

TIMP2 and MMP (activity or expression level) and IL-6 and desmosine (optionally measured by ELISA)

TIMP2 and IL-1beta and IL-6

TIMP2 and IL-1beta and IL-6 and desmosine (optionally measured by ELISA) or MMP (activity or expression level)

Other markers shown experimentally herein to be individually useful in predicting and identifying exacerbation events (and/or recovery therefrom including successful treatment) include markers selected from RBP4, creatinine, cystatin C, LEF, CRP and CC16. C-reactive protein (CRP) is an annular pentameric protein synthesised in the liver and found in blood plasma. Levels in blood plasma rise in response to inflammation. However, it was not previously observed that CRP can pass the kidney barrier and thus be detected in urine samples. Clara cell protein (CC16) is a 15.8-kDa protein secreted all along the tracheobronchial tree and especially in the terminal bronchioles where Clara cells are localized. This protein has not previously been applied as a urinary biomarker of inflammation or exacerbation of inflammation.

Other markers shown experimentally herein to be individually useful in predicting and identifying recovery from exacerbation events (and/or incidence of such events) include markers selected from MMP activity as measured according to the methods described herein (ultimate ELTABA), creatinine, LEF and CRP.

Combinations of markers that may be useful to predict or identify exacerbation events (and/or recovery therefrom, including successful treatment) include CRP together with IL1B and/or desmosine (e.g. when measured by lateral flow).

Other combinations of markers that may be useful to predict or identify exacerbation events (and/or recovery therefrom, including successful treatment) include at least one of CRP and A1AT. They may be employed together with at least one, up to all, of Ac-PGP (e.g. measured by a competitive EIA), fMLP, TIMP1, HSA and CC16. They may be employed with at least one, up to all, of Ac-PGP (e.g. measured by a competitive EIA), fMLP and TIMP1. They may be employed with at least one, up to all, of fMLP, desmosine fragments, desmosine and TIMP1. They may be employed with at least one, up to all, of of Ac-PGP (e.g. measured by a competitive EIA), fMLP and CC16.

Further useful combinations, as evidence herein, include:
TIMP2, CRP and desmosine—TIMP2 may be measured by a lateral flow assay (LF). Desmosine may be measured by an enzyme immunoassay, for example as described herein.
TIMP1, CRP and CC16—TIMP1 and CC16 may be measured by ELISA in some embodiments.
B2M, CRP and Ac-PGP. Ac-PGP may be measured by an enzyme immunoassay, for example as described herein.
MMP activity, CRP and LEF. MMP activity may be measured by Ultimate ELTABA as described herein. LEF may be measured by the Large Elastin Fragment assay described herein.
MMP activity, CRP and HSA. MMP activity may be measured by Ultimate ELTABA as described herein. LEF may be measured by the Large Elastin Fragment assay described herein. Human serum albumin may be measured by ELISA.
Creatinine, CRP, Ac-PGP. Ac-PGP may be measured by an enzyme immunoassay, for example as described herein.
fMLP, CRP and TIMP2. fMLP may be measured by an enzyme immunoassay, for example as described herein. TIMP2 may be measured by ELISA.
Ac-PGP, CRP, alternative Ac-PGP assay. Ac-PGP may be measured by an enzyme immunoassay, for example one of the range of assays as described herein.

As discussed herein, the marker levels may be normalised against a reference marker such as creatinine. In such embodiments, the following specific markers and marker combinations may be particularly useful:
TIMP2 and IL-6 or FMLP or desmosine (optionally measured by lateral flow) or MMP (activity or expression level)
TIMP2 and IL-6 and MMP (activity or expression level)
TIMP2 and IL-6 and MMP (activity or expression level) and HNE (activity or expression level) or desmosine (optionally measured by ELISA) or HSA
TIMP2 and FMLP and IL-6 or desmosine (optionally measured by ELISA)
TIMP2 and FMLP and IL-6 and desmosine (optionally measured by lateral flow) or HSA
TIMP2 and FMLP and desmosine (optionally measured by ELISA) and MMP (activity or expression level)
TIMP2 and desmosine (optionally measured by lateral flow) and A1AT or MMP (activity or expression level)
TIMP2 and desmosine (optionally measured by lateral flow) and A1AT and HNE (activity or expression level)
TIMP2 and desmosine (optionally measured by lateral flow) and MMP (activity or expression level) and HNE (activity or expression level)
TIMP2 and MMP (activity or expression level) and IL-6 or MMP measured by fluorogenic substrate assay
TIMP2 and MMP (activity or expression level) and IL-6 and HNE (activity or level) or desmosine (optionally measured by ELISA)
TIMP2 and MMP (activity or expression level) and MMP measured by fluorogenic substrate assay and desmosine (optionally measured by ELISA)

The invention may rely upon identifying the reciprocal relationship between effector and effector inhibitor molecule in some embodiments. For example, protease levels may increase as an early indicator of an exacerbation. This may result in a commensurate increase in the corresponding inhibitor to dampen the protease activity. This in turn may return the protease activity levels to normal. Depending upon at what point the sample happens to be tested, an elevation of effector molecule and/or inhibitor molecule may be observed. Detecting the early surge in effector molecule levels can predict an impending exacerbation in some embodiments. Detecting the increase in inhibitor levels can identify an exacerbation in some embodiments. Example effector molecules are discussed herein and include proteases such as MMPs. Example inhibitor molecules are also discussed herein and include protease inhibitors such as TIMPs (e.g. TIMP2) and A1AT. Representative individual examples are shown in FIG. 28 and confirm the importance of measuring multiple markers on an individual basis. In subjects 678 and 2023, levels of an effector molecule (MMP activity) increase to identify an exacerbation event. In subjects 2097 and 2505 levels of effector inhibitor molecules (A1AT and TIMP2 respectively) increase to identify an exacerbation event.

There are various known techniques by which marker levels may be measured. Thus, by marker levels is meant the level of expression and/or activity and/or amount and/or concentration of the marker. Expression levels of the markers may be measured in urine. Expression levels may correlate with activity and can thus be used as a surrogate of activity. Expression levels may be measured at the level of protein or mRNA according to any suitable method. Protein modifications, such as glycosylation may also be relevant and can be measured by any suitable method. Many such methods are well known in the art and include use of mass spectrometry (e.g. MALDI-TOF mass spectrometry). MicroRNAs may also be measured in urine samples as post-transcriptional regulators of gene expression. They are relatively stable in urine. A platform such as that offered by Exiqon may be utilised to provide high-throughput microRNA profiling. Such platforms may be array and/or PCR based.

The expression level and/or amount and/or concentration of a marker (e.g. a protein) may rely upon a binding reagent such as an antibody or aptamer that binds specifically to the marker of interest (e.g. protein). The antibody may be of monoclonal or polyclonal origin. Fragments and derivative antibodies may also be utilised, to include without limitation Fab fragments, ScFv, single domain antibodies, nanoantibodies, heavy chain antibodies, aptamers etc. which retain specific binding function and these are included in the definition of "antibody". Such antibodies are useful in the methods of the invention. They may be used to measure the level of a particular marker (e.g. protein, or in some instances one or more specific isoforms of a protein. The skilled person is well able to identify epitopes that permit specific isoforms to be discriminated from one another).

Methods for generating specific antibodies are known to those skilled in the art. Antibodies may be of human or non-human origin (e.g. rodent, such as rat or mouse) and be humanized etc. according to known techniques (Jones et al., Nature (1986) May 29-June 4; 321(6069):522-5; Roguska et al., Protein Engineering, 1996, 9(10):895-904; and Studnicka et al., Humanizing Mouse Antibody Frameworks While Preserving 3-D Structure. Protein Engineering, 1994, Vol. 7, μg 805).

In certain embodiments the expression level and/or amount and/or concentration of a marker is determined using an antibody or aptamer conjugated to a label. By label is meant a component that permits detection, directly or indirectly. For example, the label may be an enzyme, optionally a peroxidase, or a fluorophore. Gold labels may be utilised, e.g. in the form of colloidal gold.

A label is an example of a detection agent. By detection agent is meant an agent that may be used to assist in the detection of the antibody-marker (e.g. protein) complex. Where the antibody is conjugated to an enzyme the detection agent may comprise a chemical composition such that the enzyme catalyses a chemical reaction to produce a detectable product. The products of reactions catalysed by appropriate enzymes can be, without limitation, fluorescent, luminescent, or radioactive or they may absorb or reflect visible or ultraviolet light. Examples of detectors suitable for detecting such detectable labels include, without limitation, x-ray film, radioactivity counters, scintillation counters, spectrophotometers, colorimeters, fluorometers, luminometers, photodetectors and densitometers. In certain embodiments the detection agent may comprise a secondary antibody. The expression level is then determined using an unlabelled primary antibody that binds to the target protein and a secondary antibody conjugated to a label, wherein the secondary antibody binds to the primary antibody.

Additional techniques for determining expression level at the level of protein and/or the amount and/or concentration of a marker include, for example, Western blot, immunoprecipitation, immunocytochemistry, mass spectrometry, ELISA and others (see ImmunoAssay: A Practical Guide, edited by Brian Law, published by Taylor & Francis, Ltd., 2005 edition). To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Levels of protein may be detected using a lateral flow assay in some embodiments (discussed in further detail herein).

Measuring mRNA in a biological sample may be used as a surrogate for detection of the level of the corresponding protein in the urine sample. Thus, the expression level of any of the relevant markers described herein can also be detected by detecting the appropriate RNA.

Accordingly, in specific embodiments the expression level is determined by microarray, northern blotting, or nucleic acid amplification. Nucleic acid amplification includes PCR and all variants thereof such as real-time and end point methods and qPCR. Other nucleic acid amplification techniques are well known in the art, and include methods such as NASBA, 3SR and Transcription Mediated Amplification (TMA). Other suitable amplification methods include the ligase chain reaction (LCR), selective amplification of target polynucleotide sequences (U.S. Pat. No. 6,410,276), consensus sequence primed polymerase chain reaction (U.S. Pat. No 4,437,975), arbitrarily primed polymerase chain reaction (WO 90/06995), invader technology, strand displacement technology, recombinase polymerase amplification (RPA), nicking enzyme amplification reaction (NEAR) and nick displacement amplification (WO 2004/067726). This list is not intended to be exhaustive; any nucleic acid amplification technique may be used provided the appropriate nucleic acid product is specifically amplified. Design of suitable primers and/or probes is within the capability of one skilled in the art. Various primer design tools are freely available to assist in this process such as the NCBI Primer-BLAST tool. Primers and/or probes may be at least 15, 16, 17, 18, 19, 20, 21, 22, 23, 24 or 25 (or more) nucleotides in length. mRNA expression levels may be measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

RNA expression may be determined by hybridization of RNA to a set of probes. The probes may be arranged in an array. Microarray platforms include those manufactured by companies such as Affymetrix, Illumina and Agilent. RNA expression may also be measured using next generation sequencing methods, such as RNA-seq.

Similarly, activity of an effector molecule, such as enzymatic activity, may be measured in the urine sample. Enzymatic activity may be measured for example by detecting processing of a substrate, which may be labelled, in the sample. For example, the assay may be a fluorogenic substrate assay. Enzyme activity may be detected using a suitable lateral flow assay. Examples of suitable assay formats include the assays set forth in International Patent Applications WO2009/024805, WO2009/063208, WO2007/128980, WO2007/096642, WO2007/096637, WO2013/

156794 and WO2013/156795 (the content of each of which is hereby incorporated by reference).

In specific embodiments, protease activity is determined by measuring cleavage of a peptide substrate. For example, the assay may be a fluorogenic substrate assay. In certain embodiments, protease activity is determined by a method comprising:
- a. bringing an indicator molecule into contact with the test sample, said indicator molecule comprising
  - i. a cleavage region comprising at least one cleavage site, which can be cleaved by said protease if present; and
  - ii. a capture site;

wherein cleavage of the at least one cleavage site produces a novel binding site;
- b. adding to the test sample binding molecules capable of binding to the novel binding site, wherein the binding molecules are incapable of binding to the indicator molecule unless and until cleavage has occurred;
- c. capturing the part of the indicator molecule containing the novel binding site at a capture zone through binding of capture molecules in the capture zone to the capture site; and
- d. detecting cleavage of the at least one cleavage site by determining binding of the binding molecules to the novel binding site of the indicator molecule captured in the capture zone.

This assay may be referred to herein as the "ultimate ELTABA" assay.

Thus, the invention may incorporate an enzyme detection device for detecting the presence in a test sample of cleavage activity of an enzyme capable of cleaving a substrate, the device comprising:
- (i) an indicator molecule for adding to the test sample, said indicator molecule comprising
  - (a) a cleavage region comprising at least one cleavage site, which can be cleaved by said enzyme if said enzyme cleavage activity is present; and
  - (b) a capture site;

wherein cleavage of the at least one cleavage site produces a novel binding site;
- (ii) a capture zone to receive the test sample, wherein the capture zone comprises capture molecules capable of binding to the capture site of the indicator molecule in order to immobilise the indicator molecule including the novel binding site; and
- (iii) binding molecules capable of binding to the novel binding site, wherein the binding molecules are incapable of binding to the indicator molecule unless and until cleavage has occurred.

Similarly, the invention may incorporate an enzyme detection device for detecting the presence in a test sample of cleavage activity of an enzyme capable of cleaving a substrate, the device comprising:
- (i) an indicator molecule for adding to the test sample, said indicator molecule comprising
  - (a) a cleavage region comprising at least one cleavage site, which can be cleaved by said enzyme if said enzyme cleavage activity is present; and
  - (b) a capture site;

wherein cleavage of the at least one cleavage site produces at least two parts of the cleavage region, at least one part of which remains connected to the capture site;
- (ii) a capture zone to receive the test sample, wherein the capture zone comprises capture molecules capable of binding to the capture site of the indicator molecule; and
- (iii) binding molecules capable of binding to the part of the indicator molecule containing the at least one part of the cleavage region connected to the capture site, wherein the binding molecules are incapable of binding to the indicator molecule unless and until cleavage has occurred.

The two parts of the cleavage region are thus separated from one another at the site of cleavage. The cleavage event at the site of the cleavage produces the novel binding site.

These devices may be included as one or more testing devices in the systems and test kits of the invention.

The invention may further rely upon a method for detecting the presence or absence in a test sample of cleavage activity of an enzyme capable of cleaving a substrate, the method comprising:
- (i) bringing an indicator molecule into contact with the test sample, said indicator molecule comprising
  - (a) a cleavage region comprising at least one cleavage site, which can be cleaved by said enzyme if said enzyme cleavage activity is present; and
  - (b) a capture site;

wherein cleavage of the at least one cleavage site produces a novel binding site;
- (ii) adding to the test sample binding molecules capable of binding to the novel binding site, wherein the binding molecules are incapable of binding to the indicator molecule unless and until cleavage has occurred;
- (iii) capturing the part of the indicator molecule containing the novel binding site at a capture zone through binding of capture molecules in the capture zone to the capture site; and
- (iv) detecting cleavage of the at least one cleavage site by determining binding of the binding molecules to the novel binding site of the indicator molecule captured in the capture zone.

Similarly, the invention may also incorporate a method for detecting the presence or absence in a test sample of cleavage activity of an enzyme capable of cleaving a substrate, the method comprising:
- (i) bringing an indicator molecule into contact with the test sample, said indicator molecule comprising
  - (a) a cleavage region comprising at least one cleavage site, which can be cleaved by said enzyme if said enzyme cleavage activity is present; and
  - (b) a capture site wherein cleavage of the at least one cleavage site produces at least two parts of the cleavage region, at least one part of which remains connected to the capture site;
- (ii) adding to the test sample binding molecules capable of binding to the part of the indicator molecule containing the at least one part of the cleavage region connected to the capture site, wherein the binding molecules are incapable of binding to the indicator molecule unless and until cleavage has occurred;
- (iii) capturing the part of the indicator molecule containing the at least one part of the cleavage region connected to the capture site at a capture zone through binding of capture molecules in the capture zone to the capture site; and
- (iv) detecting cleavage of the at least one cleavage site by determining binding of the binding molecules to the part of the indicator molecule captured in the capture zone.

These specific devices and methods have been shown by the inventors to have exquisite sensitivity. They therefore have specific application in monitoring inflammation status by measuring activity of effector molecules in urine samples.

Thus, the invention further provides a method for monitoring inflammation status in a urine sample, in particular for predicting or identifying a PEx event, by detecting cleavage activity of an enzyme capable of cleaving a substrate, the method comprising:
- (i) bringing an indicator molecule into contact with the test sample, said indicator molecule comprising
  - (a) a cleavage region comprising at least one cleavage site, which can be cleaved by said enzyme if said enzyme cleavage activity is present; and
  - (b) a capture site;
  - wherein cleavage of the at least one cleavage site produces a novel binding site;
- (ii) adding to the test sample binding molecules capable of binding to the novel binding site, wherein the binding molecules are incapable of binding to the indicator molecule unless and until cleavage has occurred;
- (iii) capturing the part of the indicator molecule containing the novel binding site at a capture zone through binding of capture molecules in the capture zone to the capture site; and
- (iv) detecting cleavage of the at least one cleavage site by determining binding of the binding molecules to the novel binding site of the indicator molecule captured in the capture zone wherein an increased level of cleavage indicates an increased level of inflammation, in particular predicts or identifies a PEx event.

The invention also provides a method for monitoring inflammation status in a urine sample, in particular for predicting or identifying a PEx event, by detecting cleavage activity of an enzyme capable of cleaving a substrate, the method comprising:
- (i) bringing an indicator molecule into contact with the test sample, said indicator molecule comprising
  - (a) a cleavage region comprising at least one cleavage site, which can be cleaved by said enzyme if said enzyme cleavage activity is present; and
  - (b) a capture site
  - wherein cleavage of the at least one cleavage site produces at least two parts of the cleavage region, at least one part of which remains connected to the capture site;
- (ii) adding to the test sample binding molecules capable of binding to the part of the indicator molecule containing the at least one part of the cleavage region connected to the capture site, wherein the binding molecules are incapable of binding to the indicator molecule unless and until cleavage has occurred;
- (iii) capturing the part of the indicator molecule containing the at least one part of the cleavage region connected to the capture site at a capture zone through binding of capture molecules in the capture zone to the capture site; and
- (iv) detecting cleavage of the at least one cleavage site by determining binding of the binding molecules to the part of the indicator molecule captured in the capture zone, wherein an increased level of cleavage indicates an increased level of inflammation, in particular predicts or identifies a PEx event.

As discussed herein, the enzyme is an "effector molecule". Typically, the enzyme is a protease such as MMP, HNE or cathepsin G.

The enzyme detection devices useful in the invention may be supplied in a format ready for immediate use. Alternatively, the essential components may be provided as a kit of parts, optionally together with suitable reagents and/or instructions for assembly of the enzyme detection device. Accordingly, provided herein is an enzyme detection kit for detecting the presence in a urine test sample of cleavage activity of an enzyme capable of cleaving a substrate, the kit comprising:
- (i) an indicator molecule for adding to the test sample, said indicator molecule comprising
  - (a) a cleavage region comprising at least one cleavage site, which can be cleaved by said enzyme if said enzyme cleavage activity is present; and
  - (b) a capture site;
  - wherein cleavage of the at least one cleavage site produces a novel binding site;
- (ii) capture molecules capable of binding to the capture site of the indicator molecule
- (iii) a solid support to which the capture molecules can be attached (i.e. are attachable or attached) to form a capture zone to receive the test sample; and
- (iv) binding molecules capable of binding to the novel binding site, wherein the binding molecules are incapable of binding to the indicator molecule unless and until cleavage has occurred.

Also useful in the invention is an enzyme detection kit for detecting the presence in a urine test sample of cleavage activity of an enzyme capable of cleaving a substrate, the kit comprising:
- (i) an indicator molecule for adding to the test sample, said indicator molecule comprising
  - (a) a cleavage region comprising at least one cleavage site, which can be cleaved by said enzyme if said enzyme cleavage activity is present; and
  - (b) a capture site;
  - wherein cleavage of the at least one cleavage site produces at least two parts of the cleavage region, at least one part of which remains connected to the capture site;
- (ii) capture molecules capable of binding to the capture site of the indicator molecule,
- (iii) a solid support to which the capture molecules can be attached (i.e. are attachable or attached) to form a capture zone to receive the test sample; and
- (iii) binding molecules capable of binding to the part of the indicator molecule containing the at least one part of the cleavage region connected to the capture site, wherein the binding molecules are incapable of binding to the indicator molecule unless and until cleavage has occurred.

In related aspects, the invention also provides for use of an enzyme detection device as described and defined herein for monitoring inflammation status, in particular for indicating or predicting an exacerbation of inflammation in a urine test sample. Similarly, the invention also provides for use of a method as described and defined herein for indicating or predicting an exacerbation of inflammation in a urine test sample. The invention further provides for use of an enzyme detection kit as described and defined herein for indicating or predicting an exacerbation of inflammation in a urine test sample. In each of these uses, the respiratory condition may be chronic obstructive pulmonary disease or inflammation of the respiratory tract as a result of cystic fibrosis.

Central to these aspects of the invention is the indicator molecule. The indicator molecule comprises a cleavage region comprising at least one cleavage site. The cleavage site is cleaved by an effector molecule, typically an enzyme or enzymes, in the urine test sample with the relevant enzyme cleavage activity. The cleavage region provides a suitable context for the cleavage site to ensure cleavage is efficient, if the enzyme is present in the sample. In specific embodiments the cleavage region is a peptide. In addition to the peptide bond representing a protease cleavage site, the additional amino acids in the peptide may ensure specificity and sensitivity of cleavage. The cleavage region may contain multiple cleavage sites in certain embodiments, particularly where the indicator molecule is structurally constrained, for example where it also comprises a scaffold molecule.

The indicator molecule also comprises a capture site (intended to encompass at least one capture site). The capture site is a discrete region of the indicator molecule which permits immobilization of the indicator molecule, whether cleaved or uncleaved, at a capture zone. The capture site is discussed herein below in greater detail.

The indicator molecule also optionally comprises a scaffold molecule, as discussed in greater detail below.

Cleavage of the indicator molecule splits the indicator molecule to reveal or form at least one novel binding site. The two parts of the cleavage region are thus separated from one another at the site of cleavage. Typically the novel binding site comprises a conformational epitope produced as a consequence of cleavage. Use of binding molecules that bind specifically to the newly revealed binding site or sites but not to the indicator molecule prior to cleavage enables specific and sensitive detection of cleavage activity of an enzyme. Accordingly, in some embodiments, cleavage of the at least one cleavage site produces at least two parts of the indicator molecule (or cleavage region of the indicator molecule), at least one part of which contains (or remains connected to) the capture site and as a consequence of cleavage contains a binding site for binding molecules and wherein the binding molecules are incapable of binding to the binding site unless and until cleavage has occurred. In other words, the binding site is hidden or is not formed until cleavage at the cleavage site occurs.

In some embodiments, cleavage of the at least one cleavage site produces at least two separate parts of the (cleavage region of the) indicator molecule. Thus, cleavage may produce at least two parts or fragments; one part or fragment that contains or is connected to the capture site and a separate part or fragment that does not contain, or is not connected to, the capture site. The binding molecules bind to the new binding site on the part or parts of the indicator molecule that contain or include the capture site. This permits specific detection of cleavage at the site of capture of the indicator molecule through binding to the capture molecules (i.e. binding of the binding molecules is detected in the capture zone).

However, it is not essential that cleavage (at the cleavage site) produces at least two completely separate molecules, provided that cleavage produces a novel binding site for the binding molecules and wherein the binding molecules are incapable of binding to the binding site unless and until cleavage has occurred. Thus cleavage produces two parts of the cleavage region which are separated at the cleavage site. Accordingly, in some embodiments, cleavage of the at least one cleavage site produces at least two parts of the cleavage region, at least two parts of which remain connected, either directly or indirectly (for each part), to the capture site. This is shown schematically in FIG. 16A. In specific embodiments the indicator molecule contains a further linkage or connection away from the cleavage site or outside of the cleavage region such that cleavage of the at least one cleavage site produces at least two parts of the cleavage region of the indicator molecule which remain connected to one another. This does not exclude the possibility that cleavage produces at least three fragments, at least one of which does not remain connected via the further linkage or connection. This is particularly the case where the cleavage region may comprise more than one cleavage site. This is shown schematically in FIG. 16B. The further linkage or connection may comprise a disulphide bond in some embodiments. It has been found that use of scaffold molecules, linked to the indicator molecule, provides a further linkage or connection within the indicator molecules. Such scaffold molecules may act as a structural constraint that is useful for developing binding molecules that bind to the indicator molecule only after cleavage has occurred. Without being bound by theory, the structural constraint is believed to assist in producing a specific and reproducible binding site that is not present unless and until cleavage at the cleavage site has occurred. The scaffold molecule may enhance the differences in spatial conformation between the indicator molecule pre- and post-cleavage, as discussed in greater detail herein. The scaffold may also constrain the cleaved indicator molecule in a particular spatial conformation following cleavage. This may assist in improving specificity of detection in terms of the binding molecules discriminating between cleaved and uncleaved indicator molecules, by providing a clearly defined and different molecule after cleavage against which binding molecules can be designed or raised. Thus, in some embodiments, the binding molecules bind to the region of cleavage. In specific embodiments, the binding site may thus encompass both sides of the cleavage site following cleavage (i.e. at least two parts of the cleavage region). The binding molecules may bind to both parts of the indicator molecule following cleavage.

The invention therefore may also rely upon use of an indicator molecule in detecting the presence in a urine test sample of cleavage activity of an effector molecule, such as an enzyme capable of cleaving a substrate, the indicator molecule comprising:
  (a) a cleavage region comprising at least one cleavage site, which can be cleaved by said enzyme if said enzyme cleavage activity is present,
  (b) a capture site; and
  (c) a scaffold molecule which acts to connect at least two parts of the indicator molecule outside of the cleavage site, such as outside of the cleavage region
  wherein the scaffold further acts to structurally constrain the indicator molecule in a manner such that cleavage of the at least one cleavage site produces a novel binding site to which binding molecules bind, but wherein the binding molecules are incapable of binding to the indicator molecule unless and until cleavage has occurred.

The invention may also incorporate an indicator molecule for use in detecting the presence in a urine test sample of cleavage activity of an effector molecule, in particular an enzyme capable of cleaving a substrate, the indicator molecule comprising:
  (a) a cleavage region comprising at least one cleavage site, which can be cleaved by said enzyme if said enzyme cleavage activity is present to produce at least two parts of the cleavage region,
  (b) a capture site; and
  (c) a scaffold molecule which acts to connect at least two parts of the indicator molecule such that cleavage of the at least one cleavage site produces at least two parts of the cleavage region of the indicator molecule which remain connected to one another
  wherein the scaffold further acts to structurally constrain the indicator molecule in a manner such that cleavage of the at least one cleavage site produces a (novel) binding site to which binding molecules bind, but wherein the binding molecules are incapable of binding to the indicator molecule unless and until cleavage has occurred.

The scaffold molecule is typically attached to the indicator molecule away from the cleavage site so that cleavage activity of the enzyme is not inhibited by the scaffold. Thus the cleavage region may be separated from the scaffold molecule by one or more linker or spacer regions. Those linker or spacer regions may incorporate the capture site in some embodiments. The scaffold molecule is typically linked to the indicator molecule by two linkages, although it is possible that additional linkages can be employed—for example 3, 4, 5 or 6 etc.—linkages depending upon the scaffold molecule that is used and the nature of the indicator molecule. It is also possible that a single scaffold molecule can be linked to multiple indicator molecules. In embodiments where the scaffold molecules contain more than two halogen substituents, in particular bromomethyl substituents, such as 4 or 6 bromomethyl substituents the scaffold molecule may provide a structural constraint for multiple indicator molecules. Each pair of substituents may be attached to connect at least two parts of a cleavage region. Thus, the scaffold effectively links (and structurally constrains) multiple separate cleavage regions. In specific embodiments, the indicator molecules comprise more than one constrained peptide (cleavage region). The cleavage regions can also be different resulting in a single molecule containing different cleavable sequences. Here it may be possible to detect cleavage of each individual peptide cleavage region using two or more distinct binding molecules (e.g. antibodies raised against its cleaved substrate). Consequently where an assay signal is required only when two or more proteases are present it is possible that binding molecule (antibody) binding only takes place when all the distinct cleavage sites have been cleaved. In this instance the binding molecule (antibody) would have to be raised to the form of indicator molecule after cleavage by the two or more proteases.

The scaffold molecule assists in constraining the cleaved ends or parts of the indicator molecule (usually a peptide) to produce a novel and specific binding site for a binding molecule (usually an antibody binding to a newly revealed or produced epitope, in particular a conformational epitope). The binding molecule may, therefore, bind specifically to either cleaved end or part of the indicator molecule or to both sides of the cleavage site (i.e. within the cleavage region either side of the cleavage site). In specific embodiments, the scaffold further acts to structurally constrain the indicator molecule in a manner such that cleavage of the at least one cleavage site produces a binding site containing both parts of the cleavage region of the indicator molecule to which binding molecules bind, but wherein the binding molecules are incapable of binding to the indicator molecule unless and until cleavage has occurred. In specific embodiments, the binding site includes the cleavage site. In specific embodiments, the binding site represents a novel structural conformation of the indicator molecule. Cleavage may produce at least one new conformational epitope. The novel binding site for the binding molecule may comprise any part of the indicator molecule, provided that enzyme cleavage activity and capture are not substantially impeded. In certain embodiments, the binding site comprises at least a portion of the cleavage region. In specific embodiments, the binding site comprises at least a portion of the scaffold molecule.

In most embodiments, the cleavage site is specific for cleavage by a protease. However, as discussed herein, the indicator molecules of the invention may be cleaved by other enzymes which act as effector molecules in inflammatory exacerbation events. One or more different proteases may be detected according to the invention. In certain embodiments, the cleavage site is specific for cleavage by a matrix metalloproteinase (MMP). MMPs are zinc-dependent endopeptidases. They are responsible for cleaving various proteins, including extracellular matrix proteins. The MMPs include MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP26, MMP27 and MMP28. Other relevant effector molecules include HNE and cathepsin G.

The at least one cleavage site may be biased for cleavage by specific proteases in some embodiments. This permits the invention to be utilised in order to detect specific protease activity in the test sample. Many proteases are known and their sites of preferred cleavage well reported. In certain embodiments, the at least one cleavage site is biased for cleavage by specific matrix metalloproteinases. More specifically, in some embodiments, the at least one cleavage site is biased for cleavage by MMP-9 and/or MMP-8 or for MMP-13 and/or MMP-9. The at least one cleavage site may be biased for cleavage by MMP-13, 9, 2, 12 and 8. The bias may be for the group of MMPs equally or may be in that particular order of preference. As is shown herein, it is possible to design specific indicator molecules and cleavage sites within the indicator molecules that are biased for cleavage by these particular MMPs, in the specified order of preference. Accordingly, in some embodiments, the cleavage site is within the amino acid sequence GPQGIFGQ (SEQ ID NO: 1). This may be considered a specific example of the "cleavage region" of the indicator molecule. In those embodiments, cleavage produces a part of the cleavage region of the indicator molecule containing the amino acid sequence GPQG and a part of the cleavage region of the indicator molecule containing the amino acid sequence IFQG. Either part can be the part connected to the capture site. In specific embodiments, the indicator molecule comprises the amino acid sequence CGPQGIFGQC (SEQ ID NO: 2). Inclusion of the cysteine residues provides thiol groups which represent a convenient linkage point for various scaffold molecules. The cleavage region may be separated from the attachment points for the scaffold molecule by one or more linker or spacer regions in some embodiments. Thus, the indicator molecule may comprise the structure:

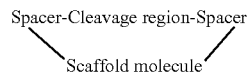

The capture site may be found within one or both of the spacers in some embodiments. Thus, the indicator molecules of the invention may comprise suitable amino acids at or near the N and C terminus to facilitate linkage to the scaffold molecule. The amino acids may comprise thiol groups. Suitable residues include cysteine and selenium. The scaffold molecules may be attached to the indicator molecules via thioether linkages.

A range of suitable scaffold molecules and methods for linking the scaffold molecules to a peptide are discussed in WO2004/077062 and WO2008/013454, the relevant disclosures of which are hereby incorporated by reference. The present invention applies these scaffold molecules in a new manner to present cleavage sites and produce new binding sites after cleavage which permit detection of enzyme cleavage activity (especially protease activity) in a test sample as an indication or prediction of an inflammatory exacerbation.

In certain embodiments, the scaffold molecule comprises a (hetero)aromatic molecule. In more specific embodiments, the (hetero)aromatic molecule comprises at least two benzylic halogen substituents. The scaffold molecule is a halomethylarene in some embodiments, such as a halomethylarene selected from the group consisting of bis(bromomethyl)benzene, tris(bromomethyl)benzene and tetra(bromomethyl)benzene, or a derivative thereof. In specific embodiments, the scaffold is selected from the group consisting of ortho-, meta- and para-dihaloxylene and 1,2,4,5 tetra halodurene, such as meta-1,3-bis(bromomethyl)benzene (m-T2), ortho-1,2-bis(bromomethyl)benzene (o-T2), para-I,4-bis(bromomethyl)benzene (p-T2), meta-I,3-bis(bromomethyl)pyridine (m-P2), 2,4,6-tris(bromomethyl)mesitylene (T3), meta-l,3-bis(bromomethyl)-5-azidobenzene (m-T3-N3) and/or 1,2,4,5 tetrabromodurene (T4).

Suitable derivatives of halomethyl arenes include ortho, meta and para bis(bromomethyl) benzenes. More specifically 1,2-bis(bromomethyl) benzene, 1,3-bis(bromomethyl) benzene and 1,4-bis(bromomethyl) benzene. Further substituted halomethylarenes include 1,3,5-tris(bromomethyl)benzene, 1,2,4,5-tetrakis(bromomethyl)benzene and 1,2,3,4,5,6-hexakis(bromomethyl)benzene. Polycyclic halomethylarenes include 2,7-bis(bromomethyl)-naphthalene, 1,4-bis(bromomethyl)-naphthalene, 1,8-bis(bromomethyl)-naphthalene, 1,3-bis(bromomethyl)-naphthalene, 1,2-bis(bromomethyl)-naphthalene, 2,3-bis(bromomethyl)-naphthalene, 2,6-bis(bromomethyl)-naphthalene, 1,2,3,4-tetrakis(bromomethyl)-naphthalene, 9,10-bis(bromomethyl)-phenanthrene, 5,10-bis(bromomethyl)-anthracene, and 1-(bromomethyl)-3-[3-(bromomethyl)benzyl]benzene. Methyl substituted halomethylarenes include 1,3-bis(bromomethyl)-5-methylbenzene, 2,5-bis(bromomethyl)-1,3-dimethylbenzene, 2,5-bis(bromomethyl)-1,4-dimethylbenzene, 2,4-bis(bromomethyl)-1,3,5-trimethylbenzene and 3,6-bis(bromomethyl)durene. Nitro substituted halomethylarenes include 3,4-bis(bromomethyl)-nitrobenzene and 2,3-bis(bromomethyl)-nitrobenzene. Hydroxy substituted halomethylarenes include 1,3-bis(bromomethyl)-5-hydroxybenzene and cyano substituted halomethylarenes include 2,6-bis(bromomethyl)-benzonitrile. Methoxy substituted halomethylarenes include 1,3-bis(bromomethyl)-5-methoxybenzene, 1,3-bis(bromomethyl)-2-methoxy-5-methylbenzene, 1,3-bis(bromomethyl)-5-hydroxybenzene, 2,3-bis(bromomethyl)-1,4-dimethoxybenzene, and 2,5-bis(bromomethyl)-1,4-dimethoxybenzene.

Some suitable scaffold molecules for use in the indicator molecules of the invention are shown in FIG. 14. A number of specific suitable scaffold molecules are also shown, together with proposed nomenclature, in FIG. 15.

Due to their relative rigidity and ease of synthetic use, the halomethyl arene derivatives are preferred candidates to act as scaffold molecules in the present invention. They are particularly convenient for creating constrained peptide substrates. However one can envisage other appropriate chemistries with which to "cyclise" the indicator molecule, such as a peptide. In the case of peptides containing thiols (eg: in the form of cysteine), a simple disulphide bond formation or a diepoxide derivative can be used to affect covalent closure of the structure. Another appropriate chemistry includes the "click chemistry" method, involving the cycloaddition reaction between azides and alkynes forming stable triazoles. Here for example a peptide bearing two azido lysine amino acids could be intramolecularly cross linked by a dialkyne reagent. Such reactions can be catalysed by copper. However in some examples such as those where a strained alkyne is used, no catalyst is required. A further chemical route includes that of stable hydrazone formation. Indicator molecules (in particular peptides) containing two phenyl hydrazine moieties may be cross linked intramolecularly via a dialdehyde reagent. A further chemical route is possible through peptide-based indicator molecules containing two tyrosine amino acids. These peptides can be intramolecularly crosslinked using a bis(diazo) scaffold to form the corresponding diazo adduct.

The scaffold molecules may also include further functionalities or reactive groups to facilitate generation of a novel binding site following enzymatic cleavage of the cleavage site. Thus, following cleavage at the cleavage site there are at least two parts of the cleavage region of the indicator molecule which are no longer connected to one another through the cleavage site. One or more of those "free" parts may become further constrained by interaction with the scaffold molecule. This may produce a significant change in structure of the overall molecule. This in turn permits specific binding molecules to be generated which will not cross-react with the indicator molecule prior to cleavage. Thus, by way of example, in the case of peptides constrained by a scaffold molecule one can envisage a specific conformational change after cleavage of the cleavage site. The afforded degrees of freedom in the peptide chain may allow it to self-assemble via non covalent interactions in a new stable conformation, creating a new conformational epitope unique to the molecule and recognised by the binding molecule (such as an antibody raised against the cleaved substrate). These non-covalent interactions may comprise hydrophobic interactions between the amino acid side chains and the aromatic rings in the scaffold molecule. The non-covalent interactions can be further enhanced in scaffolds with extended substitution patterns such that for example a negatively charged nitro substituent can interact with positively charged amino acids such as lysine, arginine or histidine included within the cleavage region. Hydrogen bond interactions are also possible between methoxy and/or hydroxyl aryl substituents and a number of amino acids, including serine, threonine and tyrosine. In addition the two cleaved peptide parts of the cleavage region may be free to self-assemble with each other inducing a secondary structure such as a helix or beta stranded structure after cleavage. In further embodiments, a combination of both peptide-peptide interactions and peptide-scaffold interactions, as described above, may produce a novel binding site recognised by a binding molecule. Such interactions serve to differentiate the structure in 3 dimensional space between its uncleaved "closed" form and its "open" form following cleavage and hence significantly enhance the specificity of interaction between the cleaved indicator molecule and the binding molecule (e.g. an antibody raised against the cleaved peptide product). The resulting high specificity of interaction is beneficial to the sensitivity of detection of enzyme cleavage activity within the sample because it facilitates use of the indicator molecule in excess without the risk of the binding molecule binding to uncleaved indicator molecule (e.g. the antibody raised against the cleaved peptide from binding to the uncleaved peptide).

The scaffold should not prevent cleavage at the one or more cleavage sites. In some embodiments, the scaffold may orientate the (cleavage region of the) indicator molecule to optimise or improve efficiency of cleavage at the cleavage site. The scaffold may effectively fix or constrain the cleavage region to present the cleavage site in a favourable manner for the enzyme activity to be detected. The effect of the scaffold molecule on cleavage of any given substrate can readily be tested by a simple time course experiment. A test may determine whether cleavage occurs in the presence of the enzyme within a reasonable time (e.g. 5-10 minutes). This testing can be qualified, for example through mass spec analysis, optionally in combination with HPLC as it should evolve a new hydrolysed molecule (with a different molecular mass) which should also retain differently on a reverse phase analytical column. Those indicator molecules incorporating a scaffold molecule can, for example, then be prepared as an immunogen in its purified cleaved form. This can be used to raise antibodies in a suitable animal such as a sheep, either as free peptide or conjugated to a carrier protein. Antisera may then be characterised by ELISA to immobilised antigen and an antigen column may be used to affinity purify and refine the polyclonal response specifically to the cleaved indicator molecule. The complete indicator molecule may then be tested according to the methods of the invention.

A range of suitable binding molecules for use in the invention are disclosed herein, which discussion applies mutatis mutandis here. Typically, the binding molecule comprises an antibody (again as defined herein).

For the avoidance of doubt, these indicator molecules may be employed in any of the aspects of the invention (devices, kits, methods, uses etc.).

In the context of the invention as a whole, the one or more cleavage sites may be any site at which an enzymatically-cleavable bond is present. For example, this bond may be present between neighbouring residues of the indicator molecule. Such residues may be selected from nucleotides, monosaccharides, and amino acids. The indicator molecule typically comprises a peptide cleavage region. Thus, in some embodiments, the cleavage region comprises a sequence of amino acids. In a preferred embodiment of the invention, the cleavage site is a specific peptide bond located between two amino acid residues.

In further embodiments of the invention, the at least one cleavage site is located within a peptide, a protein, a carbohydrate, a lipid or a nucleic acid cleavage region. In certain embodiments, the indicator molecule may be engineered such that it comprises the enzyme's natural substrate or a portion thereof, such that the enzyme is presented with its native cleavage site, optionally in its native state within the cleavage region. In certain other embodiments, the indicator molecule may be engineered such that it comprises an artificial or non-native cleavage site and/or substrate region. For example, the cleavage site in the indicator molecule may be engineered or mutated such that the rate of cleavage activity or specificity of cleavage activity exhibited by the enzyme is increased (or decreased) relative to the rate and/or specificity of cleavage activity of the enzyme measured under comparable conditions against the enzyme's natural substrate.

In certain embodiments of the invention, the cleavage region may comprise multiple cleavage sites, wherein cleavage at any one of the sites produces at least two parts of the cleavage region, at least one part of which remains connected to the capture site. In the context of the present invention, the term 'multiple' means at least two, at least three, at least four, and so forth. In certain embodiments, the cleavage region of the indicator molecule includes between 2, 3, 4, 5 and 10, 11, 12, 13, 14, 15, 16, 17, 18, 19, 20, 25, 50, 100, 500 or 1000 cleavage sites. In some embodiments, the indicator molecule includes between 2 and 5, 6, 7, 8, 9 or 10 cleavage sites.

In one embodiment, the multiple cleavage sites may all be identical. In this configuration, the repeated cleavage site may be relatively non-specific or may be highly specific for one enzyme or enzyme subtype as defined above. Moreover, use of an indicator molecule of this type may help to increase the sensitivity of the enzyme detection device by providing a means to increase the concentration of cleavage sites present within the test sample.

In other embodiments, the cleavage region of the indicator molecule may comprise multiple cleavage sites wherein there are at least two different cleavage sites present within the same indicator molecule. In preferred embodiments of the invention, the indicator molecule may comprise at least three, at least four, at least five, and up to at least 8 different cleavage sites.

In a further preferred embodiment, the different cleavage sites are recognised by different enzymes or different categories, subcategories or subtypes of enzymes as defined above, such that the device of the invention can be used to detect the activity of multiple different enzymes. This is particularly the case where multiple effector molecules are measured according to the invention. The activities may be grouped, such that the detection of enzyme activity gives a useful result. For example, a group of MMPs (e.g. MMP 8 and 9) may be involved in an exacerbation event such that detection of the relevant activity of one or more of the enzyme group is useful for predicting or identifying the inflammatory exacerbation.

Use of multiple cleavage sites (whether identical or non-identical) may be particularly useful for situations in which very low levels of enzyme activity are to be detected in a test sample. For example, an indicator molecule having multiple cleavage sites as defined above may be used to detect enzyme activity in a urine sample containing low levels of protease. Use of multiple cleavage sites may also be particularly applicable where the indicator molecule incorporates a scaffold molecule.

In addition to a cleavage region containing at least one cleavage site, the indicator molecule comprises a capture site. The capture site mediates binding of the indicator molecule to a capture molecule present within a capture zone. Thus, the capture site is the portion of the indicator molecule responsible for retaining or localising the indicator molecule within the capture zone. Following cleavage of the indicator molecule, the capture site may remain intact or substantially intact, such that the site is still recognised and bound by a capture molecule present within the capture zone of the device. Under these circumstances, both intact indicator molecules and the part of the indicator molecules comprising the capture site following cleavage will be bound to capture molecules within the capture zone. The capture site may comprise any suitable molecule, for example a biotin molecule. It is also possible for the scaffold molecule to form a part, or the entirety, of the capture site in order to permit immobilization of the indicator molecule at a capture zone. For example, the capture zone may comprise antibodies raised against the scaffold molecule, preferably in the form as attached to the indicator molecule. In these embodiments, the scaffold molecule is not substantially involved in binding to the binding molecules. Key to effectiveness of the indicator molecules is immobilization via the interaction between capture site and capture molecules at the capture zone and simultaneous binding by binding molecules after cleavage has occurred. In those embodiments in which the scaffold molecule defines a part of the binding site for the binding molecules after cleavage, the capture site must be sufficiently distinct to prevent either or both binding events from being impeded.

As noted above, the cleavage site may be within a peptide, a protein, a carbohydrate, a lipid or a nucleic acid cleavage region. In specific embodiments of the invention, the cleavage region and capture site are defined by discrete amino acids or groups of amino acids within a peptide or protein. As used herein the term "peptide" is intended to mean a length of amino acids of no more than (about) 20, 30, 40 or 50 amino acids.

Alternatively, the capture site may be present in a region of the indicator molecule which is separate to the region in which the cleavage site is located. Thus, in certain embodiments of the invention, the capture site may be present within a capture region, and the cleavage site may be present within a separate cleavage region of the indicator molecule. In embodiments wherein the capture site is in a separate region of the indicator molecule to the cleavage site, the capture site may comprise materials or residues entirely distinct from those found in the region of the molecule containing the cleavage site. For example, the cleavage region may comprise amino acid residues whilst the capture site may comprise or consist of a biotin moiety. Moreover, in embodiments wherein the indicator molecule comprises separate regions bearing the cleavage site and capture site, said regions may be associated by any means known to one of skill in the art. In a preferred embodiment, said regions may be associated via a direct covalent linkage. Said regions may be immediately adjacent or may be separated by a linker or spacer, for example, a polyethylene glycol moiety.

The effector molecules detected in urine are discussed elsewhere. These enzymes to be detected according to the invention must be capable of cleaving the indicator molecule at the cleavage site. This activity is required in order for the indicator molecule to be cleaved at the cleavage site, to produce at least two parts of the cleavage region of the indicator molecule, at least one part of which remains connected to the capture site.

Within the context of the present invention the indicator molecules (via the capture site) may bind to the capture molecules with relatively high affinity. In some embodiments, the dissociation constant (kd) for the indicator molecule will be relatively low and preferably between $1 \times 10^{-17}M$ and $1 \times 10^{-7}M$ (depending on the sensitivity required of the assay). In certain embodiments of the invention, the dissociation constant for the indicator molecule will be between $1 \times 10^{-15}M$ and $1 \times 10^{-9}M$.

In certain embodiments of the invention, such a binding interaction may be achieved as a result of direct binding of the capture site of the indicator molecule to the capture molecule present in the capture zone. In this context, direct binding means binding of the indicator molecule (via the capture site) to the capture molecule without any intermediary.

In some embodiments of the invention, the capture site of the indicator molecule and the capture molecule present in the capture zone are two halves of a binding pair. In this context, a binding pair consists of two molecules or entities capable of binding to each other. In certain embodiments of the invention, the binding interaction is specific such that each member of the binding pair is only able to bind its respective partner, or a limited number of binding partners. Moreover, as detailed above, it is preferable for the binding pair to exhibit relatively high affinity. The binding pair may be a binding pair found in nature or an artificially generated pair of interacting molecules or entities.

In some embodiments of the invention, the capture site of the indicator molecule and the capture molecule are two halves of a binding pair wherein the binding pair is selected from the following:—an antigen and an antibody or antigen binding fragment thereof; biotin and avidin, streptavidin, neutravidin or captavidin; an immunoglobulin (or appropriate domain thereof) and protein A or G; a carbohydrate and a lectin; complementary nucleotide sequences; a ligand and a receptor molecule; a hormone and hormone binding protein; an enzyme cofactor and an enzyme; an enzyme inhibitor and an enzyme; a cellulose binding domain and cellulose fibres; immobilised aminophenyl boronic acid and cis-diol bearing molecules; and xyloglucan and cellulose fibres and analogues, derivatives and fragments thereof.

In particular embodiments of the invention, the binding pair consists of biotin and streptavidin. In a further embodiment of the invention, the capture site of the indicator molecule comprises an epitope and the capture molecule comprises an antibody, which specifically binds to the epitope present at the first capture site. In the context of the present invention, the term antibody covers native immunoglobulins from any species, chimeric antibodies, humanised antibodies, F(ab')2 fragments, Fab fragments, Fv fragments, sFv fragments and highly related molecules such as those based upon antibody domains which retain specific binding affinity (for example, single domain antibodies). The antibodies may be monoclonal or polyclonal. Thus, in specific embodiments, the capture molecule comprises an antibody. In other embodiments, the capture site comprises a biotin molecule and the capture zone comprises a streptavidin molecule.

In certain embodiments of the invention, binding of the capture site of the indicator molecule to the capture molecule of the device may be indirect. In the context of the present invention, "indirect binding" means binding mediated by some intermediate entity capable of bridging the capture site of the indicator molecule and the capture molecule, for example an "adaptor" capable of simultaneously binding the capture site of the indicator molecule and the capture molecule.

Wherein binding of the indicator molecule to the capture molecule is indirect and mediated by an adaptor, it may be possible for a plurality of indicator molecules to bind to each capture molecule. In this context, a plurality means at least two, at least three, at least four, and so forth. This may be achieved by the incorporation of a multivalent adaptor molecule, for example, a streptavidin molecule capable of simultaneous binding to multiple biotin-containing indicator molecules in addition to a capture molecule consisting of or comprising biotin.

Embodiments of the device wherein a plurality of indicator molecules bind to each capture molecule, may be used to achieve improved assay accuracy as described in greater detail herein.

Another key molecule to this implementation of the invention is the binding molecule. The invention relies upon binding molecules capable of binding to the novel binding site produced on cleavage, or the part of the indicator molecule containing the capture site following cleavage, wherein the binding molecules are incapable of binding to the indicator molecule unless and until cleavage has occurred. Thus, in specific embodiments, the binding molecule comprises an antibody. For the avoidance of doubt, the term antibody covers native immunoglobulins from any species, chimeric antibodies, humanised antibodies, F(ab')2 fragments, Fab fragments, Fv fragments, sFv fragments and highly related molecules such as those based upon antibody domains which retain specific binding affinity (for example, single domain antibodies). The antibodies may be monoclonal or polyclonal. The inventors have produced antibodies which recognise the cleavage region only after cleavage and will therefore not bind to the indicator molecule (to any significant degree) unless and until cleavage at the cleavage site has occurred. Antibodies may be produced according to techniques known in the art. This may rely upon immunisation of an animal, such as a sheep, rabbit or goat, with the cleavage products. For example immunisation may be performed using the part of the cleavage region which remains connected to the capture site after cleavage, optionally including the capture site itself. Polyclonal antibodies may be isolated from serum and affinity purified. Monoclonal antibodies may be produced using well-known and characterised hybridoma technology. The binding molecule may also comprise an aptamer in some embodiments.

Thus, the invention also provides a binding molecule, typically an antibody, which binds to an indicator molecule as defined herein after cleavage. The invention provides a binding molecule, typically an antibody, which binds to a novel binding site in the indicator molecule produced as a result of cleavage wherein the binding molecule is incapable of binding to the indicator molecule unless and until cleavage has occurred. In some embodiments, the binding molecule binds in the cleavage region. In specific embodiments, cleavage of the at least one cleavage site produces at least two parts of the cleavage region of the indicator molecule, at least one part of which remains connected to the capture site and as a consequence of cleavage contains a binding site for binding molecules and wherein the binding molecules are incapable of binding to the binding site unless and until cleavage has occurred. In some embodiments, cleavage of the at least one cleavage site produces two separate parts of the indicator molecule and thus the binding molecule binds to one or both of the separate parts following cleavage. In agreement with this, the invention provides a binding molecule, optionally an antibody, which binds to an indicator molecule comprising the amino acid sequence GPQG but not to an indicator molecule comprising the amino acid sequence GPQGIFGQ (SEQ ID NO: 1) (as the cleavage region). Similarly, the invention provides a binding molecule, optionally an antibody, which binds to an indicator molecule comprising the amino acid sequence IFGQ but not to an indicator molecule comprising the amino acid sequence GPQGIFGQ (SEQ ID NO: 1) (as the cleavage region).

In those embodiments of the invention in which the indicator molecule is structurally constrained and in which cleavage of the at least one cleavage site produces at least two parts of the cleavage region of the indicator molecule which remain connected to one another, the binding molecules may bind to the cleavage region following cleavage. In specific embodiments, the binding molecules bind to both parts of the cleavage region of the indicator molecule following cleavage. Thus, the binding molecules may bind a region that effectively spans the cleavage site following cleavage. Structural constraint of the indicator molecule, for example using the scaffold molecules as discussed herein, provides a well-defined and stable binding site for the binding molecules following cleavage. In specific embodiments, the binding site to which the binding molecule binds represents a novel structural conformation of the indicator molecule. Cleavage may produce at least one new conformational epitope. The binding site for the binding molecule may comprise any part of the indicator molecule. This may be with the proviso that enzyme cleavage activity and/or capture of the indicator molecule are not substantially impeded by binding of the binding molecule. In certain embodiments, the binding site comprises at least a portion of the cleavage region and/or at least a portion of the linker or spacer region to which the scaffold molecule is attached and which separates the scaffold molecule from the cleavage region. In other embodiments, the binding molecule may bind to a novel binding site that comprises at least a portion of the scaffold molecule.

The binding molecule may be directly or indirectly labelled with a reporter molecule to permit detection of binding of the binding molecule to the indicator molecule. The reporter molecule may be any substance or moiety suitable for detection by any means available to those skilled in the art. Thus, the reporter molecule is typically capable of signal generation or production. In certain embodiments of the invention, the reporter molecule is selected from the following:—a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particular embodiment of the invention, the reporter moiety is a gold particle.

Indirect labelling of the binding molecules with a reporter molecule is also envisaged within the present invention. Thus, the reporter molecule may be attached to a further binding molecule which in turn binds to the binding molecule to provide the label. This indirect binding may be mediated by an adaptor capable of simultaneously binding the binding molecule and the reporter molecule. As an illustrative embodiment, where the binding molecule is an antibody, indirect labelling could be mediated by a further antibody that binds to the antibody binding molecule in specific fashion. The further antibody may be directly labelled with a reporter molecule such as a gold particle; a chromogen; a luminescent compound; a fluorescent molecule; a radioactive compound; a visible compound; a liposome or other vesicle containing signal producing substances; an electroactive species; or a combination of enzyme and its substrate. A suitable enzyme-substrate combination for use as a reporter moiety may be the enzyme alkaline phosphatase and the substrate nitro blue tetrazolium-5-bromo-4-chloro-3-indolyl phosphate. In a particular embodiment of the invention, the reporter moiety is a gold particle.

In embodiments of the invention wherein the reporter molecule binds to the binding molecule by virtue of an adaptor molecule, the adaptor may be pre-complexed with the binding molecule prior to the addition of the test sample to the indicator molecule, provided that the adaptor does not prevent binding of the binding molecule to the cleaved indicator molecule.

The adaptor may be any material or molecule capable of mediating the indirect interaction of the binding molecule with the reporter molecule. In some embodiments, the adaptor is streptavidin and the binding molecule comprises a biotin molecule. The adaptor may also be an "adaptor binding pair" wherein said binding pair comprises:
(i) a first member capable of binding to the binding molecule; and (ii) a second member capable of binding to the first member of the pair and to the reporter molecule. In certain embodiments of the invention, the detection region of the indicator molecule comprises biotin, the first member of the adaptor binding pair is avidin or streptavidin, the second member of the adaptor binding pair is biotin, and the reporter molecule comprises a moiety capable of binding biotin.

The inclusion of an adaptor molecule or an adaptor binding pair may facilitate the binding of multiple reporter molecules to each binding molecule. For example, the use of multivalent streptavidin as the adaptor will allow for simultaneous binding of both a biotin-containing binding molecule in addition to multiple biotin-containing reporter molecules.

The invention may be performed in lateral flow or vertical flow devices in certain embodiments. Generally, therefore, the invention (or one or more detection devices) may rely upon some form of solid support. The solid support may define a liquid flow path for the sample. In specific embodiments, the solid support comprises a chromatographic medium or a capillary flow device. The invention may be provided in a test strip format in some embodiments. A representative example is shown in FIG. 2 and described in further detail herein.

In specific embodiments of the invention, the capture zone is formed on a solid support. Any support to which the capture molecules may be attached to form a capture zone is intended to be encompassed. The solid support may take the form of a bead (e.g. a sepharose or agarose bead) or a well (e.g. in a microplate) for example. Thus, in certain embodiments the device comprises a solid support to which the capture molecules are attached to form the capture zone. In the case of the kits of the invention, the solid support may be provided without the capture molecules attached. In those embodiments, the user of the kit may immobilize the capture molecules on the solid support to form the capture zone prior to use of the device with a test sample. The kit may, therefore, also comprise means for immobilizing the capture molecules on the solid support. The immobilizing means may comprise any suitable reagents to permit the capture zone to be formed. The solid support may be pre-formed with suitable immobilizing means. For example, the solid support may comprise biotin molecules arranged to interact with avidin (e.g. streptavidin) molecules that form (part of) the capture molecules. Of course, other binding pair interactions may be used to immobilize the capture molecules on the solid support to form a capture zone, as discussed herein and as would be readily understood by one skilled in the art.

The capture zone may be defined by the immobilization therein or thereon of capture molecules capable of binding to the capture site of indicator molecules. Immobilization of capture molecules may be achieved by any suitable means. Wherein the device is a flow device comprising a chromatographic medium, the capture molecules may be immobilized by directly binding to the medium or immobilized indirectly via binding to a carrier molecule, such as a protein, associated with, or bound to, the medium.

In further embodiments, the solid support further comprises a sample application zone to which the sample is applied. The sample application zone may be pre-loaded with the indicator molecule, such that when the test sample is applied any enzyme in the sample acts upon the cleavage site of the indicator molecule within the sample application zone. The sample application zone may contain a barrier, which holds the sample in the sample application zone for a pre-determined period of time. This permits the sample to interact with the indicator molecule for a sufficient period to achieve measurable levels of cleavage. This may be 1, 2, 3, 4, 5, 6, 7, 8, 9, 10, 15, 20, 30, 60 minutes or more depending upon the enzyme to be detected, as would be readily understood by one skilled in the art. The barrier may be degraded by the sample, or otherwise removed, after this period of time thus allowing the sample to continue to flow through the device. Alternatively, the test sample and indicator molecule may be pre-mixed or pre-incubated prior to adding the mixture to the device, such as to the sample application zone. However, where the test sample and indicator molecule may be pre-mixed or pre-incubated it is possible to omit the sample application zone. Here, it may be possible to add the mixture directly to the capture zone to permit immobilization of the indicator molecules through interaction with the capture molecules. In some embodiments, the test sample may be applied to the chromatographic medium at a site upstream from the capture zone such that it is drawn, for example by capillary action, through the capture zone. The chromatographic medium may be made from any material through which a fluid is capable of passing, such as a fluidic channel or porous membrane. In certain embodiments of the invention, the chromatographic medium comprises a strip or membrane, for example a nitrocellulose strip or membrane.

The binding molecules must be provided in the device in a manner that permits interaction with the indicator molecule, if cleaved at the cleavage site. The binding molecules may, therefore, be pre-mixed with the indicator molecules prior to application to the device. This may be before or after the indicator molecules have been mixed with the test sample. It is preferably after to avoid any effect the binding molecules may have on enzyme activity (in the test sample) at the cleavage site of the indicator molecule. The binding molecules can also be provided on or in the device at any point upstream of the capture zone, such that the binding molecules encounter the test sample and indicator molecules before the indicator molecules are immobilised (via interaction between the capture site of the indicator molecule and capture molecules defining the capture zone). Alternatively, the binding molecule may be added to the capture zone after the test sample and indicator molecules have been added to the capture zone. This ensures that any indicator molecule will already be immobilized at the capture zone, providing (in the case of cleaved indicator molecule) a binding site for the binding molecules to produce a signal.

Depending upon the particular enzyme cleavage activity that is being detected, it may be necessary to incorporate suitable enzyme inhibitors into the devices or methods. This may be important to prevent the enzyme from acting upon other components of the device or method, such as the binding molecules or capture molecules. Where the test sample is pre-incubated with the indicator molecule, it may be advantageous to add an inhibitor of the enzyme activity at the end of the incubation period. This is preferably before the binding molecules come into contact with the test sample. Alternatively, the enzyme activity inhibitor or inhibitors may be included in the device at any point upstream of the binding molecules, where the binding molecules are provided on or in the device. This is upstream of the capture zone (per the discussion herein above). The inhibitor may be simply dried or passively adsorbed onto the device such that the test sample mobilises the inhibitor as it passes through the device. It should be noted that use of an inhibitor is not essential and may be excluded where the inhibitor would result in an inability to detect a further marker in the urine. For example, some of the enzyme activities detected according to the invention such as specific protease activity may be sufficiently specific that the protease will not act on any other components of the device or method than the substrate. The cleavage sites of particular enzymes are well known in the art and can be used to design the various components of the devices and methods. For example, in silico screening may be performed (e.g. using freely available tools such as BLAST according to standard settings) to confirm that the cleavage site of the enzyme to be detected is not contained within any of the relevant molecules; such as the binding molecules and capture molecules. It is also possible to check for cross-reactivity by incubating the relevant molecules (e.g. binding molecules and capture molecules) with the enzyme activity to be tested and detecting whether cleavage occurs. In some embodiments, the relevant molecules will not be acted upon due to the nature of the enzyme cleavage activity to be detected. As an example, if a nuclease activity is being detected, this should not display any cleavage activity in relation to an antibody binding molecule or streptavidin or antibody capture molecule.

The solid support may further comprise a control zone, downstream of the capture zone in relation to sample flow, and the sample application zone if present, containing further binding molecules which bind to the binding molecules to indicate successful completion of an assay using the device. Alternatively, the further binding molecules may bind to a further molecule added to the sample or to the device and which flows with the sample through the device. The further molecule may be labelled, either directly or indirectly, with a reporter molecule as defined herein. Preferably, the reporter molecule is the same reporter molecule as attached to the binding molecules, for ease of detection, although it may be different. The control zone is spatially separated from the capture zone, for example to produce two separate test lines if the reporter is bound or immobilized in each respective zone. This control zone is used to confirm that the test sample, including the binding molecules, has passed through the entire device and confirms that the device is operating correctly. A positive signal is expected at the control zone independent of whether enzyme cleavage activity is present in the sample or not. The further binding molecules are selected based upon the nature of the binding molecules which bind to the cleavage site of the indicator molecules or on the nature of the further molecule added to the sample. The binding molecules and further binding molecules or further molecules and further binding molecules may form a binding pair as defined herein. For example, if the binding molecule is a species specific antibody (e.g. a sheep antibody), the further binding molecule may be an anti-species antibody (e.g. an anti-sheep antibody). Alternatively, if the further molecule is an antibody from a different species, e.g. a chicken or a goat, the further binding molecule may be an appropriate anti-species antibody. This permits immobilization of the binding molecule or further molecule at the control zone by virtue of a specific interaction. The further binding molecules may be immobilized in the control zone by any suitable means, for example by a covalent or non-covalent interaction.

While these embodiments have been described primarily in reference to determining the levels of an effector molecule in the urine sample, the same techniques may also be applied in order to determine other markers. In particular, levels of effector inhibitor molecules may be determined by similar techniques. The inhibitor molecules are expected to reduce the activity of the effector molecules and their level in urine can thus be detected, for example by a competition assay. For example, in the presence of a known amount of effector molecule added to the sample, the level of the effector inhibitor molecule can be determined.

Some examples of suitable assay formats useful for particular markers are outlined in the table below and also table 2.1a:

| Test | Analyte | Assay |
|---|---|---|
| | Proteases & Proteolytic activity | |
| 1 | Total MMP8 | Commercial ELISA (R&D DuoSet) |
| 2 | Total MMP9 | Commercial ELISA (R&D DuoSet) |
| 3 | Human Neutrophil Elastase (HNE) | Mologic in-house ELIZA |
| 4 | MMP-9 activity | Gelatin zymography. Commercial (Invitrogen NuPage (ref MMP9) |
| 5 | MMP activity (various) | Mologic fluorogenic substrate assay (ref MMP9) |
| 6 | MMP activity (mainly MMP13, 9, 2, 8, 12 in order) | Mologic in-house lateral flow assay Ultimate ELTABA |
| | Protease Inhibitors | |
| 7 | Alpha-1 anti-Trypsin (A1AT) | Mologic in-house ELISA |
| 8 | Alpha-1 anti-Trypsin (A1AT | Mologic in-house Lateral Flow assay |
| 9 | Neutrophil Gelatinase-Associated Lipocalin (NGAL) | Commercial ELISA (R&D DuoSet) |
| 10 | Tissue inhibitor of Metalloproteinase (TIMP1) | Commercial ELISA (R&D DuoSet) |
| 11 | Tissue inhibitor of Metalloproteinase (TIMP2) | Commercial ELISA (R&D DuoSet) |
| | Metabolites & other urinary markers | |
| 12 | Desmosine | Mologic in-house ELISA |
| 13 | Desmosine | Mologic in-house Lateral Flow assay |
| 14 | Human Serum Albumin (HAS) | Commercial ELISA (R&D DuoSet) |
| 15 | Calprotectin | Commercial ELISA (Hycult) |
| 16 | Creatinine | Commercial ELISA (R&D) |
| 17 | Beta-2 Microglobulin (B2M) | Commercial ELISA (AbCam) |
| 18 | Fibrinogen | Commercial ELISA (AbCam) |
| 19 | Cystatin C | Commercial ELISA (R&D DuoSet) |
| 20 | Retinol Binding Protein 4 (RBP4) | Commercial ELISA (R&D DuoSet) |
| 21 | Interleukin 6 (IL-6) | Commercial ELISA (R&D DuoSet) |
| 22 | Interleukin 8 (IL-8) | Commercial ELISA (R&D DuoSet) |

| Test | Analyte | Assay |
|---|---|---|
| 23 | Interleukin-1 beta (IL-1β) | Commercial ELISA (R&D DuoSet) |
| 24 | Tumour necrosis factor alpha (INFa) | Commercial ELISA (R&D DuoSet) |
| 25 | N-Formylmethionine leucyl phenylalanine (FMLP) | Mologic in-house ELISA (experimental) |

Thus, it can be readily seen that ELISA and lateral flow formats are particularly applicable to the present invention. Zymography may be useful for certain markers.

The inventors have devised various assays for determining the levels of the markers described herein.

One marker useful in the present invention is N-acetyl Pro-Gly-Pro (Ac-PGP), a neutrophil chemoattractant, derived from the breakdown of extracellular matrix (ECM) and generated during airway inflammation. Ac-PGP is cleaved from collagen through the proteolytic action of neutrophil leucocytes in inflammatory diseases such as chronic obstructive pulmonary disease (COPD). According to the invention Ac-PGP may be detected by an enzyme immunoassay (EIA). In certain embodiments, the EIA is a competitive assay. The invention thus provides a competitive enzyme immunoassay for detecting Ac-PGP in a urine sample comprising:
  (a) contacting the urine sample with an immunoassay surface on which is immobilised PGP (e.g. in the form of AHX-PGP or Ac-PGP)
  (b) adding a reagent (such as an antibody, as defined herein, one specific example being CF1763) that specifically binds to PGP to the sample, which reagent is conjugated to an enzyme (such as alkaline phosphatase)
  (c) removing reagent not bound to the immunoassay surface
  (d) measuring the levels of enzyme activity at the immunoassay surface as an indication of the levels of Ac-PGP in the sample.

In the absence of Ac-PGP in the sample, the PGP immobilised on the immunocapture surface will be bound by the reagent and thus enzyme activity will be detected. As levels of Ac-PGP in the sample increase, these molecules will compete for binding to the reagent and thus will reduce levels of enzyme activity at the immunocapture surface. A preferred reagent is a sheep anti-Ac-PGP antibody CF1763. An alternative is CF1764. The reagent may be conjugated to alkaline phosphatase in some embodiments. A schematic representation of a suitable assay format is shown in FIG. 34. A representative calibration curve for this assay is shown in FIG. 35. This assay may be referred to as version 3.

An alternative assay utilises an immobilised Ac-PGP binding reagent, such as an anti-Ac-PGP antibody (e.g. CF1763—version 1 or CF1764—version 2 as capture antibody). Here, the competing reagent may be B-AHX-PGP (biotinylated AHX-PGP) which competes with Ac-PGP in the sample. The third step then utilises streptavidin AP (streptavidin alkaline phosphatase) to label any B-AHX-PGP bound to the antibody capture line in the absence of 'free' Ac-PGP in the sample.

Ac-PGP may be detected in a lateral flow format in other embodiments, including by use of lateral flow as a format for the above referenced assays.

Another marker useful in the present invention are N-formylated peptides like fMLP (N-formyl-L-methionyl-L-leucyl-phenylalanine). Neutrophils respond to bacterial infection by producing and releasing reactive oxygen species that kill bacteria and by expressing chemokines that attract other immune cells to the site of infection. N-formylated peptides like fMLP (N-formyl-L-methionyl-L-leucyl-phenylalanine) play a major role as potent chemoattractants. fMLP originates from various bacteria as a consequence of their protein processing mechanisms and/or from degraded bacterial (PAMP). It can also be produced in mitochondria of eukaryotic cell proteins (e.g. "DAMP"). The N-formyl peptide receptor is G-protein coupled and initiates/propagates phagocytosis and pro-inflammatory reactions in human neutrophils and other cells, such as the production of reactive oxygen intermediates (e.g. superoxide; $O2-\cdot$) upon stimulation with fMLP. According to the invention fMLP may be detected by an enzyme immunoassay (EIA). In certain embodiments, the EIA is a competitive assay. The invention thus provides a competitive enzyme immunoassay for detecting fMLP in a urine sample comprising:
  (a) contacting the urine sample with an immunoassay surface on which is immobilised fMLP (e.g. through conjugation to an albumin molecule such as ovalbumin on the surface)
  (b) adding a reagent (such as an antibody, as defined herein, one specific example being CF1573) that specifically binds to fMLP to the sample, which reagent is conjugated to an enzyme (such as alkaline phosphatase)
  (c) removing reagent not bound to the immunoassay surface
  (d) measuring the levels of enzyme activity at the immunoassay surface as an indication of the levels of fMLP in the sample.

In the absence of fMLP in the sample, the fMLP immobilised on the immunocapture surface will be bound by the reagent and thus enzyme activity will be detected. As levels of fMLP in the sample increase, these molecules will compete for binding to the reagent and thus will reduce levels of enzyme activity at the immunocapture surface. A preferred reagent is a sheep anti-Ac-fMLP antibody CF1573. The reagent may be conjugated to alkaline phosphatase in some embodiments. A schematic representation of a suitable assay format is shown in FIG. 36. A representative calibration curve for this assay is shown in FIG. 37.

fMLP may be detected in a lateral flow format in some embodiments.

The degradation of elastin fibres during inflammation is caused by enzymes called elastases. Two important inflammatory elastases are neutrophil elastase (released by activated neutrophils) and MMP12 (released by lung macrophages). Desmosine is cleaved from elastin and is a molecular signature of the degradation process, indicating that leukocyte activity is elevated or rising. The amount of desmosine excreted in the urine directly correlates with the extent of elastin degradation which in turn is indicative of the level of tissue damage. Desmosine is small enough to be passed through the kidney. Excess neutrophil leukocyte activity is a key driver of exacerbation. The inventors have developed desmosine fragment assays as well as Desmosine assays. The invention provides an assay able to measure Desmosine as well as Desmosine still attached to elastin fibres. This format relies upon use of multiple antibodies raised to different sized elastin fragments resulting from cleavage by human neutrophil elastase. According to the invention desmosine fragments may be detected by an enzyme immunoassay (EIA). In certain embodiments, the EIA is a competitive assay. The invention thus provides a competitive enzyme immunoassay for detecting desmosine fragments in a urine sample comprising:

(a) contacting the urine sample with an immunoassay surface on which is immobilised desmosine fragments (e.g. through conjugation to an albumin molecule such as ovalbumin on the surface)
(b) adding a series of reagents (such as a group of antibodies, as defined herein, one specific example being CF1673, CF1674 and CF1675) that specifically bind to respective desmosine fragments in the sample, each of which reagents is conjugated to an enzyme (such as alkaline phosphatase)
(c) removing reagent not bound to the immunoassay surface
(d) measuring the levels of enzyme activity at the immunoassay surface as an indication of the levels of desmosine fragments in the sample.

In the absence of the desmosine fragments in the sample, the desmosine fragments immobilised on the immunocapture surface will be bound by the reagents and thus enzyme activity will be detected. As levels of desmosine fragments in the sample increase, these molecules will compete for binding to the reagent and thus will reduce levels of enzyme activity at the immunocapture surface. A preferred reagent series are sheep anti-desmosine fragment antibodies CF1673, CF1674 and CF1675. The reagents may each be conjugated to alkaline phosphatase in some embodiments. A schematic representation of a suitable assay format is shown in FIG. 38. In some embodiments, the respective reagents in the series are utilised in separate individual assays, referred to herein as versions 1, 2, and 3. HPLC analysis of elastin breakdown products is shown in FIG. 39, which breakdown products can be used as immunogens to produce specific antibodies. The elastin fragments may be small elastin fragments. Small elastin fragments typically have a molecular weight of no more than 30,000 Da, such as between 1000 and 30,000 Da. Small elastin fragments not attached to desmosine may also, or separately, be measured in some embodiments.

Similarly, the invention provides an assay for measuring large elastin fragments (LEF). By large elastin fragments is meant fragments of elastin with a molecular weight greater than around 30,000 Da. This format relies upon use of multiple antibodies raised to the large elastin fragments resulting from cleavage by human neutrophil elastase (also see FIG. 39). According to the invention large elastin fragments may be detected by an enzyme immunoassay (EIA). In certain embodiments, the EIA is a competitive assay. The invention thus provides a competitive enzyme immunoassay for detecting large elastin fragments in a urine sample comprising:

(a) contacting the urine sample with an immunoassay surface on which is immobilised large elastin fragments (e.g. through conjugation to an albumin molecule such as ovalbumin on the surface)
(b) adding a series of reagents (such as a group of antibodies, as defined herein, such as CF1669, CF1670 and CF1673 (all purified against LEF)) that specifically bind to respective large elastin fragments in the sample, each of which reagents is conjugated to an enzyme (such as alkaline phosphatase)
(c) removing reagent not bound to the immunoassay surface
(d) measuring the levels of enzyme activity at the immunoassay surface as an indication of the levels of large elastin fragments in the sample.

In the absence of the large elastin fragments in the sample, the large elastin fragments immobilised on the immunocapture surface will be bound by the reagents and thus enzyme activity will be detected. As levels of large elastin fragments in the sample increase, these molecules will compete for binding to the reagent and thus will reduce levels of enzyme activity at the immunocapture surface. The reagents may each be conjugated to alkaline phosphatase in some embodiments.

In some embodiments, the respective reagents in the series are utilised in separate individual assays, referred to herein as versions 1, 2, and 3.

The methods of the invention rely upon identifying a change in the level of at least one marker in a urine sample. Thus, a comparison is made between the levels in the test sample and at least one urine sample taken from the same subject at an earlier time point. The comparison permits identification of whether there has been an increase, decrease or no change in the marker levels compared to the earlier urine sample or samples. One key aspect of the invention is the ability to personalise the monitoring of inflammation status in order to accurately identify and/or predict an exacerbation. Thus, according to all aspects of the invention increased levels of the at least one marker may be calculated with reference to a threshold level of the marker that is adapted (or personalised) to the subject. The invention may therefore rely upon a personalised baseline level of the relevant marker or markers against which the threshold is calculated. Calculation may be on an on-going basis to coincide with testing. Thus, the threshold may be a rolling threshold derived from the rolling baseline. The ability to measure longitudinally on a subject by subject basis is greatly facilitated by the ease of collection of urine samples. Compliance is expected to be significantly improved by provision of home monitoring using an easy to collect sample. Thus, the invention relies upon monitoring an individual's inflammation status through repeated testing of urine samples over time. In this context, it is apparent that levels of the marker or markers do not have to be measured in absolute terms and may be measured in absolute or relative terms. The markers simply have to be measured in a manner which permits a comparison to be made with marker levels in urine samples taken at different time points. Thus "level" should be interpreted accordingly throughout the specification, unless indicated otherwise. For example, levels may be measured relative to a reference analyte present at a stable concentration in urine samples irrespective of exacerbation status.

In some embodiments, the threshold level of the marker is set by determining the levels of the marker in urine samples taken from the subject at earlier time points. In its simplest form, the invention may rely upon a simple comparison between the test sample and the level of the marker in the previously taken urine sample (i.e. a single earlier time point). However, typically, the earlier time points may comprise at least two, and possibly 3, 4, 5, 6, 7, 8, 9, 10 etc, earlier measurements immediately preceding the determination of the level of the marker in the current urine sample. Those earlier measurements may be taken over a period of days or weeks, such as 1, 2, 3, 4, 5 or 6 weeks or longer. The baseline may be set during a period of stable disease to determine the initial thresholds against which future changes are measured. Stable disease may initially be identified by routine methods. Alternatively or additionally, the baseline may be set during a period of exacerbation to determine the initial thresholds against which future changes are measured. An exacerbation may initially be identified by routine methods.

Where marker levels are measured at multiple time points those levels may be averaged to provide the threshold for the test sample, above which an exacerbation is predicted or identified. In some embodiments, the threshold may be set with reference to a sliding window within which levels of the markers have been measured to provide a baseline. The threshold level is thus "learned" by the system. It is not a fixed threshold and is adapted to the subject, thereby taking into account insignificant fluctuations in marker levels from the baseline that are not predictive or indicative of an exacerbation event. Accordingly, the threshold may be set around the baseline to specify an allowable range of the marker levels beyond which a statistically significant increase (or decrease) in level is indicated. In the presence of drift of the baseline level of the marker, it is possible that the parameter limits may be narrowed such that a further change in level of the markers is deemed significant. For example, if the baseline marker level is drifting upwards over time, the difference between a measured increase and baseline may need to be smaller (compared to the situation in which the baseline is relatively stable) to be considered to have exceeded the threshold (i.e. to be significant). This is intended to prevent a "slow onset" exacerbation being missed. For example, a difference from baseline of at least 5, 10, 15, 20% or more may be considered significant generally. This difference may be reduced if there have been multiple previous measurements displaying a trend upwards or downwards but in each case by an amount less than the threshold difference. The difference (in order to be considered significant) may thus be reduced to at least 1, 2, 3, 4, 5% or more as appropriate in the event of a drift upwards or downwards in the baseline.

In some embodiments, the threshold level of the marker is set by determining the levels of the marker in urine samples taken from the subject at earlier time points at which the subject was not suffering from an exacerbation of inflammation. An exacerbation may be predicted or identified based upon observance of a statistically significant deviation from the baseline set with reference to the non-exacerbation levels. Thus, stable state levels may be measured on an individual basis to provide criteria for detecting meaningful changes in future monitoring.

In other embodiments, levels of at least one marker are determined at least twice a week. Marker levels may be determined at least 1, 2, 3, 4, 5, 6 times a week or daily in some embodiments. For the avoidance of doubt marker levels may be detected in a newly collected urine sample on each occasion.

The threshold is intended to permit detection both of a gradual move or "drift" towards an exacerbation as well as a more sudden decline in condition (reflected by an increased level of one or more markers) towards exacerbation. Thus, the threshold may be a rolling threshold personalised to the subject. It permits any significant (i.e. statistically significant) deviation from baseline in terms of the levels of the one or more markers to be detected, thus indicating or predicting an exacerbation event. The baseline and calculated threshold may be adapted or trained in relation to previous exacerbation events suffered by the same subject. The baseline and threshold calculated therefrom may be set in relation to 1, 2, 3, 4, 5, 6, 7, 8, 9, 10 etc previous measurements taken by the subject. The threshold may be weighted towards more recent measurements as would be well understood by one skilled in the art.

The threshold may be set in relation to multiple markers as discussed in greater detail herein. Thus, the prediction or identification of an exacerbation may be identified based upon a deviation from baseline that is cumulative according to the multiple markers measured. Typically, however, each marker will be measured individually with reference to a marker specific baseline and against a marker specific threshold. It is shown herein that use of multiple individual markers provides an improved ability to predict or identify an exacerbation. This seems to be because in different individuals an exacerbation may be predicted or identified more accurately with different markers. Thus, the invention may rely upon a plurality of rolling baselines/thresholds depending upon the individual markers employed (typically three or more). The methods and systems may weight the contribution of a plurality of markers. Thus, additional weight in terms of predicting or identifying an exacerbation may be given to elevation of more than one (be it 2, 3, 4, 5 etc.) markers, for example when measured in the same sample. Thus, for example, elevation of 2 markers may predict or identify an exacerbation whereas elevation of one marker may result in an increased frequency of testing to monitor more closely whether an exacerbation is or will occur.

The thresholds may also be used to guide sampling/testing frequency. For example, in some embodiments, the frequency of determining the levels of the at least one marker in urine samples taken from the subject is increased if an increase in the levels of the at least one marker is detected. This may be used to improve the sensitivity or accuracy by which an exacerbation is predicted or identified. The frequency may be increased from weekly or twice weekly to daily or from daily to twice daily for example. In certain embodiments the frequency of determining the levels of the at least one marker in urine samples taken from the subject is maintained (at the increased level) until a decrease in the levels of the at least one marker is detected. Thus, the monitoring frequency may be maintained until an exacerbation has been identified or predicted. The monitoring frequency may also be maintained (at the increased level) during a treatment phase in order to monitor the effectiveness of treatment of the exacerbation event. In some embodiments, the monitoring frequency may be further increased during the treatment phase (e.g. to testing every 6, 8 or 12 hours for example).

The invention may rely upon determining levels of a plurality, such as at least two or three (or 4, 5, 6, 7, 8, 9, 10 or more) markers in urine samples taken from the subject at multiple time points. In specific embodiments, increased levels (above threshold, relative to the personalised baseline) of at least one of the markers in a urine sample are indicative of or predictive of an exacerbation of inflammation. In some embodiments, decreased levels of at least one of markers in a urine sample following an increase are indicative or predictive of recovery from, or successful treatment of, an exacerbation of inflammation.

Where levels of multiple markers are determined, a suitable algorithm may be employed in order to interpret the data and apply it to provide the prediction or identification. In some embodiments, the marker levels may be interdependent and thus the algorithm is based on this predicted relationship (e.g. between effector and effector inhibitor molecules). In certain embodiments, the determined levels of the at least two or three (or more) markers are analysed in a pre-determined sequence to monitor the inflammation status of the subject. This may give rise to a decision tree, as explained further herein and shown in the figures, to guide future sampling and treatment of the subject. For example, FIG. 24 shows a suitable testing protocol based upon determining levels of an effector inhibitor (TIMP2), followed by effector (MMP activity) followed by a further effector inhibitor marker (A1AT). Thus, in some embodiments, for a given sample, the marker levels may be analysed in sequence until a marker is found with an increased level (or all markers have been examined). If a marker is detected at increased level the further markers may or may not also be assessed to determine if their level is also increased. The likelihood of exacerbation may be higher in the event that multiple markers are increased in a sample and the algorithm may account for this in the outcome, e.g. by weighting the observations. Thus, the sample may be "graded" based upon how many of the markers are increased in level compared to threshold. For example, Grade 1 may indicate only one of the markers is increased in the sample, Grade 2 may indicate two of the markers is increased etc. Grade 3 or above may predict or identify an exacerbation.

In some embodiments, gender is incorporated into the algorithm. As shown experimentally herein, gender may influence the markers used and the levels applied in a given algorithm.

In some embodiments, an increase in an effector molecule without a corresponding increase in a corresponding inhibitor molecule may indicate an early warning sign of an exacerbation. An increased level of both molecules may indicate an early exacerbation. An increased level of the inhibitor and a decreased level of the effector may indicate a later phase of exacerbation or predict the (beginning of a) recovery phase. If multiple markers are increased an exacerbation may be predicted or identified without the need for further sampling for example (e.g. Grade 3 or above). Increased levels of a single marker may lead to increased frequency of testing but not necessarily to immediate referral/treatment. In some embodiments, the determined levels of the at least two or three markers are weighted. Weighting is a well-known method of applying a degree of relative significance to the multiple markers. The algorithm may be a threshold based algorithm as discussed herein.

As already discussed, in some embodiments, levels of at least one marker are determined by normalising against the levels of a reference marker, also measured in urine. Suitable reference markers useful in the invention may include urinary creatinine or fibrinogen. Other markers may include urine volume, conductivity and albumin levels. Specific gravity and colour may be other normalising or reference markers.

In illustrative embodiments, relating to use of at least three markers, an increase in the levels of each of the at least three markers indicates or predicts an exacerbation of inflammation. These embodiments may be applied mutatis mutandis to situations in which 2, 4, 5, 6, 7, 8, 9, 10 etc. markers are measured in urine samples as would readily be appreciated by the skilled person.

In specific embodiments, where an exacerbation is indicated or predicted, the subject's exacerbation is treated. Suitable treatments for an exacerbation are known in the art. They include use of inhalers, which may be bronchodilator inhalers (short or long acting). Short-acting bronchodilators include beta-2 agonist inhalers, such as salbutamol and terbutaline and antimuscarinic inhalers, such as ipratropium. Long acting bronchodilators include beta-2 agonist inhalers, such as salmeterol and formoterol and antimuscarinic inhalers, such as tiotropium. Steroid or corticosteroid inhalers may also be used. Further useful therapeutic agents include theophylline, mucolytics such as carbocisteine, antibiotics and steroids. Nebulisers may be employed. They may for example be employed in place of an inhaler where the exacerbation is not managed or does not improve through use of an inhaler. Such monitoring is encompassed by the present invention. Oxygen therapy or non-invasive ventilation may also be employed. Rehabilitation programmes involving physical exercise may also be utilised as appropriate. Again the invention permits monitoring of such programmes to determine whether they are having the desired effect in terms of stabilising the condition (against exacerbations).

In some embodiments, if no increase in the levels of any of the markers is determined, the inflammation status is considered stable. In those circumstances the frequency of testing may be maintained (for example at a basal level). Thus, monitoring includes the detection of no change in levels of the marker(s). Similarly, once an exacerbation has been identified or predicted no change in levels of the marker(s) may indicate an on-going exacerbation. Further increases may indicate a worsening of the exacerbation.

In certain embodiments, if an increase in the level of one of the markers is determined but not in the other two markers the frequency of testing is increased. In specific embodiments, the frequency of testing is increased unless the increased level of one of the markers reverts to a non-increased level within a set number of repeat tests. That set number can be any suitable number. For example it may be 1, 2, 3, 4 or 5 (or more). The increased frequency may be daily or twice daily for example.

In further embodiments, if the level of one of the markers reverts to a non-increased level within the set number of repeat tests, the frequency of testing reverts to the original frequency. The original frequency may be one to three times a week for example. In related embodiments, if the level of one of the markers remains at an increased level within the set number of repeat tests, the frequency of testing is increased further. That set number can be any suitable number. For example it may be 1, 2, 3, 4 or 5 (or more). The further increased frequency of testing may be on a 6, 8 or 12 hourly basis for example.

In certain embodiments, if the level of one (or more) of the markers remains at an increased level within a further set number of repeat tests at increased frequency an exacerbation of inflammation is indicated or predicted. That set number can be any suitable number. For example it may be 1, 2, 3, 4 or 5 (or more). In those circumstances, the patient's exacerbation may then be treated.

In related embodiments, if the level of one (or more) of the markers reverts to a non-increased level within the further set number of repeat tests at increased frequency, the frequency of testing reverts to the increased (but not further increased) frequency of testing. That set number can be any suitable number. For example it may be 1, 2, 3, 4 or 5 (or more). Thus, the invention may enable a step-down in frequency of monitoring where there has been a reversion in levels of the one or more markers without reaching prediction or identification of an exacerbation. More generally, the invention permits stepping up and down of frequency of testing according to the data generated for the individual subject with a view to accurately managing that patient's inflammation status.

In specific embodiments, if the level of one (or more) of the markers remains at the non-increased level within the set number of repeat tests, the frequency of testing reverts to the original frequency. Thus, there may be a second step-down to the original testing protocol.

According to all of these exemplary embodiments, if an increase in the level of two of the markers is determined but not in the other marker (or markers if more than three are used) the frequency of testing may be increased. In specific embodiments, the frequency of testing is increased to a frequency greater than if an increased level in only one of the markers is detected. Thus, the algorithm may categorise an increased level of a plurality of markers as potentially more dangerous than a single marker and adjust the frequency of testing accordingly. This may be a double step-up in frequency of testing.

In some embodiments, if the level of at least one of the markers reverts to a non-increased level within the set number of repeat tests, the frequency of testing reverts to a frequency of testing indicative of a determined increase in the level of one of the markers. Thus monitoring may be flexible to allow a step-down in frequency to a level suitable for, or commensurate with, elevation of a single marker. However, in some embodiments, if the level of the one of the markers remains at an increased level within the set number of repeat tests (which may be 1, 2, 3, 4, 5, or more), the frequency of testing is increased again. This permits a persistent increase in a single marker to be monitored. In specific embodiments, if the level of the one of the markers remains at an increased level within a further set number of repeat tests at increased frequency an exacerbation of inflammation is indicated or predicted. In those circumstances, the patient's exacerbation may be treated.

Alternatively, if the level of two of the markers remains at an increased level within a further set number of repeat tests at increased frequency an exacerbation of inflammation is indicated or predicted. That set number can be any suitable number. For example it may be 1, 2, 3, 4 or 5 or more. In those circumstances, the patient's exacerbation may be treated.

The subject may continue monitoring during treatment in order to assess the effectiveness of the treatment and/or recovery from the exacerbation. This monitoring may continue at the increased level (e.g. every 6, 8 or 12 hours) or may revert to a single (e.g. twice daily or daily) or double stepped down level (e.g. one, twice or three times a week). If no response is observed to the treatment given (i.e. no decrease in the marker levels is seen in the urine samples), alternative treatments may then be explored. Thus, the invention also relates to monitoring treatment of an exacerbation event.

Accordingly, the invention further provides a method for monitoring inflammation status of a subject, the method comprising determining levels of at least one neutrophil activation marker in urine samples taken from the subject at multiple time points, wherein decreased levels of the at least one neutrophil activation marker in a urine sample are indicative of or predictive of recovery from, or successful treatment of, an exacerbation of inflammation.

The method is preferably implemented in a system or kit for home use monitoring. Accordingly, the invention also provides a system or test kit for monitoring inflammation status in a subject, comprising:
a. One or more testing devices for determining levels of at least one neutrophil activation marker in a urine sample
b. A processor; and
c. A storage medium comprising a computer application that, when executed by the processor, is configured to:
i. Access and/or calculate the determined levels of the at least one neutrophil activation marker in the urine sample on the one or more testing devices
ii. Calculate whether there is an increased or decreased level of the at least one neutrophil activation marker in the urine sample; and
iii. Output from the processor the current inflammation status of the subject, wherein decreased levels of the at least one neutrophil activation marker in a urine sample are indicative of or predictive of recovery from, or successful treatment of, an exacerbation of inflammation.

The invention also relates to a corresponding computer application for use in the system or test kit.

The inventors have determined that specific and sensitive results may be achieved by combining a plurality of urinary markers in order to monitor or predict PEx events. Accordingly, the invention also provides a method for monitoring inflammation status of a subject, the method comprising determining levels of at least 2, 3, 4, 5, 6, 7, 8, 9, 10 or more markers in urine samples taken from the subject at multiple time points, wherein decreased levels of at least one of the markers in a urine sample indicates or predicts recovery from, or successful treatment of, an exacerbation of inflammation.

Similarly, the invention also provides a system or test kit for monitoring inflammation status in a subject, comprising:
a. One or more testing devices for determining levels of at least 2, 3, 4, 5, 6, 7, 8, 9, 10 or more markers in a urine sample
b. A processor; and
c. A storage medium comprising a computer application that, when executed by the processor, is configured to:
i. Access and/or calculate the determined levels of each marker in the urine sample on the one or more testing devices
ii. Calculate whether there is an increased or decreased level of at least one of the markers in the urine sample; and
iii. Output from the processor the current inflammation status of the subject, wherein decreased levels of at least one of the markers in a urine sample are indicative of or predictive of an exacerbation of inflammation.

The invention also relates to a corresponding computer application for use in the system or test kit.

All embodiments discussed herein are also applicable to the treatment monitoring aspects of the invention, where a decrease indicates successful treatment or recovery from an exacerbation. Thus, in these embodiments, the baseline from which personal thresholds are derived may be a baseline measured at exacerbation, to include measurement of levels of the marker or markers in at least one urine sample taken during exacerbation.

In terms of further monitoring, decreased levels of at least one of the markers in a urine sample following an increase may be indicative or predictive of recovery from, or successful treatment of, an exacerbation of inflammation. The algorithm may also account for the relationship between effector and effector inhibitor molecules as discussed herein, with a recovery ultimately indicated by a return to baseline levels in both types of marker but an increase in inhibitor being expected as part of the subject's response to the effector level increase.

In all of these embodiments, the determined levels of the plurality of markers (e.g. at least three) may be analysed in a pre-determined sequence to monitor the inflammation status of the subject. The determined levels of the at least two or three (or more) markers may be weighted.

In specific embodiments of the invention, such as those outlined above, the first marker may be TIMP2 (level/activity), the second marker may be MMP (level/activity) and the third marker may be A1AT (level/activity). A suitable algorithm is described in further detail herein in relation to these three markers, although it would be readily apparent that the algorithm can be adapted to any combination of markers.

The methods, systems and test kits of the invention may be used in conjunction with monitoring other indicators of exacerbation of inflammation. In specific embodiments, the other indicators of exacerbation of inflammation comprise or are selected from one or more of shortness of breath, increased wheeze, increased pulse rate, dyspnoea, increased sputum purulence, increased sputum colour, sore throat, increased cough, cold and fever. Similarly, treatment may be monitored in relation to these additional indicators. Another indicator that may be monitored is Forced Expiratory Volume in one second ($FEV_1$)

From the foregoing, it is apparent that the personalised nature of the methods of the invention requires significant computational input in order to define relevant thresholds on a continuous or semi-continuous basis, relative to baseline, and to interpret marker levels against those thresholds. Thus, the methods of the invention typically incorporate suitable software to perform the relevant technical steps. Accordingly, the methods of the invention may be performed using systems or test kits. In particular, the invention provides a system or test kit for monitoring inflammation status in a subject, comprising:
a. One or more testing devices for determining levels of at least one neutrophil activation marker in a urine sample
b. A processor; and
c. A storage medium comprising a computer application that, when executed by the processor, is configured to:
  i. Access and/or calculate the determined levels of the at least one neutrophil activation marker in the urine sample on the one or more testing devices
  ii. Calculate whether there is an increased or decreased level of the at least one neutrophil activation marker in the urine sample; and
  iii. Output from the processor the current inflammation status of the subject, wherein increased levels of the at least one neutrophil activation marker in a urine sample are indicative of or predictive of an exacerbation of inflammation.

Similarly the invention provides a system or test kit for monitoring inflammation status in a subject, comprising:
a. One or more testing devices for determining levels of at least three markers in a urine sample
b. A processor; and
c. A storage medium comprising a computer application that, when executed by the processor, is configured to:
  i. Access and/or calculate the determined levels of each marker in the urine sample on the one or more testing devices
  ii. Calculate whether there is an increased or decreased level of at least one of the markers in the urine sample; and
  iii. Output from the processor the current inflammation status of the subject, wherein increased levels of at least one of the markers in a urine sample are indicative of or predictive of an exacerbation of inflammation.

The invention also relates to the computer applications used in the systems and test kits. Thus, in certain embodiments, the computer-implemented method, system, and computer program product may be embodied in a computer application, for example, that operates and executes on a processor, such as in the context of a computing machine. When executed, the application performs the relevant analyses to output the current inflammation status of the subject, wherein increased levels of at least one of the markers in a urine sample are indicative of or predictive of an exacerbation of inflammation.

As used herein, the processor may be comprised within any computer, server, embedded system, or computing system. The computer may include various internal or attached components such as a system bus, system memory, storage media, input/output interface, and a network interface for communicating with a network, for example.

The computer may be implemented as a conventional computer system, an embedded controller, a laptop, a server, a customized machine, any other hardware platform, such as a laboratory computer or device, for example, or any combination thereof. The computing machine may be a distributed system configured to function using multiple computing machines interconnected via a data network or bus system, for example.

The processor may be configured to execute code or instructions to perform the operations and functionality described herein, manage request flow and address mappings, and to perform calculations and generate commands. The processor may be configured to monitor and control the operation of the components in the computing machine. The processor may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor may be a single processing unit, multiple processing units, a single processing core, multiple processing cores, special purpose processing cores, co-processors, or any combination thereof. According to certain example embodiments, the processor, along with other components of the computing machine, may be a virtualized computing machine executing within one or more other computing machines.

The storage medium may be selected from a hard disk, a floppy disk, a compact disc read only memory ("CD-ROM"), a digital versatile disc ("DVD"), a Blu-ray disc, a magnetic tape, a flash memory, other non-volatile memory device, a solid-state drive ("SSD"), any magnetic storage device, any optical storage device, any electrical storage device, any semiconductor storage device, any physical-based storage device, any other data storage device, or any combination or multiplicity thereof. The storage media may store one or more operating systems, application programs and program modules such as module, data, or any other information. The storage media may be part of, or connected to, the computing machine. The storage media may also be part of one or more other computing machines that are in communication with the computing machine, such as servers, database servers, cloud storage, network attached storage, and so forth.

The storage media may therefore represent examples of machine or computer readable media on which instructions or code may be stored for execution by the processor. Machine or computer readable media may generally refer to any medium or media used to provide instructions to the processor. Such machine or computer readable media associated with the module may comprise a computer software product.

The input/output ("I/O") interface may be configured to couple to one or more external devices, to receive data from the one or more external devices, and to send data to the one or more external devices. Such external devices along with the various internal devices may also be known as peripheral devices. The I/O interface may include both electrical and physical connections for operably coupling the various peripheral devices to the computing machine or the processor. The I/O interface may be configured to communicate data, addresses, and control signals between the peripheral devices, the computing machine, or the processor. The I/O interface may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface may be configured to implement only one interface or bus technology.

Alternatively, the I/O interface may be configured to implement multiple interfaces or bus technologies. The I/O interface may be configured as part of, all of, or to operate in conjunction with, the system bus. The I/O interface may include one or more buffers for buffering transmissions between one or more external devices, internal devices, the computing machine, or the processor.

The I/O interface may couple the computing machine to various input devices including mice, touch-screens, scanners, electronic digitizers, sensors, receivers, touchpads, trackballs, cameras, microphones, keyboards, any other pointing devices, or any combinations thereof. The I/O interface may couple the computing machine to various output devices including video displays, speakers, printers, projectors, tactile feedback devices, automation control, robotic components, actuators, motors, fans, solenoids, valves, pumps, transmitters, signal emitters, lights, and so forth.

The computing machine may operate in a networked environment using logical connections through the network interface to one or more other systems or computing machines across the network. The network may include wide area networks (WAN), local area networks (LAN), intranets, the Internet, wireless access networks, wired networks, mobile networks, telephone networks, optical networks, or combinations thereof. The network may be packet switched, circuit switched, of any topology, and may use any communication protocol. Communication links within the network may involve various digital or an analog communication media such as fiber optic cables, free-space optics, waveguides, electrical conductors, wireless links, antennas, radio-frequency communications, and so forth.

The processor may be connected to the other elements of the computing machine or the various peripherals discussed herein through the system bus. It should be appreciated that the system bus may be within the processor, outside the processor, or both. According to some embodiments, any of the processor, the other elements of the computing machine, or the various peripherals discussed herein may be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement one or more of the disclosed embodiments described herein. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The methods, systems and test kits may incorporate means for Automatic Identification and Data Capture (AIDC), such as a Radio-frequency identification tag or card (RIF)

For the avoidance of doubt, the discussion of the invention hereinabove applies to the systems and test kits of the invention and all embodiments can be applied accordingly. However, for clarity and by way of exemplification of how the discussion applies directly to the systems and test kits, further specific embodiments are outlined below.

The systems or test kits may be suitable for home use by a subject, in particular a subject in need of monitoring as defined herein. In some embodiments, the test system or kit takes the form of a portable system. An example system upon which the systems of the invention may be based is the Alere™ DDS® 2 mobile test system. This system comprises an analyser, into which a test cartridge is inserted. The user then also inserts a sample collection device into the analyser. The analyser incorporates a full colour screen to read the results. The analyser thus houses the processor and storage medium which permits the assays to be run. The test cartridge represents the one or more testing devices for determining levels of the urinary markers. The systems or test kits of the invention may incorporate a separate sample collection device or this may be integrated into the one or more testing devices.

In specific embodiments, the system or test kit further comprises a display for the output from the processor. This is intended to give a simple visual and/or audible read-out of the assays performed on the urine sample. The display may be operably connected to the processor running the computer application. The output or read-out may be an instruction to the subject in some embodiments. Depending upon the algorithm employed suitable read-outs may be selected from "increase/decrease frequency of testing", which may be to a specified level or frequency for example or "visit practitioner" or equivalent wordings. The output may be colour coded or numerical to reflect the various possible outcomes of monitoring as discussed herein. It is possible for the display to provide levels of the markers measured in the sample and provide suitable training and/or documentation to assist the user in interpretation of the data. However, this is not preferred for obvious reasons of susceptibility to human error. A combination of both types of information may, however, be presented in some embodiments. Thus, the display may present both quantitative and qualitative read-outs in some embodiments. Probability values related to the predictive and identification outcomes may also represent an output in some embodiments.

The one or more testing devices can be of any form suitable for home use. The various methods of detecting markers are discussed herein and from this discussion the skilled person would be well able to determine the form of a suitable corresponding home use device.

In specific embodiments, the one or more testing devices comprise disposable single use devices to which the urine sample is applied. Typically the one or more testing devices may comprise a sample application zone to which the sample is added. Generally, the sample application zone can receive a relatively large volume of sample, for example 10, 20, 30, 40 or 50 ml or more. The devices typically also incorporate a solid support which defines a liquid/capillary flow path for the sample once applied to the sample application zone. The sample application zone may be an integral part of the solid support. The solid support may comprise a chromatographic medium, such as a membrane material in some embodiments (e.g. nitrocellulose). A urine sample applied to the sample application zone will typically rehydrate the necessary reagents to detect the marker. The reagents may include a binding reagent which specifically interacts with the marker or a substrate for effector molecules where activity is measured. A further reagent may be immobilized further along the flow path. This reagent may bind to the complex of marker and binding reagent. The binding reagent is typically labelled to provide a signal at the site of immobilization of the complex of marker and binding reagent (through binding to the further reagent). Suitable labels include fluorescent labels, magnetic labels, latex or gold as would be readily understood by one skilled in the art.

The binding reagent and further reagent are typically antibodies (as defined herein). Thus, in specific embodiments, the one or more testing devices may comprise a lateral flow test strip. In some embodiments, a single lateral flow test strip is employed to permit detection of all markers that are to be determined in the test sample. In other embodiments, a separate lateral flow test strip is provided for each marker that is determined.

The devices may also include a control zone to confirm sample has passed through the device satisfactorily. In the event this is not the case the system or test kit may indicate an invalid result to the user, for example via the display. The devices may act as competitive or sandwich assays, as discussed herein. ELISA (enzyme linked immunosorbent assay) is an example of a suitable assay format that may be incorporated in the testing devices used in the invention. Again, typically all reagents to detect the levels of the one or more markers are pre-loaded onto the testing device such that they can interact with the urine sample once added to the device. This minimizes intervention and thus error caused by the subject. Thus, effectively, the device may only require the user to apply the sample and subsequently observe the output of the assay.

The systems and test kits require a quantitative read-out to permit inflammation status to be monitored over time in the subject. Thus, the systems or test kits, may incorporate a suitable reader to provide a quantitative output (in conjunction with the processor and storage medium). As already mentioned this output can be an absolute or a relative output. Suitable readers may incorporate an illuminator to expose the device to a specific wavelength or wavelengths of light and a suitable detector for the reflected or emitted light. The devices also incorporate a suitable processor and computer application to output the current inflammation status of the subject based upon the detected signal. Thus, the processor running the computer application will be in operable connection with the reader. By "operable connection" is meant a functional connection that permits the exchange of a signal or information between the elements.

The testing device may comprise one or more specific binding reagents to bind to the marker whose level is detected in the urine sample. As discussed above, where protein levels are measured the reagent may comprise an antibody (to include derivatives, fragments and aptamers). Where RNA levels are measured suitable reagents may comprise nucleic acid amplification reagents such as primers, probes, dNTPs, polymerases etc. to permit amplification reactions to be run and results reported from the testing device.

The one or more testing devices may comprise an enzyme detection device as discussed in greater detail hereinabove. These devices may be particularly useful for investigating enzymatic activity (e.g. of effector molecules such as MMPs, cathepsin G and HNE). The one or more testing devices may comprise a testing device for measuring cleavage of a peptide substrate as an indicator of protease activity.

In specific embodiments, the testing device comprises:
a. an indicator molecule for adding to the urine sample, said indicator molecule comprising
   i. a cleavage region comprising at least one cleavage site, which can be cleaved by said protease activity if present; and
   ii. a capture site;
   wherein cleavage of the at least one cleavage site produces a novel binding site;
b. a capture zone to receive the urine sample, wherein the capture zone comprises capture molecules capable of binding to the capture site of the indicator molecule in order to immobilise the indicator molecule including the novel binding site; and
c. binding molecules capable of binding to the novel binding site,
   wherein the binding molecules are incapable of binding to the indicator molecule unless and until cleavage has occurred.

Where a plurality of markers is determined in the sample, the system or test kit may incorporate the appropriate number of testing devices to permit each marker to be determined. This is particularly the case where the markers are detecting using different platforms. Thus, in some embodiments, the one or more testing devices for determining levels of an effector molecule comprise one or more lateral flow activity assays, ELISAs, fluorogenic substrate assays etc. In some embodiments, the one or more testing devices for determining levels of an effector inhibitor molecule comprise one or more lateral flow activity assays, ELISAs or competition assays. In some embodiments, the one or more testing devices for determining levels of a signalling molecule comprise one or more lateral flow assays and ELISAs.

As discussed above, the invention relies upon personalised subject thresholds, which may be calculated against a baseline for the subject (e.g. on a marker by marker basis).

Accordingly, in some embodiments, the computer application causes the processor to calculate levels of the at least one marker with reference to a threshold level of the marker that is adapted to the subject. Also as discussed above, the threshold level of the marker is set based upon determined levels of the marker in urine samples taken from the subject at earlier time points. Those earlier time points may comprise at least two earlier measurements immediately preceding the determination of the level of the marker in the current urine sample. Thus, the threshold may be set with reference to a sliding window within which levels of the markers have been measured to provide a baseline. The threshold level is thus "learned" by the system. It is not a fixed threshold and is adapted to the subject, thereby taking into account insignificant fluctuations in marker levels from the baseline that are not predictive or indicative of an exacerbation event. Accordingly, the threshold may be set around the baseline to specify an allowable range of the marker levels beyond which a statistically significant increase (or decrease) in level is indicated. In the presence of drift of the baseline level of the marker, it is possible that the parameter limits may be narrowed such that a further change in level of the markers is deemed significant. For example, if the baseline marker level is drifting upwards over time, the difference between a measured increase and baseline may need to be smaller to be considered to have exceeded the threshold (i.e. to be significant). This is intended to prevent a "slow onset" exacerbation being missed. The threshold level of the marker may be set based upon determined levels of the marker in urine samples taken from the subject at earlier time points at which the subject was not suffering from an exacerbation of inflammation. Suitable approaches which can be adopted for such analyses are known in the art and include fluctuation analyses, such as detrended fluctuation analysis (DFA) or other forms of line fitting.

In certain embodiments, the computer application causes the processor to indicate to the subject the requirement to determine the levels of at least one marker. In other embodiments, the computer application is further configured to output from the processor a requirement to increase the frequency of determining the levels of the at least one marker in urine samples taken from the subject where an increase in the levels of the at least one marker is calculated. The computer application may be further configured to output via the processor a requirement to maintain the increased frequency of determining the levels of the at least one neutrophil activation marker until a decrease in the levels of the at least one marker is calculated.

In specific embodiments, the system or test kit comprises one or more testing devices for determining levels of at least two or three markers in urine samples taken from the subject at multiple time points. In some embodiments, the computer application is configured to calculate increased levels of at least one of the markers and provide an output via the processor that a calculated increase in levels of at least one of the markers is indicative of or predictive of an exacerbation of inflammation. The computer application may be configured to calculate decreased levels of at least one of the neutrophil activation markers and provide an output from the processor that a calculated decrease in levels of at least one of the markers following an increase are indicative or predictive of recovery from, or successful treatment of, an exacerbation of inflammation. In further embodiments, the computer application is configured to analyse the calculated levels of the at least two or three markers in a pre-determined sequence to monitor the inflammation status of the subject. As discussed above, the markers may be weighted. Thus, the computer application may be configured to apply and/or calculate as appropriate a weighting to the determined levels of the at least two or three markers.

In specific embodiments, the computer application is configured to calculate levels of at least one marker by normalising against the levels of a reference marker, typically also measured in the same urine sample. Suitable reference markers are discussed herein and include urinary creatinine or fibrinogen. Further markers may include urine volume, for example measured by testosterone glucuronide. Specific gravity and colour may be other normalising or reference markers.

In certain embodiments, the computer application is further configured to incorporate inputs from other indicators of exacerbation of inflammation into the calculation of the current inflammation status of the subject. Those other indicators of exacerbation of inflammation may comprise shortness of breath, increased wheeze, increased pulse rate, dyspnoea, increased sputum purulence, increased sputum colour, sore throat, increased cough, cold and fever. Another indicator that may be monitored is Forced Expiratory Volume in one second ($FEV_1$)

The computer application thus runs the relevant algorithms to enable subject monitoring, particularly in reference to the personalised "rolling" threshold. In certain embodiments, the computer application is configured to output from the processor an indication or prediction of exacerbation of inflammation if an increase in the levels of each of the at least 2, 3, 4, 5, 6, 7, 8, 9, 10 or more markers is calculated. In specific embodiments, the output is an indication that the subject should receive treatment. In other embodiments, the computer application is configured to output from the processor an indication the inflammation status is considered stable and/or the frequency of testing is maintained in the event that no increase in the levels of any of the markers is determined. In some embodiments, the computer application is configured to output from the processor an indication that the frequency of testing is increased if an increase in the level of one of the markers is calculated but not in the other two markers. The computer application may be configured to output from the processor an indication that the frequency of testing is increased unless the increased level of one of the markers reverts to a non-increased level within a set number of repeat tests. The computer application may calculate whether the level of one of the markers has reverted to a non-increased level within the set number of repeat tests. In specific embodiments, if the level of one of the markers has reverted to a non-increased level within the set number of repeat tests the computer application produces an output from the processor that the frequency of testing reverts to the original frequency. In further embodiments, if the level of one of the markers remains at an increased level within the set number of repeat tests, the computer application produces an output from the processor that the frequency of testing is increased further. In still further embodiments, if the level of one of the markers remains at an increased level within a further set number of repeat tests at increased frequency the computer application produces an output from the processor that an exacerbation of inflammation is indicated or predicted and/or the subject should be treated.

In some embodiments, if the level of one of the markers reverts to a non-increased level within the further set number of repeat tests at increased frequency, the computer application produces an output from the processor that the frequency of testing reverts to the increased (but not further increased) frequency of testing. In further embodiments, if the level of one of the markers remains at the non-increased level within the set number of repeat tests, the computer application produces an output from the processor that the frequency of testing reverts to the original frequency (i.e. a baseline level of testing). In specific embodiments, if an increase in the level of two of the markers is determined but not in the other marker the computer application produces an output from the processor that the frequency of testing is increased. In such embodiments, the frequency of testing may be increased to a frequency greater than if an increased level in only one of the markers is detected. In certain embodiments, if the level of at least one of the markers reverts to a non-increased level within the set number of repeat tests, the computer application produces an output from the processor that the frequency of testing reverts to a frequency of testing indicative of a determined increase in the level of one of the markers. If the level of the one of the markers remains at an increased level within the set number of repeat tests, the computer application may produce an output from the processor that the frequency of testing is increased again. If the level of one of the markers remains at an increased level within a further set number of repeat tests at increased frequency the computer application may produce an output from the processor that an exacerbation of inflammation is indicated or predicted and/or the subject should be treated.

In other embodiments, if the level of two of the markers remains at an increased level within a further set number of repeat tests at increased frequency the computer application produces an output from the processor that an exacerbation of inflammation is indicated or predicted and/or the subject should be treated.

In the invention, the computer application may be configured to calculate decreased levels of at least one of the neutrophil activation markers and provide an output from the processor that a calculated decrease in levels of at least one of the markers following an increase are indicative or predictive of recovery from, or successful treatment of, an exacerbation of inflammation. For the avoidance of doubt all of the outputs described may be displayed by a suitable display module, which is in operable connection with the processor/computer application.

Generally, the computer application may be configured to analyse the calculated levels of the at least three markers in a pre-determined sequence to monitor the inflammation status of the subject. The computer application may be configured to apply a weighting to the determined levels of the at least three markers. In specific embodiments, the first marker is TIMP2, the second marker is MMP activity and the third marker is A1AT. Other preferred markers and combinations are described hereinabove.

DESCRIPTION OF THE FIGURES

The invention will now be described by way of example with respect to the accompanying drawings in which:

FIG. 2A and FIG. 2B are a schematic view of an enzyme detection device useful in the present invention and shows operation of the device in the absence (FIG. 2A) or presence (FIG. 2B) of enzyme cleavage activity.

In FIG. 5A initially, a linear peptide (1) is synthesised, for example using solid phase Fmoc chemistry. The peptide may be purified for example by High Performance Liquid Chromatography (HPLC). The peptide is then constrained, or cyclised, by reaction between thiol groups on the peptide (2) and the scaffold molecule (3). This reaction produces a structurally constrained "clipped" peptide (4).

In FIG. 5B, the indicator molecule is synthesised to include the capture site (1), for example by synthesis of the linear peptide on a pre-loaded Biotin-PEG resin.

FIG. 7A shows reader values across the entire concentration range of MMP-9, whereas FIG. 7B is an expanded view at MMP-9 concentrations between 0 and 15 ng/ml.

FIG. 11A shows reader values across the entire concentration range of MMP-9, whereas FIG. 11B is an expanded view at MMP-9 concentrations between 0 and 50 ng/ml. Both figures demonstrate that the method of the invention produced a steeper curve. According to both assays, colour development as shown by the absorbance values was seen at 4 ng/ml MMP9, the lowest standard tested.

FIG. 14 shows a number of scaffold molecules useful in the indicator molecules described herein, together with proposed nomenclature.

FIG. 15A shows products of cleavage at a single cleavage site and FIG. 15B shows products of cleavage at two separate cleavage sites.

FIG. 27—Showing performance of the MMP/TIMP/A1AT cluster in terms of identifying onset of a COPD exacerbation.

Additional markers increase the sensitivity of detection as shown by the percentage values.

Figure 33:
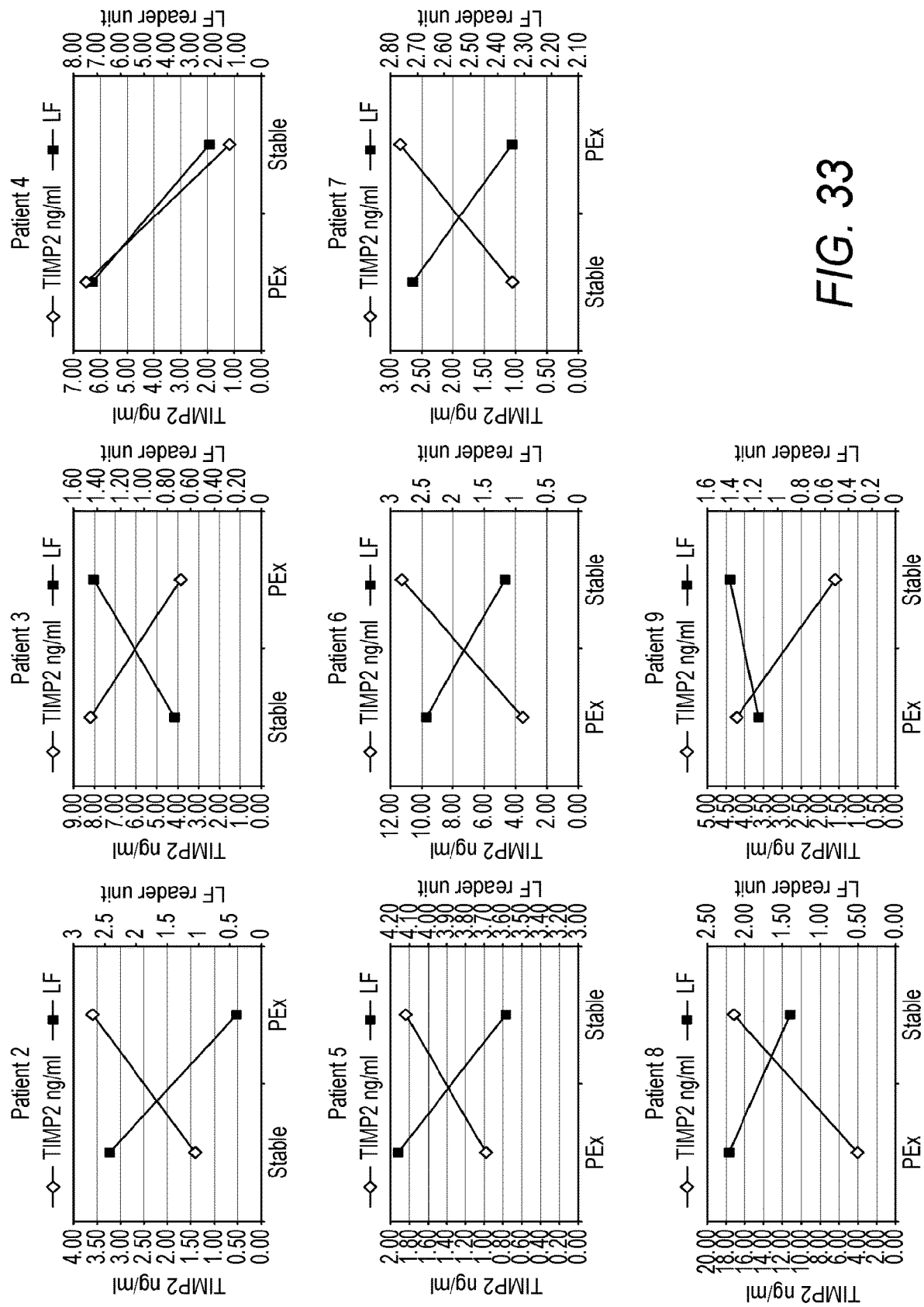

FIG. 33—showing the significance in cystic fibrosis of certain urinary markers. Exacerbation is characterised by an imbalance between MMP and TIMP2 levels.

Figure 34:
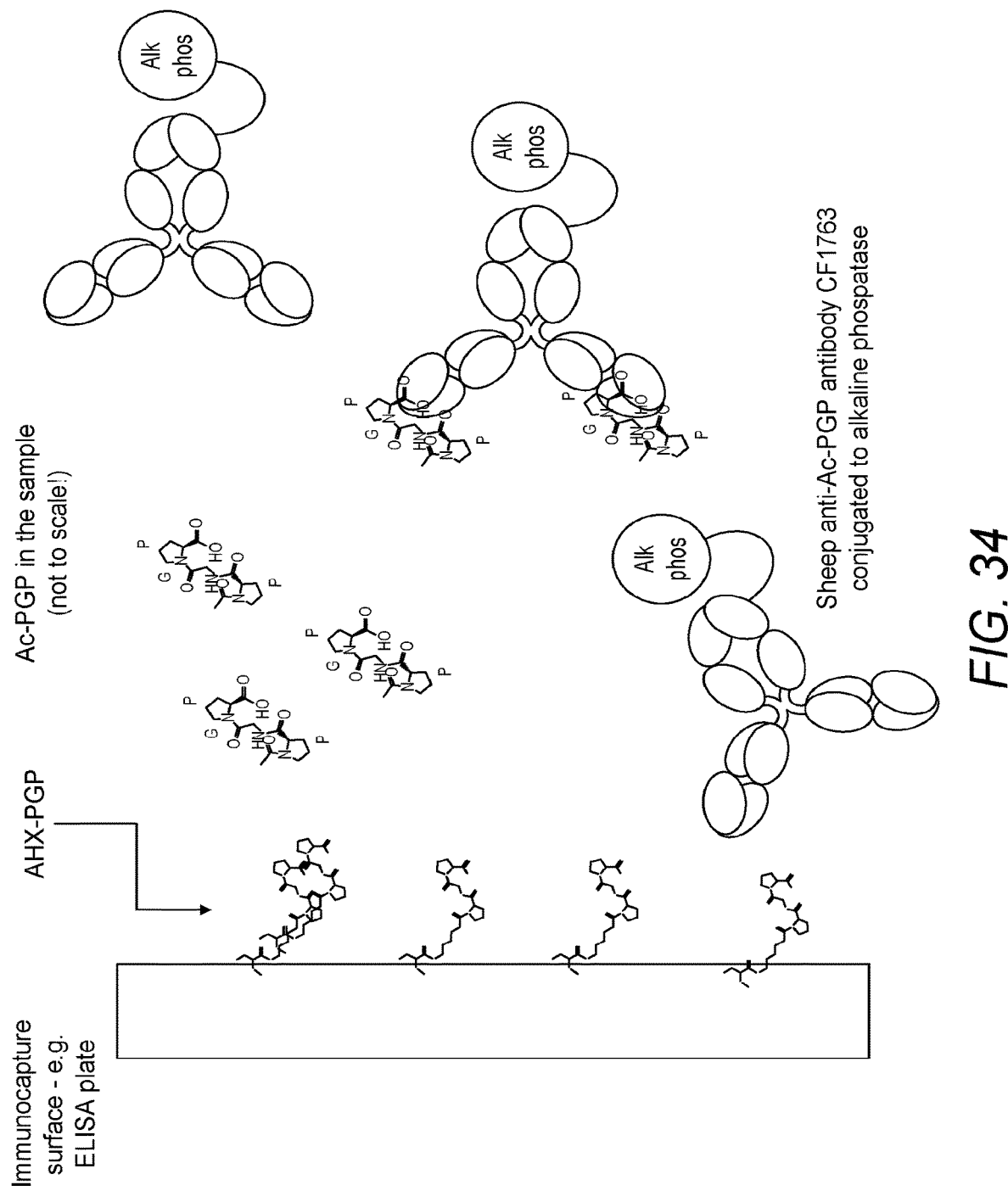

FIG. 34 shows a schematic of one of the Ac-PGP competitive EIA assays.

Figure 35:
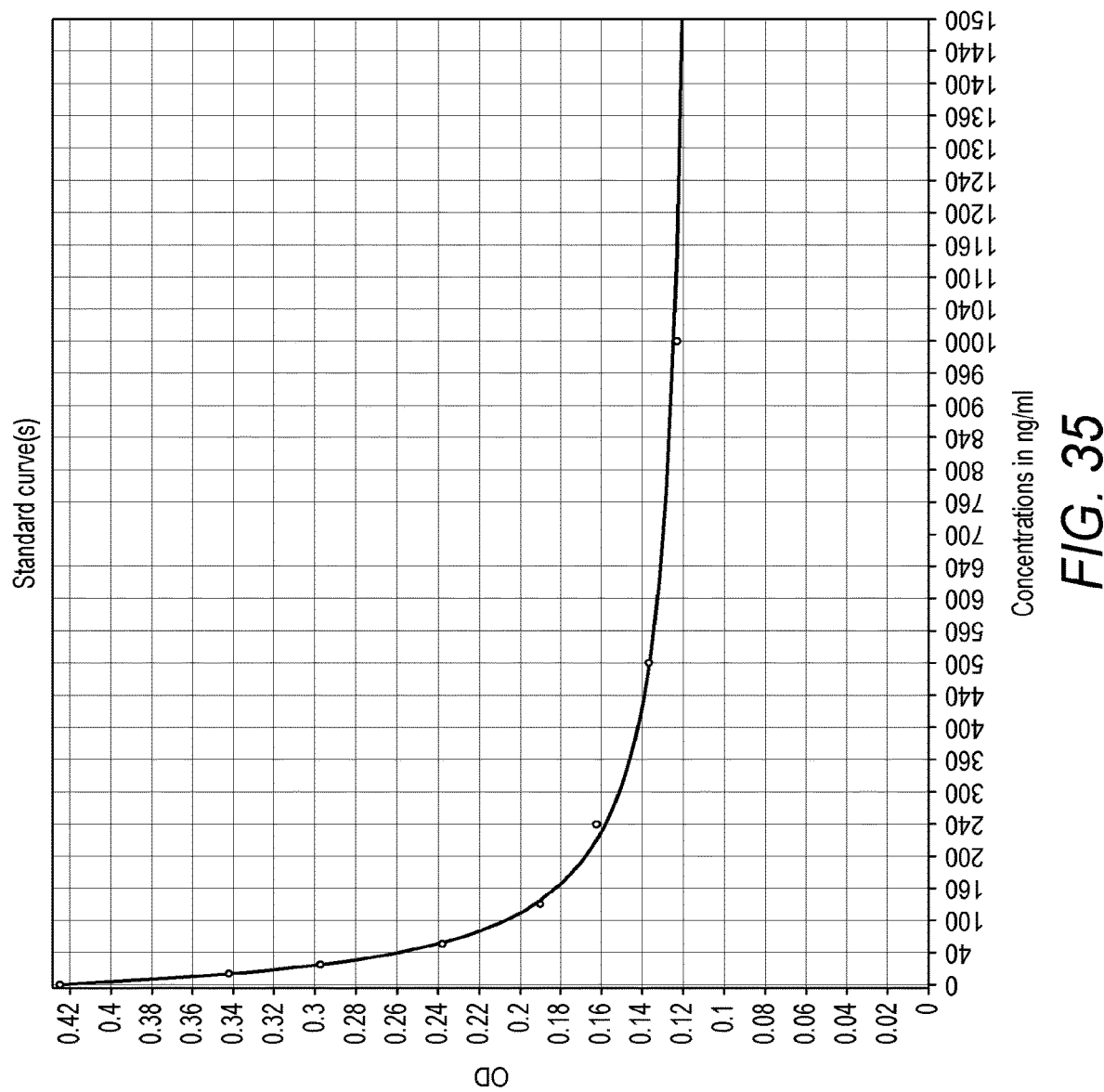

FIG. 35 presents the calibration curve obtained using the Ac-PGP competitive EIA assay binding format with standards ranging from 1000 ng/ml down to 15.625 ng/ml.

Figure 36:
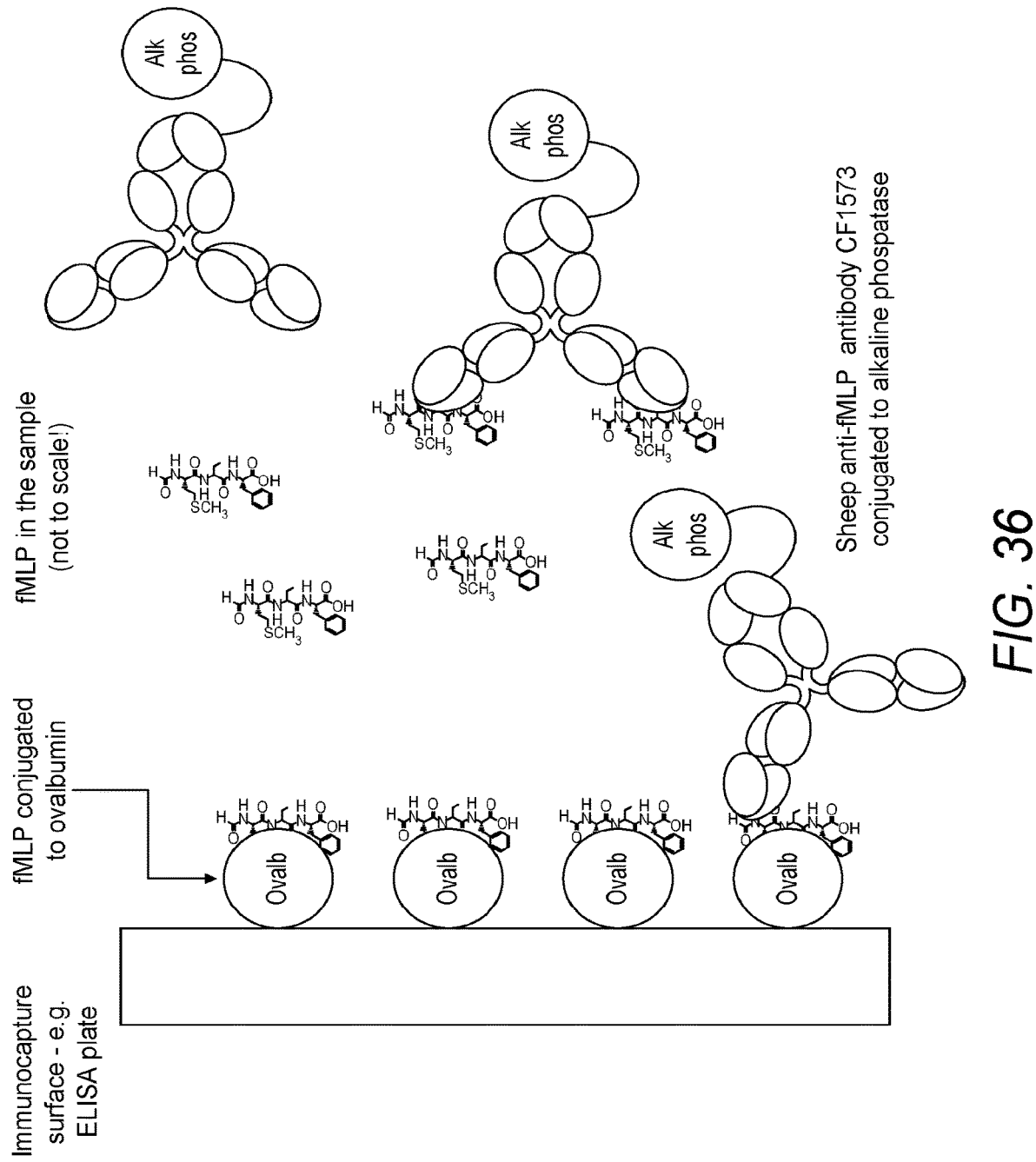

FIG. 36 shows a schematic of an fMLP competitive EIA assay format.

Figure 37:
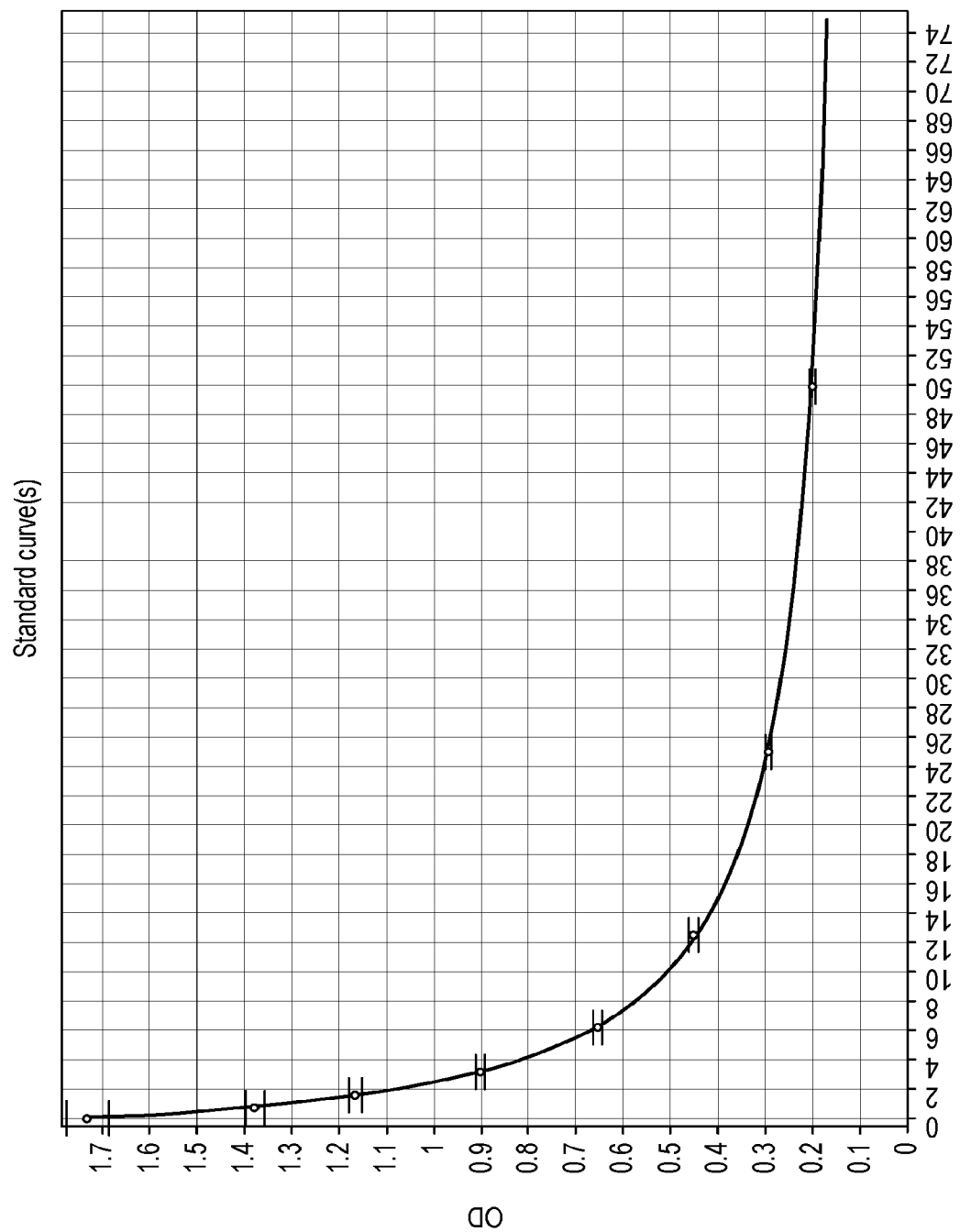

FIG. 37 presents the calibration curve obtained using the fMLP competitive binding format with standards ranging from 50 ng/ml down to 0.78 ng/ml.

Figure 38:
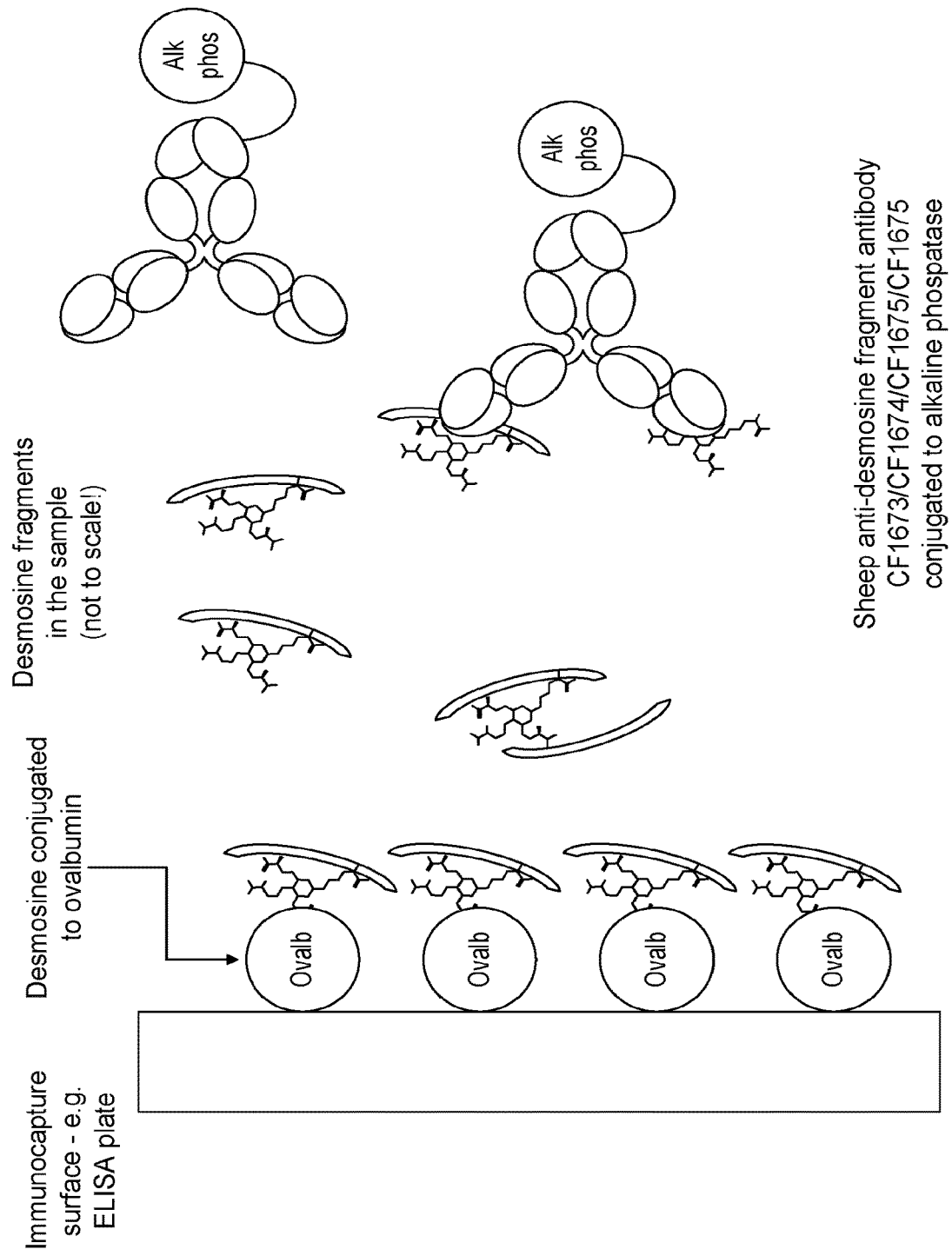

FIG. 38 is a schematic of a Desmosine fragment competitive EIA assay.

Figure 39:
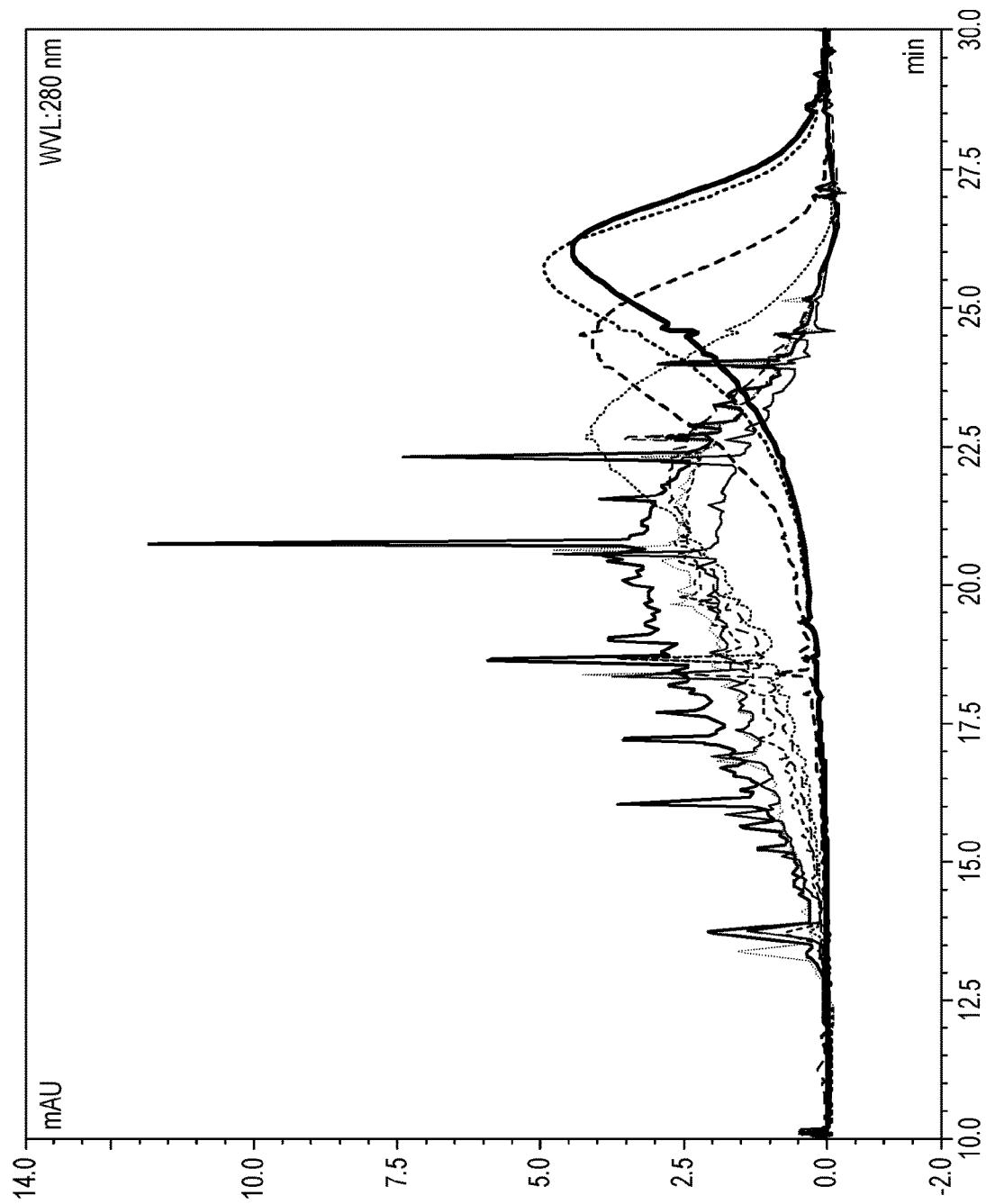

FIG. 39 presents HPLC analysis to show profiles for whole elastin (peak on the right) broken down by increased concentration of enzyme (HNE).

Figure 40:
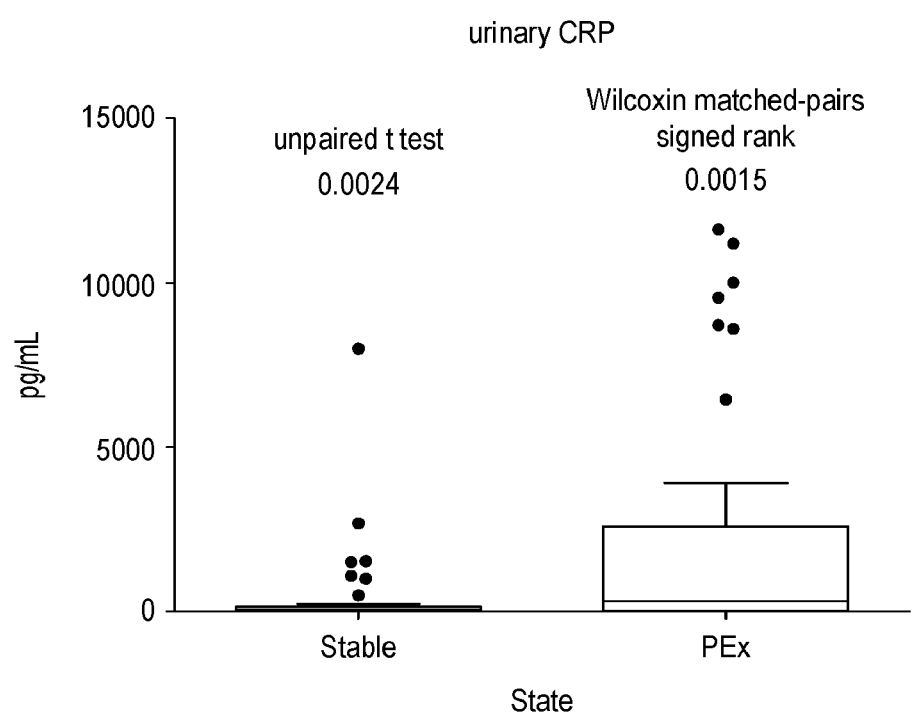

FIG. 40 shows urinary CRP levels in stable versus exacerbation samples.

Figure 41A:
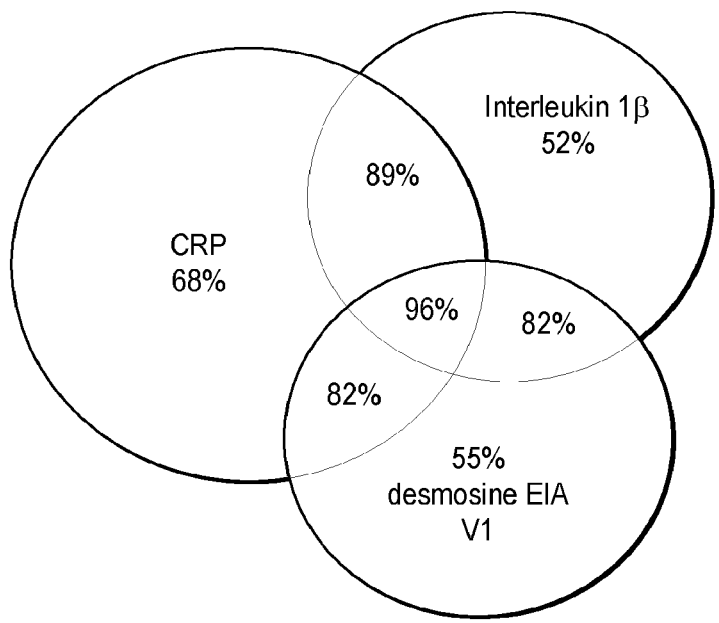

FIG. 41A shows performance of a combination of CRP, desmosine and IL1β in PEx prediction.

Figure 41B:
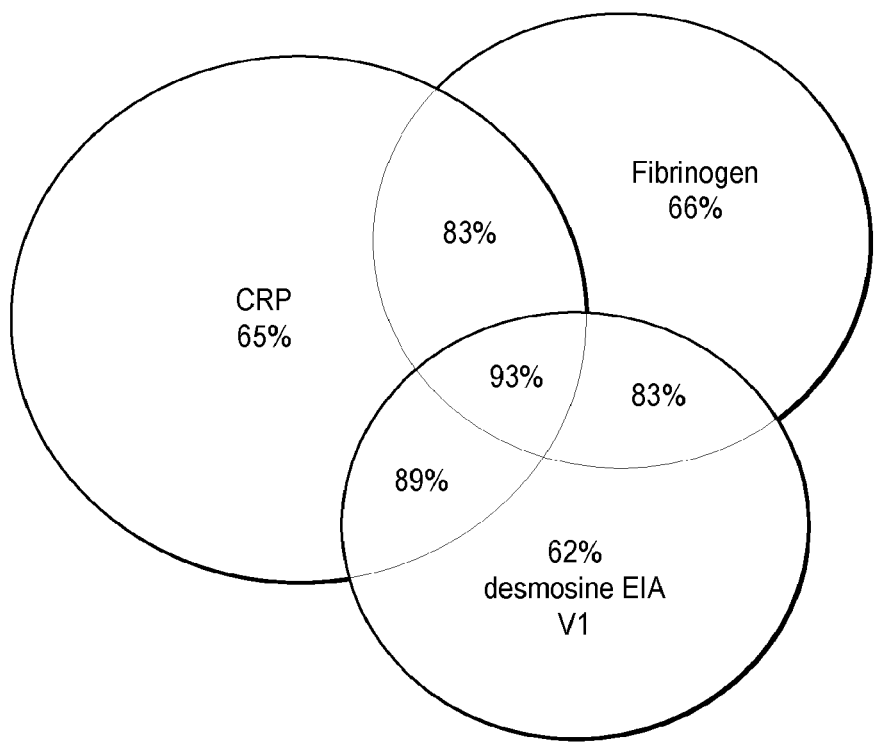

FIG. 41B shows performance of CRP, desmosine and fibrinogen in PEx recovery.

Figure 42A:
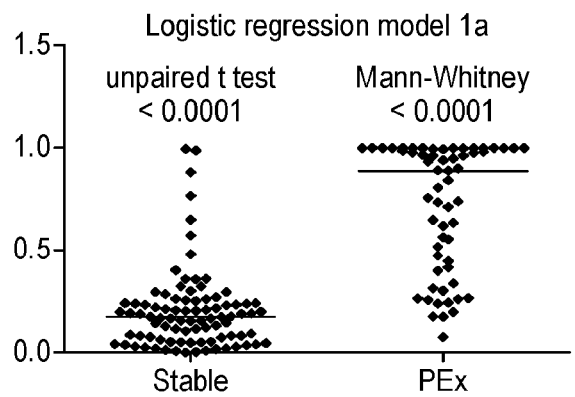
Figure 42B:
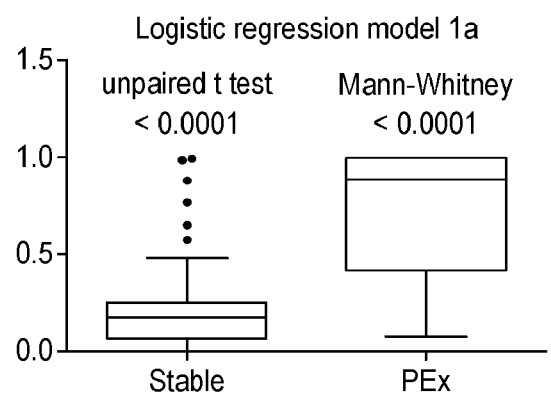
Figure 42C:
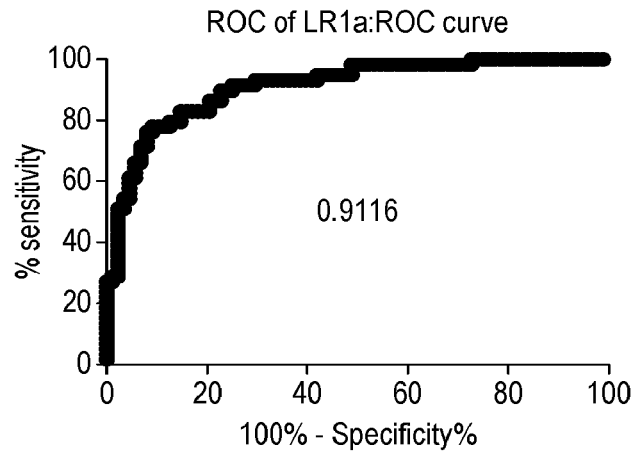

FIG. 42 shows Logistic regression and ROC plots for model 1a

Figure 43A:
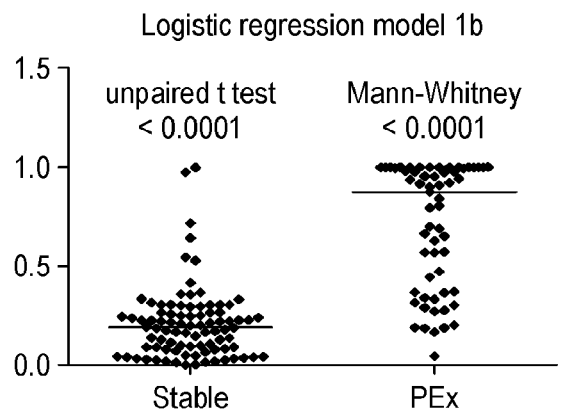
Figure 43B:
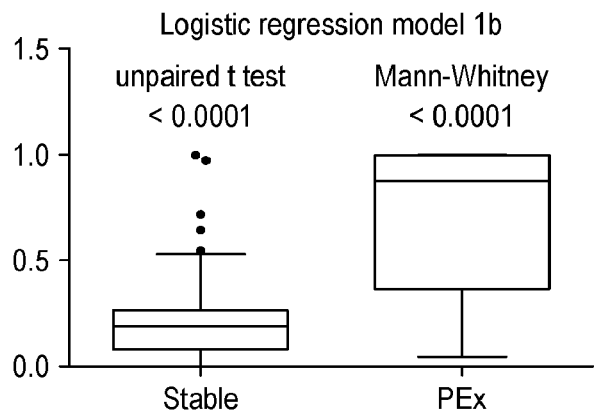
Figure 43C:
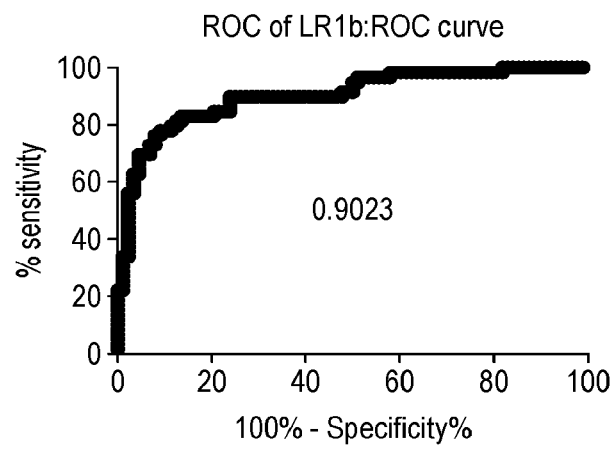

FIG. 43 shows Logistic regression and ROC plots for model 1b

Figure 44A:
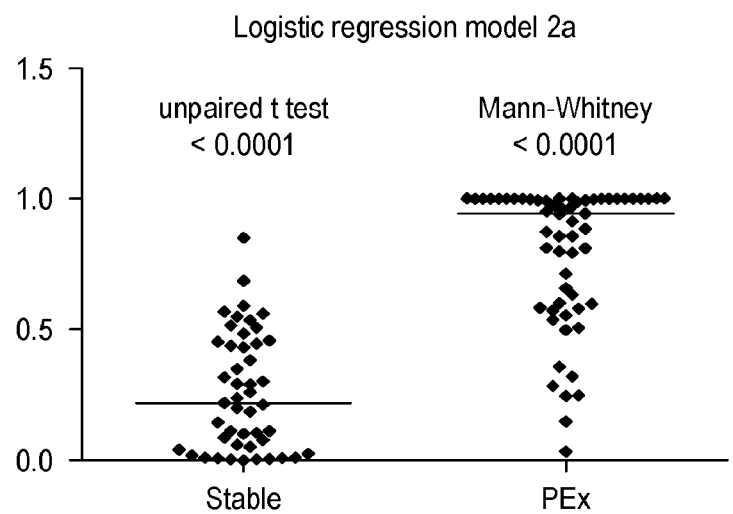
Figure 44B:
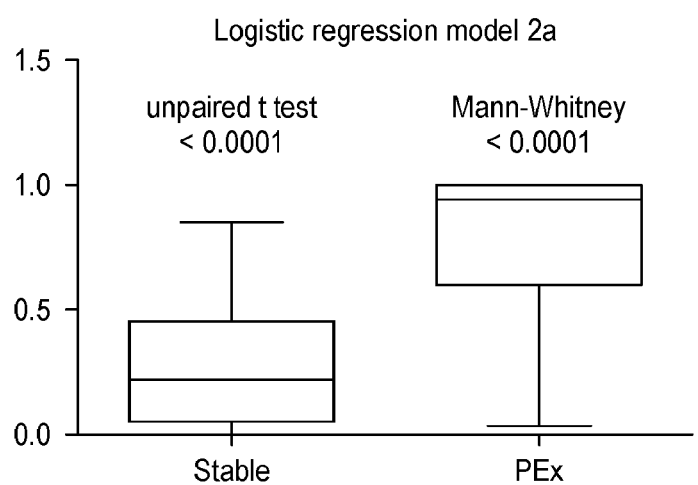

FIG. 44 shows logistic regression plot for model 2a

Figure 45A:
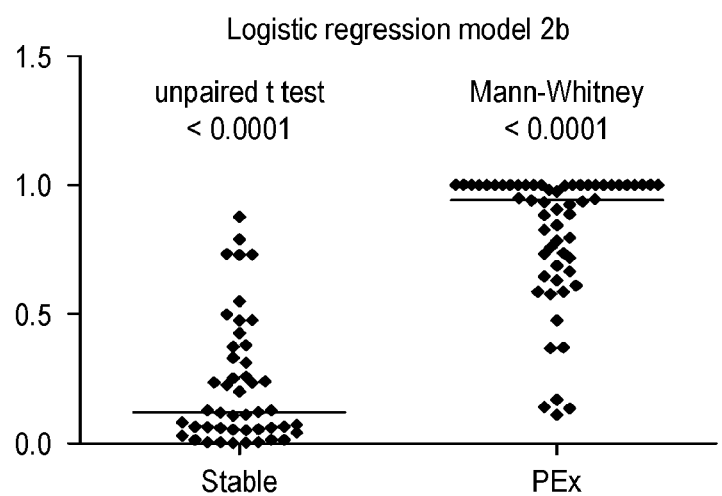
Figure 45B:
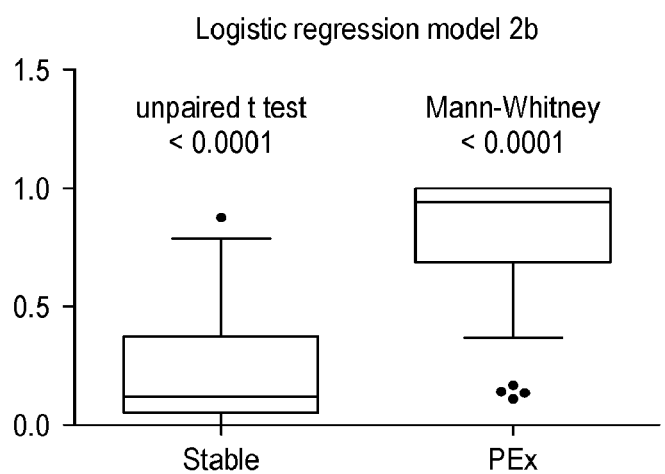

FIG. 45 shows logistic regression plot for model 2b

Figure 46A:
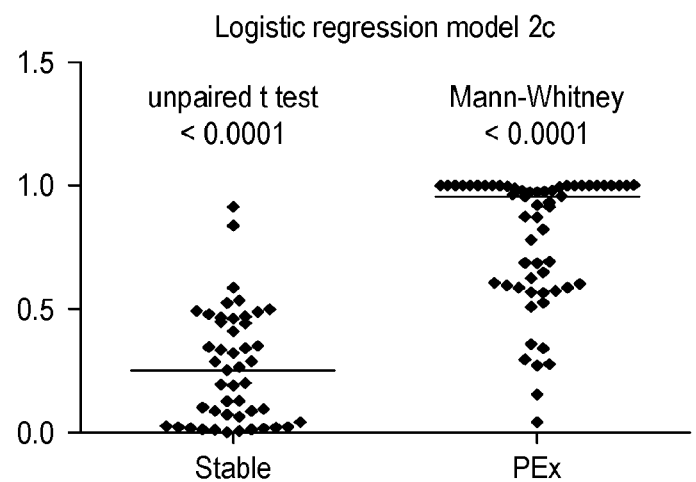
Figure 46B:
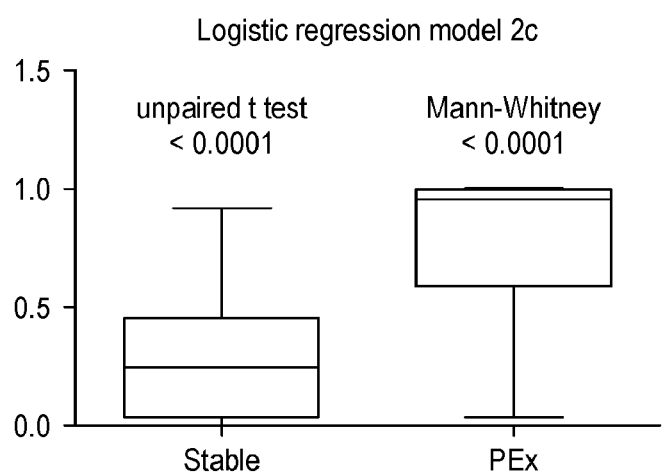

FIG. 46 shows logistic regression plot for model 2c

Figure 47A:
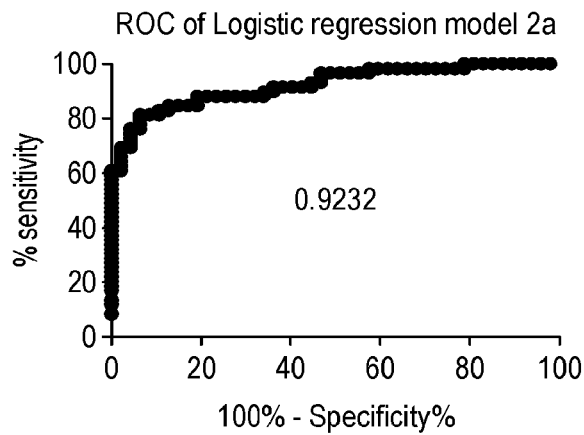
Figure 47B:
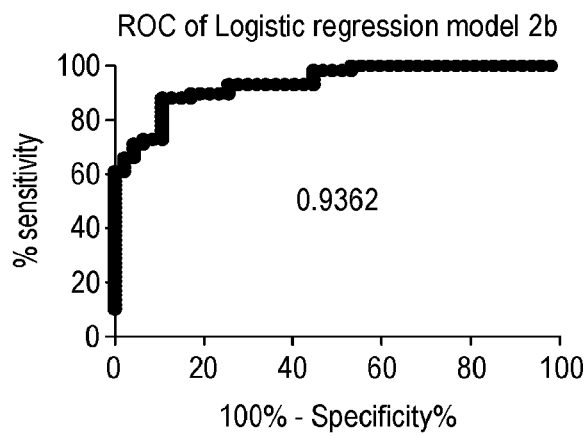
Figure 47C:
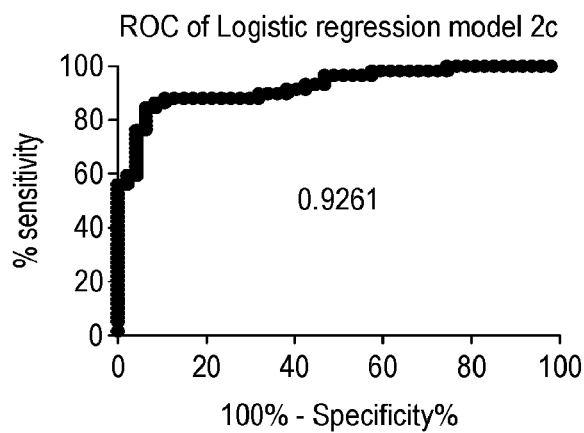

FIG. 47 shows ROC plots for model 2a, 2b and 2c

Figure 48:
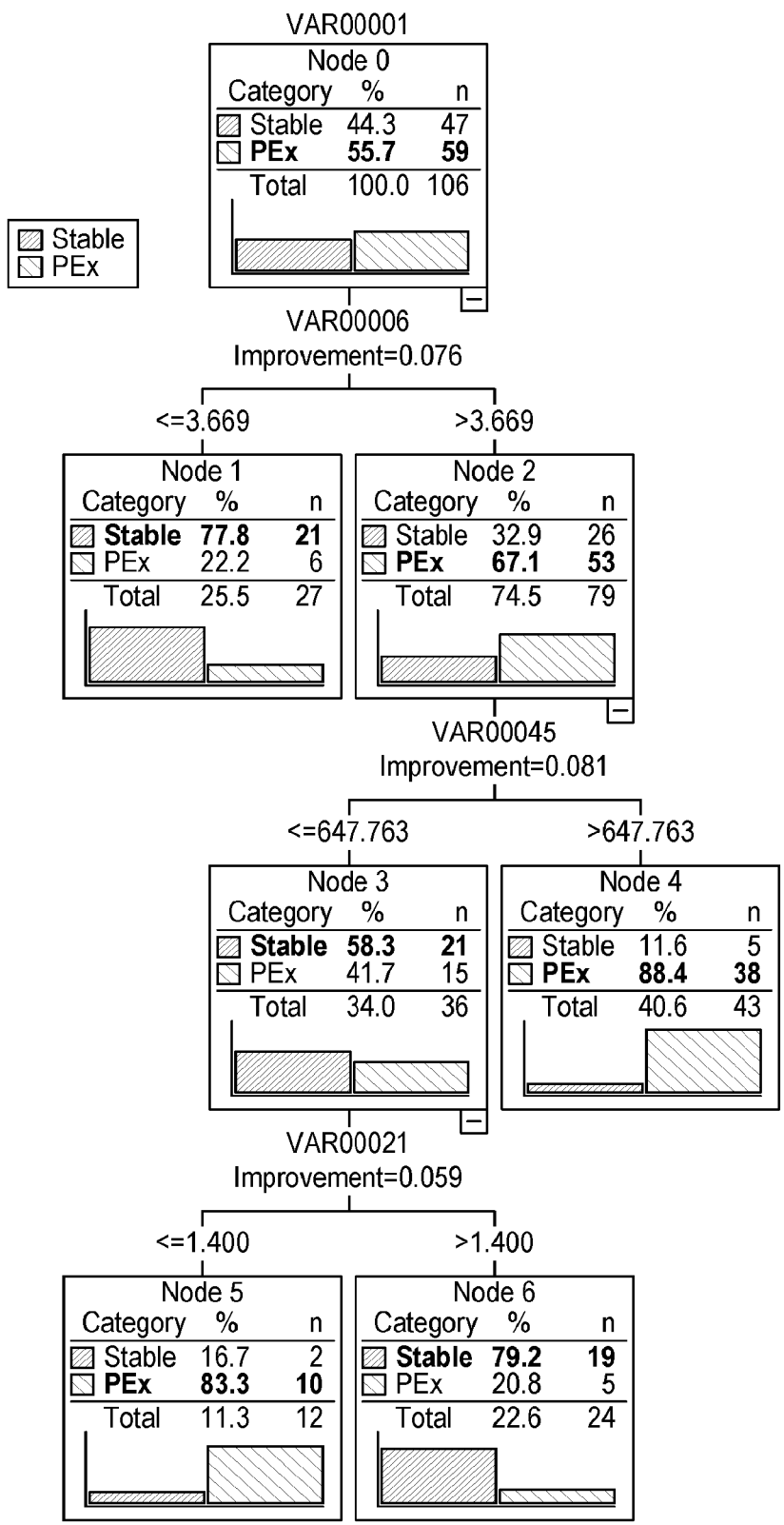

FIG. 48 shows a decision tree for combination 1

Figure 49:
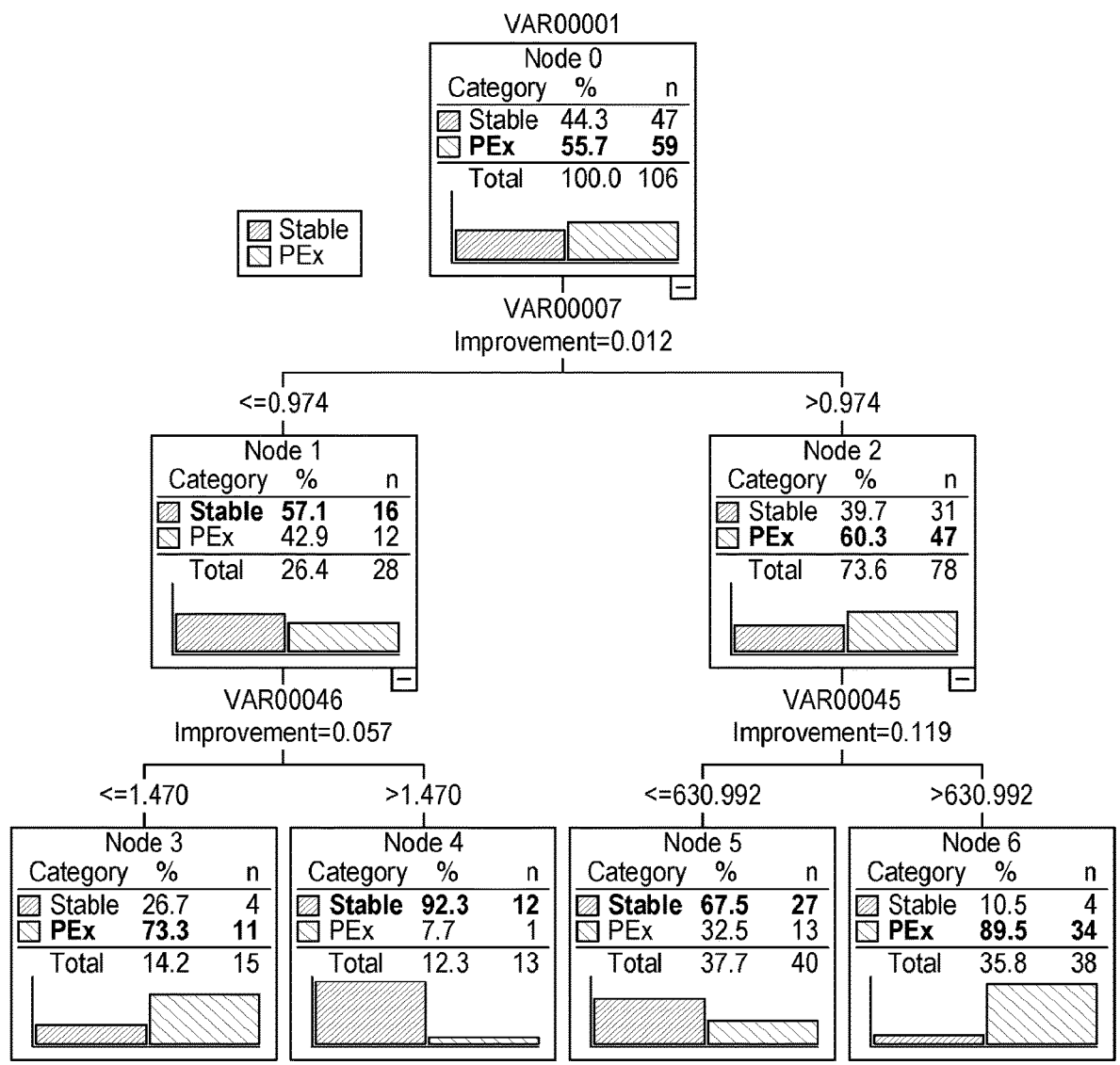

FIG. 49 shows a decision tree for combination 2

Figure 50:
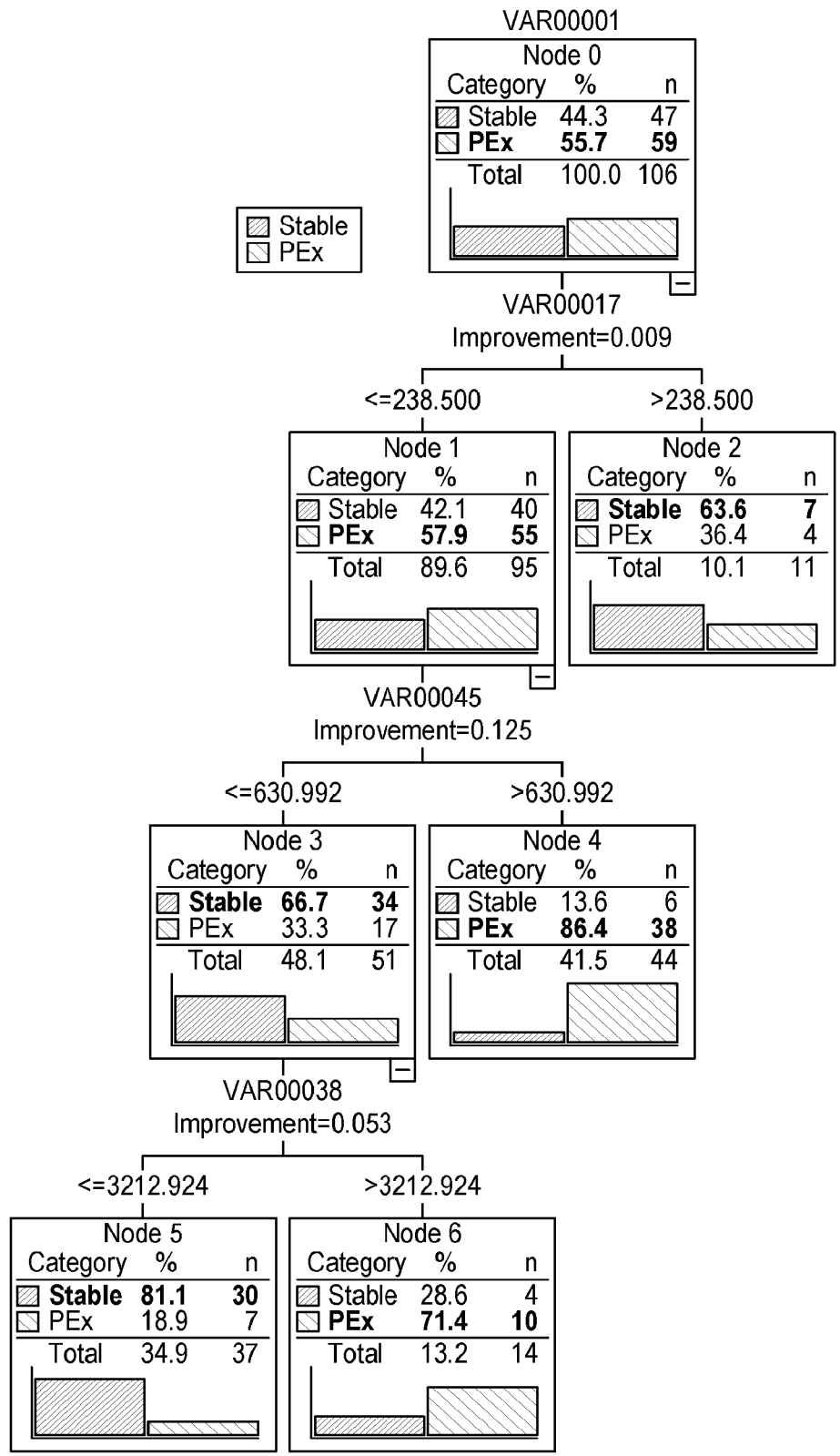

FIG. 50 shows a decision tree for combination 3

Figure 51:
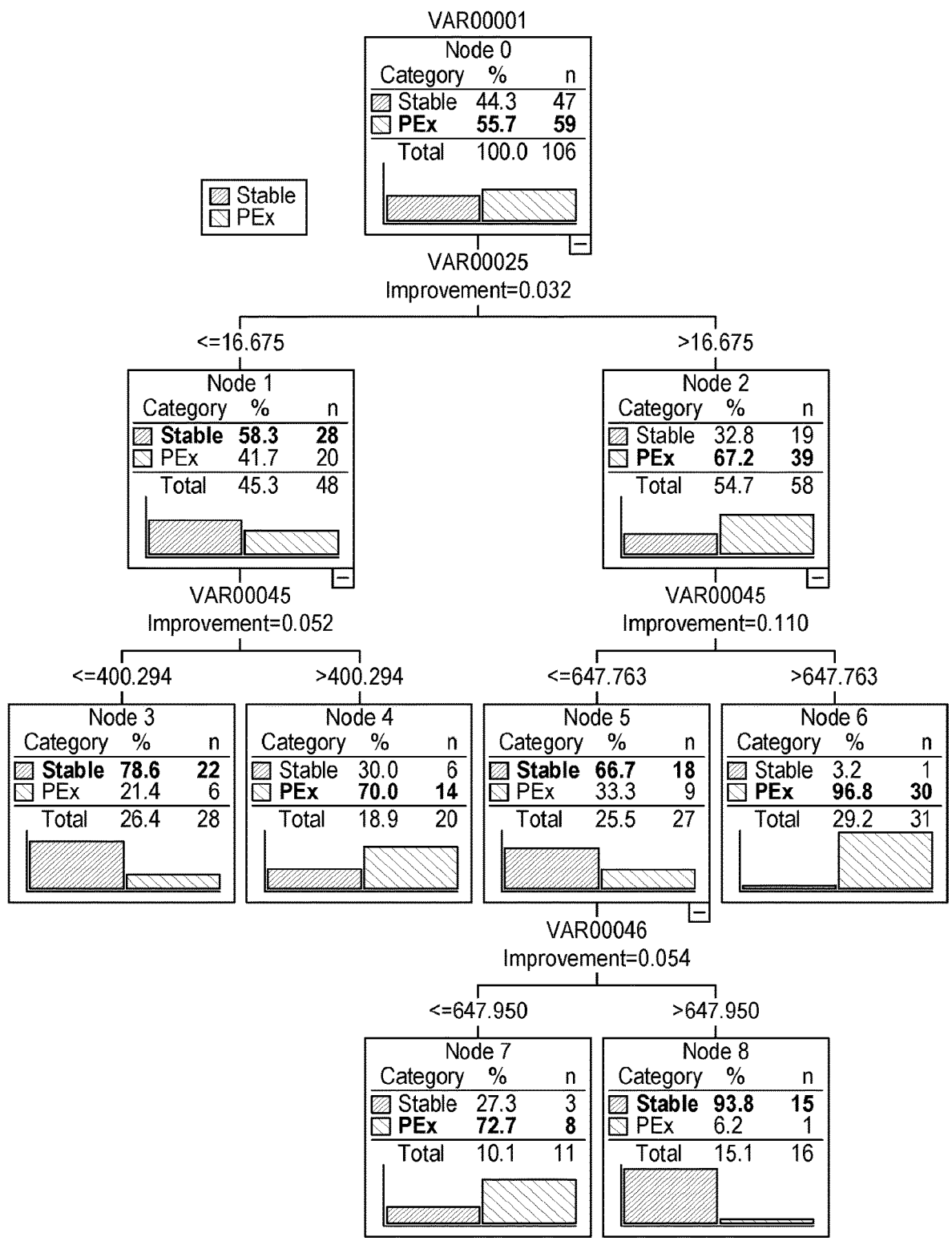

FIG. 51 shows a decision tree for combination 4

Figure 52:
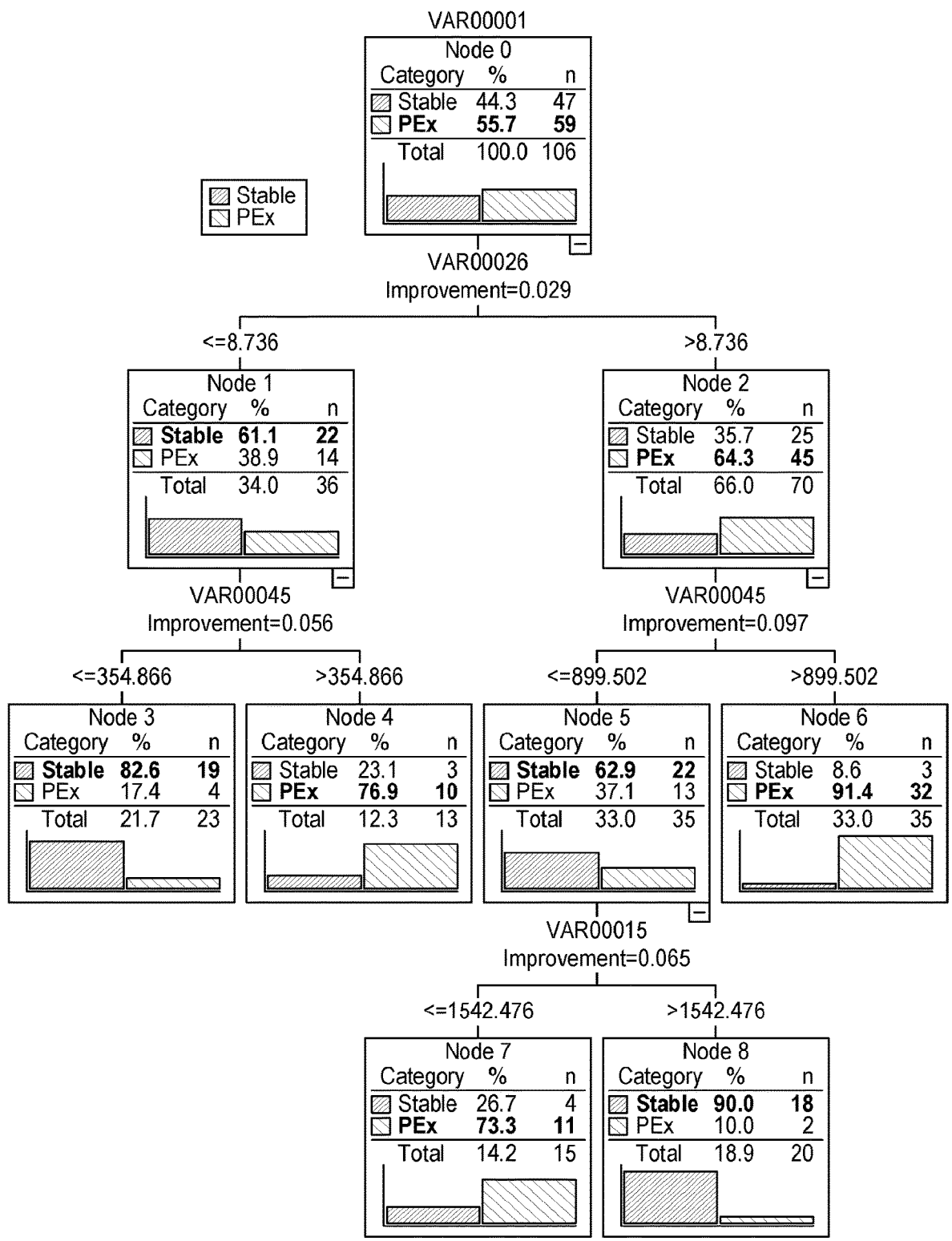

FIG. 52 shows a decision tree for combination 5

Figure 53:
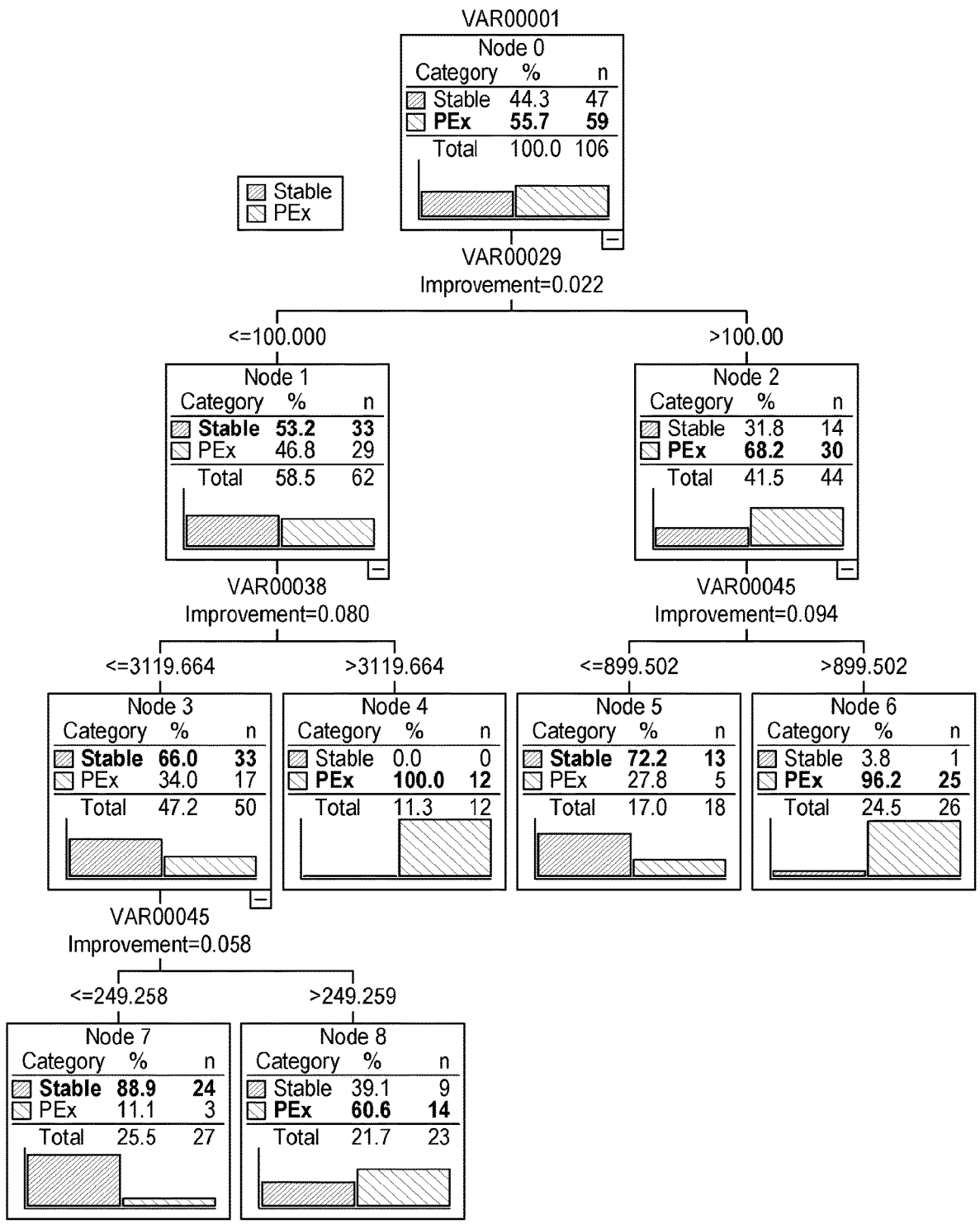

FIG. 53 shows a decision tree for combination 6

Figure 54:
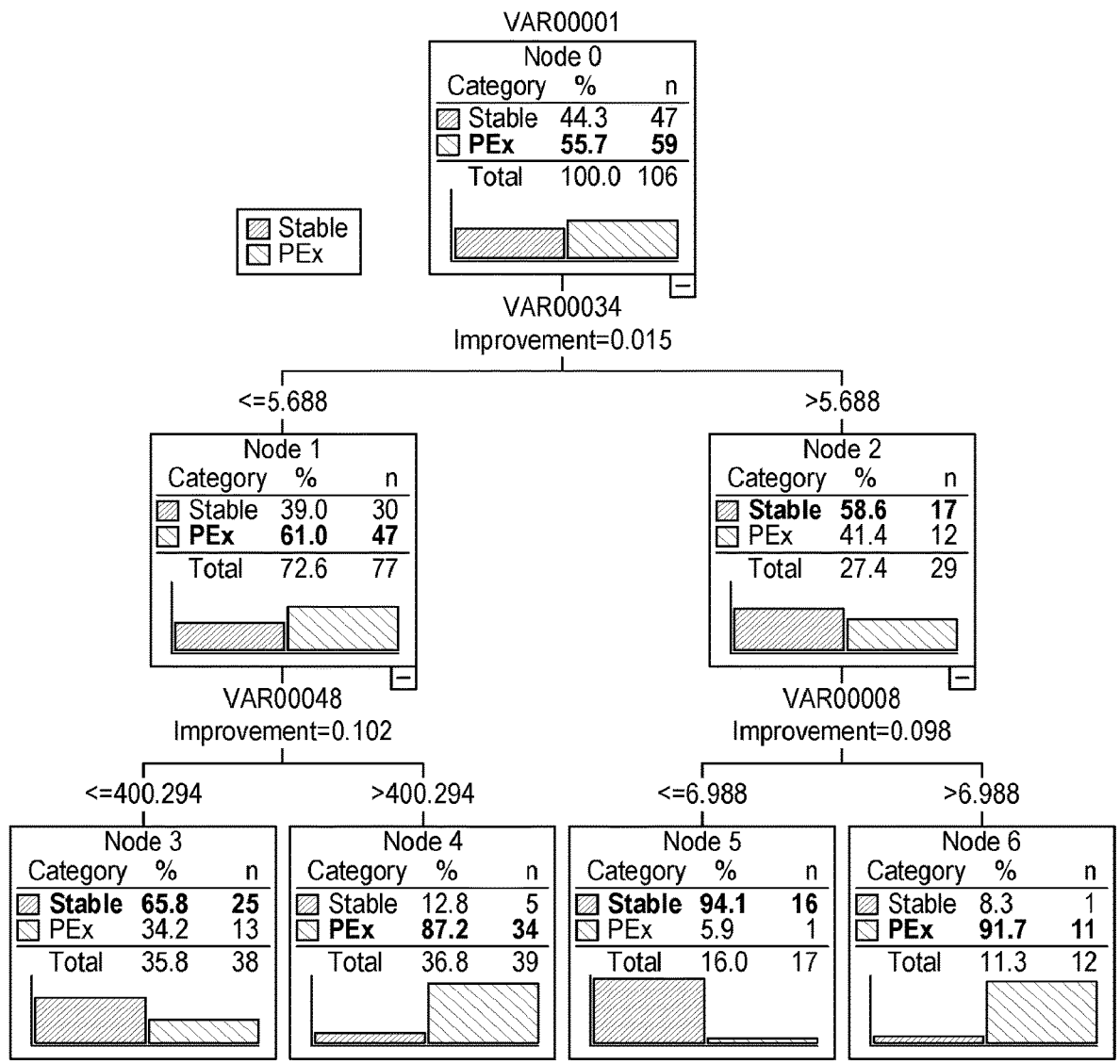

FIG. 54 shows a decision tree for combination 7

Figure 55:
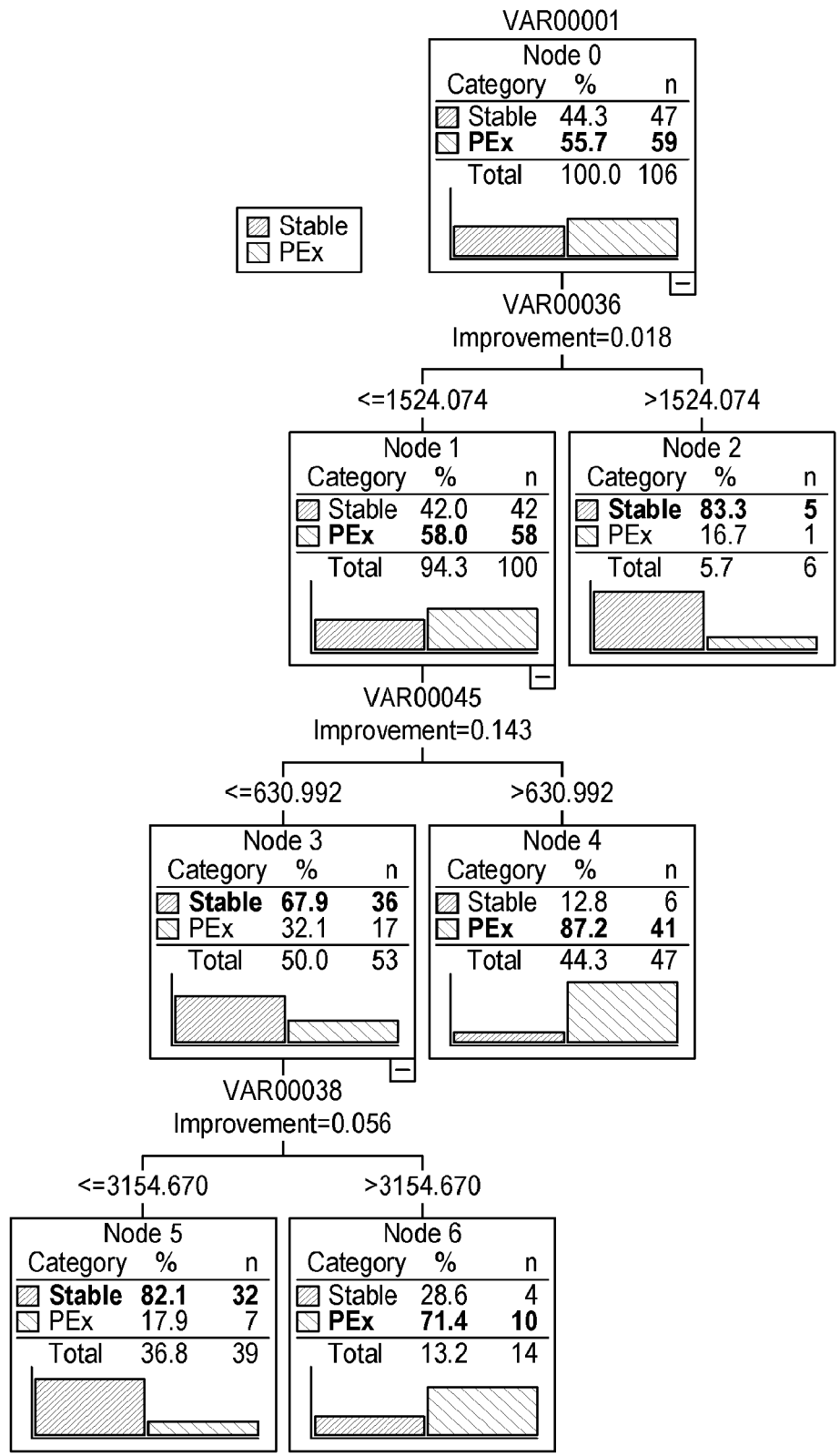

FIG. 55 shows a decision tree for combination 8

DETAILED DESCRIPTION AND EXAMPLES

Figure 1:
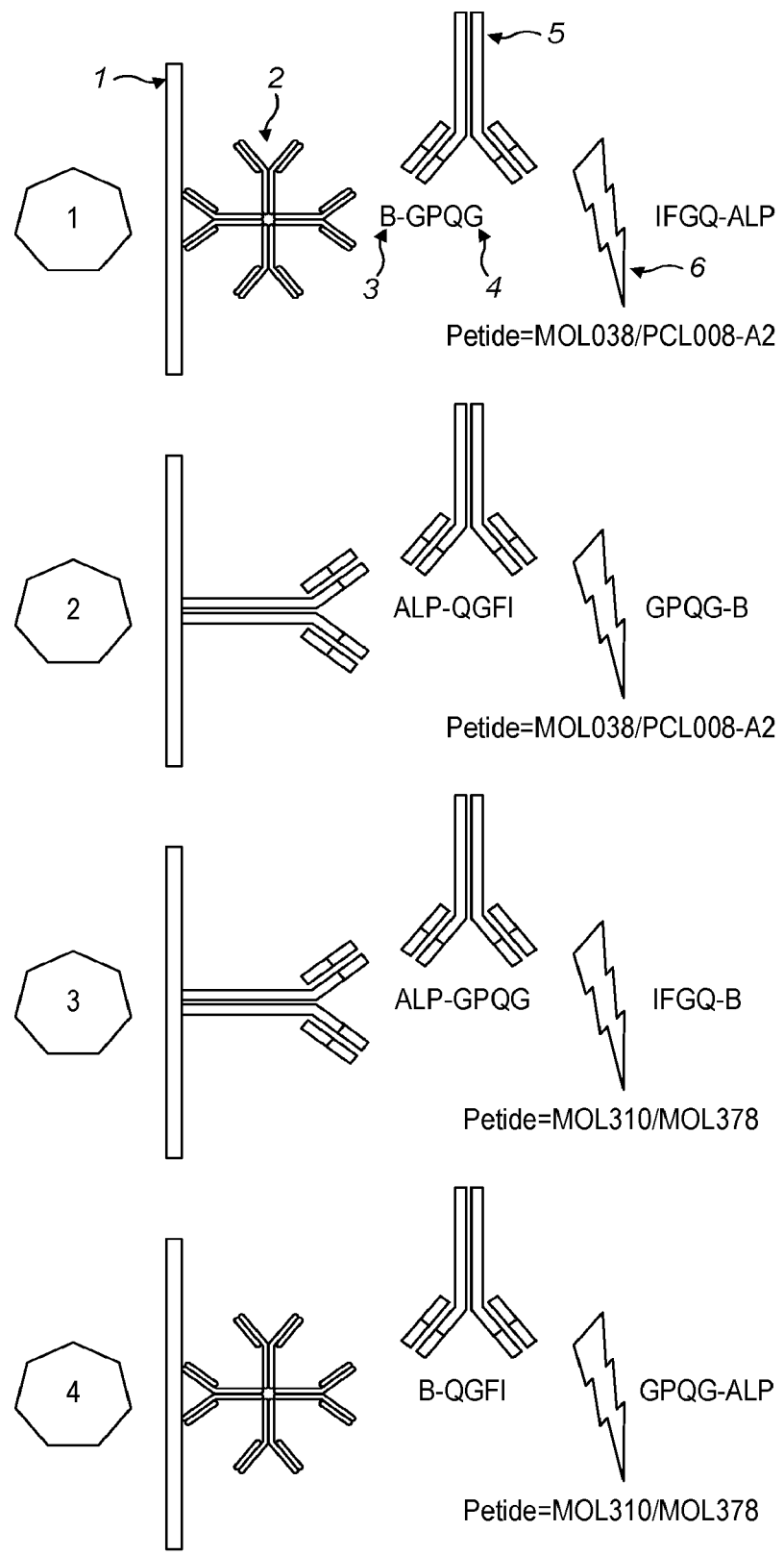
FIG. 1 is a schematic view of four different formats of the assay useful in the invention. Each format relies upon the same basic components of solid support (1), capture molecule (2), an indicator molecule containing a capture site (3) and a cleavage site (4) and a binding molecule (5) that binds to the indicator molecule only after cleavage (6) has occurred.

FIG. 1 is a schematic view of four different formats of an assay useful for performance of the invention, in particular for detecting effector molecules (and especially proteases such as MMPs) in urine samples. Each format relies upon the same basic components of solid support (1), capture molecule (2), an indicator molecule containing a capture site (3) and a cleavage site (4) and a binding molecule (5) that binds to the indicator molecule only after cleavage (6) has occurred.

In formats 1 and 4, the capture molecule (2) is streptavidin. Here, the capture molecule (2) binds to a biotin capture site (3) within the indicator molecule. In formats 2 and 3, the capture molecule (2) is an antibody. Here, the capture molecule (2) binds to an epitope capture site (3) within the indicator molecule. The epitope is found in the alternative long peptide (ALP) which is derived from human chorionic gonadotropin (hCG).

Once the indicator molecule is added to a test sample, any enzyme specifically recognising the cleavage site (4) present, may cleave the indicator molecule (6). This cleavage event (6) produces a binding site for the specific antibody binding molecule (5). The binding molecule (5) is unable to bind to the indicator molecule until cleavage (6) has occurred. Thus, in formats 1 and 3 the antibody binding molecule (5) binds to the amino acid sequence GPQG produced as a result of cleavage of the GPQGIFGQ sequence. In formats 2 and 4, on the other hand, the antibody binding molecule (5) binds to the amino acid sequence QGFI, also produced as a result of cleavage of the GPQ-GIFGQ sequence. In each format, the antibody binding molecule (5) does not bind to the GPQGIFGQ sequence prior to cleavage (not shown).

FIG. 2 is a schematic view of an enzyme detection device used in the present invention and shows operation of the device in the absence (FIG. 2A) or presence (FIG. 2B) of enzyme cleavage activity in the urine sample. The test strip includes an adhesive liner (1) upon which the other components of the device are assembled. From right to left, the sample application zone (2) is in the form of an absorbent pad. This is laid partially overlapping the conjugate pad (3), which is impregnated with the labelled binding molecules (7). In alternative embodiments, the labelled binding molecules may be impregnated in the sample application zone and this removes the need for a separate conjugate pad. The conjugate pad (3) is in fluid connection with a nitrocellulose membrane (4). The nitrocellulose membrane (4) contains immobilized streptavidin molecules (5) which define a capture zone. The membrane (4) further contains immobilized further binding molecules (6) downstream of the capture zone which bind to further labelled molecules (11) which pass through the device with the sample and form a separate control zone. Alternatively, the immobilised further binding molecules may bind to labelled binding molecules (7). The device optionally further comprises an absorbent pad (8) to absorb any test sample and reagents reaching the end of the device.

In use, the indicator molecule (9) is added to the test sample prior to bringing the test sample into contact with the sample application zone (8) of the device. As shown in FIG. 2A, in the absence of enzyme cleavage activity in the test sample, the indicator molecule (9) remains uncleaved at the cleavage site. Upon sample flow into the conjugate pad (3), the binding molecules (7) are unable to bind to the indicator molecule (9) because cleavage of the cleavage site has not occurred. The indicator molecules become bound at the capture zone via the interaction between streptavidin (5) and the biotin capture site (10) of the indicator molecule (9). The labelled binding molecules (7) are not immobilised at the capture zone because they cannot bind to the indicator molecules (9). Accordingly, the labelled binding molecules flow through to the control zone and beyond. Further labelled molecules (11) also pass through the device to the control zone where they are immobilized by binding to the immobilized further binding molecules (6). Thus, absence of enzyme cleavage activity is displayed as a signal only at the control zone, but not at the capture zone. Excess sample, potentially containing labelled binding molecules (7), flows into the absorbent pad (8).

As shown in FIG. 2B, in the presence of enzyme cleavage activity in the test sample, the indicator molecule (9) is cleaved at the cleavage site. Upon sample flow into the conjugate pad (3), the binding molecules (7) are able to bind to the indicator molecule (9) because cleavage of the cleavage site has occurred. The indicator molecules become bound at the capture zone via the interaction between streptavidin (5) and the biotin capture site (10) of the indicator molecule (9). The labelled binding molecules (7) are immobilized at the capture zone due to binding to the indicator molecules (9) at the cleavage site. Due to the relative excess of labelled binding molecule (7) to binding sites at the capture zone some labelled binding molecules (7) still flow through to the control zone and beyond. Further labelled molecules (11) also pass through the device to the control zone where they are immobilized by binding to the immobilized further binding molecules (6). Thus, level of enzyme cleavage activity may be measured via a signal at the capture zone (and a signal will also be present at the control zone). Excess sample, potentially containing cleavage products of the indicator molecule that do not contain the biotin capture site (10), flows into the absorbent pad (8).

It should be noted that the control zone is optional. The level of enzyme cleavage activity in the urine sample can be monitored based upon a measurement of the corresponding signal at the capture zone.

Figure 3:
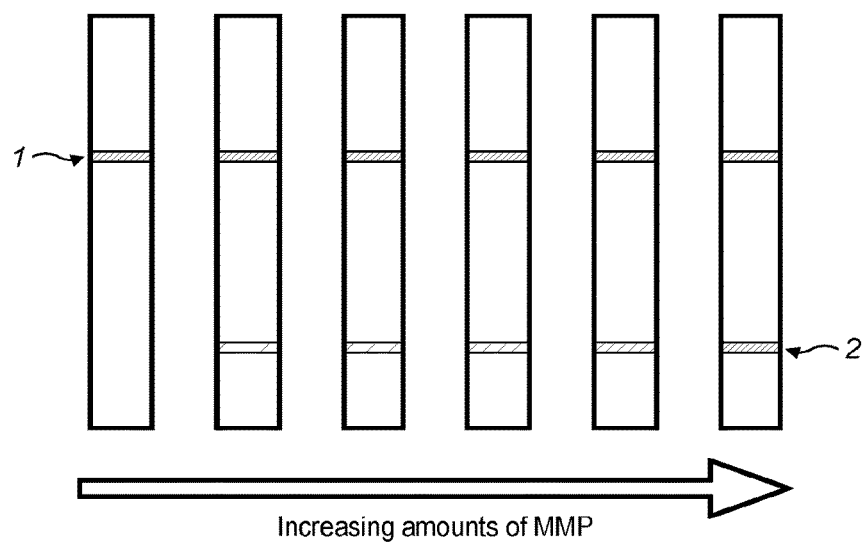
FIG. 3 shows the visual read-out of the assay (shown in FIG. 2) as levels of MMP activity in the test sample are increased.

FIG. 3 shows the visual read-out of the assay (shown in FIG. 2) as levels of MMP activity in the test sample are increased. As can readily be seen, the signal at the control zone (1) is constant as MMP amounts increase. In contrast, as MMP amounts increase, the signal at the capture zone (2) also increases. This is due to cleavage of the indicator molecule at the cleavage site by MMP activity. This reveals a binding site, enabling binding of the binding molecules which is detected at the capture zone (2) via interaction between capture molecules defining the capture zone and the capture site of the indicator molecules. The intensity of the signal at the capture zone can be measured to provide the level of effector molecule in the urine sample. This may employ a suitable reader.

Figure 4:
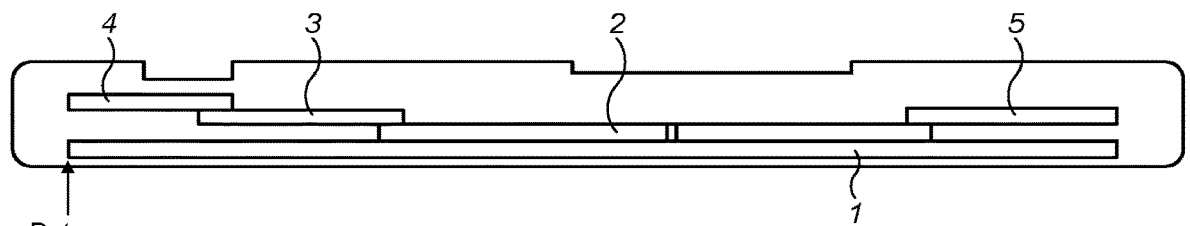
FIG. 4 is a schematic view of an enzyme detection device useful in the present invention. The figure specifies the exact longitudinal dimensions and position of each of the card components.

FIG. 4 is a schematic view of one specific enzyme detection device useful with the present invention. The table below provides a legend for the figure and specifies the longitudinal dimensions and position of each of the card components in this particular embodiment. Of course, the dimensions and positions may be varied as would be readily understood by one skilled in the art.

| Component | Size | Position from Datum point |
| --- | --- | --- |
| Backing card (1) | 60 mm | 0 mm |
| Nitrocellulose Membrane (2) | 25 mm | 20 mm |
| Conjugate Pad (3) | 17 mm | 5 mm |
| Sample Pad (4) | 10 mm | 0 mm |
| Absorbent Pad (5) | 22 mm | 38 mm |

FIG. 5 shows an example of synthesis of a structurally constrained indicator molecule. It should be noted that additional spacer or linker regions may be included between the cleavage region and the site of attachment of the scaffold molecule.

Figure 5A:
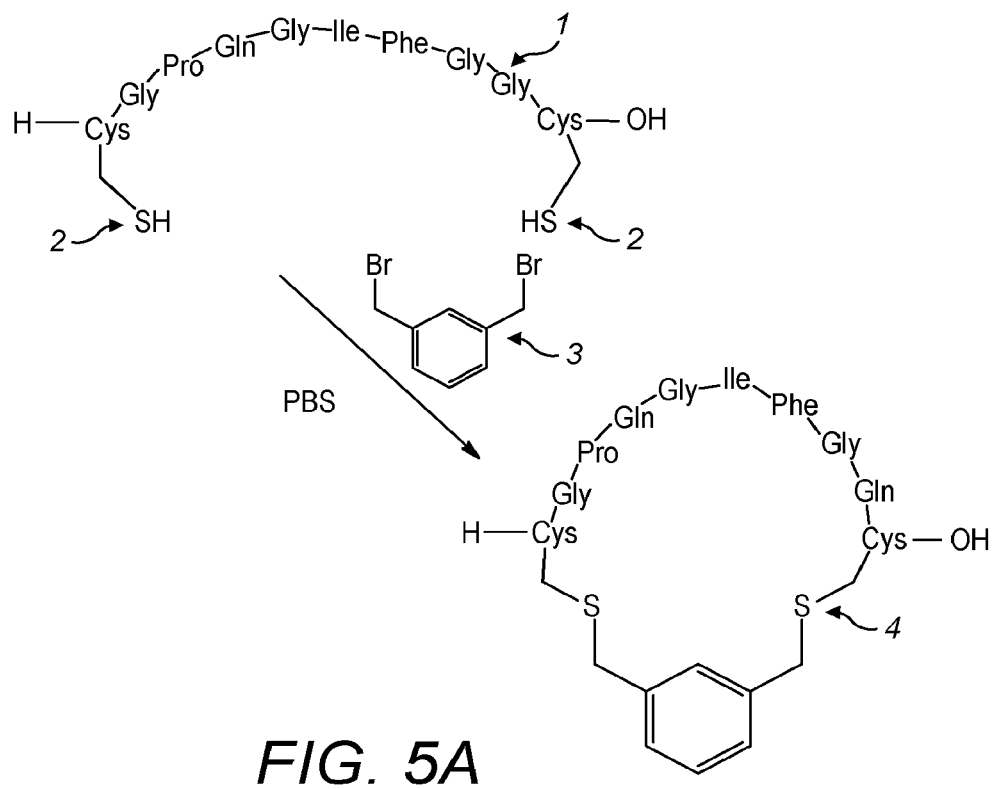
FIG. 5A and FIG. 5B show an example of synthesis of a structurally constrained indicator molecule.

In FIG. 5A initially, a linear peptide (1) is synthesised, for example using solid phase Fmoc chemistry. The peptide may be purified for example by High Performance Liquid Chromatography (HPLC). The peptide is then constrained, or cyclised, by reaction between thiol groups on the peptide (2) and the scaffold molecule (3). This reaction produces a structurally constrained "clipped" peptide (4).

Figure 5B:
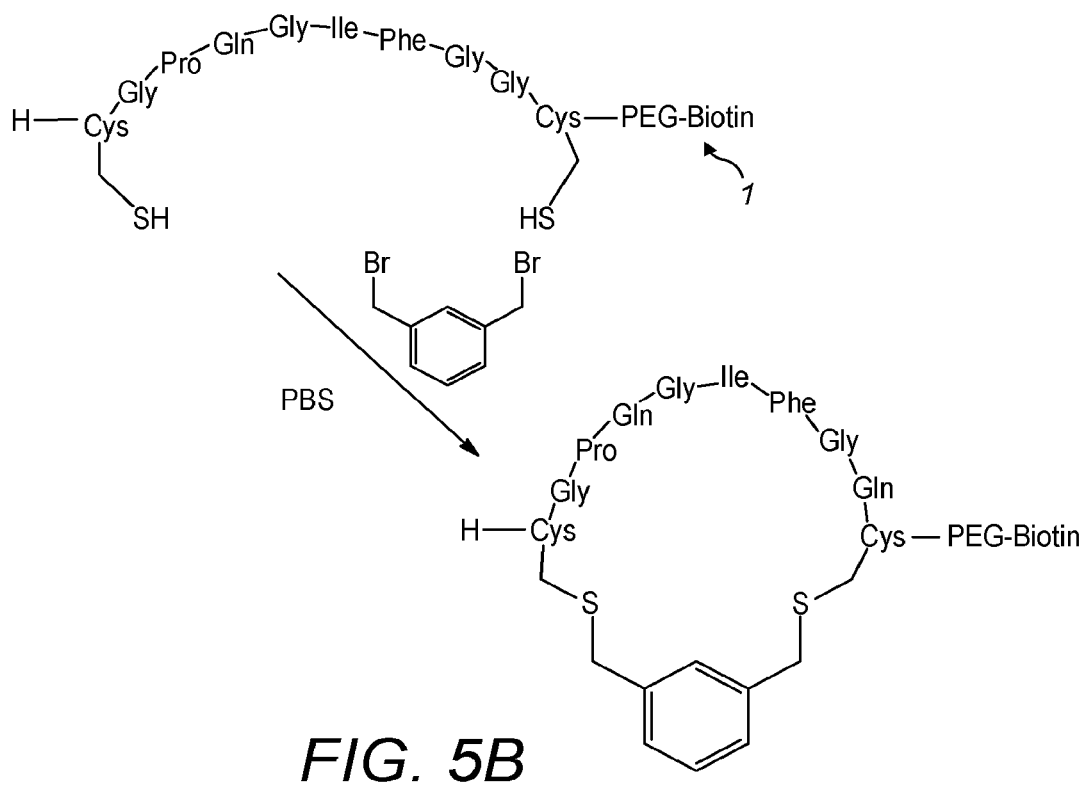

In FIG. 5B, the indicator molecule is synthesised to include the capture site (1), for example by synthesis of the linear peptide on a pre-loaded Biotin-PEG resin.

Figure 6:
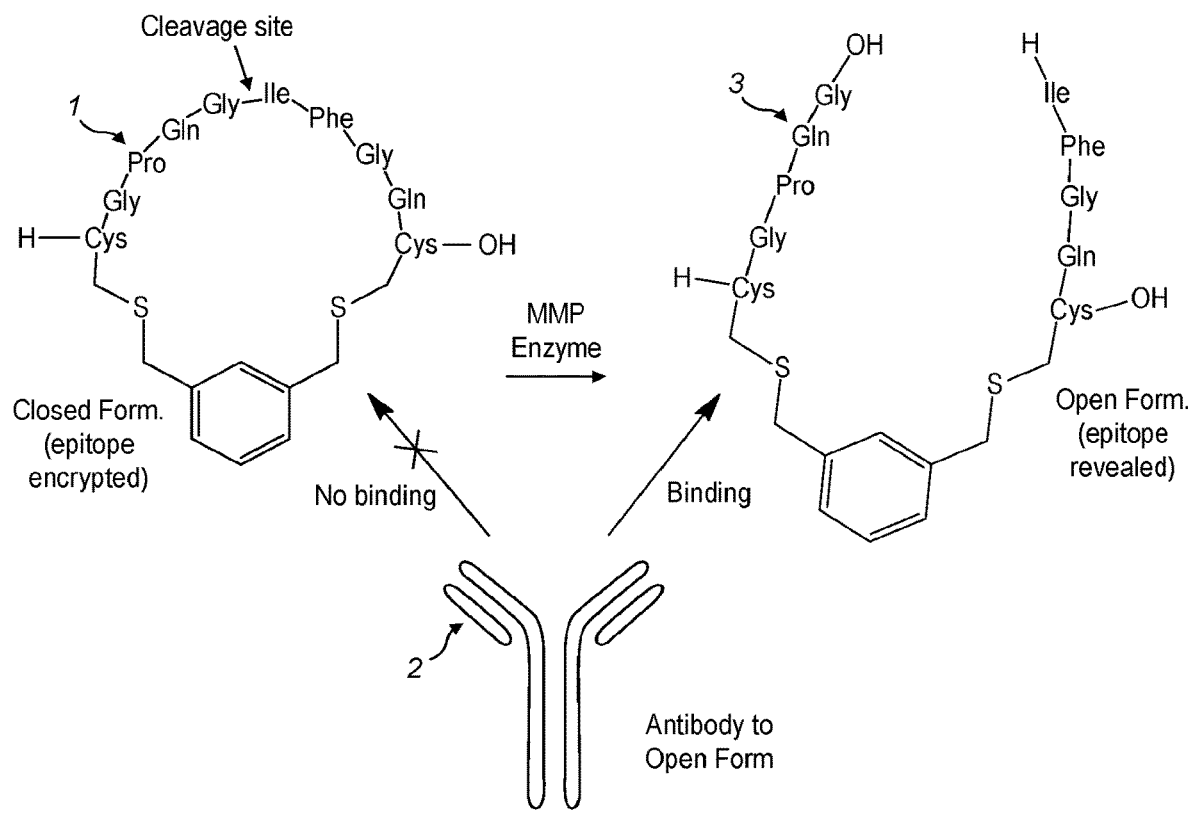
FIG. 6 shows schematically the ability of the binding molecules used in the invention to bind exclusively to the cleaved indicator molecule. In the absence of enzyme cleavage activity, the structurally constrained indicator molecule (1) is not bound by the antibody binding molecule (2). This antibody is generated using the cleaved indicator molecule (3) as antigen and thus only binds to this "open" form of the molecule.

FIG. 6 shows schematically the ability of the binding molecules used in some embodiments of the invention to bind exclusively to the cleaved indicator molecule. In the absence of enzyme cleavage activity, the structurally constrained indicator molecule (1) is not bound by the antibody binding molecule (2). This antibody is generated using the cleaved indicator molecule (3) as antigen and thus only binds to this "open" form of the molecule.

Figure 13:
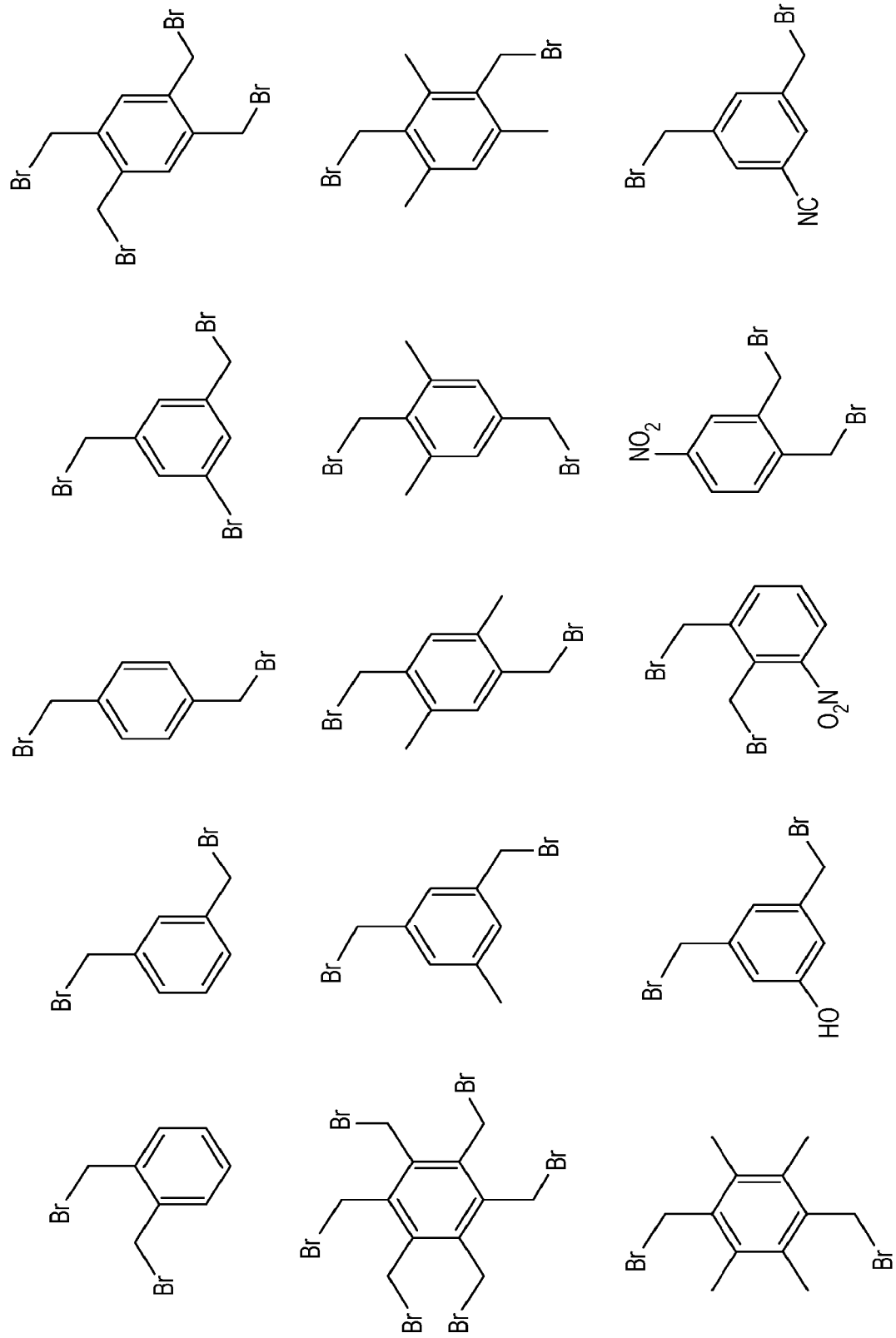
FIG. 13 shows a number of scaffold molecules useful in the indicator molecules described herein.
Figure 13:
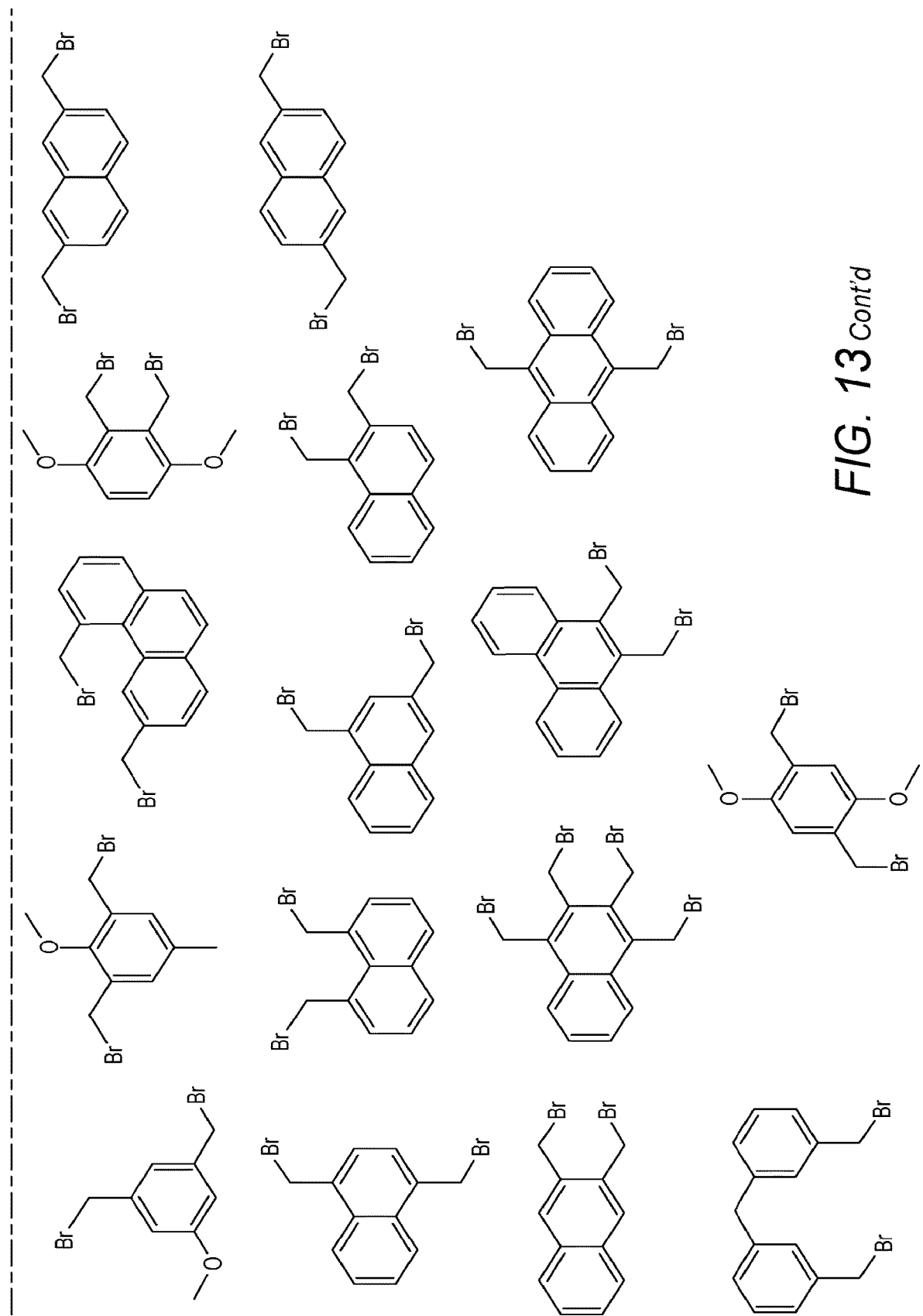

FIGS. 13 and 14 show a range of suitable scaffold molecules for use in the invention.

Figure 15A:
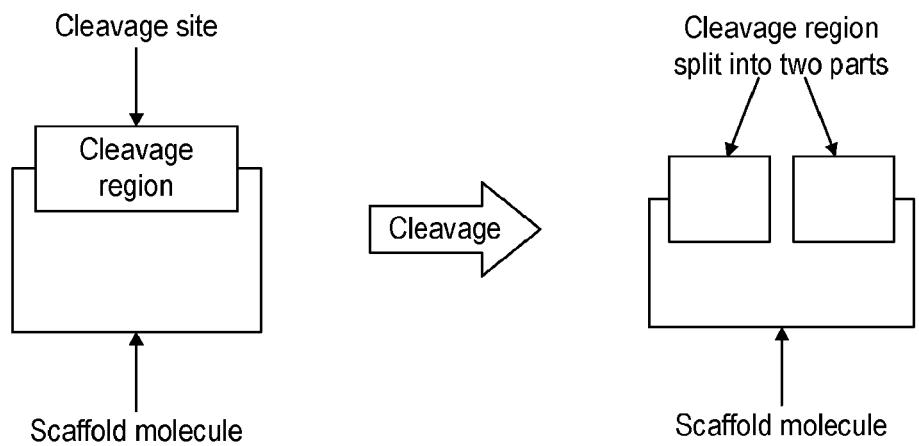
FIG. 15A and FIG. 15B show some attachment options for scaffold molecules to the indicator molecules.
Figure 15B:
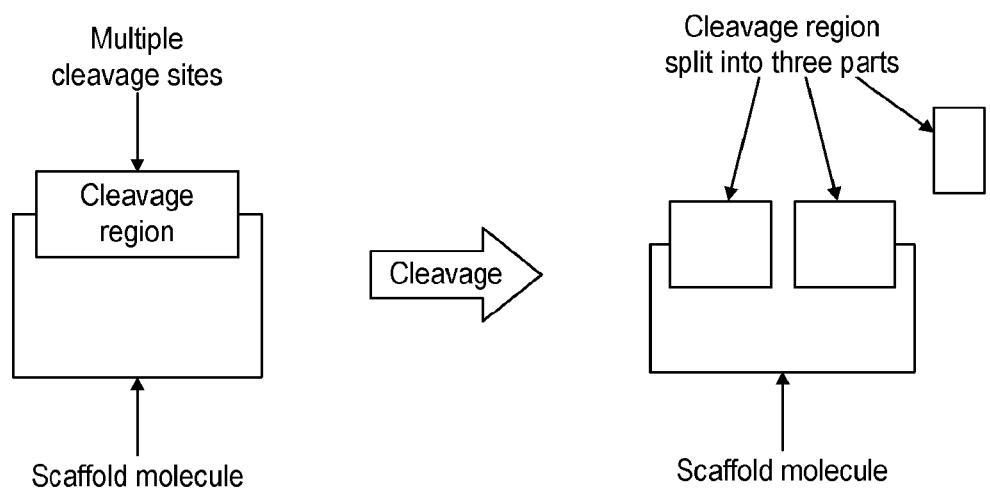

FIG. 15 shows, in schematic form, some attachment options for scaffold molecules to the indicator molecules. FIG. 15A shows products of cleavage at a single cleavage site and FIG. 15B shows products of cleavage at two separate cleavage sites.

Figure 24:
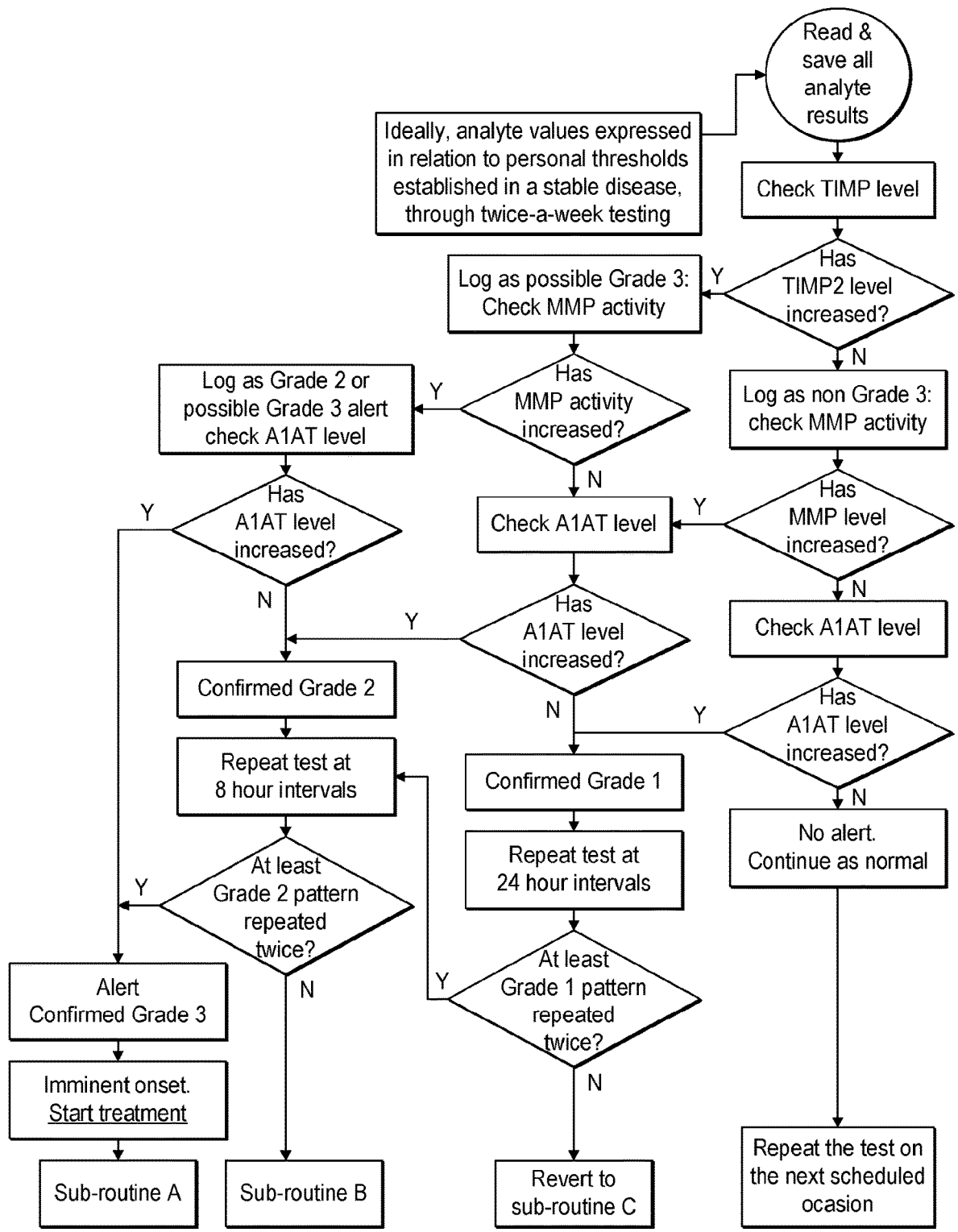
FIG. 24—Possible algorithm for COPD patient management based upon the MMP/TIMP/A1AT cluster of markers.

FIG. 24 presents an algorithm useful in the invention. This particular algorithm was designed based on the observed TIMP-2 concentration, MMP activity and A1AT concentration in urine samples taken during stable disease and during exacerbation. The algorithm is also based on biomarker profiles and patterns of change observed before, during and after exacerbation. This particular algorithm is designed to make sense of critical changes in balance between the neutrophil derived proteases and protease inhibitor shield. However, the principles applied and developed with this algorithm are clearly applicable to the other urinary markers and combinations described herein. The algorithm goes beyond the initial data analysis process of a simple, sequential search for alternative biomarker values that are raised individually at the time of exacerbation. Such simple procedures are a useful way of identifying which biomarkers are appropriate to include in an algorithm, as they clearly can be combined to identify exacerbation in the vast majority of cases, by one or other of them being elevated at a particular test event.

The algorithm, in use as a predictor of exacerbation, considers a range of other important factors, such as:
frequency of sampling
extra weighting of observations when more than one biomarker is elevated
increased frequency of sampling triggered by individual marker elevation
rolling personal biomarker thresholds
appropriate subroutines to switch-in when certain defined conditions prevail.

The algorithm shown in FIG. 24 takes all of these factors into account, to provide a rational means of interpreting biomarker changes into a trigger for therapeutic intervention. The algorithm incorporates personal threshold establishment by repeat testing in the stable disease state, to provide robust criteria for detection of meaningful changes in the biomarker profile.

The invention may be further defined in the following set of numbered clauses:
1. A method for monitoring inflammation status of a subject, the method comprising determining levels of at least one neutrophil activation marker in urine samples taken from the subject at multiple time points, wherein increased levels of the at least one neutrophil activation marker in a urine sample are indicative of or predictive of an exacerbation of inflammation and/or wherein decreased levels of the at least one neutrophil activation marker in a urine sample following an increase are indicative or predictive of recovery from, or successful treatment of, an exacerbation of inflammation.
2. The method according to clause 1 wherein the at least one neutrophil activation marker is selected from a signalling molecule or an effector/effector inhibitor molecule.
3. The method according to clause 2 wherein the effector molecule is selected from a protease activity, Neutrophil gelatinase-associated lipocalin (NGAL) (either free or in complex), calprotectin or myeloperoxidase (MPO).
4. The method according to clause 3 wherein the protease activity is selected from matrix metalloproteinase (MMP) activity, HNE activity and cathepsin G activity.
5. The method according to clause 4 wherein MMP activity comprises MMP9 and/or MMP8 activity.
6. The method according to any one of clauses 3 to 5 wherein protease activity is determined by measuring cleavage of a peptide substrate.
7. The method according to any one of clauses 3 to 6 wherein protease activity is determined by a method comprising:
  a. bringing an indicator molecule into contact with the test sample, said indicator molecule comprising
    i. a cleavage region comprising at least one cleavage site, which can be cleaved by said protease if present; and
    ii. a capture site;
  wherein cleavage of the at least one cleavage site produces a novel binding site;
  b. adding to the test sample binding molecules capable of binding to the novel binding site, wherein the binding molecules are incapable of binding to the indicator molecule unless and until cleavage has occurred;
  c. capturing the part of the indicator molecule containing the novel binding site at a capture zone through binding of capture molecules in the capture zone to the capture site; and
  d. detecting cleavage of the at least one cleavage site by determining binding of the binding molecules to the novel binding site of the indicator molecule captured in the capture zone.
8. The method according to any one of clauses 2 to 4 wherein the effector inhibitor molecule is a protease inhibitor molecule.
9. The method according to clause 5 wherein the protease inhibitor molecule is selected from Tissue Inhibitor of metalloproteinase (TIMP), cystatin C and alpha-1 antitrypsin (A1AT).
10. The method according to clause 2 wherein the signalling molecule is selected from ICAM-1, IL-6, IL-1β, IL-8, N-formyl-Met-Leu-Phe (fMLP), IL-6 induced fibrinogen and cytokine induced beta-2-microglobulin (B2M).
11. The method according to any preceding clause wherein the at least one neutrophil activation marker comprises or further comprises a molecule produced as a consequence of inflammation.
12. The method according to clause 5 wherein the molecule produced as a consequence of inflammation comprises a degradation product of protease activity, such as an extracellular matrix breakdown product (e.g. Ac-PGP, elastin fragments/peptides, desmosine) and/or a product of oxidative damage such as chlorinated peptides and/or metabolites such as lactic acid and free fatty acid.
13. The method according to any preceding clause wherein the inflammation status is lung inflammation status.
14. The method according to any preceding clause wherein the exacerbation of inflammation is a pulmonary exacerbation.
15. The method according to any preceding clause wherein the subject is suffering from a respiratory disorder.
16. The method according to clause 15 wherein the respiratory disorder is chronic obstructive pulmonary disease (COPD) or cystic fibrosis (CF).
17. The method according to any preceding clause wherein increased or decreased levels of the at least one 18. The method according to clause 19 wherein the threshold level of the marker is set by determining the levels of the marker in urine samples taken from the subject at earlier time points.
19. The method according to clause 19 wherein the earlier time points comprise at least two earlier measurements immediately preceding the determination of the level of the marker in the current urine sample.
20. The method according to clause 19 or 20 wherein the threshold level of the marker is set by determining the levels of the marker in urine samples taken from the subject at earlier time points at which the subject was not suffering from an exacerbation of inflammation and an increase above threshold predicts or identifies an exacerbation.
21. The method according to clause 19 or 20 wherein the threshold level of the marker is set by determining the levels of the marker in urine samples taken from the subject at earlier time points at which the subject was suffering from an exacerbation of inflammation and a decrease below threshold predicts or identifies recovery from, or successful treatment of, an exacerbation of inflammation.
22. The method according to any preceding clause wherein levels of at least one neutrophil activation marker are determined at least twice a week.
23. The method according to any preceding clause wherein the frequency of determining the levels of the at least one neutrophil activation marker in urine samples taken from the subject is increased if an increase in the levels of the at least one marker is detected.
24. The method according to clause 23 wherein the wherein the frequency of determining the levels of the at least one neutrophil activation marker in urine samples taken from the subject is maintained until a decrease in the levels of the at least one marker is detected.
25. The method according to any preceding clause comprising determining levels of at least two or three neutrophil activation markers in urine samples taken from the subject at multiple time points.
26. The method according to clause 25 wherein increased levels of at least one of the neutrophil activation markers in a urine sample are indicative of or predictive of an exacerbation of inflammation.
27. The method according to clause 25 or 26 wherein decreased levels of at least one of the neutrophil activation markers in a urine sample following an increase are indicative or predictive of recovery from, or successful treatment of, an exacerbation of inflammation.
28. The method according to any one of clauses 25 to 27 wherein the determined levels of the at least two or three markers are analysed in a pre-determined sequence to monitor the inflammation status of the subject.
29. The method according to any one of clauses 25 to 27 wherein the determined levels of the at least two or three markers are weighted.
30. The method according to any preceding clause wherein levels of at least one neutrophil activation marker are determined by normalising against the levels of a reference marker.
31. The method according to clause 31 wherein the reference marker comprises urinary creatinine or fibrinogen.
32. The method according to any preceding clause further comprising monitoring other indicators of exacerbation of inflammation.
33. The method according to clause 32 wherein the other indicators of exacerbation of inflammation comprise shortness of breath, increased wheeze, increased pulse rate, dyspnoea, increased sputum purulence, increased sputum colour, sore throat, increased cough, cold and fever.
34. A system or test kit for monitoring inflammation status in a subject, comprising:
   a. One or more testing devices for determining levels of at least one neutrophil activation marker in a urine sample
   b. A processor; and
   c. A storage medium comprising a computer application that, when executed by the processor, is configured to:
      i. Access and/or calculate the determined levels of the at least one neutrophil activation marker in the urine sample on the one or more testing devices
      ii. Calculate whether there is an increased or decreased level of the at least one neutrophil activation marker in the urine sample; and
      iii. Output from the processor the current inflammation status of the subject, wherein increased levels of the at least one neutrophil activation marker in a urine sample are indicative of or predictive of an exacerbation of inflammation and/or wherein decreased levels of the at least one neutrophil activation marker in a urine sample following an increase are indicative or predictive of recovery from, or successful treatment of, an exacerbation of inflammation.
35. The system or test kit of clause 34 further comprising a display for the output from the processor.
36. The system or test kit of clause 34 or 35 wherein the one or more testing devices are disposable single use devices.
37. The system or test kit of any one of clauses 34 to 36 wherein the one or more testing devices comprise lateral flow test strips.
38. The system or test kit of clause 37 comprising a lateral flow test strip for each marker that is determined.
39. The system or test kit of any one of clauses 34 to 38 wherein the at least one neutrophil activation marker is selected from a signalling molecule or an effector/effector inhibitor molecule.
40. The system or test kit of clause 39 wherein the effector molecule is selected from a protease activity, Neutrophil gelatinase-associated lipocalin (NGAL) (either free or in complex), calprotectin or myeloperoxidase (MPO).
41. The system or test kit of clause 40 wherein the protease activity is selected from matrix metalloproteinase (MMP) activity, HNE activity and cathepsin G activity.
42. The system or test kit of clause 41 wherein MMP activity comprises MMP9 and/or MMP8 activity.
43. The system or test kit of any one of clauses 40 to 42 wherein the one or more testing devices comprises a testing device for measuring cleavage of a peptide substrate as an indicator of protease activity.

44. The system or test kit of clause 43 wherein the testing device comprises:
   a. an indicator molecule for adding to the urine sample, said indicator molecule comprising
      i. a cleavage region comprising at least one cleavage site, which can be cleaved by said protease activity if present; and
      ii. a capture site;
   wherein cleavage of the at least one cleavage site produces a novel binding site;
   b. a capture zone to receive the urine sample, wherein the capture zone comprises capture molecules capable of binding to the capture site of the indicator molecule in order to immobilise the indicator molecule including the novel binding site; and
   c. binding molecules capable of binding to the novel binding site, wherein the binding molecules are incapable of binding to the indicator molecule unless and until cleavage has occurred.
45. The system or test kit of any one of clauses 39 to 44 wherein the effector inhibitor molecule is a protease inhibitor molecule.
46. The system or test kit of clause 45 wherein the protease inhibitor molecule is selected from Tissue Inhibitor of metalloproteinase (TIMP), cystatin C and alpha-1 antitrypsin (A1AT).
47. The system or test kit of clause 39 wherein the signalling molecule is selected from ICAM-1, IL-6, IL-1β, IL-8, N-formyl-Met-Leu-Phe (fMLP), IL-6 induced fibrinogen and cytokine induced beta-2-microglobulin (B2M).
48. The system or test kit of any one of clauses 34 to 47 wherein the at least one neutrophil activation marker comprises or further comprises a molecule produced as a consequence of inflammation.
49. The system or test kit of clause 48 wherein the molecule produced as a consequence of inflammation comprises a degradation product of protease activity, such as an extracellular matrix breakdown product (e.g. Ac-PGP, elastin fragments/peptides, desmosine) and/or a product of oxidative damage such as chlorinated peptides and/or metabolites such as lactic acid and free fatty acid.
50. The system or test kit of any one of clauses 34 to 49 wherein the inflammation status is lung inflammation status.
51. The system or test kit of any one of clauses 34 to 50 wherein the exacerbation of inflammation is a pulmonary exacerbation.
52. The system or test kit of any one of clauses 34 to 51 wherein the subject is suffering from a respiratory disorder.
53. The system or test kit of any one of clauses 34 to 52 wherein the respiratory disorder is chronic obstructive pulmonary disease (COPD) or cystic fibrosis (CF).
54. The system or test kit of any one of clauses 34 to 52 wherein the computer application causes the processor to calculate levels of the at least one neutrophil activation marker with reference to a threshold level of the marker that is adapted to the subject.
55. The system or test kit of clause 54 wherein the threshold level of the marker is set based upon determined levels of the marker in urine samples taken from the subject at earlier time points.
56. The system or test kit of clause 55 wherein the earlier time points comprise at least two earlier measurements immediately preceding the determination of the level of the marker in the current urine sample.
57. The system or test kit of clauses 55 or 56 wherein the threshold level of the marker is set based upon determined levels of the marker in urine samples taken from the subject at earlier time points at which the subject was not suffering from an exacerbation of inflammation and an increase above threshold predicts or identifies an exacerbation.
58. The system or test kit of clauses 55 or 56 wherein the threshold level of the marker is set based upon determined levels of the marker in urine samples taken from the subject at earlier time points at which the subject was suffering from an exacerbation of inflammation and a decrease below threshold predicts or identifies recovery from, or successful treatment of, an exacerbation of inflammation.
59. The system or test kit of any one of clauses 34 to 58 wherein the computer application causes the processor to indicate to the subject the requirement to determine the levels of at least one neutrophil activation marker.
60. The system or test kit of any one of clauses 34 to 59 wherein the computer application is further configured to output from the processor a requirement to increase the frequency of determining the levels of the at least one neutrophil activation marker in urine samples taken from the subject where an increase in the levels of the at least one marker is calculated.
61. The system or test kit of clause 60 wherein the computer application is further configured to output from the processor a requirement to maintain the increased frequency of determining the levels of the at least one neutrophil activation marker until a decrease in the levels of the at least one marker is calculated.
62. The system or test kit of any one of clauses 34 to 61 comprising one or more testing devices for determining levels of at least two or three neutrophil activation markers in urine samples taken from the subject at multiple time points.
63. The system or test kit of clause 62 wherein the computer application is configured to calculate increased levels of at least one of the neutrophil activation markers and provide an output from the processor that a calculated increase in levels of at least one of the markers is indicative of or predictive of an exacerbation of inflammation.
64. The system or test kit of clause 62 or 63 wherein the computer application is configured to calculate decreased levels of at least one of the neutrophil activation markers and provide an output from the processor that a calculated decrease in levels of at least one of the markers following an increase are indicative or predictive of recovery from, or successful treatment of, an exacerbation of inflammation.
65. The system or test kit of any one of clauses 62 to 64 wherein computer application is configured to analyse the calculated levels of the at least two or three markers in a pre-determined sequence to monitor the inflammation status of the subject.
66. The system or test kit of any one of clauses 62 to 65 wherein the computer application is configured to apply a weighting to the determined levels of the at least two or three markers.
67. The system or test kit of any one of clauses 34 to 66 wherein the computer application is configured to calculate levels of at least one neutrophil activation marker by normalising against the levels of a reference marker.
68. The system or test kit of clause 67 wherein the reference marker comprises urinary creatinine or fibrinogen.
69. The system or test kit of any one of clauses 34 to 67 wherein the computer application is further configured to incorporate inputs from other indicators of exacerbation of inflammation into the calculation of the current inflammation status of the subject.
70. The system or test kit of clause 69 wherein the other indicators of exacerbation of inflammation comprise shortness of breath, increased wheeze, increased pulse rate, dyspnoea, increased sputum purulence, increased sputum colour, sore throat, increased cough, cold and fever.
71. A computer application as defined in any one of clauses 34 to 70.
72. A method for monitoring inflammation status of a subject, the method comprising determining levels of at least three markers in urine samples taken from the subject at multiple time points, wherein increased levels of at least one of the markers in a urine sample indicates or predicts an exacerbation of inflammation and/or wherein decreased levels of at least one of the markers in a urine sample following an increase indicate or predict recovery from, or successful treatment of, an exacerbation of inflammation.
73. The method according to clause 71 or 72 wherein at least one of the markers is selected from a signalling molecule or an effector/effector inhibitor molecule.
74. The method according to clause 73 wherein the effector molecule is selected from a protease activity, Neutrophil gelatinase-associated lipocalin (NGAL) (either free or in complex), calprotectin or myeloperoxidase (MPO).
75. The method according to clause 74 wherein the protease activity is selected from matrix metalloproteinase (MMP) activity, HNE activity and cathepsin G activity.
76. The method according to clause 75 wherein MMP activity comprises MMP9 and/or MMP8 activity.
77. The method according to any one of clauses 74 to 76 wherein protease activity is determined by measuring cleavage of a peptide substrate.
78. The method according to any one of clauses 74 to 77 wherein protease activity is determined by a method comprising:
  a. bringing an indicator molecule into contact with the test sample, said indicator molecule comprising
    i. a cleavage region comprising at least one cleavage site, which can be cleaved by said protease if present; and
    ii. a capture site;
  wherein cleavage of the at least one cleavage site produces a novel binding site;
  b. adding to the test sample binding molecules capable of binding to the novel binding site, wherein the binding molecules are incapable of binding to the indicator molecule unless and until cleavage has occurred;
  c. capturing the part of the indicator molecule containing the novel binding site at a capture zone through binding of capture molecules in the capture zone to the capture site; and
  d. detecting cleavage of the at least one cleavage site by determining binding of the binding molecules to the novel binding site of the indicator molecule captured in the capture zone.
79. The method according to any one of clauses 73 to 78 wherein the effector inhibitor molecule is a protease inhibitor molecule.
80. The method according to clause 79 wherein the protease inhibitor molecule is selected from Tissue Inhibitor of metalloproteinase (TIMP), cystatin C and alpha-1 antitrypsin (A1AT).
81. The method according to clause 73 wherein the signalling molecule is selected from ICAM-1, IL-6, IL-1β, IL-8, N-formyl-Met-Leu-Phe (fMLP), IL-6 induced fibrinogen and cytokine induced beta-2-microglobulin (B2M).
82. The method according to any one of clauses 72 to 81 wherein at least one of the markers comprises or further comprises a molecule produced as a consequence of inflammation.
83. The method according to clause 82 wherein the molecule produced as a consequence of inflammation comprises a degradation product of protease activity, such as an extracellular matrix breakdown product (e.g. Ac-PGP, elastin fragments/peptides, desmosine) and/or a product of oxidative damage such as chlorinated peptides and/or metabolites such as lactic acid and free fatty acid.
84. The method according to any one of clauses 72 to 83 wherein the inflammation status is lung inflammation status.
85. The method according to any one of clauses 72 to 84 wherein the exacerbation of inflammation is a pulmonary exacerbation.
86. The method according to any one of clauses 72 to 85 wherein the subject is suffering from a respiratory disorder.
87. The method according to clause 86 wherein the respiratory disorder is chronic obstructive pulmonary disease (COPD) or cystic fibrosis (CF).
88. The method according to any one of clauses 72 to 87 wherein increased or decreased levels of the markers is calculated with reference to a threshold level of each marker that is adapted to the subject.
89. The method according to clause 89 wherein the threshold level of each marker is set by determining the levels of each marker in urine samples taken from the subject at earlier time points.
90. The method according to clause 90 wherein the earlier time points comprise at least two earlier measurements immediately preceding the determination of the level of the marker in the current urine sample.
91. The method according to clause 90 or 91 wherein the threshold level of each marker is set by determining the levels of the marker in urine samples taken from the subject at earlier time points at which the subject was not suffering from an exacerbation of inflammation and an increase above threshold predicts or identifies an exacerbation.
92. The method according to clause 90 or 91 wherein the threshold level of the marker is set by determining the levels of the marker in urine samples taken from the subject at earlier time points at which the subject was suffering from an exacerbation of inflammation and a decrease below threshold predicts or identifies recovery from, or successful treatment of, an exacerbation of inflammation.

93. The method according to any one of clauses 72 to 92 wherein levels of the markers are determined at least twice a week.
94. The method according to any one of clauses 72 to 93 wherein the frequency of determining the levels of the markers is increased if an increase in the levels of at least one marker is detected.
95. The method according to clause 94 wherein the frequency of determining the levels of the markers is maintained until a decrease in the levels of at least one of the markers is detected.
96. The method according to any one of clauses 72 to 93 wherein if an increase in the levels of each of the at least three markers is detected, the subject indicates or predicts an exacerbation of inflammation.
97. The method of clause 96 wherein the subject's exacerbation is treated.
98. The method according to any one of clauses 72 to 97 wherein if no increase in the levels of any of the markers is determined, the inflammation status is considered stable and/or the frequency of testing is maintained.
99. The method according to any one of clauses 72 to 98 wherein if an increase in the level of one of the markers is determined but not in the other two markers the frequency of testing is increased.
100. The method according to clause 99 wherein the frequency of testing is increased unless the increased level of one of the markers reverts to a non-increased level within a set number of repeat tests.
101. The method of clause 100 wherein if the level of one of the markers reverts to a non-increased level within the set number of repeat tests, the frequency of testing reverts to the original frequency.
102. The method of clause 100 wherein if the level of one of the markers remains at an increased level within the set number of repeat tests, the frequency of testing is increased further.
103. The method of clause 102 wherein if the level of one of the markers remains at an increased level within a further set number of repeat tests at increased frequency an exacerbation of inflammation if indicated or predicted.
104. The method of clause 103 wherein the patient's exacerbation is treated.
105. The method of clause 102 wherein if the level of one of the markers reverts to a non-increased level within the further set number of repeat tests at increased frequency, the frequency of testing reverts to the increased (but not further increased) frequency of testing.
106. The method of clause 105 wherein if the level of one of the markers remains at the non-increased level within the set number of repeat tests, the frequency of testing reverts to the original frequency.
107. The method according to any one of clauses 72 to 106 wherein if an increase in the level of two of the markers is determined but not in the other marker the frequency of testing is increased.
108. The method according to clause 107 wherein the frequency of testing is increased to a frequency greater than if an increased level in only one of the markers is detected.
109. The method of clause 108 wherein if the level of at least one of the markers reverts to a non-increased level within the set number of repeat tests, the frequency of testing reverts to a frequency of testing indicative of a determined increase in the level of one of the markers.
110. The method of clause 109 wherein if the level of the one of the markers remains at an increased level within the set number of repeat tests, the frequency of testing is increased again.
111. The method of clause 110 wherein if the level of one of the markers remains at an increased level within a further set number of repeat tests at increased frequency an exacerbation of inflammation if indicated or predicted.
112. The method of clause 111 wherein the patient's exacerbation is treated.
113. The method of clause 107 or 108 wherein if the level of two of the markers remains at an increased level within a further set number of repeat tests at increased frequency an exacerbation of inflammation is indicated or predicted.
114. The method of clause 113 wherein the patient's exacerbation is treated.
115. The method according to any one of clauses 72 to 114 wherein decreased levels of at least one of the markers in a urine sample following an increase are indicative or predictive of recovery from, or successful treatment of, an exacerbation of inflammation.
116. The method according to any one of clauses 72 to 115 wherein the determined levels of the at least three markers are analysed in a pre-determined sequence to monitor the inflammation status of the subject.
117. The method according to any one of clauses 72 to 116 wherein the determined levels of the at least two or three markers are weighted.
118. The method according to any one of clauses 72 to 117 wherein the first marker is TIMP2, the second marker is MMP activity and the third marker is A1AT.
119. The method according to any preceding clause wherein levels of at least one marker are determined by normalising against the levels of a reference marker.
120. The method according to clause 119 wherein the reference marker comprises urinary creatinine or fibrinogen.
121. The method according to any one of clauses 72 to 120 further comprising monitoring other indicators of exacerbation of inflammation.
122. The method according to clause 121 wherein the other indicators of exacerbation of inflammation comprise shortness of breath, increased wheeze, increased pulse rate, dyspnoea, increased sputum purulence, increased sputum colour, sore throat, increased cough, cold and fever.
123. A system or test kit for monitoring inflammation status in a subject, comprising:
   a. One or more testing devices for determining levels of at least three markers in a urine sample
   b. A processor; and
   c. A storage medium comprising a computer application that, when executed by the processor, is configured to:
      i. Access and/or calculate the determined levels of each marker in the urine sample on the one or more testing devices
      ii. Calculate whether there is an increased or decreased level of at least one of the markers in the urine sample; and
      iii. Output from the processor the current inflammation status of the subject, wherein increased levels of at least one of the markers in a urine sample are indicative of or predictive of an exacerbation of inflammation and/or wherein decreased levels of at least one of the markers in a urine sample following an increase are indicative or predictive of recovery from, or successful treatment of, an exacerbation of inflammation.
124. The system or test kit of clause 123 further comprising a display for the output from the processor.
125. The system or test kit of clause 123 or 124 wherein the one or more testing devices are disposable single use devices.
126. The system or test kit of any one of clauses 123 to 125 wherein the one or more testing devices comprise lateral flow test strips.
127. The system or test kit of clause 126 comprising a lateral flow test strip for each marker that is determined.
128. The system or test kit of any one of clauses 123 to 127 wherein at least one of the markers is selected from a signalling molecule or an effector/effector inhibitor molecule.
129. The system or test kit of clause 128 wherein the effector molecule is selected from a protease activity, Neutrophil gelatinase-associated lipocalin (NGAL) (either free or in complex), calprotectin or myeloperoxidase (MPO).
130. The system or test kit of clause 129 wherein the protease activity is selected from matrix metalloproteinase (MMP) activity, HNE activity and cathepsin G activity.
131. The system or test kit of clause 130 wherein MMP activity comprises MMP9 and/or MMP8 activity.
132. The system or test kit of any one of clauses 129 to 131 wherein the one or more testing devices comprises a testing device for measuring cleavage of a peptide substrate as an indicator of protease activity.
133. The system or test kit of clause 132 wherein the testing device comprises:
   a. an indicator molecule for adding to the urine sample, said indicator molecule comprising
      i. a cleavage region comprising at least one cleavage site, which can be cleaved by said protease activity if present; and
      ii. a capture site;
   wherein cleavage of the at least one cleavage site produces a novel binding site;
   b. a capture zone to receive the urine sample, wherein the capture zone comprises capture molecules capable of binding to the capture site of the indicator molecule in order to immobilise the indicator molecule including the novel binding site; and
   c. binding molecules capable of binding to the novel binding site, wherein the binding molecules are incapable of binding to the indicator molecule unless and until cleavage has occurred.
134. The system or test kit of any one of clauses 128 to 133 wherein the effector inhibitor molecule is a protease inhibitor molecule.
135. The system or test kit of clause 134 wherein the protease inhibitor molecule is selected from Tissue Inhibitor of metalloproteinase (TIMP), cystatin C and alpha-1 antitrypsin (A1AT).
136. The system or test kit of clause 128 wherein the signalling molecule is selected from ICAM-1, IL-6, IL-1β, IL-8, N-formyl-Met-Leu-Phe (fMLP), IL-6 induced fibrinogen and cytokine induced beta-2-microglobulin (B2M).
137. The system or test kit of any one of clauses 123 to 136 wherein the markers comprise or further comprise a molecule produced as a consequence of inflammation.
138. The system or test kit of clause 137 wherein the molecule produced as a consequence of inflammation comprises a degradation product of protease activity, such as an extracellular matrix breakdown product (e.g. Ac-PGP, elastin fragments/peptides, desmosine) and/or a product of oxidative damage such as chlorinated peptides and/or metabolites such as lactic acid and free fatty acid.
139. The system or test kit of any one of clauses 123 to 138 wherein the inflammation status is lung inflammation status.
140. The system or test kit of any one of clauses 123 to 139 wherein the exacerbation of inflammation is a pulmonary exacerbation.
141. The system or test kit of any one of clauses 123 to 140 wherein the subject is suffering from a respiratory disorder.
142. The system or test kit of any one of clauses 123 to 141 wherein the respiratory disorder is chronic obstructive pulmonary disease (COPD) or cystic fibrosis (CF).
143. The system or test kit of any one of clauses 123 to 142 wherein the computer application causes the processor to calculate levels of the markers with reference to a threshold level of each marker that is adapted to the subject.
144. The system or test kit of clause 143 wherein the threshold level of each marker is set based upon determined levels of the marker in urine samples taken from the subject at earlier time points.
145. The system or test kit of clause 144 wherein the earlier time points comprise at least two earlier measurements immediately preceding the determination of the level of the marker in the current urine sample.
146. The system or test kit of clauses 144 or 145 wherein the threshold level of each marker is set based upon determined levels of the marker in urine samples taken from the subject at earlier time points at which the subject was not suffering from an exacerbation of inflammation.
147. The system or test kit of any one of clauses 123 to 146 wherein the computer application causes the processor to indicate to the subject the requirement to determine the levels of the markers and an increase above threshold predicts or identifies an exacerbation.
148. The system or test kit of clauses 123 to 146 wherein the threshold level of the marker is set based upon determined levels of the marker in urine samples taken from the subject at earlier time points at which the subject was suffering from an exacerbation of inflammation and a decrease below threshold predicts or identifies recovery from, or successful treatment of, an exacerbation of inflammation.
149. The system or test kit of any one of clauses 123 to 148 wherein the computer application is further configured to output from the processor a requirement to increase the frequency of determining the levels of the markers where an increase in the levels of at least one marker is calculated.
150. The system or test kit of clause 149 wherein the computer application is further configured to output from the processor a requirement to maintain the increased frequency of determining the levels of the markers until a decrease in the levels of the at least one marker is calculated.

151. The system or test kit of any one of clauses 123 to 150 wherein the computer application is configured to output from the processor an indication or prediction of exacerbation of inflammation if an increase in the levels of each of the at least three markers is calculated.

152. The system or test kit of clause 151 wherein the output is an indication that the subject should receive treatment.

153. The system or test kit of any one of clauses 123 to 150 wherein the computer application is configured to output from the processor an indication the inflammation status is considered stable and/or the frequency of testing is maintained in the event that no increase in the levels of any of the markers is determined.

154. The system or test kit of any one of clauses 123 to 153 wherein the computer application is configured to output from the processor an indication that the frequency of testing is increased if an increase in the level of one of the markers is calculated but not in the other two markers.

155. The system or test kit of clause 154 wherein the computer application is configured to output from the processor an indication that the frequency of testing is increased unless the increased level of one of the markers reverts to a non-increased level within a set number of repeat tests.

156. The system or test kit of clause 154 wherein the computer application calculates whether the level of one of the markers has reverted to a non-increased level within the set number of repeat tests.

157. The system or test kit of clause 156 wherein if the level of one of the markers has reverted to a non-increased level within the set number of repeat tests the computer application produces an output from the processor that the frequency of testing reverts to the original frequency.

158. The system or test kit of any one of clauses 154 to 157 wherein if the level of one of the markers remains at an increased level within the set number of repeat tests, the computer application produces an output from the processor that the frequency of testing is increased further.

159. The system or test kit of clause 158 wherein if the level of one of the markers remains at an increased level within a further set number of repeat tests at increased frequency the computer application produces an output from the processor that an exacerbation of inflammation is indicated or predicted and/or the subject should be treated.

160. The system or test kit of clause 158 or 159 wherein if the level of one of the markers reverts to a non-increased level within the further set number of repeat tests at increased frequency, the computer application produces an output from the processor that the frequency of testing reverts to the increased (but not further increased) frequency of testing.

161. The system or test kit of clause 160 wherein if the level of one of the markers remains at the non-increased level within the set number of repeat tests, the computer application produces an output from the processor that the frequency of testing reverts to the original frequency.

162. The system or test kit of any one of clauses 123 to 161 wherein if an increase in the level of two of the markers is determined but not in the other marker the computer application produces an output from the processor that the frequency of testing is increased.

163. The system or test kit of clause 162 wherein the frequency of testing is increased to a frequency greater than if an increased level in only one of the markers is detected.

164. The system or test kit of clause 163 wherein if the level of at least one of the markers reverts to a non-increased level within the set number of repeat tests, the computer application produces an output from the processor that the frequency of testing reverts to a frequency of testing indicative of a determined increase in the level of one of the markers.

165. The system or test kit of clause 164 wherein if the level of the one of the markers remains at an increased level within the set number of repeat tests, the computer application produces an output from the processor that the frequency of testing is increased again.

166. The system or test kit of clause 165 wherein if the level of one of the markers remains at an increased level within a further set number of repeat tests at increased frequency the computer application produces an output from the processor that an exacerbation of inflammation is indicated or predicted and/or the subject should be treated.

167. The system or test kit of clause 162 or 163 wherein if the level of two of the markers remains at an increased level within a further set number of repeat tests at increased frequency the computer application produces an output from the processor that an exacerbation of inflammation is indicated or predicted and/or the subject should be treated.

168. The system or test kit of any one of clauses 123 to 167 wherein the computer application is configured to calculate decreased levels of at least one of the neutrophil activation markers and provide an output from the processor that a calculated decrease in levels of at least one of the markers following an increase are indicative or predictive of recovery from, or successful treatment of, an exacerbation of inflammation.

169. The system or test kit of any one of clauses 123 to 168 wherein the computer application is configured to analyse the calculated levels of the at least three markers in a pre-determined sequence to monitor the inflammation status of the subject.

170. The system or test kit of any one of clauses 123 to 169 wherein the computer application is configured to apply a weighting to the determined levels of the at least three markers.

171. The system or test kit of any one of clauses 123 to 170 wherein the first marker is TIMP2, the second marker is MMP activity and the third marker is A1AT.

172. The system or test kit of any one of clauses 123 to 171 wherein the computer application is configured to calculate levels of at least one marker by normalising against the levels of a reference marker.

173. The system or test kit of clause 172 wherein the reference marker comprises urinary creatinine or fibrinogen.

174. The system or test kit of any one of clauses 123 to 173 wherein the computer application is further configured to incorporate inputs from other indicators of exacerbation of inflammation into the calculation of the current inflammation status of the subject.

175. The system or test kit of clause 174 wherein the other indicators of exacerbation of inflammation comprise shortness of breath, increased wheeze increased pulse rate, dyspnoea, increased sputum purulence, increased sputum colour, sore throat, increased cough, cold and fever.

176. A computer application as defined in any one of clauses 123 to 175.

The invention as discussed in these clauses may also be applied to further markers. Examples include CRP, LEF and CC16 which may be applied in combination with any other specific marker described herein.

The invention will be further understood with reference to the following experimental examples.

EXAMPLES

Example 1

A Lateral Flow Platform Used in the Invention for Detection of Matrix Metalloprotease-9 (MMP-9)

A kit comprises the following components:
1) A device for urine sample collection
2) A lateral flow test-strip, which is mounted in a plastic case. The test strip has a capture zone comprising polystreptavidin as a first test line across the flow-path of the test strip. A second capture zone comprising anti-chicken antibodies adsorbed as a control line across the flow-path of the test strip, downstream of the test line may be included as a control line. There is an observation window in the plastic case through which to view the test and control line. There is also an integrated sample-receiving pad, upstream of the first test line. In addition, the test strip has gold particles bearing sheep antibody (CF1522) dried into the test strip, downstream of the sample-receiving pad which can be reconstituted by the addition of the sample.
3) A tube, in which the sample collection device may be placed, together with the indicating molecule.
4) An indicator molecule containing the cleavable sequence, in this example, (GPQGIFGQ) which carries a terminal biotin group connected via a polyethylene glycol spacer/linker which allows it to form a complex with the capture line, polystreptavidin.

The Test Strip

A test strip for the detection of protease activity in a sample was constructed as described below. The assay was based on the cleavage of the indicator molecule in the presence of various MMPs to expose an epitope visible to the Sheep antibody (CF1522) conjugated to gold particles.

The methods used were all in accordance with standard procedures well known in the art.

A. Preparation of CF1522:40 nm Gold Conjugate

Affinity purified sheep antibody CF1522 (Ig Innovations, CF1522) was conjugated to 40 nm gold particles at a concentration giving an OD of 5 at 520 nm (BBI International, GC40). The antibody was loaded at a concentration of 15 µg/ml in a 20 mM BES buffer pH 7.8. 0.2% BSA (Sigma, A7906) was used as a blocking solution to minimise non-specific binding.

B. Preparation of Gold-Impregnated Conjugate Pads

A glass fibre conjugate pad (Millipore, G041, 17 mm×300 mm) was sprayed with CF1522:40 nm gold conjugate (Mologic) at OD4, diluted in gold drying buffer (1M Tris, 150 mM sodium chloride, 20 mM sodium Azide, 3% BSA, 5% Sucrose, 1% Tween 20 at pH 9.4) at 0.8 µl/mm with the Isoflow dispenser (15 mm spray height). The processed conjugate band was dried in a tunnel dryer at 60° C. at a speed of 5 mm/sec. The dried gold conjugate-impregnated conjugate pads were stored dried in a sealed foil pouch with desiccant at room temperature.

C. Preparation of Antibody-Impregnated Nitrocellulose Membrane

All reagents were striped on Unistart CN140 membrane (Sartorius, CN140, 25 mm×300 mm) at a dispense rate of 0.1 µl/mm. A test line polystreptavidin (BBI, Polystrep N 01041048K) at a concentration of 1 mg/ml was positioned 7 mm from base of membrane. Processed membrane was dried in a tunnel dryer at 60° C. at a speed of 10 mm/sec. The dried antibody-impregnated Nitrocellulose Membrane was stored in a sealed foil pouch with desiccant at room temperature.

D. Card Assembly

A test card was assembled according to the following procedure and in accordance with FIG. 4 which specifies the exact longitudinal dimensions and position of each of the card components.

1. A 60×300 mm piece of clear plastic film with a release liner protected adhesive, serving as the back laminate, designated 1 in FIG. 4, (G&L Precision Die Cutting, GL-48077) was placed on top of a worktable. The release liner was peeled to expose the adhesive.
2. The reaction membrane (prepared as in section C) was attached on top of the adhesive side of the back cover, 20 mm from the lower end.
3. The impregnated conjugate pad (prepared as in section B) was attached on top of the back cover with 2 mm overlap on top of the reaction membrane.
4. The sample pad (MDI, FR-1, 10×300 mm) was placed on top of the back cover with 5 mm overlap on top of the conjugate pad.
5. The absorbent pad (Gel blotting paper, Ahlstrom, grade 222, 22×300 mm) was placed on top of the upper side of the back cover with a 2 mm overlap on top of the reaction membrane.

The card was trimmed to 5 mm width strips using an automated die cutter (Kinematic, 2360) and assembled into plastic housings (Forsite). The devices were closed using a pneumatic device clamp specifically manufactured for these devices at Mologic.

The table lists the strip components and respective positioning on a backing card.

| Component | Size | Position from Datum point |
|---|---|---|
| Backing card (1) | 60 mm | 0 mm |
| Nitrocellulose Membrane (2) | 25 mm | 20 mm |
| Conjugate Pad (3) | 17 mm | 5 mm |
| Sample Pad (4) | 10 mm | 0 mm |
| Absorbent Pad (5) | 22 mm | 38 mm |

Buffer standards were produced containing different concentrations of active MMP-9 (Alere San Diego) ranging from 1000 ng/ml down to 1 ng/ml.

STEP 1: Each standard was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 7A:
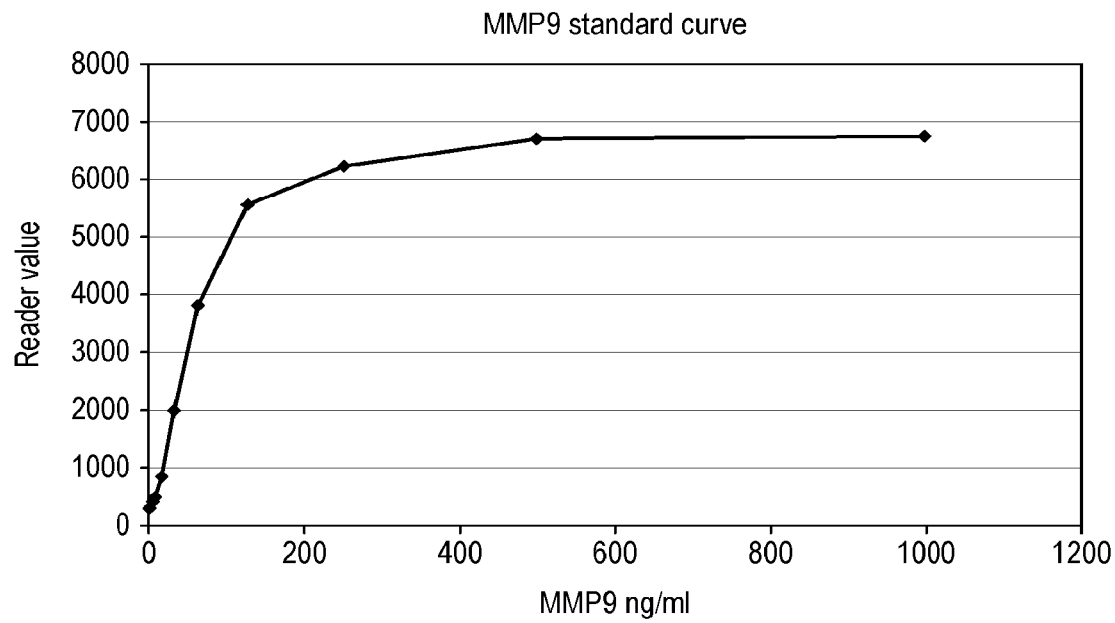
FIGS. 7A and 7B demonstrate the sensitivity of the assay useful in the invention when run with spiked MMP-9 buffer samples. The detectable limit for MMP-9 was approximately 4 ng/ml with a sample volume of 75 µl.
Figure 7B:
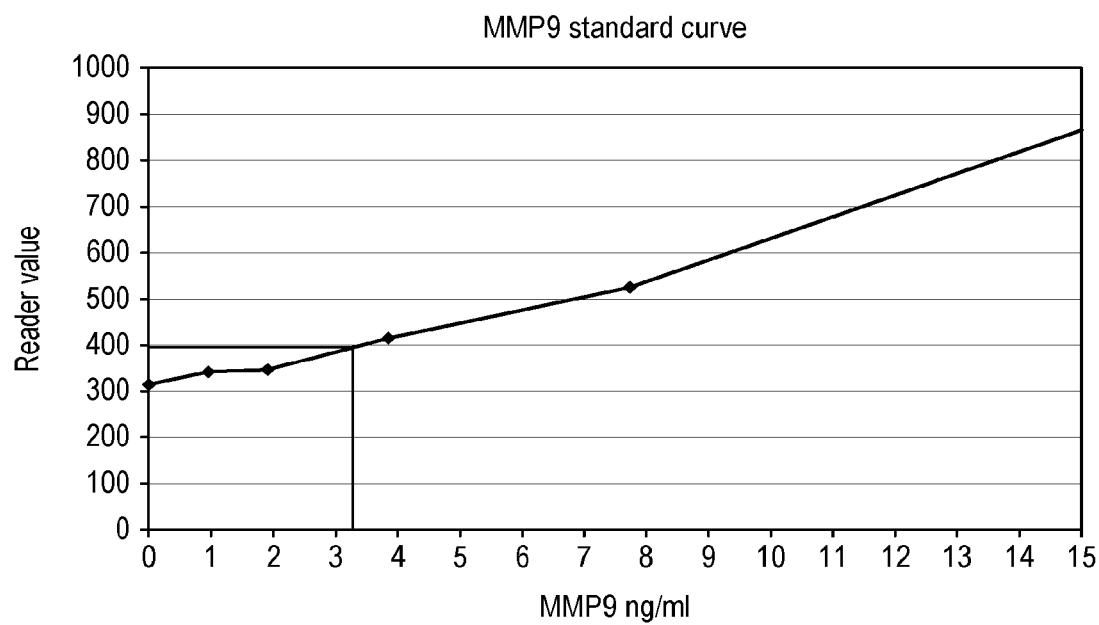

FIG. 7 (FIGS. 7A and 7B) demonstrates the sensitivity of the assay when run with spiked MMP-9 buffer samples. The detectable limit for MMP-9 was approximately 4 ng/ml with a sample volume of 75 µl. FIG. 7A shows reader values across the entire concentration range of MMP-9, whereas FIG. 7B is an expanded view at MMP-9 concentrations between 0 and 15 ng/ml.

The reader units are displayed in the table below where a value above 400 was deemed a positive result:

| ng/ml MMP9 | reader value |
|---|---|
| 1000 | 6770 |
| 500 | 6729 |
| 250 | 6225 |
| 125 | 5581 |
| 62.5 | 3826 |
| 31.25 | 2029 |
| 15.625 | 882 |
| 7.8125 | 524 |
| 3.90625 | 413 |
| 1.953125 | 343 |
| 0.9765625 | 338 |
| 0 | 312 |

Example 2

Matrix Metalloprotease (MMP) Specificity of a Lateral Flow Format of an Assay Used in the Invention The kit and test strip synthesis were performed as for Example 1.

Various MMP's (Enzo) were prepared in buffer (Aq. Solution of 50 mM Tris, 150 mM sodium chloride, 20 mM sodium azide, 1% vol/vol Tween 20, at pH 8.0) at 0.5 µg/ml.

STEP 1: Each MMP solution was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 8:
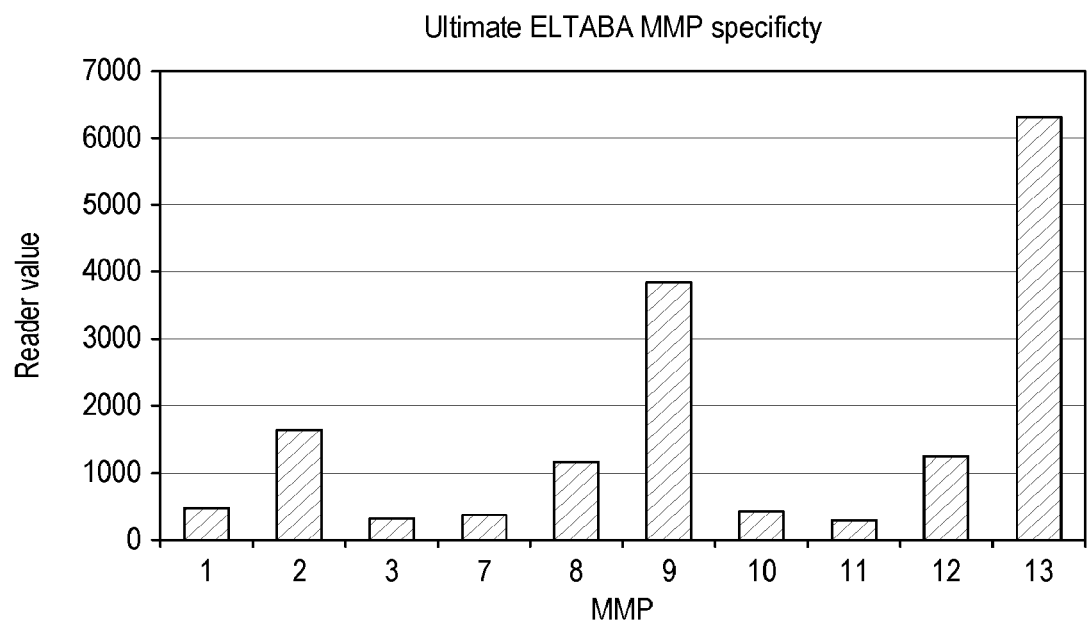
FIG. 8 demonstrates that the specific version of an assay useful in the invention uses a cleavable sequence that is biased towards MMP13, MMP12, MMP9, MMP8 and MMP2. Other versions of the assays of the invention may use sequences with different targets depending on the application required.

FIG. 8 demonstrates that this version of the invention uses a cleavable sequence that is biased towards MMP13, MMP12, MMP9, MMP8 and MMP2. Other versions of this invention may use sequences with different targets depending on the application required.

The table below shows the read-out values for each of the MMPs tested:

| MMP | Reader value |
|---|---|
| 1 | 477.5 |
| 2 | 1608.5 |
| 3 | 336.5 |
| 7 | 373 |
| 8 | 1140.5 |
| 9 | 3844 |
| 10 | 444 |
| 11 | 279.5 |
| 12 | 1252.5 |
| 13 | 6348.5 |

Example 3

Detection of Enzyme Activity in Urine

The kit and test strip synthesis were performed as for Example 1.

Samples were collected from healthy volunteers (9) and from patients suffering from a respiratory disease. Samples were donated from nine patients with Cystic Fibrosis (CF) and seven patients with Chronic Obstructive Pulmonary Disease (COPD) and stored at −80° C. until used.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 9:
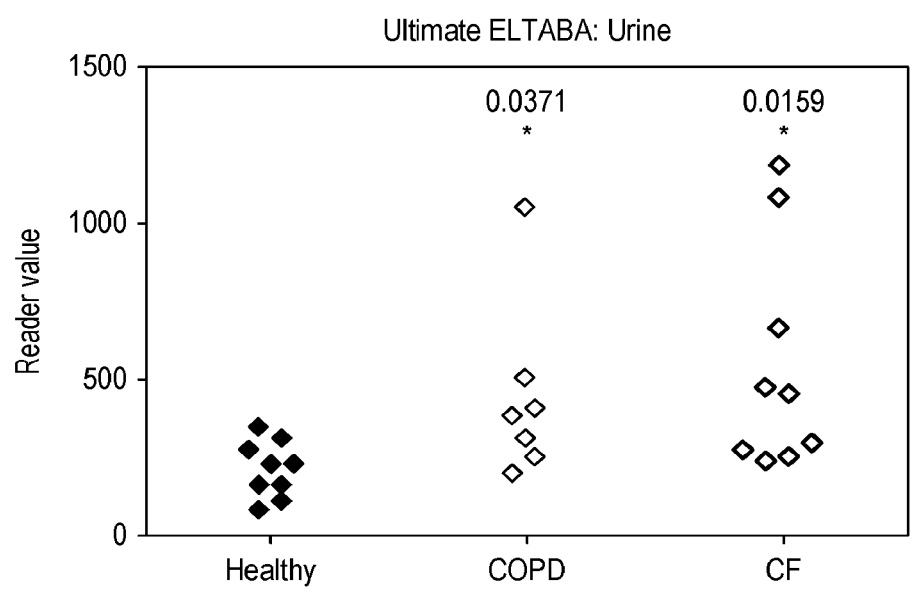
FIG. 9 demonstrates that measurable amounts of active proteases (in particular MMPs, including MMP-9) can be found in urine samples and that higher levels are present in samples obtained from patients with a respiratory disease. A significant difference was observed with COPD samples when compared to samples collected from healthy controls (P=0.03) and CF samples to healthy controls (P=0.01).

FIG. 9 demonstrates that measurable amounts of active proteases (in particular MMPs, including MMP-9) can be found in urine samples and that higher levels are present in samples obtained from patients with a respiratory disease. A significant difference was observed with COPD samples when compared to samples collected from healthy controls (P=0.03) and CF samples to healthy controls (P=0.02).

Example 4

Detection of Enzyme Activity in Wound Fluid

The kit and test strip synthesis were performed as for Example 1.

Wound samples from 18 patients were tested on the ultimate ELTABA device to measure active MMP's in this biologic matrix. The samples were extracted from a swab (Copan, 552C.US) in MMP buffer buffer (Aq. Solution of 50 mM Tris, 100 mM sodium chloride, 10 mM Calcium Chloride, 50 µM 20 mM zinc chloride, 0.025% Brij 35, 0.05% sodium azide at pH 8.0) and then frozen at −20° C. until use. The addition of a chelating agent (5 mM EDTA) determined the specificity of the device to calcium dependent enzymes e.g. MMP's.

STEP 1: Each wound sample was diluted 1 in 20 in MMP buffer and 75 µl was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried biotin attached to the gold particles. Intact indicator molecule was not recognised by the gold conjugate and migrated in an uncomplexed state towards the Polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 10:
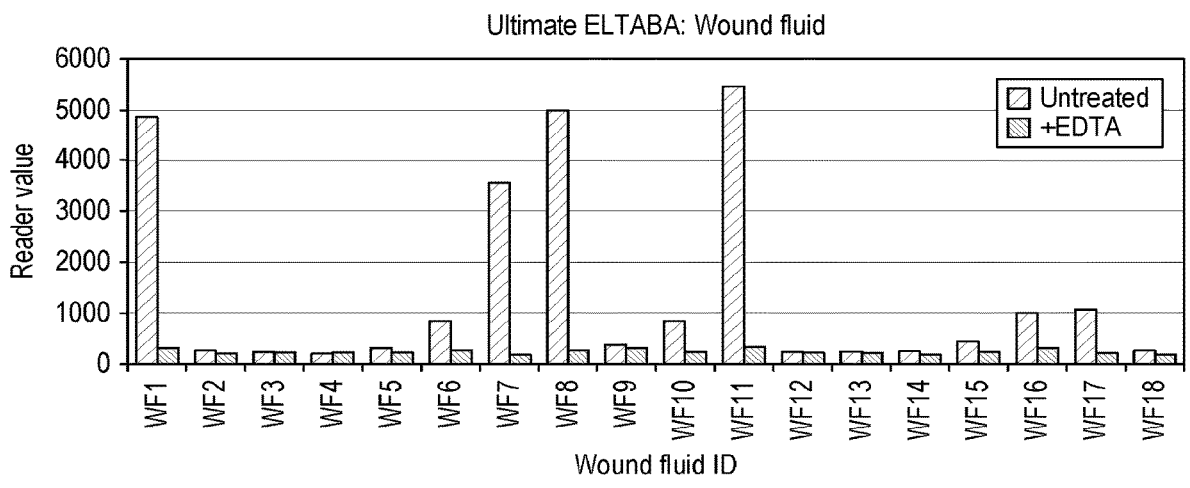
FIG. 10 is a graph comparing the ability of the assay to detect MMP activity in the presence or absence of EDTA. The graph shows that addition of EDTA to the wound samples inhibits the readout, confirming the presence of MMP in the samples and also confirming that the assay is specifically measuring active MMPs.

FIG. 10 shows that addition of EDTA to the wound samples inhibits the readout, confirming the presence of MMP in the samples and also confirms that the assay is specifically measuring active MMPs.

Example 5

Comparison of Sensitivity of the Invention to a Commercial MMP-9 Activity Assay Kit The commercial kit is designed for specifically detecting MMP-9 in biologic samples such as culture medium, serum, plasma, synovial fluid, and tissue homogenate. A monoclonal anti-human MMP is used to pull down both pro and active forms of MMP from the mixture first, and then the activity of MMP9 is quantified using fluorescence resonance energy transfer (FRET) peptide. An MMP-9 standard AMPA activated in-house was run on both the kit and a lateral flow format at a range of 250 ng/ml-4 ng/ml. For the commercial assay the MMP-9 was diluted in an MMP buffer supplied in the kit and a Tris buffer saline 1% Tween20 for lateral flow devices.

The lateral flow kit and test strip synthesis were performed as for Example 1.

Buffer standards were produced containing different concentrations of active MMP-9 (Alere San Diego) ranging from 250 ng/ml down to 4 ng/ml in a Tris buffer saline 1% Tween (Aq. Solution of 50 mM Tris, 150 mM sodium chloride, 20 mM sodium azide, 1% vol/vol Tween 20, at pH 8.0).

STEP 1: Each standard was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with a Forsite Lateral flow device reader. A semi-quantitative scoring system with a scale of 0-10, in which 1 was the lowest detectable colour intensity and 10 was the highest observed colour intensity was used for the visual readings.

Figure 11A:
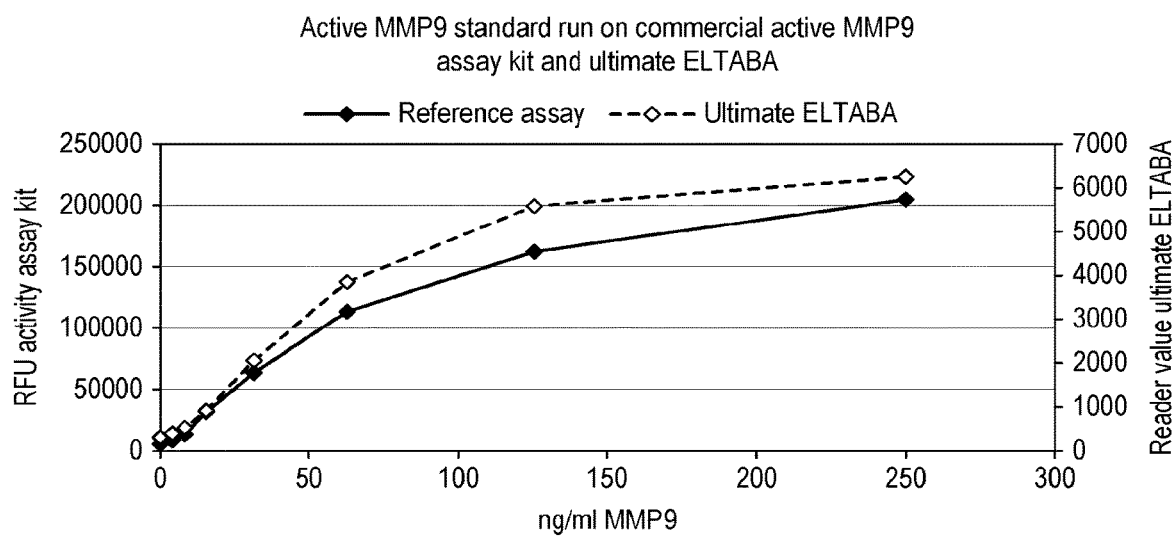
FIGS. 11A and 11B contain graphs comparing the ability of a commercially available active MMP-9 assay kit and the assay of the invention to detect MMP9.
Figure 11B:
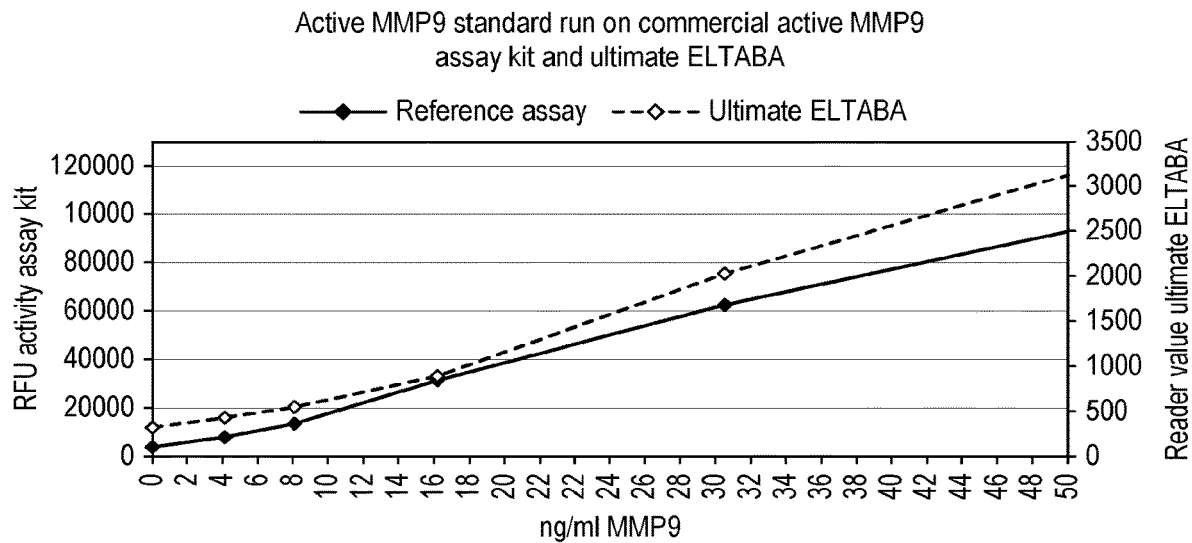

FIG. 11 (FIGS. 11A and 11B) is a graph comparing the ability of a commercially available active MMP-9 assay kit and the assay of the invention to detect MMP9. FIG. 11A shows reader values across the entire concentration range of MMP-9, whereas FIG. 11B is an expanded view at MMP-9 concentrations between 0 and 50 ng/ml. Both figures demonstrate that the lateral flow assay described herein is particularly useful for urine testing according to the invention and produced a steeper curve. According to both assays, colour development as shown by the absorbance values was seen at 4 ng/ml MMP9, the lowest standard tested.

Numerical read-outs for each assay are shown in the table below:

| ng/ml MMP9 | Reference assay | Ultimate ELTABA |
|---|---|---|
| 250 | 204465.5 | 6225 |
| 125 | 162522 | 5581 |
| 62.5 | 112706.5 | 3826 |
| 31.25 | 62301.5 | 2029 |
| 15.625 | 31295 | 882 |
| 7.8125 | 13140.5 | 524 |
| 3.90625 | 7601 | 413 |
| 0 | 3818.5 | 312 |

Example 6

Testing of Substrate in Both ELISA and LF Format

ELISA Format
1) A device for sample collection (e.g. for urine)
2) A 96 well plate coated with polystreptavidin
3) A tube, in which the sample collection device may be placed, together with the indicating molecule.
4) An indicator molecule containing the cleavable sequence, in this example, (GPQGIFGQ) which carries a terminal biotin group connected via a polyethylene glycol spacer/linker which allows it to form a complex with the capture line, polystreptavidin.
5) A sheep antibody CF1522 conjugated to alkaline phosphatase (AP)
6) An Alkaline phosphatase substrate p-nitrophenylphosphate (pNPP) that enables the development of a soluble yellow reaction product that may be read at 405 nm.

Samples were collected from healthy volunteers (9) and from patients suffering from a respiratory disease. Samples were donated from nine patients with Cystic Fibrosis (CF) and seven patients with Chronic Obstructive Pulmonary Disease (COPD) and stored at −80° C. until used.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of sample was added to the streptavidin plate (Nunc, 442404) and incubated for a further 1 hr at ambient where the biotin labelled indicator molecule becomes immobilized by the streptavidin bound to the plate.

STEP 3: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 4: CF1522-AP (Mologic) was diluted 1/500 in 1% BSA in PBST and incubated on the plate for 1 hr at ambient. The antibody will form a complex with the cleaved stubs exposed by any MMP present in the sample and in the absence of the cleaved stub there will be no binding of the antibody.

STEP 5: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 6: The plate was incubated with pNPP substrate and then read at 405 nm after 30 minute incubation at 37° C. An MMP9 standard curve is represented in FIG. 14b used as a reference. The colour of the wells indicate different levels of protease in the test sample represented by the OD 405 nm in FIG. 14b, Lateral Flow Format The kit and test strip synthesis were performed as for Example 1.

Buffer standards were produced containing different concentrations of active MMP-9 (Alere San Diego) ranging from 50 ng/ml down to 0.39 ng/ml and 62.5 ng/ml down to 0.97 ng/ml for the ELISA and lateral flow device respectively.

STEP 1: Each sample was placed in a collection device with a defined amount of peptide (25 ng/test). The collection device was rotated vigorously in order for the sample to mix sufficiently with the substrate solution. This reaction mixture was incubated at ambient temperature for a defined period of time (e.g. 10 minutes).

STEP 2: At the end of the incubation period, a defined volume of liquid was dropped onto the sample receiving pad which subsequently made contact with the conjugate pad and re-hydrated the dried CF1522 antibody attached to the gold particles. Intact indicator molecule was not recognised by the gold conjugate and migrated in an uncomplexed state towards the polystreptavidin test line where it was immobilised via the biotin attached to the indicator molecule. Any MMP-9 present in the sample cleaved the indicator molecule at the cleavage site, exposing the recognisable epitope thus allowing the gold conjugate to form a complex with the cleaved stub.

The lines that were formed were assessed by their relative intensities. The presence of a test line indicated that there was protease present in the test sample. A negative test line indicated a zero or low level of protease that was below the detectable limit. Stages in between these extremes indicated different levels of protease in the test sample. The intensity of the developed coloured lines was measured visually and with an NES Lateral flow device reader.

Figure 12:
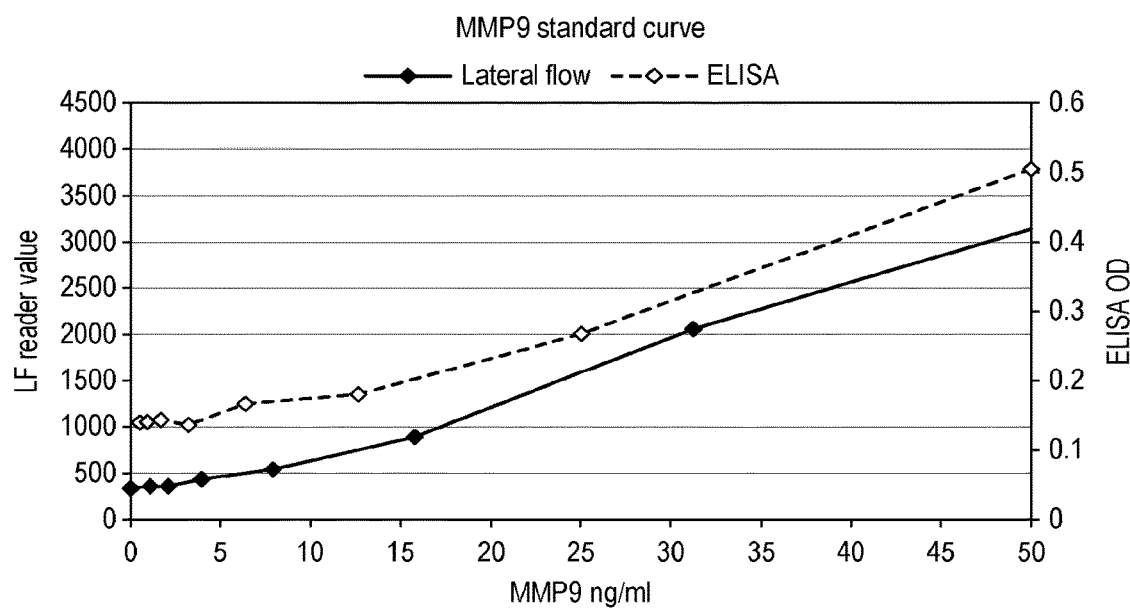
FIG. 12 shows MMP9 standard curves using ELISA and lateral flow embodiments of the invention.

The results of an MMP9 standard curve can be seen in FIG. 12. FIG. 12 demonstrates that the two MMP9 standard curves produced by the ELISA and the Lateral Flow are similar with sensitivity down to 4 ng/ml.

The numerical read-outs from the two assays are also shown in the table below:

| ELISA standard curve | | Lateral Flow standard curve | |
|---|---|---|---|
| ng/ml MMP9 | OD405 | ng/ml MMP9 | Reader value |
| 50.00 | 0.50 | 62.50 | 3826.00 |
| 25.00 | 0.27 | 31.25 | 2029.00 |
| 12.50 | 0.18 | 15.63 | 882.00 |
| 6.25 | 0.17 | 7.81 | 524.00 |
| 3.13 | 0.13 | 3.91 | 413.00 |
| 1.56 | 0.14 | 1.95 | 343.00 |
| 0.78 | 0.14 | 0.98 | 338.00 |
| 0.39 | 0.14 | 0.00 | 312.00 |

Example 7

Synthesis of an Example Indicator Molecule

A peptide termed MOL386 (amino acid sequence: CGPQ-GIFGQC) was synthesised on solid phase using Fmoc-chemistry. Briefly, synthesis was performed on a microwave assisted automated synthesiser (CEM Liberty).Coupling steps were carried out on PEG-polystyrene resin preloaded with Fmoc-Cys(Trt) in DMF solvent with a fivefold excess of amino acid building block, HBTU activator and a tenfold excess of DIPEA base. Deprotection steps were carried out in 5% Piperazine/DMF. Completed peptide resin was dried and then cleaved using 95% TFA, 2.5% TIPS and 2.5% water for 2 hours. TFA liquors were dried in vacuo and precipitated in ether to afford colourless peptide solid.

Figure 16:
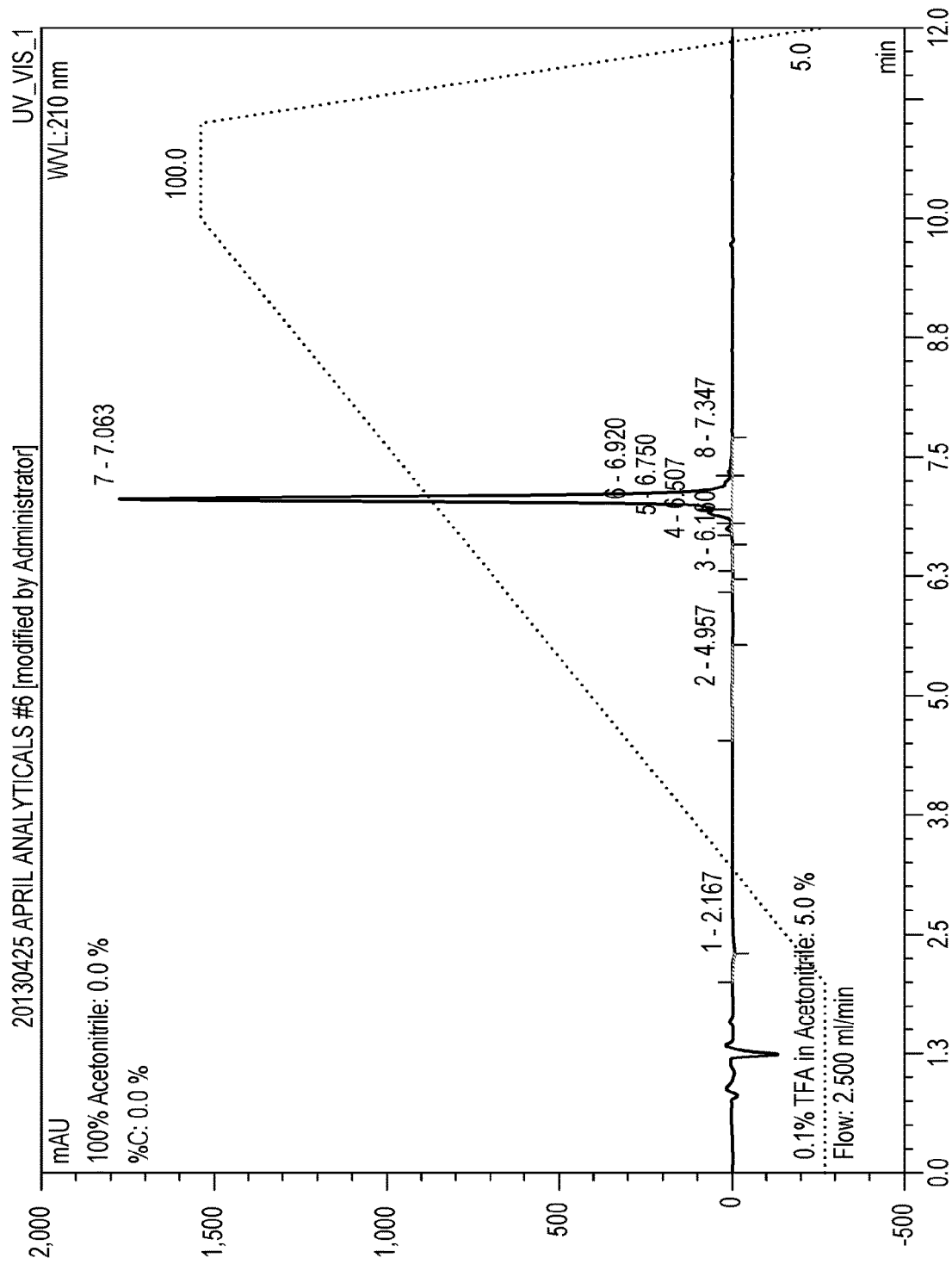
FIG. 16 shows analytical HPLC of the MOL386 peptide.
Figure 17:
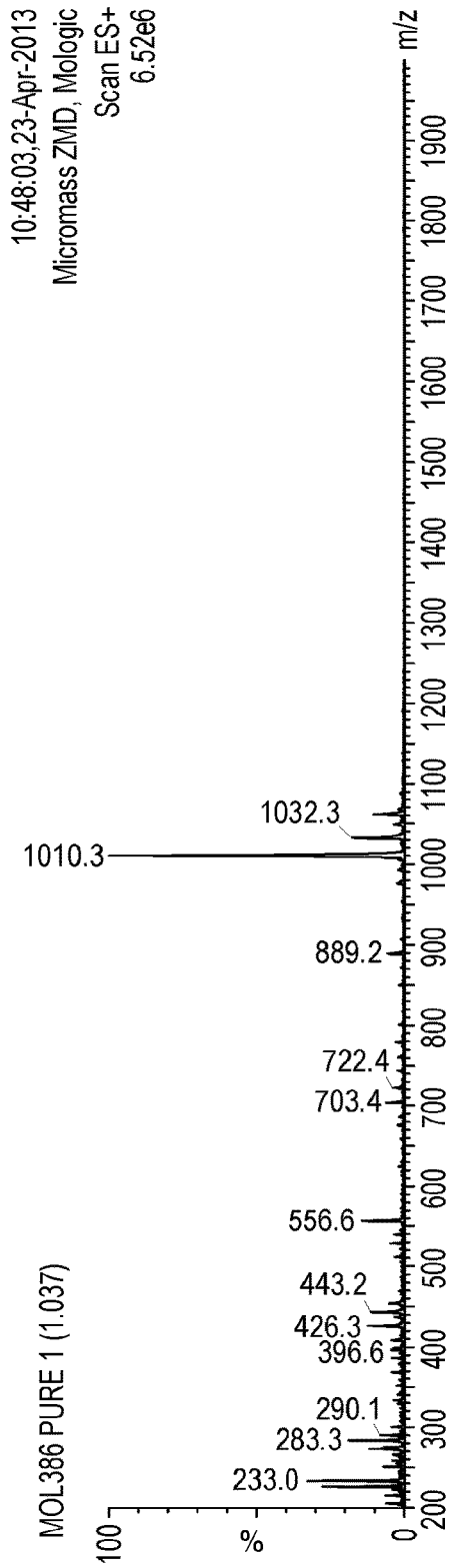
FIG. 17 is a mass spectrum of the MOL386 peptide.
Figure 18:
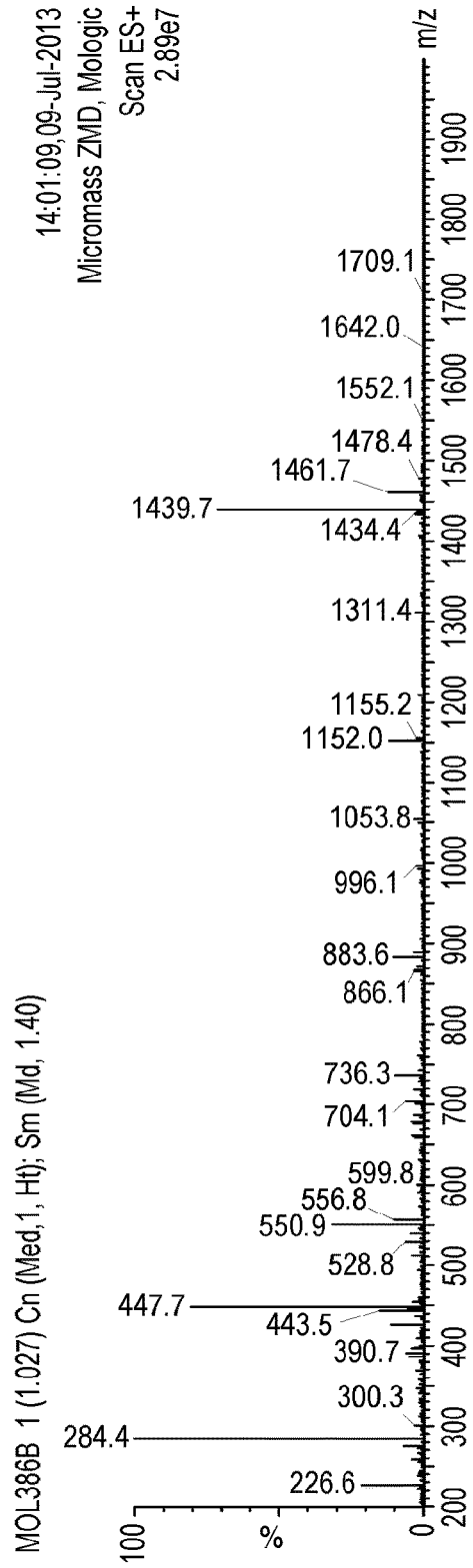
FIG. 18 is a mass spectrum of the MOL386 peptide modified with PEG-biotin.

Recovered peptide was freeze dried from 50% acetonitrile and purified by HPLC (FIG. 16) using a C18 reverse phase column and a gradient of 5% acetonitrile/water (0.1% TFA) to 100% acetonitrile (0.1% TFA). Isolated fractions were combined and freeze dried and analysed by electrospray mass spectrometry (FIG. 17) to identify target peptide (expected MH+ 1010.17, measured 1010.3). The biotinylated form (CGPQGIFGQC-PEG-biotin) was synthesised from preloaded Biotin-PEG-NovaTag Resin (Merck) (expected MH+ 1438.76, measured 1439.7, FIG. 18). The biotin provides a capture site for immobilization of the indicator molecule.

Attachment of the Scaffold Molecule (Synthesis of Cyclised Peptide)

Figure 19:
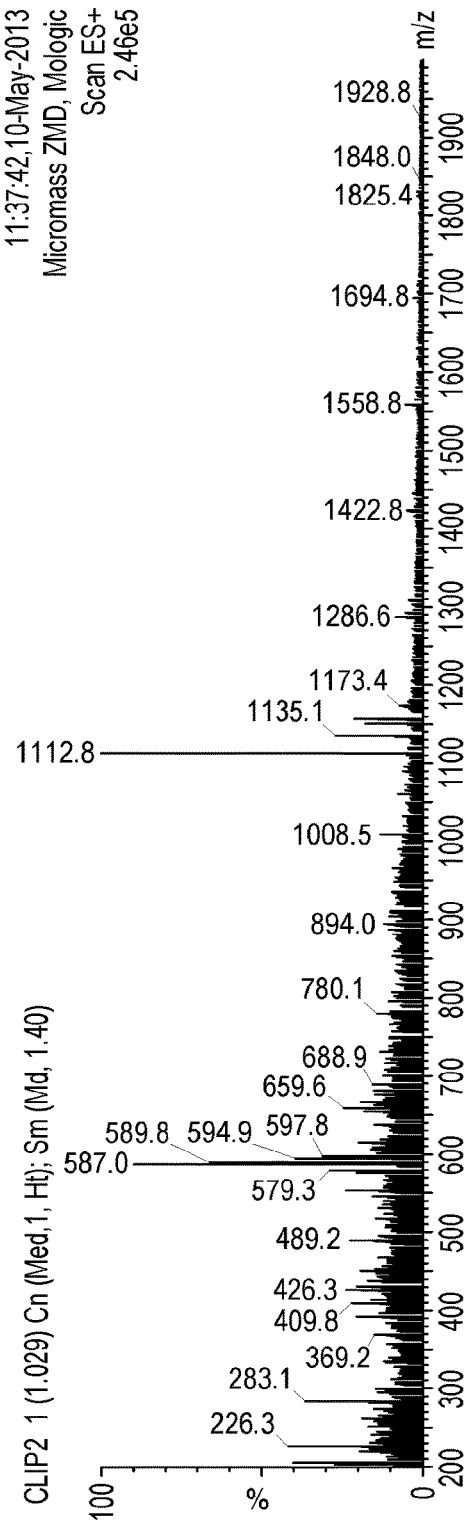
FIG. 19 is a mass spectrum analysis of the cyclised MOL386 peptide.
Figure 20:
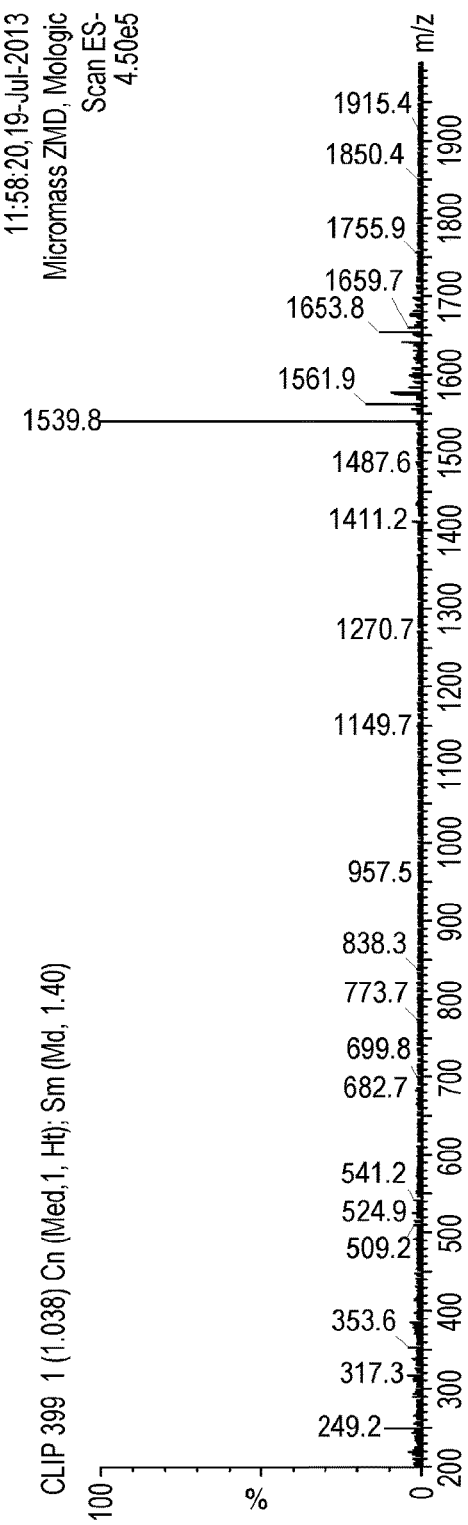
FIG. 20 is a mass spectrum analysis of the cyclised MOL386 peptide modified with PEG-biotin.

Peptide (1 mg) was dissolved in PBS 250 ul along with 1 mg of 1,3-dibromomethylbenzene and agitated gently overnight. The reaction was then diluted with 1 ml of water and injected directly on to HPLC for purification using a C18 reverse phase column and a gradient of 5% acetonitrile/water (0.1% TFA) to 100% acetonitrile (0.1% TFA). Product peak was isolated and freeze dried to afford a colourless solid (expected MH+ 1112.30, measured 1112.8, FIG. 19). The same procedure was used for the biotinylated peptide (expected MH+ 1540.89, measured 1539.8, FIG. 20).

Example 8

Test Format Generation

Antibodies were generated to recognise a cleaved peptide sequence. In this example (GPQGIFGQ), a target for MMP digestion, is used in an immunoassay to measure the enzyme activity in a clinical sample. The antibodies were raised to peptide KLH conjugates using methods known to those skilled in the art. Sheep antibodies CF1522 and CF1523 were generated to recognise cleaved stub 'IFGQ' whereas sheep antibodies CF1524 and CF1525 were generated to recognise cleaved stub 'GPQG'. The antibodies were affinity purified using the specific peptides they were raised against and then analysed by ELISA to determine the most appropriate assay format to give the best sensitivity.

Peptides containing the cleavable sequence (GPQGIFGQ) were synthesised with a biotin or Pegylated biotin attached to either the C-terminus (MOL038 and PCL008-A2 respectively) or the N-terminus (MOL310 and MOL378 respectively).

| Peptide | Sequence |
|---|---|
| MOL038 | Biotin-GPQGIFGQESIRLPGCPRGVNPVVS SEQ ID NO: 3 |
| PCL008-A2 | Biotin-PEG-Asp-AEEAc-AEEAc-GPQGIFGQESIRLPGCPRGVNPVVS SEQ ID NO: 4 |

| Peptide | Sequence |
|---|---|
| MOL310 | SIRLPGCPRGVNPVVSGPQGIFGQ-Biotin SEQ ID NO: 5 |
| MOL378 | SIRLPGCPRGVNPVVSGPQGIFGQ-AEEAc-AEEAc-PEG-Asp Biotin SEQ ID NO: 6 |

The peptide can be anchored to either streptavidin capture via the biotin or to sheep antibody CF1060 capture via the ALP sequence. The proposed formats shown schematically in FIG. 1 were evaluated.

ELISA Format
1) A device for urine sample collection
2) A 96 well plate coated with polystreptavidin (Nunc, 442404) or CF1060 overnight at ambient (Nunc, Maxisorb)
3) A tube, in which the sample collection device may be placed, together with the indicating molecule.
4) An indicator molecule containing the cleavable sequence, in this example, (GPQGIFGQ) which carries a terminal biotin group which may be connected via a polyethylene glycol spacer/linker on the N or the C-terminus.
5) Sheep antibodies CF1522, CF1523, CF1524 and CF1525 conjugated to alkaline phosphatase (AP)
6) An Alkaline phosphatase substrate p-nitrophenylphosphate (pNPP) that enables the development of a soluble yellow reaction product that may be read at 405 nm.

Active MMP9 (Alere San Diego) was diluted to 2, 0.25, 0.062, 0.0156 and 0.039 µg/ml in MMP buffer (Aq. Solution of 50 mM Tris, 100 mM sodium chloride, 10 mM Calcium Chloride, 50 µM 20 mM zinc chloride, 0.025% Brij 35, 0.05% sodium azide at pH 8.0)

STEP 1: Each MMP9 standard was placed in a collection device with a defined amount of each peptide (20 ng/test). The collection device was rotated vigorously in order for the sample to mix sufficiently with the substrate solution. This reaction mixture was incubated at ambient temperature for a defined period of time (e.g. 30 minutes).

STEP 2: At the end of the incubation period, a defined volume of sample was added to the streptavidin plate and CF1060 sensitised plate and incubated for a further 1 hr at ambient where the peptides becomes immobilized by the streptavidin or CF1060 bound to the plate.

STEP 3: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

STEP 4: sheep antibodies conjugated to Alkaline Phosphatase (Mologic) were diluted 1/500 in 1% BSA in PBST and incubated on the plate for 1 hr at ambient. The antibody will form a complex with the cleaved stubs exposed by any MMP9 present in the sample, in the absence of the cleaved stub there will be no binding of the antibody.

STEP 5: The plate was washed 3 times with 100 µl in a wash buffer, Tris buffer saline 0.1% Tween (Aq. Solution of 50 mM Tris, 150 mM sodium chloride, 20 mM sodium azide, 0.1% vol/vol Tween 20, at pH 8.0).

Figure 21:
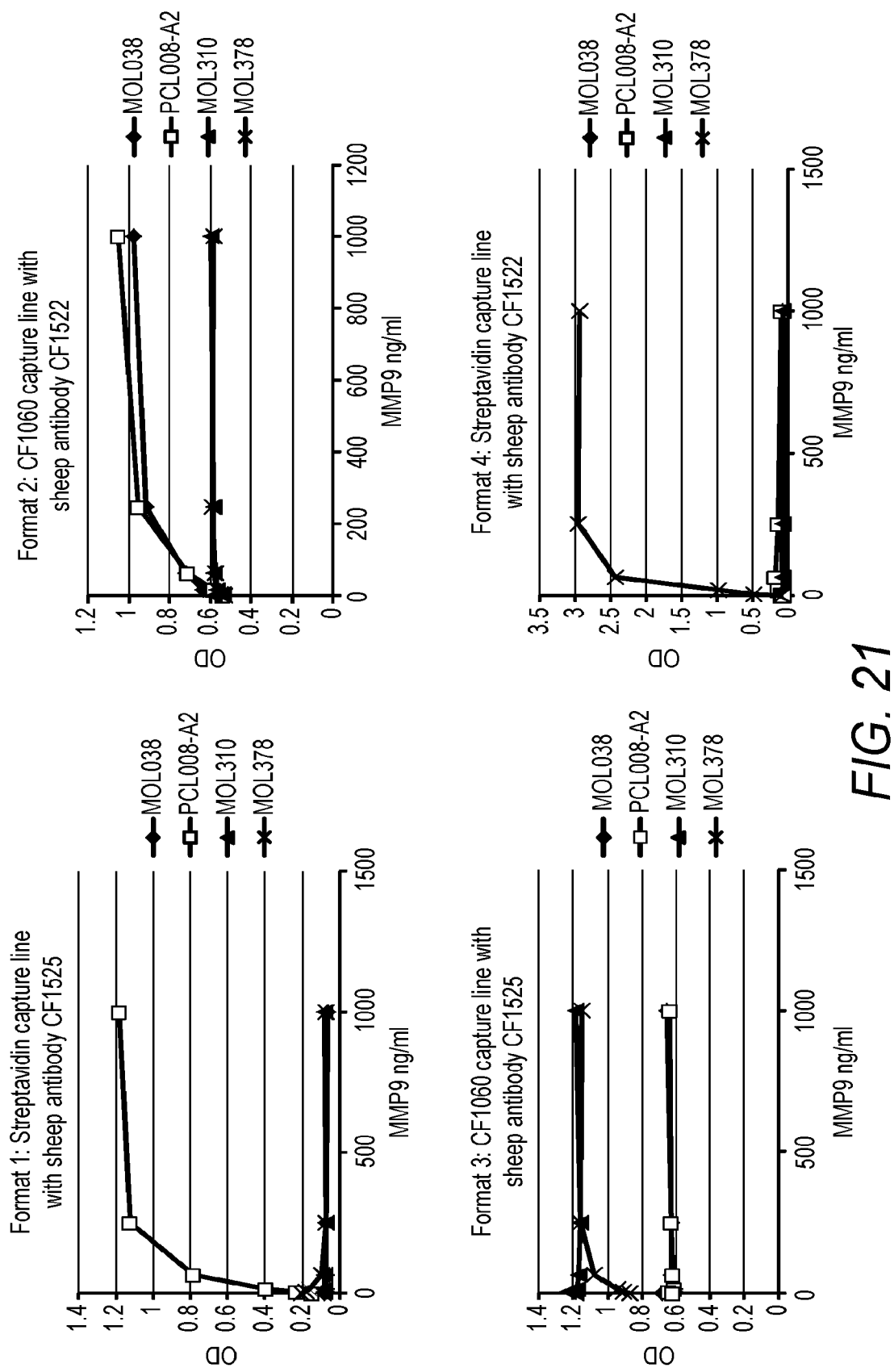
FIG. 21 shows MMP9 standard curves for all combinations shown in FIG. 1.

STEP 6: The plate was incubated with pNPP substrate and then read at 405 nm after 30 minute incubation at 37° C. MMP9 standard curves are represented in FIG. 21 for all combinations. A difference in colour of the wells indicates different levels of protease in the test sample represented by the OD 405 nm.

Figure 22:
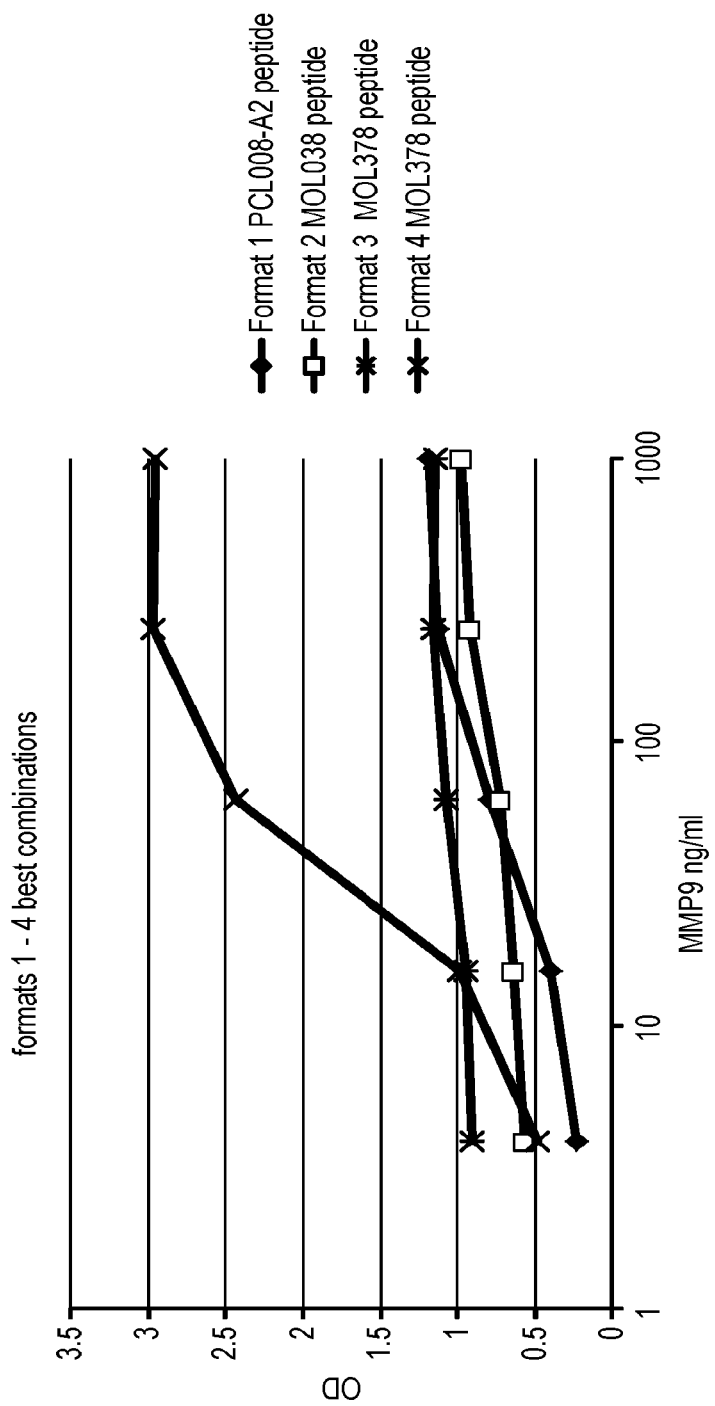
FIG. 22 presents the performance of the best combinations derived from the results shown in FIG. 21.
Figure 23:
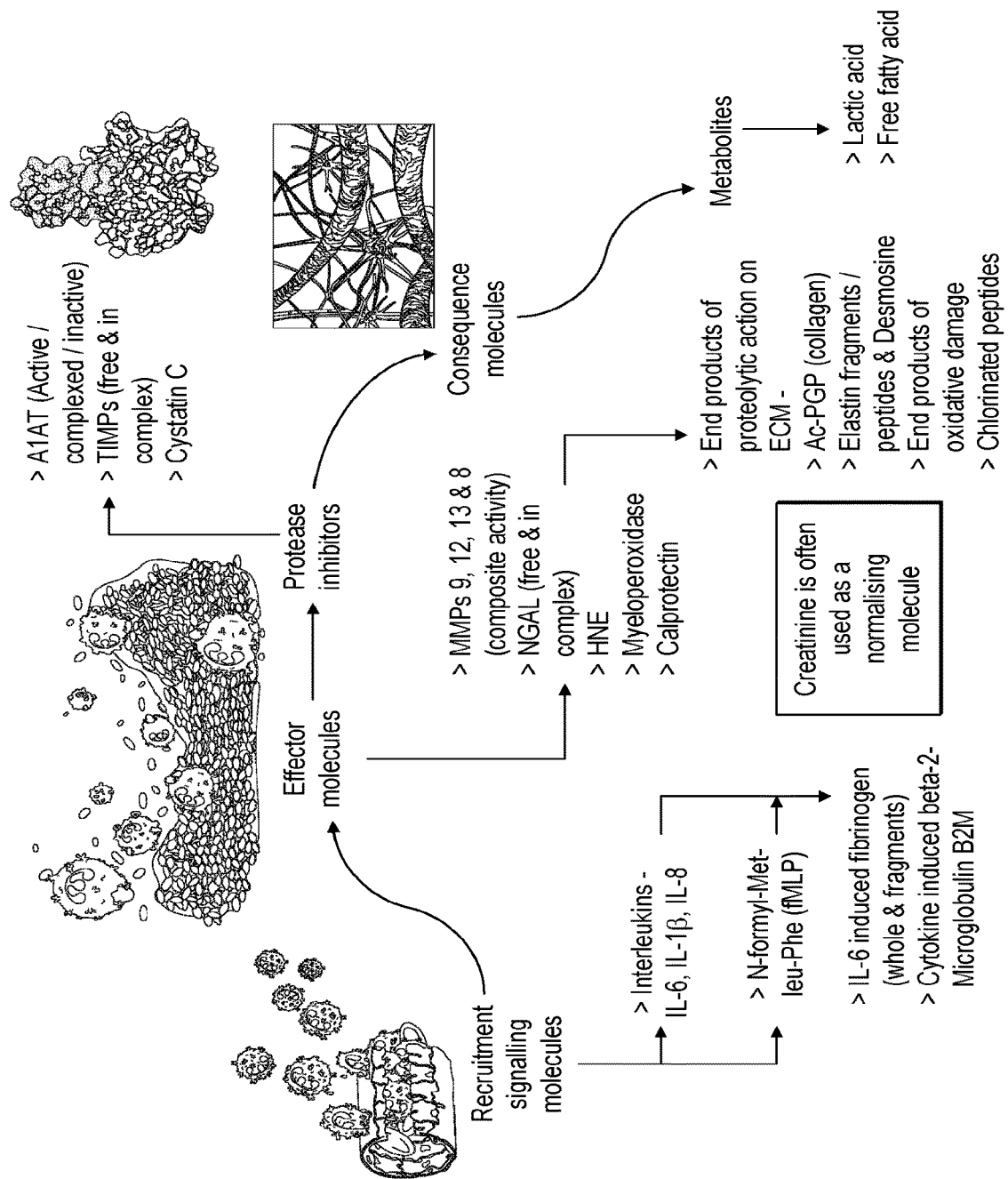
FIG. 23—An indication of inflammation biomarkers useful in the invention, including in combination. The markers are categorised according to the inflammatory pathway and reflect the neutrophil activation processes that characterise pulmonary exacerbation.

FIG. 21 shows the results of testing each format. With a streptavidin capture line, the selected peptide is MOL378 with sheep antibody CF1522 and PCL008-A2 with sheep antibody CF1525 as predicted. Both peptides contained a PEG-Asp-AEEAc-AEEAc required to reduce any steric hindrance. With a CF1060 capture line, the selected peptide is MOL038 or PCL008-A2 with sheep antibody CF1522 and MOL378 with sheep antibody CF1525 as predicted. The performance of the best combinations is shown in FIG. 22. Here, format 4 using sheep antibody CF1522 with peptide MOL378 shows the most promise.

Example 9

Rationale

Acute exacerbations of chronic obstructive pulmonary disease (AECOPD) involve both proteolytic alveolar destruction and systemic inflammation. Inflammatory proteins, proteinases, and their breakdown products have been extensively investigated as systemic markers of AECOPD, and some are excreted in a detectable state in urine, providing the opportunity to develop a minimally-invasive biomarker test of AECOPD.

Other groups have found urinary excretion levels of elastase breakdown products to be higher in AECOPD patients compared to patients with stable COPD, but only a few studies of small cohorts have investigated renal biomarker excretion in patients sequentially experiencing both AECOPD and stable phase COPD.

We aimed to identify a urinary biomarker of AECOPD. Objectives were to 1) identify biologically plausible urinary biomarkers and 2) compare biomarker excretion at exacerbation and at stable state in a longitudinal study of patients admitted with AECOPD.

Methods

73 COPD patients admitted to hospital with AECOPD were invited to take part in the study and gave written informed consent to participate. Medical history, examination and urine sampling were conducted at time of exacerbation (day 0) and at day 56 when patients were clinically well.

A panel of candidate urinary biomarkers of AECOPD was chosen, based on recent publications and a rational analysis of inflammation biochemistry and cytology. Candidates included proteinases, proteinase inhibitors and interleukins. Biomarker levels at day 0 and day 56 were quantified using a range of ELISA or in house assay designs.

At time of analysis, day 0 and day 56 data were available for 34 patients. Biomarker levels at exacerbation and stable state were compared using paired t-tests and Wilcoxon tests for normal and non-normal data respectively. Multiple hypotheses testing corrections were applied to all significance cut-off values.

Results

TIMP1, a tissue inhibitor of metalloproteinases, and cystatin c, a lysosomal proteinase inhibitor, were excreted in the urine at significantly higher levels during exacerbation compared to stable state (n=34, Wilcoxon signed rank test p=0.005 and p=0.013 for TIMP1 and cystatin c respectively).

Conclusion

The significant increase in levels of urinary TIMP1 and cystatin c during AECOPD above the levels observed during subsequent stable COPD may reflect responses to increased pulmonary proteinase activity. These findings warrant further investigation of these proteins as biomarkers of AECOPD.

Example 10

Urinary Biomarkers at Exacerbation of Chronic Obstructive Pulmonary Disease

Introduction

There is an unmet need for a reliable biomarker of a COPD exacerbation that can alert patients to seek medical care, guide therapeutic interventions and validate these events during clinical trials. The minimum requirement of any biomarker is a change at exacerbation. The aim of this study was to determine a set of candidate urinary biomarkers that respond at exacerbation.

Methods 50 patients (35 male) were recruited from the London COPD cohort. They were aged 73.2 years (SD 7.1) and had a FEV1 as % predicted of 49.0% (SD 17.6) and FEV1/FVC ratio=47.7 (13.7). Sixty-five urine samples were collected within 3 days (IQR 2-5) of the symptomatic onset of exacerbation. Each exacerbation had a separate baseline sample taken a median of 91 days prior to onset (IQR=39-132). Lung function and blood samples were taken at each clinic visit.

Urinary biomarkers were measured in a combination of in-house assays (Mologic Ltd, Thurleigh, UK) and commercial assay kits. The assay systems, ELISA, Lateral flow, substrate assays and zymography, were all optimised to ensure high precision and accuracy while also delivering the sensitivity and specificity required to detect biological levels of each biomarkers in urine.

Results

Of the 65 exacerbations: 45 were treated with antibiotics and oral corticosteroids; 9 with antibiotics alone; 6 with oral corticosteroids alone; 4 with increased corticosteroid and/or beta-2 agonist inhaler use.

Between baseline and onset, FEV1 fell from 1.27 to 1.22 l (t-test p=0.027; n=57) and c-reactive protein in plasma rose from 3 mg/dl (1-7) to 5 (3-28) (p<0.001; n=60). There was no change in heamatocrit (0.42 vs 0.41; p=0.337) suggesting that plasma volumes were unchanged.

Table 1 shows 23 urinary biomarkers—twelve of which changed significantly (wilcoxon signed-rank test; p<0.05) at exacerbation.

Conclusion

Urine is a potential source of biomarkers that can detect COPD exacerbations and also possibly assess their severity. This approach may have direct application to the home monitoring and management of COPD exacerbations.

TABLE 1

Urinary biomarkers at baseline and exacerbation.

| Biomarker (ng/ml) | unit | Baseline (median) | IQR | Onset (Median) | IQR | Wilcoxon signed-rank test p-value |
|---|---|---|---|---|---|---|
| MMP substrate | ng/ml | 0 | (0-1.6) | 0 | (0-4.0) | 0.059 |
| HNE substrate | ng/ml | 7 | (0-34) | 8 | (0-24) | 0.775 |
| MMP8 Total | ng/ml | 0 | (0-0) | 0 | (0-1.4) | 0.092 |
| MMP9 Total | ng/ml | 0.51 | (0-2.7) | 0.96 | (0-3.4) | 0.926 |
| TIMP1 | ng/ml | 2.1 | (0.7-5.5) | 2.6 | (1.1-6.3) | 0.357 |
| TIMP2 | ng/ml | 2.4 | (1.1-4.6) | 3.5 | (1.9-6.0) | 0.001 |
| NGAL | ng/ml | 26.5 | (0-44) | 32.7 | (0-68) | 0.042 |
| HNE | ng/ml | 0 | (0-41) | 11.3 | (0-76.2) | 0.797 |
| A1AT | ng/ml | 36 | (14.9-108) | 77.4 | (12.4-165.4) | 0.011 |
| A1AT LF | ng/ml | 64 | (36-126) | 96 | (50-270) | 0.027 |
| Desmosine ELISA F1 | ng/ml | 0.9 | (0-2.8) | 1.6 | (0.5-4.5) | 0.019 |
| Desmosine LF | ng/ml | 31 | (7-55) | 40 | (10.5-75) | 0.071 |
| Fibrinogen | ng/ml | 10.9 | (7-26) | 17.9 | (8.9-39.4) | 0.151 |
| IL-6 | pg/ml | 1.9 | (0-3.3) | 2.7 | (0-5.5) | 0.003 |
| IL-8 | pg/ml | 18 | (10-49) | 20.2 | (7.6-78.5) | 0.427 |
| Calprotectin | ng/ml | 25 | (12-52) | 28.9 | (13.2-60.7) | 0.565 |
| FMLP | ng/ml | 0.8 | (0.5-1.4) | 0.9 | (0.5-2.1) | 0.024 |
| IL1b | pg/ml | 1.2 | (0-6.2) | 1.9 | (0-6.5) | 0.660 |
| Creatinine | mg/ml | 84 | (48-104) | 92.7 | (71-131) | 0.004 |
| Cystatin C | ng/ml | 58 | (41-85) | 60 | (46-102) | 0.012 |
| H.S.A | ng/ml | 1353 | (736-2415) | 1575 | (873-3530) | 0.046 |
| RBP4 | ng/ml | 134 | (93-186) | 140 | (105-213) | 0.050 |
| beta 2 Microglobulin | ng/ml | 60 | (31-121) | 101 | (47-203) | 0.005 |

Figure 25:
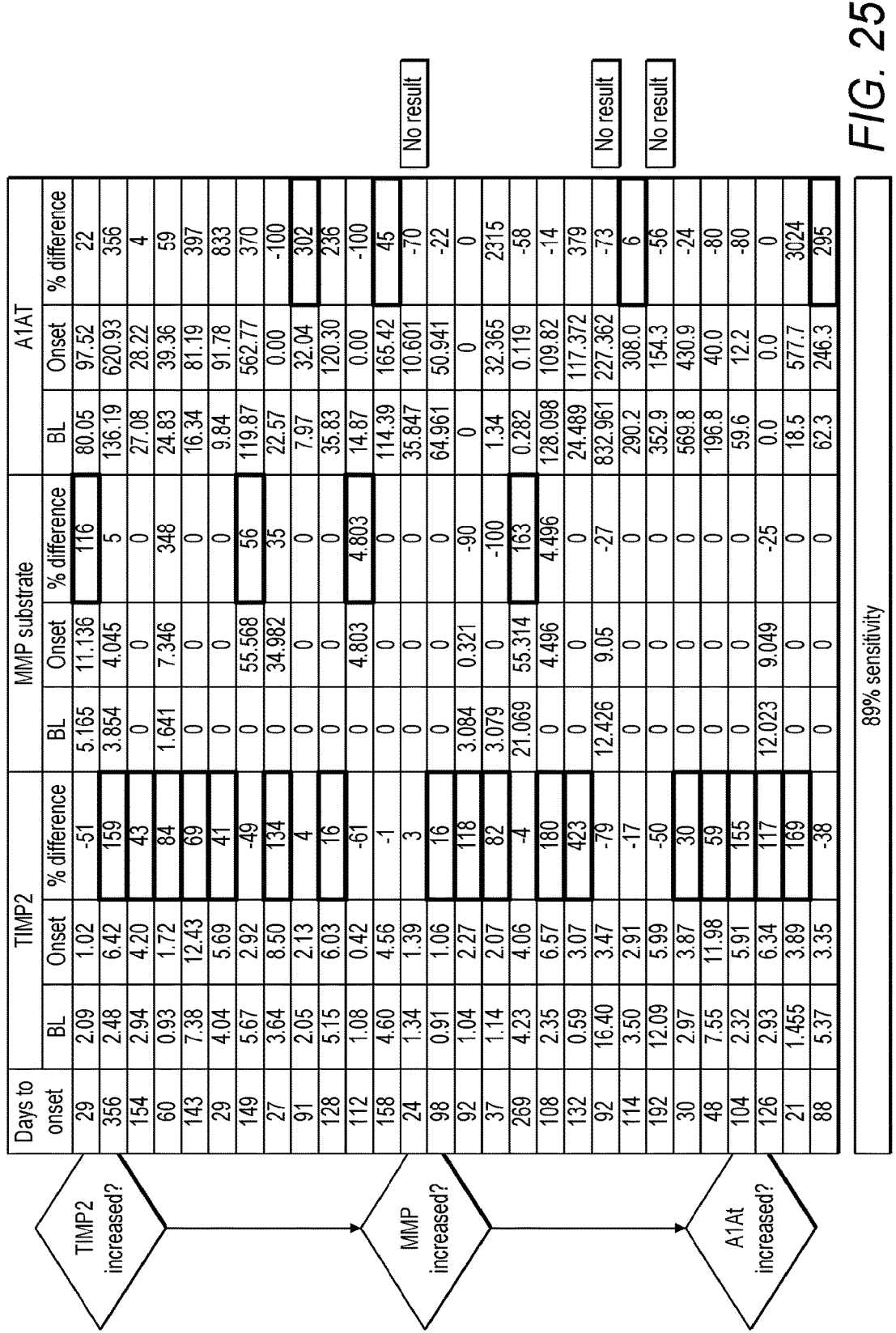
FIG. 25—Showing performance of the MMP/TIMP/A1AT cluster in terms of identifying onset of a COPD exacerbation.

FIG. 25 illustrates an initial analysis (or provisional algorithm) of biomarker testing results from urine samples donated by 28 COPD patients (from the London COPD cohort). The results included in this table are for three biomarkers relating to the balance between neutrophil derived proteases and the protease inhibitor shield—TIMP2, MMP substrate (activity) and A1AT. The outcome was part of the selection process for the biomarkers to be used as the basis of the algorithm shown in FIG. 24. Each patient donated a first sample during a period of stable disease and second sample at a later date, when they were experiencing a clinically confirmed episode of pulmonary exacerbation. The first column in the table indicates the timing of the "stable" sample in terms of number of days that elapsed before the start of the exacerbation episode. There are three columns for each of the three biomarkers. The first, headed "BL" (Base Line) shows the value for that biomarker in the sample donated during stable disease. The second column, headed "Onset", shows the value for that biomarker in the sample donated during exacerbation. The third column shows the Onset value expressed as a percentage of the BL value.

The objective of this provisional algorithm was to answer the following question: "In how many of the 28 patients is an exacerbation accompanied by a rise in the value of at least one of the three biomarkers?"

The process followed was a sequential search for alternative biomarker values that are raised individually at the time of exacerbation. This identifies which biomarkers are appropriate to include in an algorithm for subject monitoring. By reference to the table and the three sequential questions in the triple component flow chart on the left hand side, it is possible to follow the process for each patient. Taking patient 356, for example, the reader can start to scan across the nine numerical values, seeking the answer to the first question—"Is TIMP2 increased?". At the third column, the question is answered with a "yes", at which point the search is complete for patient 356, for the purpose of this provisional algorithm (even though both MMP substrate and A1AT were also raised). In a more complex algorithm increased levels of the additional markers would also be taken into account in terms of outcome of the test (e.g. in the manner described with reference to FIG. 24).

Repeating the process for patient 29, the answer for TIMP2 is "No", but a "Yes" answer comes for MMP substrate. For patient 91, Both TIMP2 and MMP substrate return "No" answers, but A1AT returns a "Yes". Only three patients (numbers 24, 92 and 192) returned "No" answers for all three biomarkers, giving the overall result of 89% of samples in which at least one of the three biomarkers was raised in exacerbation. This was considered to be a suitable basis for a full algorithm, in which certain additional factors (as described in relation to FIG. 24) are included.

Figure 26:
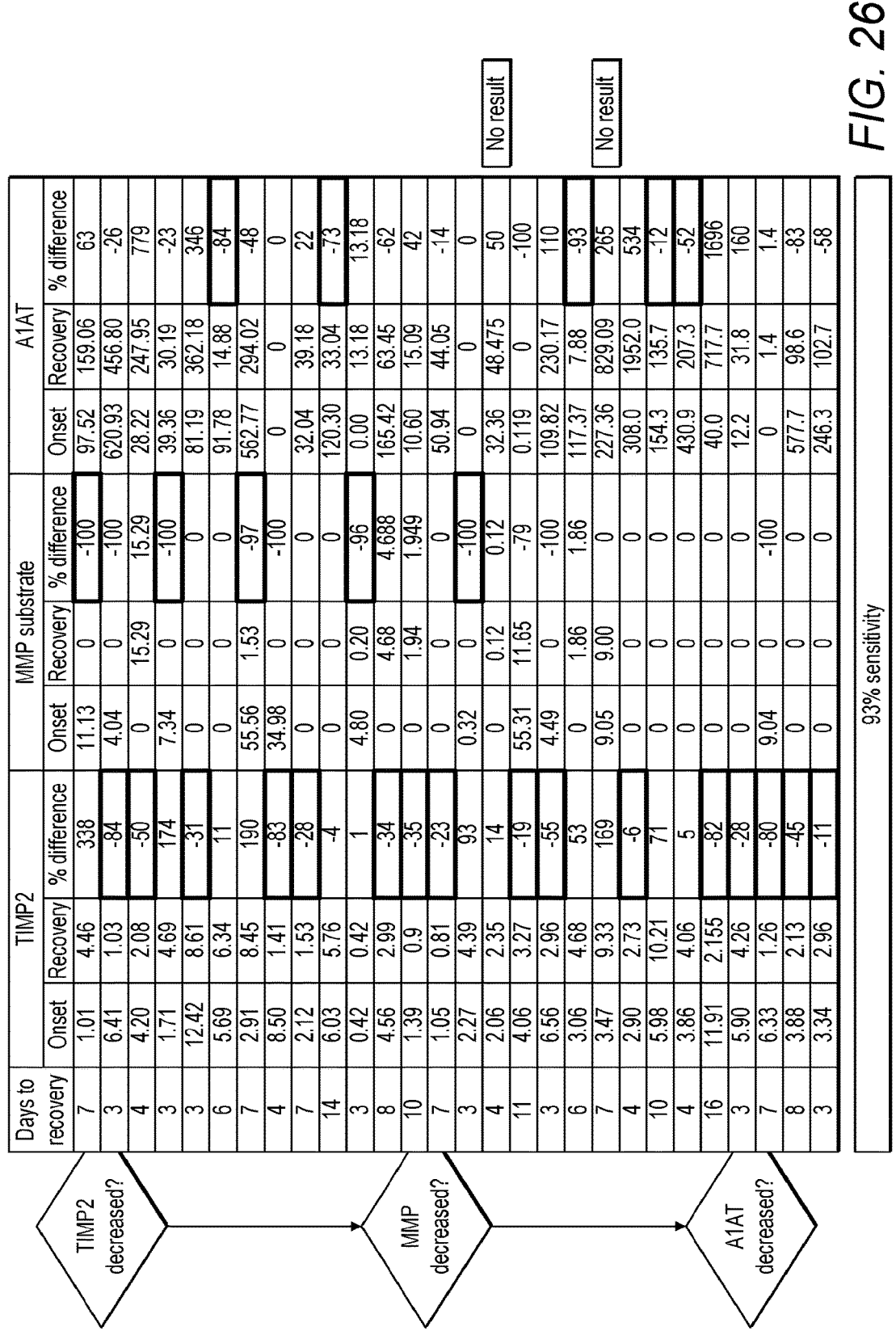
FIG. 26—Showing performance of the MMP/TIMP/A1AT cluster in terms of identifying recovery from a COPD exacerbation.

FIG. 26 illustrates a provisional algorithm which is closely similar to that shown in FIG. 25. In this case, the two samples covered the opposite clinical event—recovery from exacerbation and return to a stable disease state. Thus the reasoning and process applied to FIG. 25 also apply here, except that the questions relate to a decrease in biomarker value, rather than an increase. The underlying question is: "In how many of the 28 patients is a recovery from exacerbation accompanied by a decrease in the value of at least one of the three biomarkers?". This was considered to be an important question to answer because it has a major bearing on the credibility of the biomarker choice. If the majority of the patient samples did not reveal a decrease in one or more of the three biomarkers on recovery from exacerbation, then their essential association with exacerbation would not be validated.

The results shown in FIG. 26 confirm the validity of the three biomarkers, with only 2 of the patients returning a "No" answer for all three biomarkers. This can be defined as an overall 93% sensitivity.

FIG. 27 is based on the same underlying rationale as that of FIG. 25, but the data is simplified by only showing the percentage change in biomarker values, rather than including the two absolute values from which the percentages were derived. As with FIG. 25, the differences were between samples taken during stable disease on the one hand and samples taken at exacerbation on the other. The purpose of this figure is to further illustrate the robustness of the combined, triple (protease-related) biomarker set in working as a diagnostic index that correlates with exacerbation. Sixteen of the 28 patients whose exacerbation events were tracked in FIG. 25 had also provided a second "stable" and "exacerbation" sample pair. These second samples were donated either before or after the exacerbation episodes featured in FIG. 25. In the table, the time interval between the previously studied episode and this episode is listed in the column headed "Days since recovery". A negative value indicates that the samples were taken before the FIG. 25 episode, and samples taken afterwards do not have a negative value.

The data for each exacerbation episode are contained in rows, started by the identity number of the sample pair. The next 3 columns list the percentage difference values previously observed in the data set reported in FIG. 25. For example, in the "ID 1" row, the first three percentage values are the same as those in the first row of FIG. 25 (−51, 116 and 22), indicating that these values were from the same patient. In the next column, the value of 140 indicates that the next exacerbation had occurred in that patient 140 days after recovery. The final three columns of the row indicate the percentage difference between the stable and exacerbation values in the second exacerbation episode. For ID 25 data, it can be seen that the second sample pair analysed (in the final 3 columns) had been donated 320 days before the sample pair reported in FIG. 25, as indicated by the minus sign.

These results confirm the robustness of the combined, triple (protease-related) biomarker set, because the sensitivity was calculated to be 94% in this group of independent, repeat exacerbation events in 16 of the same patients.

Figure 28:
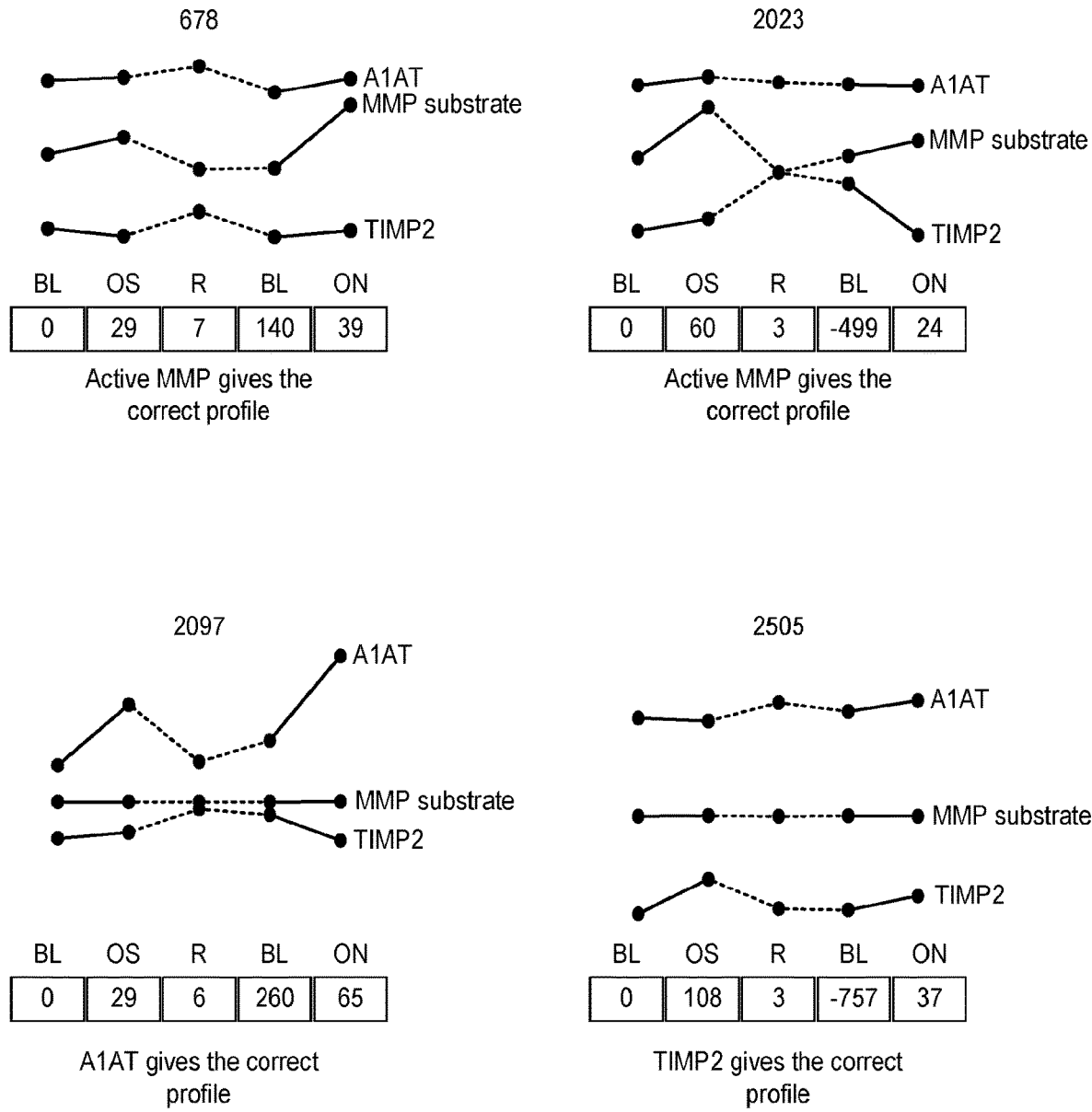
FIG. 28—Showing examples of some personal profiles. Each sample is graphed as a percentage difference from the first baseline (BL) sample (no scale)

FIG. 28 shows some of the data trends behind the values presented in FIG. 27 presented in a different way to illustrate the profiles of biomarker concentrations through repeat exacerbations. The purpose of this figure is to highlight the value of personalised thresholds and patient-specific baseline values. Four examples are displayed, each one of which shows 5 data points for each of the three biomarkers. For the sake of clarity and simplicity, there is no vertical axis, as the key points can best be made without specific, absolute values. The graphs display the fluctuations and trends. The values in each curve are normalised against the first value (at baseline 1 (BL)).

The following abbreviations are shown on the horizontal axes, defining the points at which urine samples were taken (in this order):
BL (BaseLine 1)
OS (OnSet 1)
R (Recovery)
BL (BaseLine 2)
ON (Onset 2)

Note that the horizontal axis is not calibrated in elapsed time, as each sampling event is given the same spacing from the next, regardless of the size of the interval between them. However, the intervals are defined by the set of numbers beneath the horizontal axis. Each number defines the number of days between its position and the position preceding it.

Thus, turning to the graph set under the 678 heading, it can be seen that the first BL has the number 0 beneath it, because there are no preceding events. The OS (1st onset) sampling event took place 29 days after the 1st BL sampling event, as shown by the number beneath it. The R (recovery) sample was taken 7 days later, and so on.

The axis of the 2023 graph set is slightly different, in that the day number under the second BL is a minus number (−499). This indicates that the so-called "second exacerbation" BL sample was, in fact, collected 499 days before the first BL. The exacerbation sample "ON" was collected 24 days after the −499 day BL sample. Although this may seem un-necessarily confusing, it is presented in this way because this is the order in which the data was generated and, hence the order in which the discoveries were made.

Turning to the curves in each graph set, it can be seen that for patient 678, the biomarker which most closely tracked the exacerbation history was MMP activity (MMP substrate), because there are clear increases in level at both exacerbations. The same is true for patient 2023. For patient 2097, the systemic protease inhibitor, A1AT is strikingly efficient at tracking exacerbations. For patient 2505, TIMP2 is the most efficient biomarker for tracking exacerbation.

Taken together these results indicate that:
each of the three biomarkers can function alone as an exacerbation-tracking biomarker in specific patients.
the three biomarkers are good choices for inclusion into an integrated algorithm.

To maximise sensitivity of the approach for all subjects, it is advantageous to apply more frequent sampling to determine subject specific baseline (BL) values and to utilise these values to calculate rolling baseline and threshold values from which to determine meaningful trends away from the baseline at exacerbation. These approaches are discussed herein in further detail. Nevertheless, the trends observed provide justification for the approach taken and specific markers selected.

Figure 29:
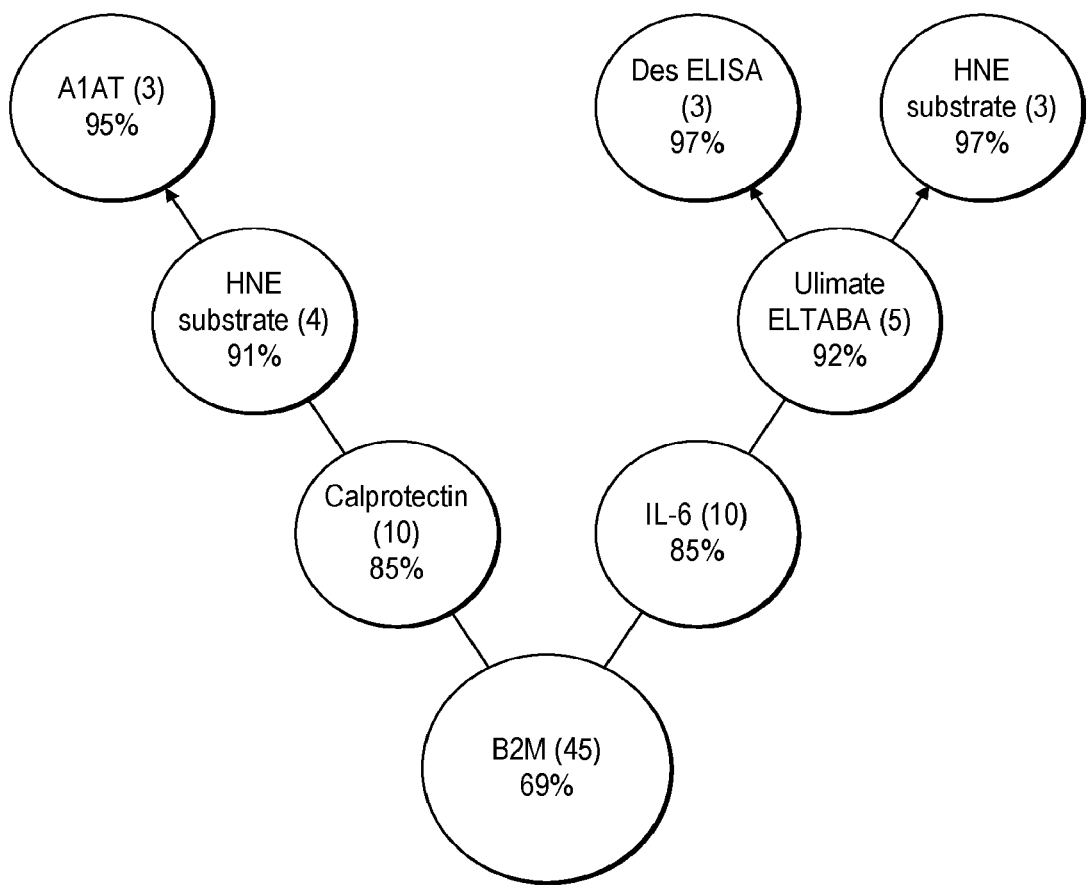
FIG. 29—Showing performance of various marker combinations for identifying a pulmonary exacerbation. Additional markers increase the sensitivity of detection as shown by the percentage values.

FIG. 29 illustrates the various biomarker clusters that can be formed to achieve the best sensitivity. 65 matched baseline and exacerbation-onset samples from 50 patients were analysed and the following approach was used to identify which markers could be combined to identify more than 90% of patients at exacerbation (assuming that biomarker values increased at exacerbation). The rationale was essentially the same as in FIG. 25.

The starting focus was on B2M, which was at an elevated concentration in 45 episodes (increased levels from baseline to exacerbation-onset) giving a sensitivity of 69%. For the 20 episodes that were 'missed' 2 routes could be taken, as shown on the diagram.
1. 10 of the B2M negative episodes had increased calprotectin levels raising the sensitivity to 85%. From the remaining 10 episodes, 4 episodes had increased active HNE levels, bringing the sensitivity up to 91%. Finally, a further 3 patients were identified with increased A1AT levels.
2. 10 of the B2M negative episodes had increased IL-6 levels raising the sensitivity to 85%. From the remaining 10 episodes, 5 episodes had increased active MMP levels (as measured by Ultimate ELTABA), bringing the sensitivity up to 92%. Finally, a further 3 patients were identified with increased desmosine OR increased active HNE levels.

The combination of B2M, calprotectin, active HNE and A1AT gave an overall sensitivity of 95%. Alternatively, the combination of the biomarkers identified in route 2 gave 97% sensitivity.

Figure 30:
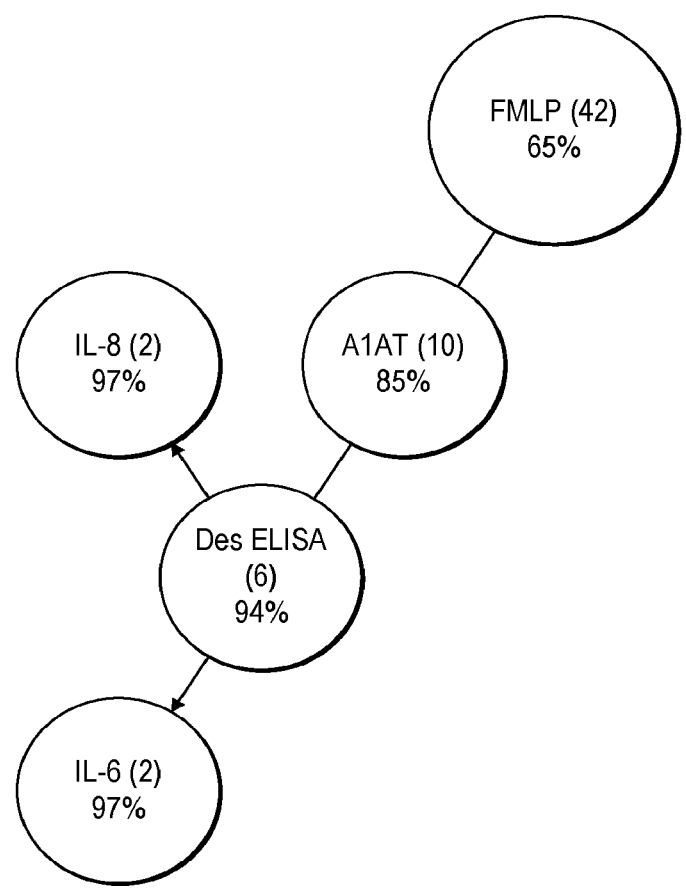
FIG. 30—Showing performance of various marker combinations for identifying a pulmonary exacerbation. Additional markers increase the sensitivity of detection as shown by the percentage values.

FIG. 30 identifies the various biomarkers clusters formed to achieve the best sensitivity with a starting focus on fMLP. This rational is the same as in FIG. 29.
1. fMLP alone gives a sensitivity of 65% with the identification of 42 episodes with elevated fMLP concentrations from baseline to exacerbation onset. With the sequential additions of A1AT, Desmosine and IL-6 the sensitivity can be raised to 97%.
2. fMLP alone gives a sensitivity of 65% with the identification of 42 episodes with elevated fMLP concentrations from baseline to exacerbation onset. With the sequential additions of A1AT, Desmosine and IL-8 the sensitivity can be raised to 97%.

Figure 31:
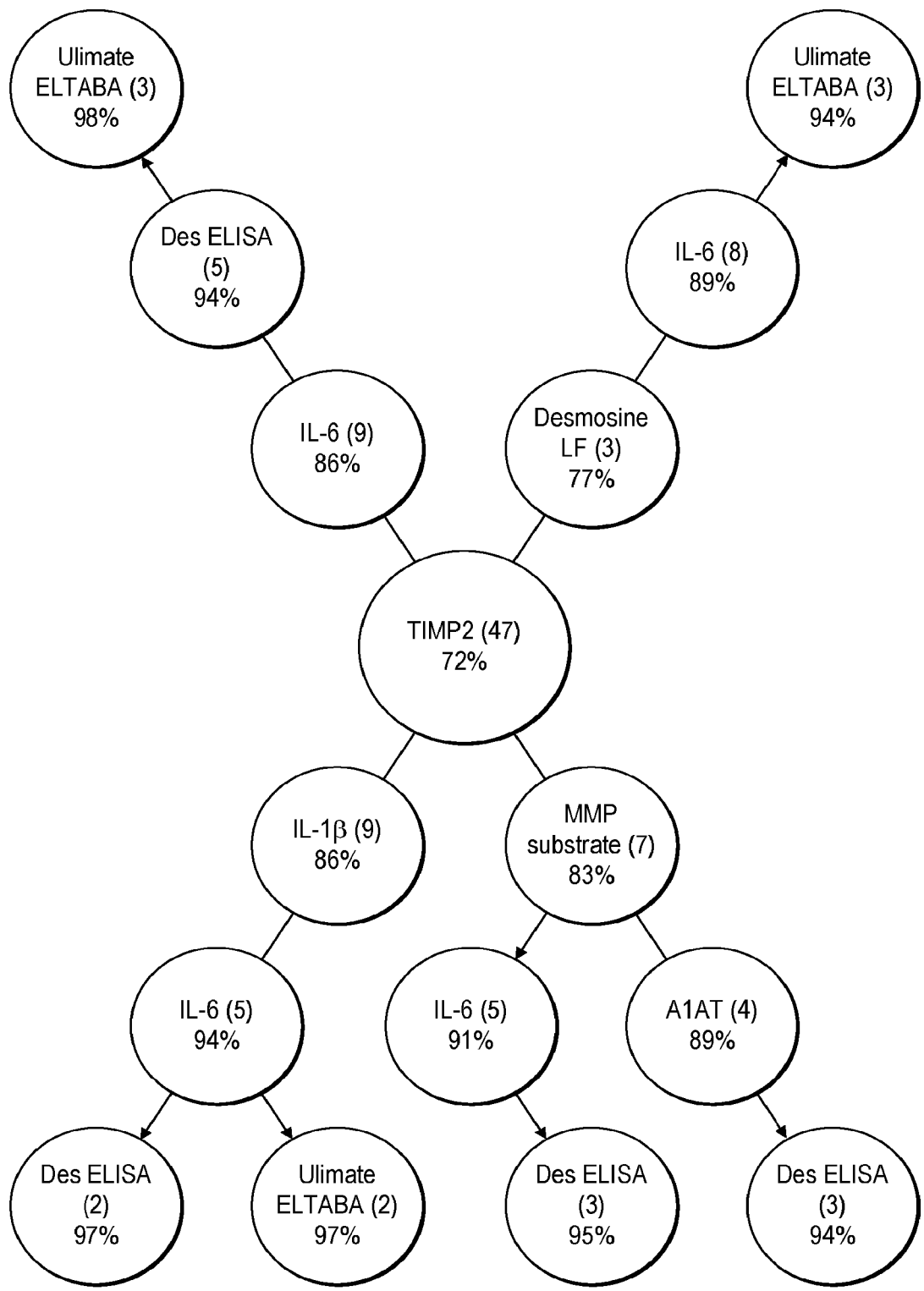
FIG. 31—Showing performance of various marker combinations for identifying a pulmonary exacerbation. Additional markers increase the sensitivity of detection as shown by the percentage values.

FIG. 31 identifies the various biomarkers clusters formed to achieve the best sensitivity with a starting focus on TIMP2. This rational is the same as in FIG. 29. TIMP2 alone gives a sensitivity of 72% with the identification of 47 episodes with elevated TIMP2 concentrations from baseline to exacerbation-onset. The following routes could be taken as shown on the diagram.
1. With the sequential additions of IL-6, Desmosine (as measured by the ELISA) and active MMP (as measured by Ultimate ELTABA) the sensitivity can be raised to 98%.
2. With the sequential additions of Desmosine (as measured by Lateral flow), IL-6 and active MMP (as measured by Ultimate ELTABA) the sensitivity can be raised to 93%.
3. With the sequential additions of IL-1β, IL-6 and desmosine (as measured by ELISA), the sensitivity can be raised to 97%.
4. With the sequential additions of IL-1β, IL-6 and active MMP (as measured by Ultimate ELTABA) the sensitivity can be raised to 97%.
5. With the sequential additions of active MMP (as measured by substrate assay), IL-6 and desmosine the sensitivity can be raised to 95%.
6. With the sequential additions of active MMP (as measured by substrate assay), A1AT and desmosine (as measured by ELISA) the sensitivity can be raised to 94%.

Figure 32:
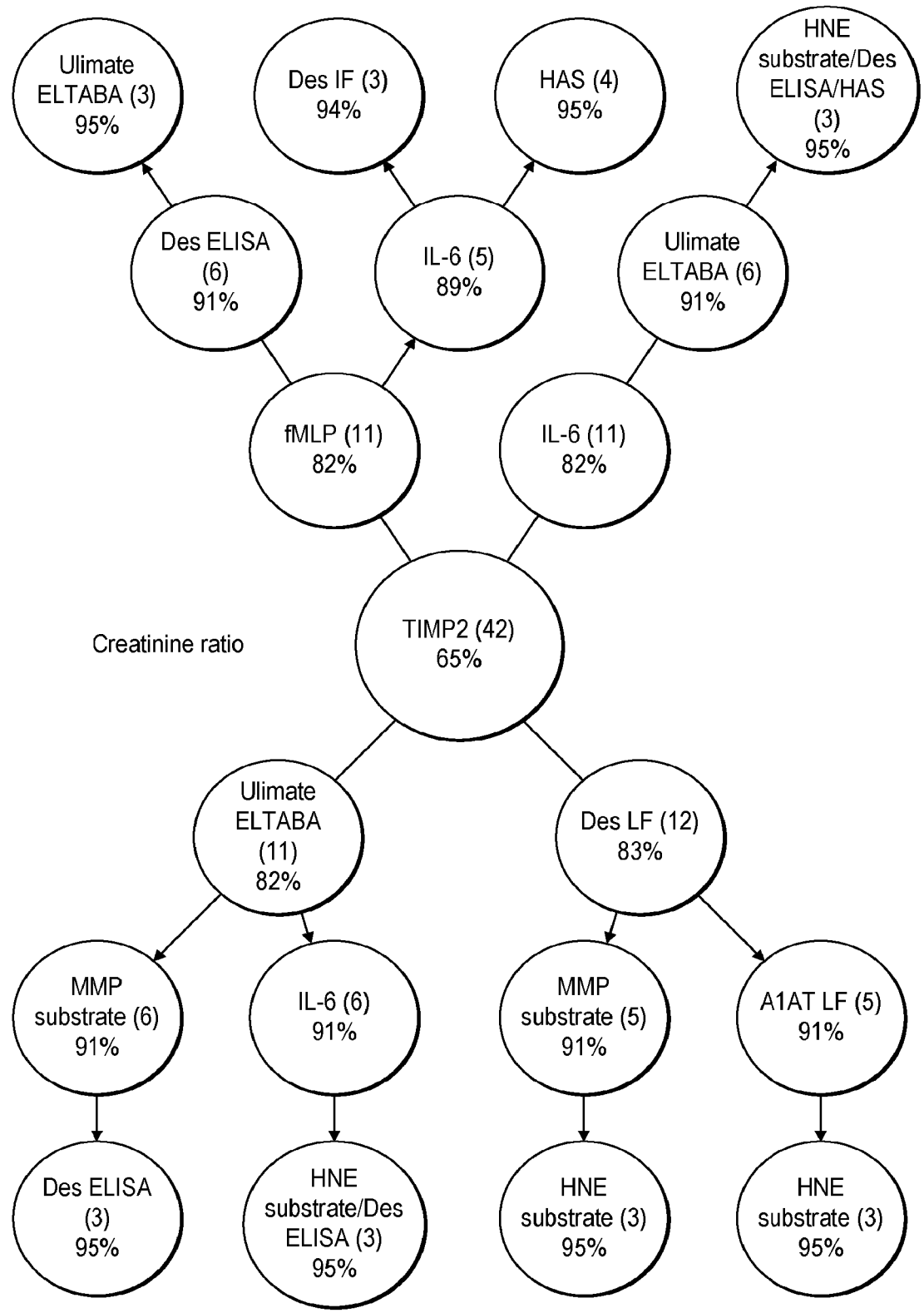
FIG. 32—Showing performance of various marker combinations for identifying a pulmonary exacerbation when normalised against creatinine levels to give a ratio.

FIG. 32 identifies the various biomarkers clusters formed to achieve the best sensitivity with a starting focus on TIMP2. The difference here is that the markers are based on creatinine ratios. This rationale is the same as in FIG. 29. TIMP2 alone gives a sensitivity of 65% with the identification of 42 episodes with elevated TIMP2 concentrations from baseline to exacerbation-onset. The following routes could be taken as shown on the diagram.
1. With the sequential additions of fMLP, desmosine (as measured by ELISA) and active MMP (as measured with Ultimate ELTABA) the sensitivity can be raised to 95%.
2. With the sequential additions of fMLP, IL-6 and desmosine (as measured by lateral flow) the sensitivity can be raised to 94%.
3. With the sequential additions of fMLP, IL-6 and HSA the sensitivity can be raised to 95%.
4. With the sequential additions of IL-6, active MMP (as measured by Ultimate ELTABA) and active HNE etc the sensitivity can be raised to 95%.
5. With the sequential additions of active MMP (as measured by Ultimate ELTABA and substrate assay) and Desmosine (as measured by ELISA) the sensitivity can be raised to 95%.
6. With the sequential additions of active MMP (as measured by Ultimate ELTABA), IL-6 and active HNE etc the sensitivity can be raised to 95%.
7. With the sequential additions of desmosine (as measured by lateral flow), active MMP (as measured by substrate assay) and active HNE the sensitivity can be raised to 95%.
8. With the sequential additions of desmosine (as measured by lateral flow), A1AT and active HNE the sensitivity can be raised to 95%.

These data show that various markers can usefully be applied to provide an algorithm to identify exacerbations with high levels of sensitivity. Other starting points and combinations can readily be derived by one skilled in the art based upon the information contained herein. As also mentioned herein, combinations of markers when simultaneously increased (or indeed decreased) may also be given additional weight in terms of directing future testing and predicting or identifying exacerbations and recovery therefrom or treatment thereof.

Methods for Analysing Marker Levels in Examples 9 and 10

Total MMP9, MMP8, NGAL, TIMP1, TIMP2, HSA, Cystatin C, RBP4, IL-6, IL-8, IL-1β and TNFα were all measured using commercial ELISA kits (R&D systems). These DuoSet ELISA development Systems containing the basic components required to develop a sandwich immunoassay for measuring analytes in biological fluids were validated with urine prior to testing. Plates were sensitised overnight and run according to the manufacturer's instructions.

Calprotectin was measured using a ready to use solid phase ELISA (Hycult HK325) based on a sandwich principle. The analyte was sandwiched by an immobilised antibody and biotinylated tracer antibody, which was recognised by a streptavidin peroxidase conjugate. All unbound material was washed away and a peroxidase enzyme substrate was added, subsequent colour was measured at 450 nm.

Fibrinogen (B2M ab108841) and Beta-2-Microglobulin (Abcam ab108885) were measured using ready to use solid phase ELISA that employed a quantitative sandwich immunoassay technique. The analytes were sandwiched by the immobilised polyclonal antibody and biotinylated polyclonal antibody, which was recognised by a streptavidin peroxidase conjugate. All unbound material was washed away and a peroxidase enzyme substrate was added, subsequent colour was measured at 450 nm. Creatinine measurements were achieved using the creatinine Parameter Assay (R&D systems KGE005). Diluted samples were added to a microplate followed by the addition of alkaline picrate reagent to initiate the Jaffe reaction. After a 30 minute incubation period the plate was read at 490 nm.

3 different methods were used for protease measurements including zymography (MMPs), Flurogenic substrate assay (MMP's and HNE) and Ultimate ELTABA (MMPs):
Zymography was performed using pre-cast gelatin gels from Invitrogen, samples were run under denaturing conditions and visualized as clear bands against a dark background following a renaturing, developing, and staining protocol. The image analysis was carried out using image J software. Active MMP9 at a known concentration was run on all gels to normalise the sample data.

For substrate assays, 10 μm of MMP flurogenic substrate (R&D systems ES010) or 20 μm HNE flurogenic substrate (Enzo P-224) was added to 5 μl sample, the fluorescence was read on a BMG plate reader. The conditions for reading were as manufacturer's instructions for 30 minutes at 1 minute intervals.

For Ultimate ELTABA (Mologic in-house Lateral flow assay), 12.5 μl MMP substrate (Mologic MOL378) was added to 75 μl sample and incubated for 10 minutes before addition to the cassette. The device was read after 15 minutes using an immunochromatography reader from Forsite diagnostics.

A1AT and HNE was measured using in-house developed ELISA based on a sandwich principle. The analytes were sandwiched by an immobilised mouse Fab and a mouse Fab directly labelled with alkaline phosphatase (AP). After washing, an alkaline phosphate enzyme substrate was added and subsequent colour was measured at 405 nm.

Desmosine was measured using an in-house developed ELISA lateral flow assay based on a competition principle, where free desmosine in the sample competed with bound desmosine on a solid phase for a sheep polyclonal antibody conjugated to alkaline phosphatase. After washing, an alkaline phosphate enzyme substrate was added and subsequent colour was measured at 405 nm.

fMLP was measured using an in-house developed ELISA based on a competition principle, where free fMLP in the sample competed with bound fMLP on a solid phase for a sheep polyclonal antibody conjugated to alkaline phosphatase. After washing, an alkaline phosphate enzyme substrate was added and subsequent colour was measured at 405 nm.

Example 11

Exacerbation in Cystic Fibrosis Patients

FIG. 33 illustrates an important aspect of the algorithm from urine samples donated from Cystic Fibrosis patients relating to the time of collection. Two samples were donated from the patient during a period of stable disease and also when they were experiencing a Pulmonary Exacerbation (PEx). The order of when the sample was taken is different for each patient, some had a previous 'stable' sample collected before admission, and some were admitted first and a 'stable' sample collected soon after. It is predicted that when the TIMP2 levels are high, MMP activity (as measured by the lateral flow) should be low. This was demonstrated in all patients with the exception of patient 4. It is also predicted that the MMP activity should be elevated at exacerbation as seen for 5 of the patients (3, 5, 6, 7, 8). However, for 2 of the patients (2, 9), active MMP was lower at PEx then at stable state indicating that the sample was donated after the protease shield has cut in i.e. the presence of active MMP9 would trigger a TIMP2 response. This has great predictive significance and highlights the importance of the use of these indicators for tracking an exacerbation episode based upon regular sampling.

Example 12

Exacerbation in COPD Patients

1. Introduction

The frequent occurrence of exacerbations is an important feature of COPD. Sample sets of urine were collected from a subgroup of COPD subjects. Urine samples were provided from each planned monthly clinic visit during the first 12 months of the study for 35 patients. In addition, urine samples collected at the time of each unscheduled clinic visit for a COPD exacerbation was provided.

2. Biomarkers and Assays
2.1 Biomarker Selection

On the basis of work undertaken by the inventors in previous lung inflammation studies (COPD and CF), the biomarkers in Table 2.1a were selected as the test menu for the study. A combination of in-house assays and commercial assay kits were used to measure the biomarkers. The assays were evaluated, selected and validated prior to the start of testing in this project by means of COPD samples from other projects.

TABLE 2.1a

Biomarkers and Test procedures

| Assay | Method Used | unit | Assay Cut Off | Validation status | Name of commercial kit | Reference of commercial kit |
|---|---|---|---|---|---|---|
| Desmosine Lateral flow Version 1 | Lateral flow | ng/ml | 2.05 | validated in-house | | |
| Desmosine Lateral flow Version 2 | Lateral flow | ng/ml | 2.05 | experimental | | |
| TIMP2 lateral flow | Lateral flow | ng/nl | 0.39 | validated in-house | | |
| TIMP1 ELISA | ELISA | ng/ml | 0.31 | commercial kit | R&D Duoset | DY970 |
| TIMP2 ELISA | ELISA | ng/ml | 0.31 | commercial kit | R&D Duoset | DY971 |
| MPO ELISA | ELISA | ng/ml | 0.62 | commercial kit | R&D Duoset | DY3174 |
| MMP8 Total ELISA | ELISA | ng/ml | 0.62 | commercial kit | R&D Duoset | DY908 |
| MMP9 Total ELISA | ELISA | ng/ml | 0.31 | commercial kit | R&D Duoset | DY911 |
| HNE ELISA | ELISA | ng/ml | 3.90 | validated in-house | | |
| NGAL ELISA | ELISA | ng/ml | 7.80 | commercial kit | R&D Duoset | DY1757 |
| RBP4 ELISA | ELISA | ng/ml | 46.00 | commercial kit | R&D Duoset | DY3378 |
| H.S.A ELISA | ELISA | ng/ml | 250.00 | commercial kit | R&D Duoset | DY1455 |
| beta 2 Microglobulin Abcam ELISA | ELISA | ng/ml | 1.20 | commercial kit | ABCAM | Ab108885 |
| beta 2 Microglobulin mologic ELISA | ELISA | ng/ml | 1.20 | experimental | | |
| A1AT ELISA | ELISA | ng/ml | 25.00 | validated in-house | | |
| A1AT Lateral Flow | Lateral flow | ng/nl | 8.80 | validated in-house | | |
| Desmosine ELISA Version 1 | ELISA | ng/ml | 8.19 | validated in-house | | |
| Desmosine ELISA Version 2 | ELISA | ng/ml | 8.19 | experimental | | |
| Calprotectin ELISA | ELISA | ng/ml | 6.25 | commercial kit | Hycult | HK325-02 |
| HNE substrate assay | enzymatic assay | ng/ml | 430.00 | commercial kit | Bachem flurogenic peptide substrate | L-1779 |
| MMP substrate assay | enzymatic assay | ng/ml | 2.73 | commercial kit | R&S flurogenic peptide substrate | ES010 |
| Ultimate ELTABA V1 | enzymatic assay | ng/ml | 7.80 | experimental | | |

TABLE 2.1a-continued

Biomarkers and Test procedures

| Assay | Method Used | unit | Assay Cut Off | Validation status | Name of commercial kit | Reference of commercial kit |
|---|---|---|---|---|---|---|
| Ultimate ELTABA V2 | enzymatic assay | ng/ml | 7.80 | experimental | | |
| Fibrinogen abcam ELISA | ELISA | ng/ml | 2.50 | commercial kit | ABCAM | Ab108841 |
| Fibrinogen mologic ELISA | ELISA | ng/ml | 1.25 | experimental | | |
| Creatinine plate assay | Chemical analysis plate assay | mg/dL | 6.26 | commercial kit | R&D | K GE005 |
| IL-6 ELISA | ELISA | pg/mL | 62.50 | commercial kit | R&D Duoset | DY206 |
| IL-1b ELISA | ELISA | pg/mL | 7.81 | commercial kit | R&D Duoset | DY201 |
| IL-8 ELISA | ELISA | pg/mL | 62.50 | commercial kit | R&D Duoset | DY208 |
| Cystatin C ELISA | ELISA | ng/ml | 15.50 | commercial kit | R&D Duoset | DY1196 |
| FMLP ELISA | ELISA | ng/ml | 7.81 | experimental | | |
| FMLP Lateral flow | Lateral flow | ng/ml | 3.91 | experimental | | |
| Ac-PGP version 1 | ELISA | ng/ml | 312.50 | experimental | | |
| Ac-PGP version 2 | ELISA | ng/ml | 312.50 | experimental | | |
| Ac-PGP version 3 | ELISA | ng/ml | 312.50 | experimental | | |
| Desmosine Fragments ELISA V2 | ELISA | ng/ml | 4.10 | experimental | | |
| Desmosine Fragments ELISA V3 | ELISA | ng/ml | 4.10 | experimental | | |
| Desmosine Fragments V4 | ELISA | ng/ml | 4.10 | experimental | | |
| Large Elastin Fragment ELISA V1 | ELISA | ng/ml | 78.13 | experimental | | |
| Large Elastin Fragment ELISA V2 | ELISA | ng/ml | 78.13 | experimental | | |
| Large Elastin Fragment ELISA V3 | ELISA | ng/ml | 78.13 | experimental | | |
| CRP ELISA | ELISA | pg/ml | 0.16 | commercial kit | | |
| CC16 ELISA | ELISA | ng/ml | 0.31 | commercial kit | | |

2. In-House Assays Developed for the Study 2.2.1 The Ac-PGP Assay

N-acetyl Pro-Gly-Pro (Ac-PGP), a neutrophil chemoattractant, is derived from the breakdown of extracellular matrix (ECM) and is generated during airway inflammation. AcPGP was selected as a biomarker because it is cleaved from collagen through the proteolytic action of neutrophil leucocytes in inflammatory diseases such as chronic obstructive pulmonary disease (COPD).

Three Ac-PGP competitive EIA assays were developed. A schematic of one of the Ac-PGP competitive EIA assays is shown in FIG. 34.

FIG. 35 presents the calibration curve obtained using this competitive binding format with standards ranging from 1000 ng/ml down to 15.625 ng/ml.

2.2.2 The fMLP Assay

Neutrophils respond to bacterial infection by producing and releasing reactive oxygen species that kill bacteria and by expressing chemokines that attract other immune cells to the site of infection. N-formylated peptides like fMLP (N-formyl-L-methionyl-L-leucyl-phenylalanine) play a major role as potent chemoattractants. fMLP originates from various bacteria as a consequence of their protein processing mechanisms and/or from degraded bacterial (PAMP). It can also be produced in mitochondria of eukaryotic cell proteins (e.g. "DAMP"). The N-formyl peptide receptor is G-protein coupled and initiates/propagates phagocytosis and pro-inflammatory reactions in human neutrophils and other cells, such as the production of reactive oxygen intermediates (e.g. superoxide; O2-·) upon stimulation with fMLP.

A competitive EIA assay was developed. A schematic of the fMLP competitive EIA assays is shown in FIG. 36.

FIG. 37 presents the calibration curve obtained using this competitive binding format with standards ranging from 50 ng/ml down to 0.78 ng/ml.

2.2.3 The Desmosine Fragment Assays

The degradation of elastin fibres during inflammation is caused by enzymes called elastases. The two most important inflammatory elastases are neutrophil elastase (released by activated neutrophils) and MMP12, released by lung macrophages. Desmosine is cleaved from elastin and is a molecular signature of the degradation process, indicating that leukocyte activity is elevated or rising. The amount of desmosine excreted in the urine directly correlates with the extent of elastin degradation which in turn is indicative of the level of tissue damage. Desmosine is small enough to be passed through the kidney. Excess neutrophil leukocyte activity is a key driver of exacerbation. The desmosine fragment assays are an addition to the Desmosine assay that we have already developed and validated. The assays have been specially designed to be are able to measure Desmosine as well as Desmosine still attached to elastin fibres by the generation of multiple antibodies raised to different sized elastin fragments resulting from cleavage by human neutrophil elastase.

FIG. 39 presents HPLC analysis to show profiles for whole elastin (peak on the right) broken down by increased concentration of enzyme (HNE). The different fragments produced were used to immunize sheep for specific antibody production.

FIG. 38 is a schematic of the Desmosine fragment competitive EIA assay.

2.2.4 The MMP Activity Assay (Ultimate ELTABA)

This unique assay (described herein in further detail) is capable of measuring the activity of certain Matrix matalloproteinases (MMPs) by the addition of a specially designed substrate capable of being cleaved by MMPs which is then recognized by a specific labelled sheep antibody CF1522.

3 Sample Analysis 71 exacerbation events were selected, each event had a pre-stable and a post-stable sample Pre-exacerbation sample was collected between 3-66 days before the exacerbation Post-exacerbation sample was collected between 6 and 73 days after the exacerbation event Using paired t-test analysis, markers that were significantly different between exacerbations and pre-exacerbation and post-exacerbation were calculated. The markers were also normalised with creatinine. The p values are shown in the table below with significant values <0.05 highlighted.

CRP was unaffected by normalisation. There was an increase and decrease pre and post exacerbation. Other markers were different with normalisation, in particular, 6 additional markers changed significantly from stable to exacerbation, the collagen and elastin degradation markers Ac-PGP and desmosine-like markers, 4 of which decreased back to recovery. The signalling molecules IL-1β, IL-6 and fMLP were not increased pre-exacerbation to exacerbation but were decreased at recovery, indicating the importance of catching the sample at the correct time point. With the non-normalised samples, a decrease in MMP activity (ultimate ELTABA version 1 and version 2, calprotectin and CC16 were shown to be significant.

|  | paired test | | | |
| --- | --- | --- | --- | --- |
|  | no normalisaion | | creatinine normalisation | |
|  | pre Pex-Pex | Pex-post Pex | pre Pex-Pex | Pex-post Pex |
| des Fab | 0.11180 | 0.09699 | 0.01336 | 0.01921 |
| A1AT | 0.09984 | 0.04965 | 0.80687 | 0.59202 |
| Calprotectin | 0.53099 | 0.02838 | 0.03607 | 0.13506 |
| Ultimate ELTABA v1 | 0.35643 | 0.00797 | 0.89972 | 0.06278 |
| Ultimate ELTABA v2 | 0.54691 | 0.02260 | 0.83052 | 0.37969 |
| Fibrinogen mologic | 0.21482 | 0.04873 | 0.08596 | 0.41560 |
| Il-6 | 0.95479 | 0.06800 | 0.45222 | 0.02485 |
| Il-1b | 0.62240 | 0.78016 | 0.34679 | 0.04435 |
| FMLP | 0.45917 | 0.61272 | 0.20326 | 0.00136 |
| PGP 1 | 0.35747 | 0.27800 | 0.02786 | 0.00004 |
| PGP2 | 0.40539 | 0.84519 | 0.06261 | 0.00230 |
| Des Frag 3 | 0.27688 | 0.45086 | 0.00717 | 0.01947 |
| LEF 1 | 0.07413 | 0.04572 | 0.30559 | 0.68892 |
| LEF 2 | 0.88849 | 0.95918 | 0.03232 | 0.01235 |
| LEF 3 | 0.88849 | 0.76501 | 0.02681 | 0.06060 |
| CRP | 0.00013 | 0.00272 | 0.00009 | 0.00191 |
| CC16 | 0.08358 | 0.01211 | 0.48307 | 0.30098 |

Individual threshold values are important as baseline values vary from patient to patient. When taking this into account, a combination of 3 markers are able to collectively group 94% of the exacerbation events into the exacerbation group from stable and 93% in the recovery group post exacerbation i.e. increase at PEx and decrease at recovery. Urinary CRP and desmosine are common markers.

Focusing on 'predicting the exacerbation event', CRP alone increase from baseline to exacerbation for 48 of the 71 events equating to 68%, combined with desmosine this was increased to 82% and to 96% with the addition of IL1β. This is shown in FIG. 41A.

Focusing on 'predicting the recovery event', CRP alone increase from exacerbation to recovery for 46 of the 71 events equating to 65%, combined with Desmosine this was increased to 89% and to 93% with the addition of fibrinogen. This is shown in FIG. 41B.

Example 13

Change in Urinary Biomarkers at Exacerbation

From the same cohort as above, a subset of samples were selected based on blood CRP measurements
Stable/Pex Based on Blood CRP Measurements
A blood biomarker was used to stratify the groups to confirm the status of the samples. Blood CRP measurements were available for some patients. From the stable group, samples were selected with blood CRP <10 and from the PEx samples with CRP >10, resulting in 88 stable samples and 59 PEx samples.
Model 1 a and 1 b.
Logistic regression analysis performed on the concentration values identified CRP,Ac-PGPv3, fMLP, TIMP1, HSA and CC16 as a promising combination in being able to differentiate the 2 groups (Model 1a):

| Logistic regression | | Predicted | | Percentage |
| --- | --- | --- | --- | --- |
| Model 1a | | Stable | PEx | correct |
| observed | Stable | 81 | 5 | 94.2 |
|  | PEx | 17 | 42 | 71.2 |
| Overall percentage | | | | 84.8 |

This uses a cut off value of 0.5, if adjusted to 0.38, the sensitivity can be increased with an acceptable specificity of 91% in the stable group.

| Logistic regression | | Predicted | | Percentage |
| --- | --- | --- | --- | --- |
| Model 1a | | Stable | PEx | correct |
| observed | Stable | 80 | 8 | 90.9 |
|  | PEx | 13 | 46 | 77.8 |
| Overall percentage | | | | 85.7 |

Logistic regression and ROC plots are shown in FIG. 42.
Logistic regression analysis performed on the concentration values identified CRP,Ac-PGPv3, fMLP, TIMP1 and A1AT as a promising combination in being able to differentiate the 2 groups (Model 1b)

| Logistic regression | | Predicted | | Percentage |
| --- | --- | --- | --- | --- |
| Model 1b | | Stable | PEx | correct |
| observed | Stable | 81 | 5 | 94.2 |
|  | PEx | 18 | 41 | 69.5 |
| Overall percentage | | | | 84.8 |

This uses a cut off value of 0.5, if adjusted to 0.3146, the sensitivity can be increased with an acceptable specificity of 86% in the stable group and good sensitivity

| Logistic regression | | Predicted | | Percentage |
| --- | --- | --- | --- | --- |
| Model 1b | | Stable | PEx | correct |
| observed | Stable | 76 | 12 | 86.4 |
|  | PEx | 11 | 48 | 81.4 |
| Overall percentage | | | | 84.4 |

Logistic regression and ROC plots are shown in FIG. 43.
A further group was defined which included only those patients who had more than 1 exacerbation that year. The PEx group consisted of 59 samples and 47 stable samples. The following 3 models generated were as follows:
Model 2a, 2b and 2c
Logistic regression analysis performed on the concentration values identified CRP, fMLP, Ac-PGP version 3, A1AT and TIMP1 as a promising combination in being able to differentiate the 2 groups (Model 2a)

| Logistic regression | Predicted | | Percentage |
|---|---|---|---|
| Model 2a | Stable | PEx | correct |
| observed  Stable | 37 | 9 | 80.4 |
| PEx | 8 | 51 | 86.4 |
| Overall percentage | | | 83.8 |

Logistic regression plots are shown in FIG. 44.

Logistic regression analysis performed on the concentration values identified CRP, fMLP, Desmosine fragment V4, Desmosine Lateral flow assay V2, A1AT. TIMP1 and GENDER as a promising combination in being able to differentiate the 2 groups (Model 2b)

| Logistic regression | Predicted | | Percentage |
|---|---|---|---|
| Model 2b | Stable | PEx | correct |
| observed  Stable | 41 | 6 | 87.2 |
| PEx | 7 | 52 | 88.1 |
| Overall percentage | | | 87.7 |

Logistic regression plots are shown in FIG. 45.

Logistic regression analysis performed on the concentration values identified CRP, fMLP, Ac-PGP version 3, A1AT and CC16 as a promising combination in being able to differentiate the 2 groups (Model 2c)

| Logistic regression | Predicted | | Percentage |
|---|---|---|---|
| Model 2c | Stable | PEx | correct |
| Observed  Stable | 42 | 5 | 89.4 |
| PEx | 7 | 52 | 88.1 |
| Overall percentage | | | 88.7 |

Logistic regression plots are shown in FIG. 46.

ROC curves for each of models 2a, 2b and 2c are presented in FIG. 47 (A, B and C respectively).

The common markers for all 3 models are CRP and A1AT. All models were able to detect most exacerbations.

Example 14

Change in Urinary Biomarkers at Exacerbation

Decision Tree Analysis

Using the limited samples set from which algorithms 21-2c were derived from, the data was analysed using decision tree. Decision Trees can be used as predictive models to predict the values of a dependent (target) variable based on values of independent (predictor) variables. This approach is applied as an alternative to methods such as Logistic Regression.

There were many marker combinations that gave preference to sensitivity or specificity, eight of which were selected based on achieving at least 75% for both.

Combination 1

TIMP2, CRP and desmosine (6: TIMP2 LF 45: CRP 21: Desmosine EIA V2)

Classification

| | Predicted | | |
|---|---|---|---|
| Observed | Stable | PEx | Percent Correct |
| Stable | 40 | 7 | 85.1% |
| PEx | 11 | 48 | 81.4% |
| Overall Percentage | 48.1% | 51.9% | 83.0% |

Growing Method: CRT
Dependent Variable: VAR00001
Decision tree is shown in FIG. 48.
Combination 2
TIMP1, CRP and CC16 (7: TIMP1 ELISA 45: CRP 46:CC16 ELISA)
Classification

| | Predicted | | |
|---|---|---|---|
| Observed | Stable | PEx | Percent Correct |
| Stable | 39 | 8 | 83.0% |
| PEx | 14 | 45 | 76.3% |
| Overall Percentage | 50.0% | 50.0% | 79.2% |

Decision tree is shown in FIG. 49.
Combination 3
B2M, CRP, Ac-PGP (17: B2M (Mologic) 45: CRP 38: Ac-PGP EIA V3)
Classification

| | Predicted | | |
|---|---|---|---|
| Observed | Stable | PEx | Percent Correct |
| Stable | 37 | 10 | 78.7% |
| PEx | 11 | 48 | 81.4% |
| Overall Percentage | 45.3% | 54.7% | 80.2% |

Decision tree is shown in FIG. 50.
Combination 4
MMP activity, CRP and LEF (25: Ultimate ELTABA V1 45: CRP 43: Large Elastin Fragment assay (LEF) V2)
Classification

| | Predicted | | |
|---|---|---|---|
| Observed | Stable | PEx | Percent Correct |
| Stable | 37 | 10 | 78.7% |
| PEx | 7 | 52 | 88.1% |
| Overall Percentage | 41.5% | 58.5% | 84.0% |

Decision tree is shown in FIG. 51.
Combination 5
MMP activity, CRP and HSA (26: Ultimate ELTABA V2 45: CRP 15: Human serum albumin ELISA)
Classification

| | Predicted | | |
|---|---|---|---|
| Observed | Stable | PEx | Percent Correct |
| Stable | 37 | 10 | 78.7% |
| PEx | 6 | 53 | 89.8% |
| Overall Percentage | 40.6% | 59.4% | 84.9% |

Decision tree is shown in FIG. 52.

Combination 6

Creatinine, CRP, Ac-PGP (29: Creatinine 45: CRP 38: Ac-PGP V3)

|  | Predicted | | |
| --- | --- | --- | --- |
| Observed | Stable | PEx | Percent Correct |
| Stable | 37 | 10 | 78.7% |
| PEx | 8 | 51 | 86.4% |
| Overall Percentage | 42.5% | 57.5% | 83.0% |

Decision tree is shown in FIG. 53.

Combination 7 fMLP, CRP and TIMP2 (34: fMLP EIA 45: CRP 8: TIMP2 ELISA)

Classification

|  | Predicted | | |
| --- | --- | --- | --- |
| Observed | Stable | PEx | Percent Correct |
| Stable | 41 | 6 | 87.2% |
| PEx | 14 | 45 | 76.3% |
| Overall Percentage | 51.9% | 48.1% | 81.1% |

Decision tree is shown in FIG. 54.

Combination 8

Ac-PGP, CRP, alternative Ac-PGP assay (36: Ac-PGP EIA V1 45: CRP 38: Ac-PGP EIA V3).

Classification

|  | Predicted | | |
| --- | --- | --- | --- |
| Observed | Stable | PEx | Percent Correct |
| Stable | 37 | 10 | 78.7% |
| PEx | 8 | 51 | 86.4% |
| Overall Percentage | 42.5% | 57.5% | 83.0% |

Decision tree is shown in FIG. 55.

Example 15

Change in Urinary Biomarkers at Exacerbation 49 patients provided at stable and exacerbation samples. Urinary CRP increased from a median 60.7 pg/ml to 317.3 pg/ml (p=0.0015). With interquartile ranges 0-143.9 for stable state and 23.6-2584 for exacerbation state. Results are shown in FIG. 40.

Other biomarkers that were significantly different in this cohort were MMP substrate (p=0.0466), TIMP2 (p=0.0095), A1AT (p=0.0035), HSA (p=0.0424) and RBP4 (p=0.0478).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate. Various publications are cited herein, the disclosures of which are incorporated by reference in their entireties.

The invention claimed is:

1. A method comprising determining levels of at least three markers in urine samples taken from a subject suffering from chronic obstructive pulmonary disease (COPD) at multiple time points, wherein the at least three markers are selected from C-Reactive Protein (CRP), Clara Cell Protein (CC16), and Tissue Inhibitor of metalloproteinase (TIMP).

2. The method according to claim 1, comprising determining levels of at least five markers in the urine samples, wherein the at least five markers are selected from CRP, CC16, Fibrinogen, Neutrophil gelatinase-associated lipocalin (NGAL) and TIMP.

3. The method according to claim 1, wherein the TIMP is TIMP 1.

4. The method according to claim 1, further comprising determining levels of at least one further marker in the urine samples, wherein the at least one further marker is selected from myeloperoxidase (MPO), large elastin fragments (LEF), cystatin C, alpha-1 antitrypsin (A1AT), ICAM-1, IL-6, IL-1β, IL-8, N-formyl-Met-Leu-Phe (fMLP), IL-6 induced fibrinogen, cytokine induced beta-2-microglobulin (B2M), retinol binding protein 4 (RBP4), calprotectin; a protease activity selected from matrix metalloproteinase (MMP) activity, human neutrophil elastase (HNE) activity or cathepsin G activity; N-acetyl Pro-Gly-Pro (Ac-PGP), desmosine, human serum albumin (HSA), chlorinated peptides, lactic acid, free fatty acids, an extracellular matrix breakdown product or elastin fragments/peptides.

5. The method according to claim 4, wherein MMP activity comprises MMP9 and/or MMP8 activity.

6. The method according to claim 4, wherein the protease activity is determined by measuring cleavage of a peptide substrate.

7. The method according to claim 1, wherein the levels of at least one marker are determined by normalising against the levels of a reference marker.

8. The method according to claim 1, comprising using a lateral flow strip or device to determine the levels of the at least 3 markers.

* * * * *

UNITED STATES PATENT AND TRADEMARK OFFICE
CERTIFICATE OF CORRECTION

PATENT NO. : 11,953,506 B2
APPLICATION NO. : 16/783567
DATED : April 9, 2024
INVENTOR(S) : Gita Parekh et al.

Page 1 of 1

It is certified that error appears in the above-identified patent and that said Letters Patent is hereby corrected as shown below:

In the Specification

Column 29, Line 4, "(INFa)" should be --(INFα)--.

Column 73, Line 8, "204465.5" should be --204466.5--.

Column 73, Line 9, "162522" should be --162622--.

Signed and Sealed this
Fifteenth Day of October, 2024

Katherine Kelly Vidal
*Director of the United States Patent and Trademark Office*